US010981963B2

(12) United States Patent
Rosenlöf et al.

(10) Patent No.: US 10,981,963 B2
(45) Date of Patent: Apr. 20, 2021

(54) ALPHA-1-MICROGLOBULIN DERIVED PROTEINS AND THEIR USE

(71) Applicant: Guard Therapeutics International AB, Lund (SE)

(72) Inventors: Lena Wester Rosenlöf, Hörby (SE); Anneli Edström Hägerwall, Lund (SE); Bo Åkerström, Lund (SE)

(73) Assignee: Guard Therapeutics International AB, Lund (SE)

(*) Notice: Subject to any disclaimer, the term of this patent is extended or adjusted under 35 U.S.C. 154(b) by 233 days.

(21) Appl. No.: 16/085,500

(22) PCT Filed: Mar. 17, 2017

(86) PCT No.: PCT/EP2017/056436
§ 371 (c)(1),
(2) Date: Sep. 14, 2018

(87) PCT Pub. No.: WO2017/158181
PCT Pub. Date: Sep. 21, 2017

(65) Prior Publication Data
US 2019/0161524 A1  May 30, 2019

(30) Foreign Application Priority Data
Mar. 18, 2016 (DK) .......................... PA 2016 70158

(51) Int. Cl.
C07K 14/47 (2006.01)
A61P 13/12 (2006.01)
A61K 38/00 (2006.01)

(52) U.S. Cl.
CPC .......... *C07K 14/4717* (2013.01); *A61P 13/12* (2018.01); *A61K 38/00* (2013.01)

(58) Field of Classification Search
None
See application file for complete search history.

(56) References Cited

U.S. PATENT DOCUMENTS

| | | | |
|---|---|---|---|
| 9,758,554 B2* | 9/2017 | Skerra ................ | C07K 14/8114 |
| 10,226,570 B2* | 3/2019 | La Berge ................ | A61G 5/10 |
| 10,350,268 B2* | 7/2019 | Åkerstrom .............. | A61P 13/12 |

FOREIGN PATENT DOCUMENTS

| | | | | |
|---|---|---|---|---|
| WO | WO-2010/006809 A2 | 1/2010 | | |
| WO | WO-2010006809 A2 * | 1/2010 | ................ | A61P 9/00 |
| WO | WO-2014/037390 A1 | 3/2014 | | |
| WO | WO-2014037390 A1 * | 3/2014 | ................ | A61P 9/00 |

OTHER PUBLICATIONS

Kwasek et al., Protein Expr Purif. May 2007 53(1):145-52. doi: 10.1016/j.pep.2006.10.023. Epub Nov. 1, 20060. PMID: 17169572.*

Åkerström et al., "A1M, an extravascular tissue cleaning and housekeeping protein," Free Radical Biology and Medicine, 74 (2014) 274-282 (Available online Jul. 2014).
Åkerström et al., "Formation of the $_{60\ 1}$-microglobulin chromophore in mammalian and insect cells: a novel post-translational mechanism?," FEBS Letters 362, 50-54 (1995).
Åkerström et al., "Lipocalins: An Introduction," Lipocalins Chapter 1, pp. 1-4 (Jan. 2006).
Åkerström et al., "The Lipocalin $\alpha_1$-Microglobulin Has Radical Scavenging Activity," The Journal of Biological Chemistry vol. 282, No. 43, pp. 31493-31503, (Oct. 2007).
Allhorn et al., "Processing of the lipocalin $\alpha_1$-microglobulin by hemoglobin induces and heme-binding and heme-degradation properties," Blood, vol. 99, No. 6, pp. 1894-1901 (Mar. 2002).
Allhorn et al., "Redox properties of the lipocalin $\alpha_1$-microglobulin: Reduction of cytochrome c, hemoglobin, and free iron," Free Radical Biology & Medicine 38, 557-567 (2005) (Available Online Dec. 2004).
Anderson et al., "Fetal hemoglobin and $\alpha_1$-microglobulin as first- and early second-trimester predictive biomarkers for preeclampsia," American Journal of Obstetrics & Gynecology, 204, 1.e1-1.e5 (Mar. 2011).
Berggård et A., "$\alpha_1$-Microglobulin chromophores are located to three lysine residues semiburied in the lipocalin pocket and associated with a novel lipophilic compound," Protein Science, 8:2611-2620, (1999).
Berggård et al., "Prothrombin, albumin and immunoglobulin A form covalent complexes with $\alpha_1$-microglobulin in human plasma," Eur. J. Biochem. 245, 676-683 (1997).
Bratt et al., "Cleavage of the $\alpha_1$-microglobulin-bikunin precursor is localized to the Golgi apparatus of rat liver cells," Biochimica et Biophysica Acta, 1157, 147-154 (1993).
Centlow et al., "Placental expression profiling in preeclampsia: local overproduction of hemoglobin may drive pathological changes," Fertil Steril., 90(5): 1834-1843, (Nov. 2008).
Ekström et al., "Human $\alpha_1$-Microglobulin, Purification Procedure, Chemical and Phystcochemical Properties", The Journal of Biological Chemistry, vol. 252, No. 22, Issue of Nov. 25, pp. 8048-8057 (1977).
Escribano et al., "Location and characterization of the three carbohydrate prosthetic groups of human protein Hc," FEBS Letters, vol. 266, No. 1,2, 167-170, (Jun. 1990).
Flower et al., "The lipocalin protein family: structure and function," Biochem. J., 318, 1-14 (1996).
Hansson et al., "Fetal hemoglobin in preeclampsia: a new causative factor, a tool for prediction/diagnosis and a potential target for therapy," Curr Opin Obstet Gynecol, vol. 25, No. 6, 448-455 (2013).
Karnaukhova et al., "Characterization of heme binding to recombinant $\alpha_1$-microglobulin," Frontiers in Pathsiology, vol. 5, Article 465, pp. 1-11, (Dec. 2014).
Kaumeyer et al., "The mRNA for a proteinase inhibitor related to the HI-30 domain of inter-α-trypsin inhibitor also encodes $\alpha_1$-microglobulin (protein HC)," Nucleic Acids Research, vol. 14 No. 20 (1986).
Kwasek et al., "Production of recombinant human $\alpha_1$-microglobulin and mutant forms involved in chromophore formation," Protein Expression and Purification 53, pp. 145-152, (2007) (Available online Nov. 2006).

(Continued)

*Primary Examiner* — Michael Szperka
(74) *Attorney, Agent, or Firm* — Dinsmore & Shohl LLP; Weston R. Gould

(57) ABSTRACT

This invention relates to an alpha-1-microglobulin derived protein for medical use.

10 Claims, 26 Drawing Sheets

Specification includes a Sequence Listing.

(56) References Cited

OTHER PUBLICATIONS

Larsson et al., "Distribution of iodine 125—labeled $_{\alpha 1}$-microglobulin in rats after intravenous injection," J Lab Clin Med vol. 137, pp. 165-175, (Mar. 2001).

Lindqvist et al., "Rat $_{\alpha 1}$-microglobulin: co-expression in liver with the light chain of inter-α-trypsin inhibitor," Biochimica et Biophysica Acta, 1130 (1992) 63-67.

May et al., "Perfusion of human placenta with hemoglobin introduces preeclampsia-like injuries that are prevented by $_{\alpha 1}$-microglobulin," Placenta 32 (2011) 323-332.

Meining et al., "The crystal structure of human $_{\alpha 1}$-microglobulin reveals a potential haem-binding site," Biochem. J. (2012) 445, 175-182.

Nääv et al., "A1M Ameliorates Preeclampsia-Like Symptoms in Placenta and Kidney Induced by Cell-Free Fetal Hemoglobin in Rabbit," PLoS One, 10(5): e0125499 (May 2015).

Olsson et al., "Increased levels of cell-free hemoglobin, oxidation markers, and the antioxidative heme scavenger $_{\alpha 1}$-microglobulin in preeclampsia," Free Radical Biology & Medicine 48, 284-291, t2010).

Olsson et al., "The lipocalin $_{\alpha 1}$-microglobulin protects erythroid K562 cells against oxidative damage induced by heme and reactive oxygen species," Free Radical Research,42:8, 725-736, (Aug. 2008).

Olsson et al., "The Radical-Binding Lipocalin A1M Binds to a Complex I Subunit and Protects Mitochondrial Structure and Function," Antioxidants & Redox Signaling, vol. 18, No. 16, pp. 2017-2028 (2013).

Olsson et al., "Up-Regulation of A1M/$_{\alpha 1}$-Microglobulin in Skin by Heme and Reactive Oxygen Species Gives Protection from Oxidative Damage," PLoS One, 6(11): e27505 (Nov. 2011).

Rutardottir et al., "Structural and biochemical characterization of two heme binding sites on $_{\alpha 1}$-microglobulin using site directed mutagenesis and molecular simulation," Biochimica et Biophysica Acta 1864, 29-41 (2016) (Available online Oct. 2015).

Sala et al., "Human $_{\alpha 1}$-Microglobulin Is Covalently Bound to Kynurenine-derived Chromophores," The Journal of Biological Chemistry, vol. 279, No. 49, Issue of Dec. 3, pp. 5103351041, (Sep. 2004).

Sverrisson et al., "Extracellular fetal hemoglobin induces increases in glomerular permeability: inhibition with $_{\alpha 1}$-microglobulin and tempol," Am J Physiol Renal Physiol, 306: F442-F448, (2014) (First published Dec. 2013).

Wester-Rosenlof et al.,"A1M/$_{\alpha 1}$-Microglobulin Protects from Heme-Induced Placental and Renal Damage in a Pregnant Sheep Model of Preeclampsia," PLoS ONE 9(1): e86353 (Jan. 2014).

\* cited by examiner

Figure 1

Figure 5:
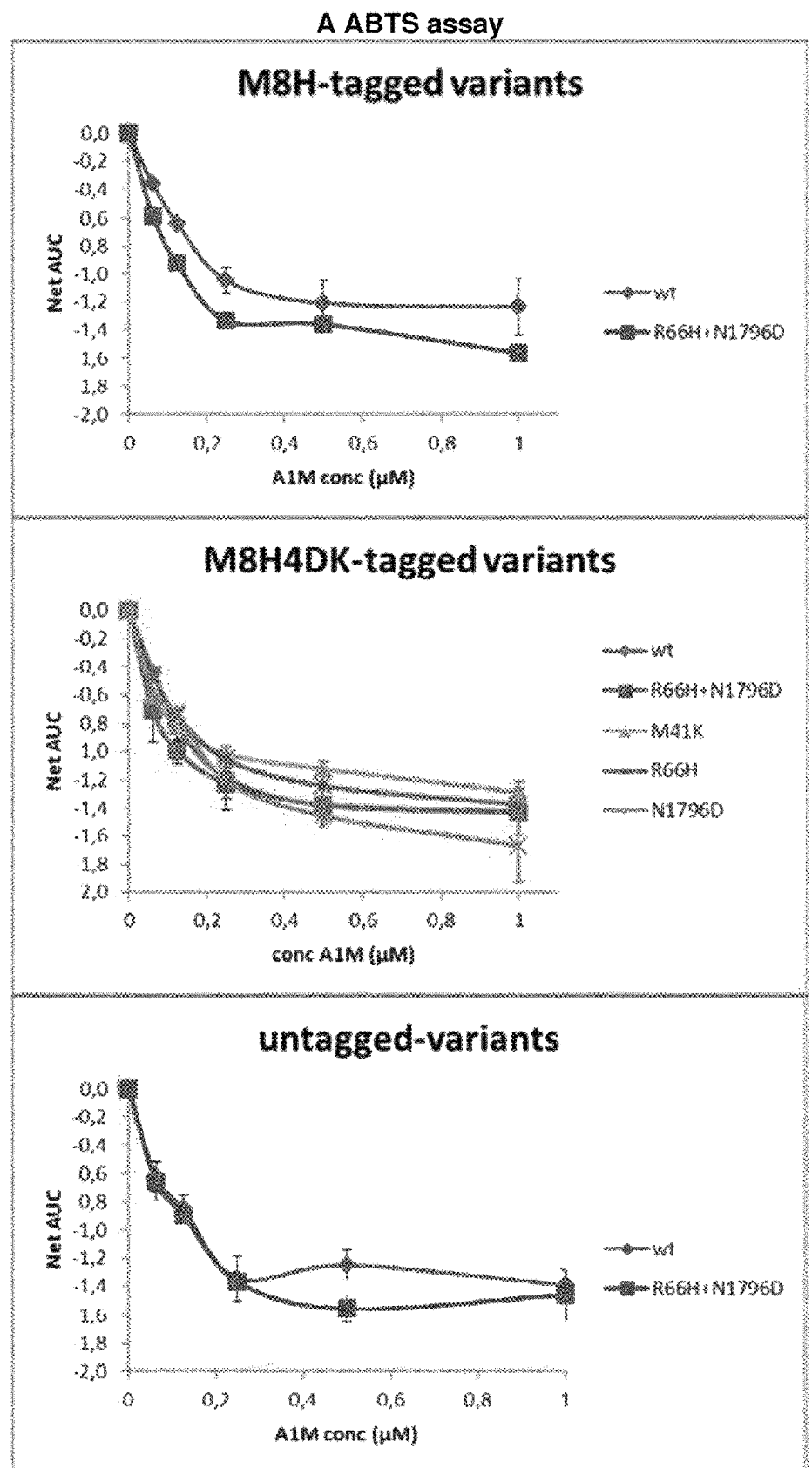

Figure 5 – continued
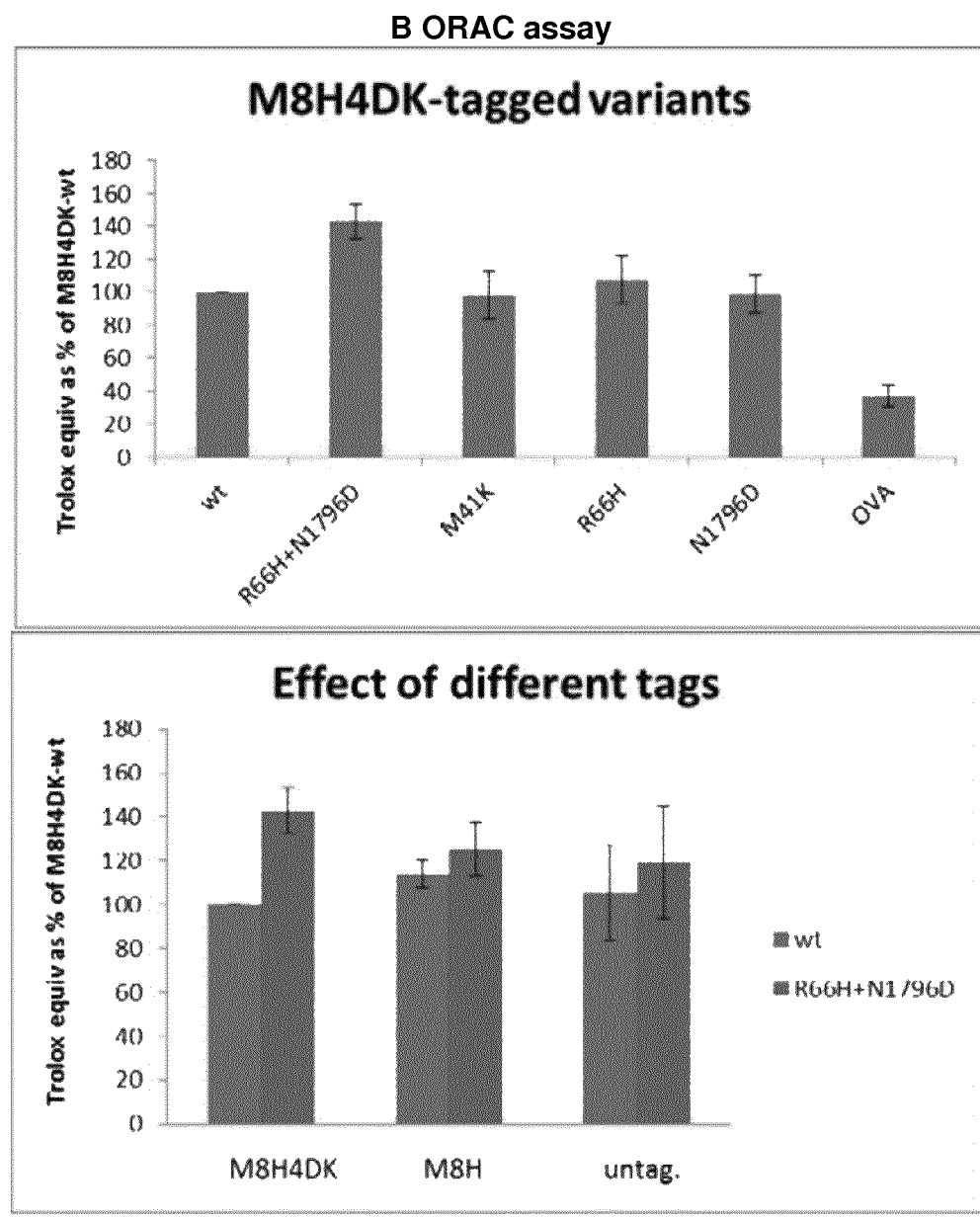

Figure 6:
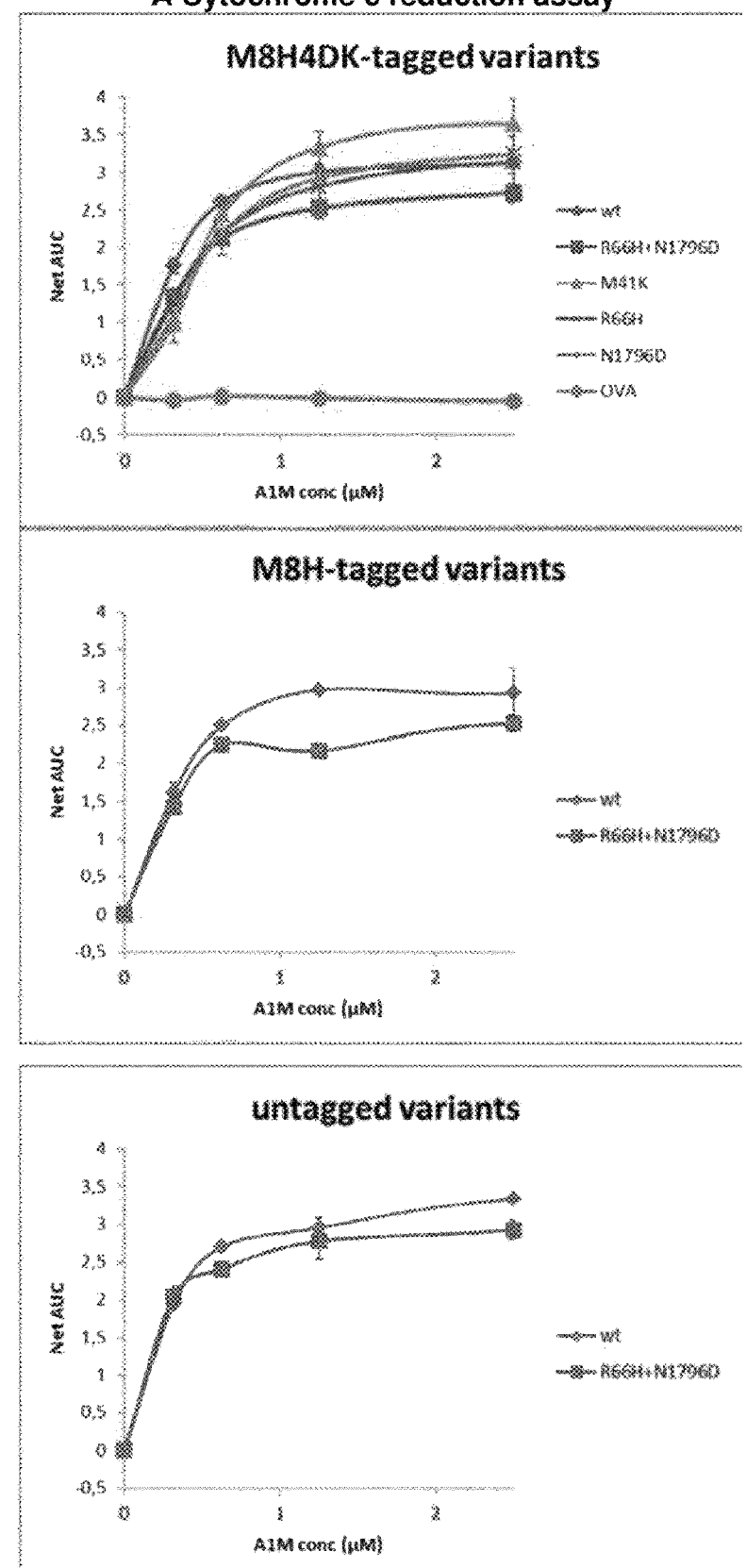

Figure 6 – continued
B Free heme reduction/incorporation red-shift assay
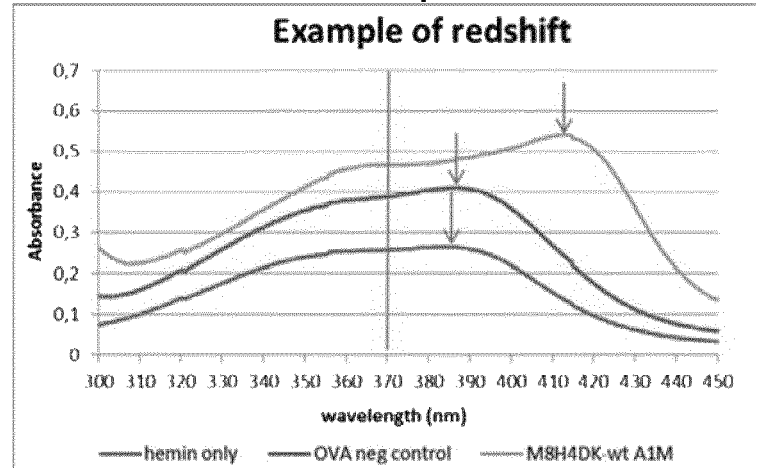
| # | variant | max (370-450nm) | ratio 413:386 |
|---|---|---|---|
|  | heme only | 386 | 0.52 |
|  | OVA | 387 | 0.59 |
| 60 | M8H4DK-wt (rhA1M) | 413 | 1.13 |
| 35 | M8H4DK-R66H+N17,96D | 411 | 1.11 |
| 37 | M8H4DK-M41K | 415 | 1.27 |
| 38 | M8H4DK-R66H | 412 | 1.12 |
| 39 | M8H4DK-N17,96D | 413 | 1.15 |
| 40 | M8H-wt | 415 | 1.34 |
| 41 | M8H-R66H+N17,96D | 415 | 1.41 |
| 61 | M-wt | 386 | 0.87 |
| 42 | MR66H+N1796D | 387 | 0.76 |
C Heme-agarose binding
| # | variant | µM bound/ µM protein |
|---|---|---|
|  | OVA | 0.008 |
| 60 | M8H4DK-wt (rhA1M) | 0.71 |
| 35 | M8H4DK-R66H+N17,96D | 0.72 |
| 37 | M8H4DK-M41K | 0.76 |
| 38 | M8H4DK-R66H | 0.66 |
| 39 | M8H4DK-N17,96D | 0.69 |
| 40 | M8H-wt | 0.68 |
| 41 | M8H-R66H+N17,96D | 0.72 |
| 61 | M-wt | 0.68 |
| 42 | MR66H+N17,96D | 0.66 |

Figure 8:
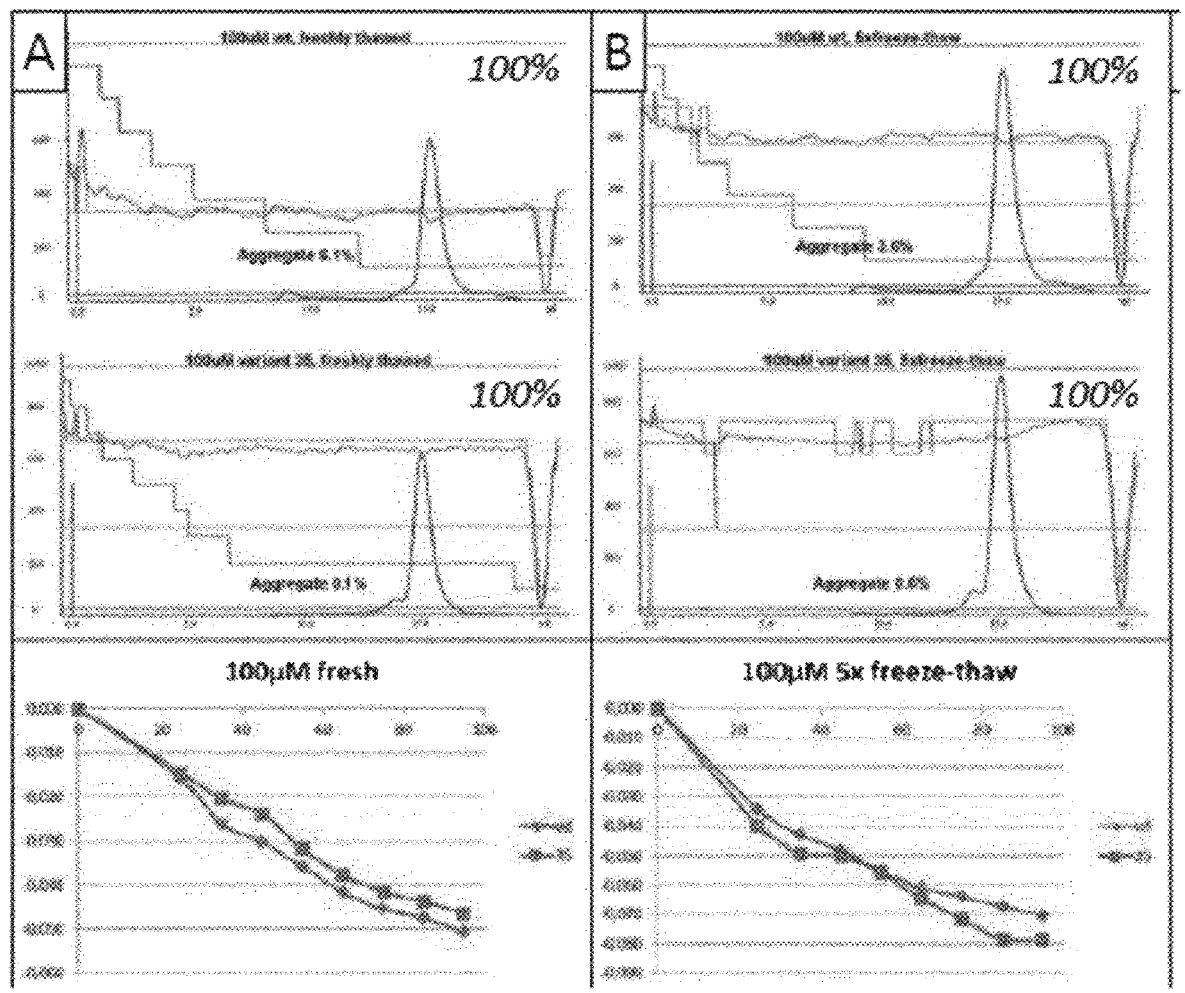

Figure 8 – continued
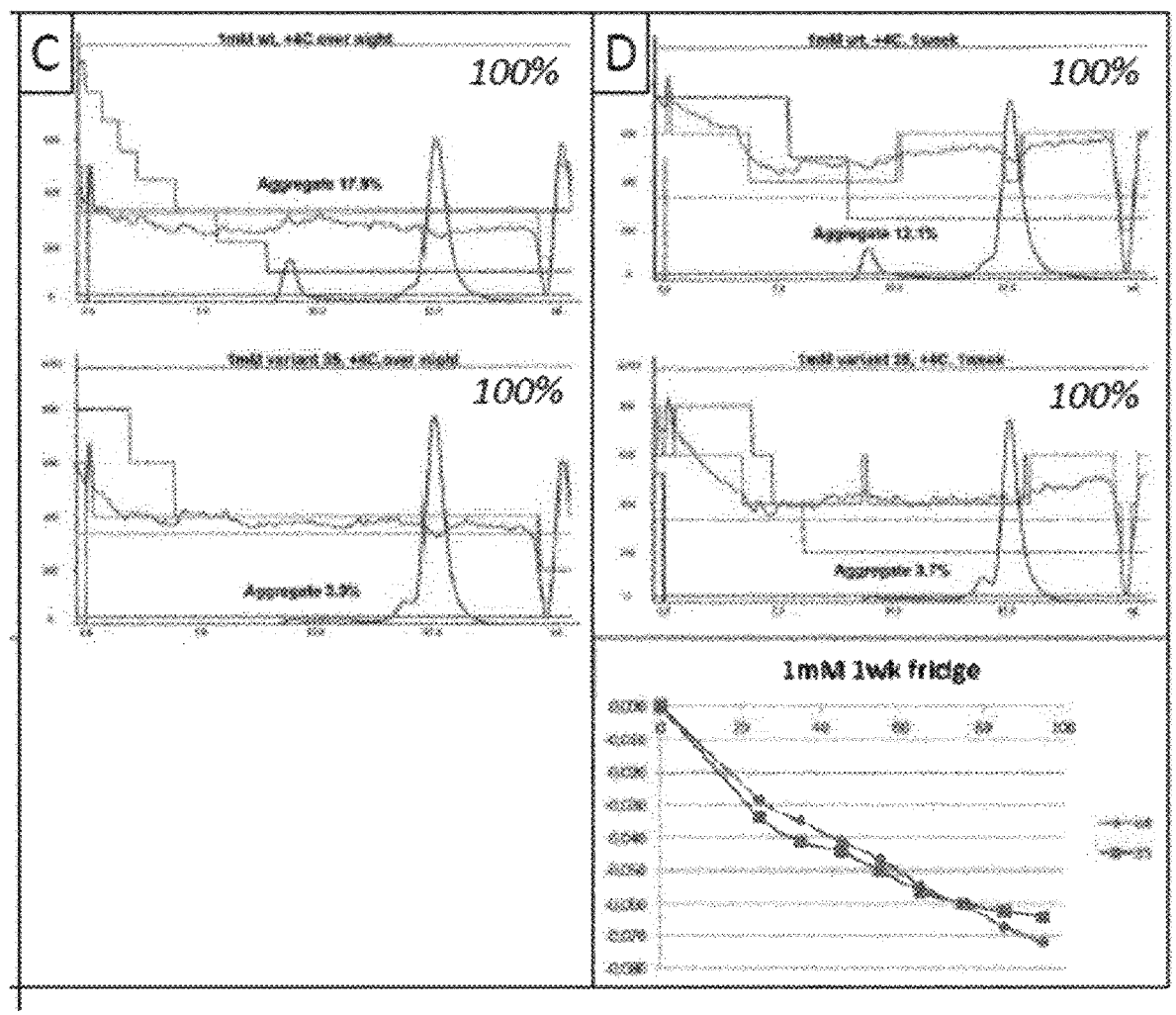

Figure 8 – continued
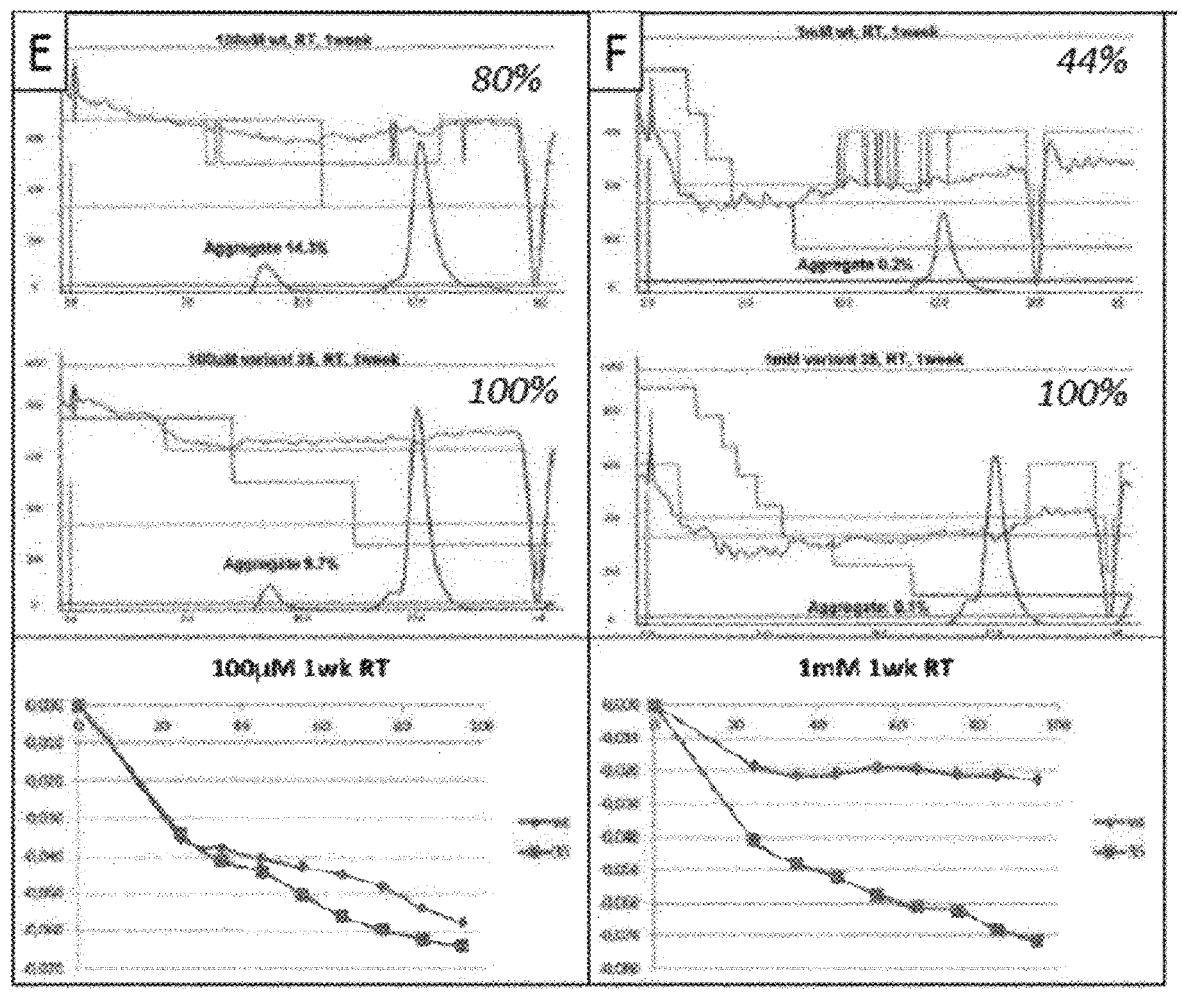

Figure 9:
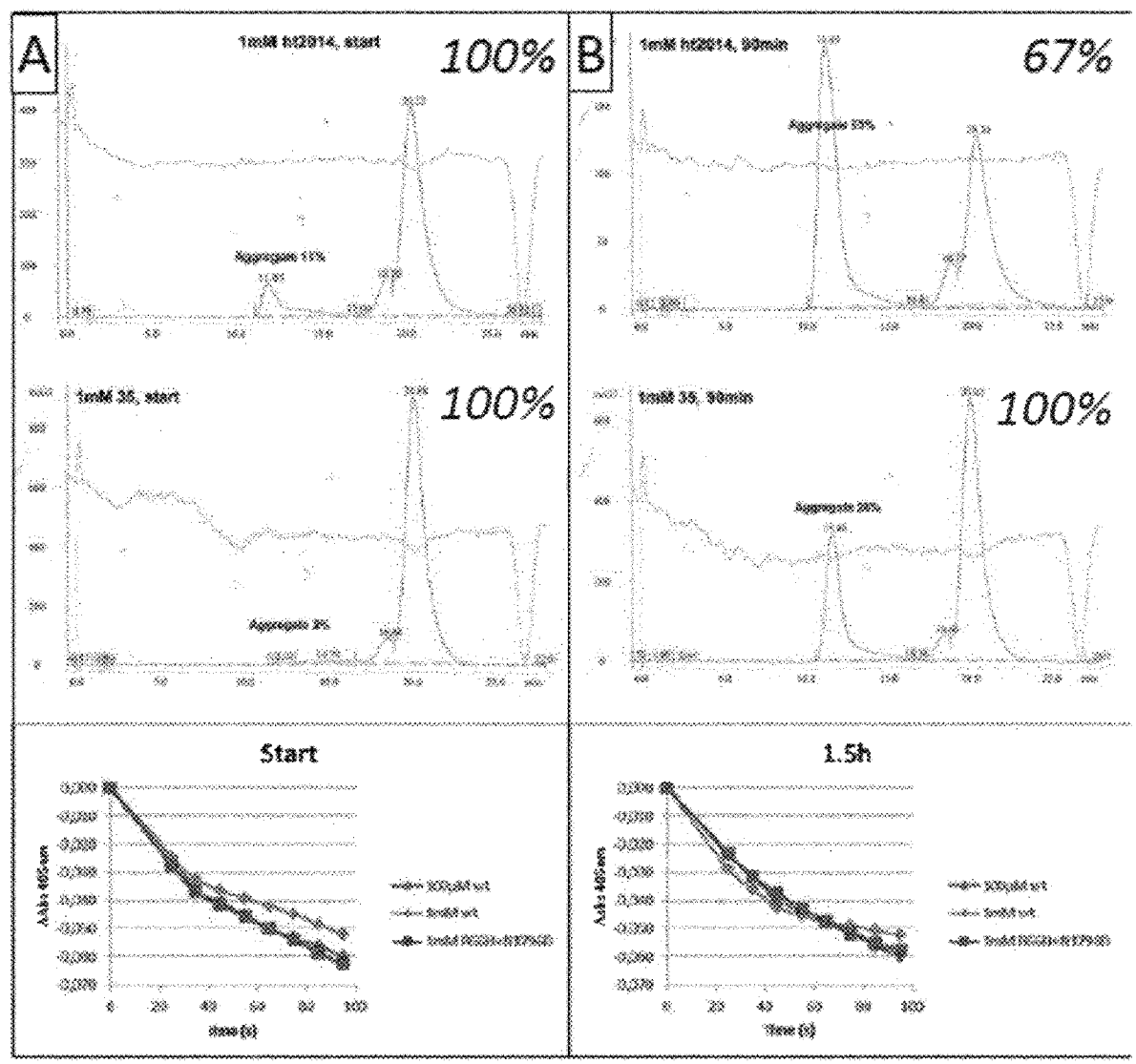

Figure 9 – continued
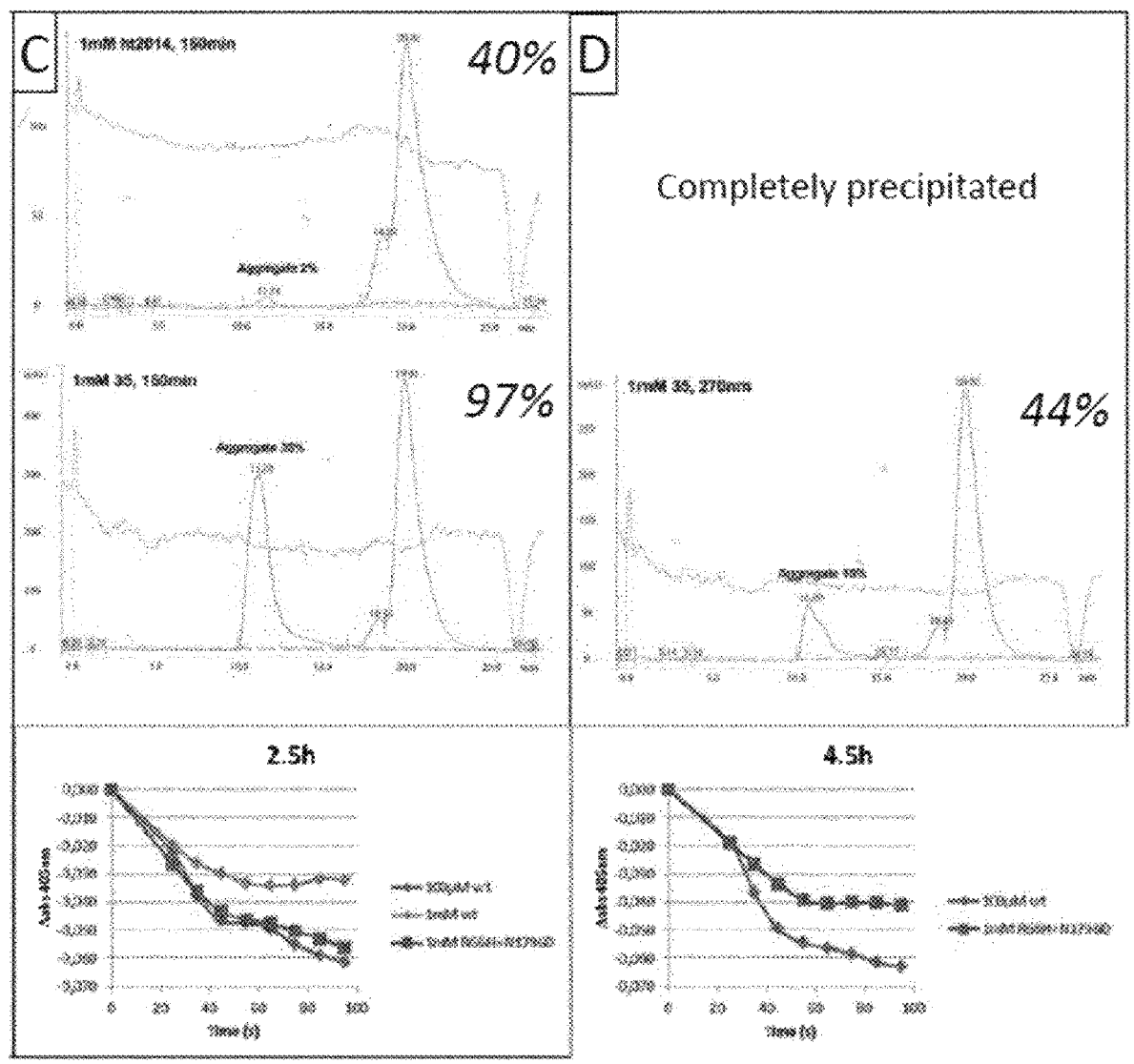

Table 4. Solubility, Stability and functional properties of phase I variants.

| | | Stability and solubility properties | | | | | | | Functional Properties | | | |
|---|---|---|---|---|---|---|---|---|---|---|---|---|
| | | Aggregation at 0.1mM | | Thermo-stability | Shearing stability at 0.1mM | | Aggregation at 1mM | Free Thiols | Binding of heme | Reduction of heme | Reduction of ABTS |
| | | PAGE | DLS | DSF | DLS | | PAGE | | | | |
| No | Name | Aggregates (%) | Average radius (nm) | Measurements used (# of 6) | $T_m$ | Average radius (nm) | Measurements used (# of 6) | Aggregates (%) | nmol L-cystein/nmol A1M | µM bound /µM added | Peak λ (380-420nm) | Average Max Net AUC |
| 60 | human, wt | 4.8 | 3.2 | 6 | 46.6 | 3.8 | 4 | 22.3 | 0.6 | 0.81 | 405 | -1.84 to -2.04 |
| 1 | mouse | 45.8 | 20 | 6 | 43 | 32.8 | 6 | 93.7 | 0.3 | 0.71 | 393 | -1.43 |
| 2 | naked mole rat | 54.8 | 2.7 | 6 | 51.6 | 3 | 6 | 80.1 | 0.1 | 0.69 | 397 | -1.42 |
| 3 | frog | 9.9 | 2.8 | 5 | NM | 3 | 1 | 24.1 | 0.1 | 0.81 | 410 | -1.33 |
| 4 | chicken | 2.4 | 3.3 | 5 | 67.5 | 3.4 | 6 | 3.5 | 0.1 | 0.66 | 391 | -1.98 |
| 5 | rabbit | 50.2 | 33 | 6 | 48.7 | 43.4 | 6 | 28.2 | 0.1 | 0.65 | 395 | -1.50 |
| 6 | sq. monkey | 20.2 | 3.2 | 3 | 49.9 | 3 | 6 | 38.3 | 0.3 | 0.72 | 407 | -1.98 |
| 7 | walrus | 4.0 | 3.8 | 6 | NM | 3.9 | 1 | 52.3 | 0.3 | 0.81 | 398 | -1.33 |
| 8 | manatee | 1.7 | 3.5 | 6 | 53.2 | 3.6 | 5 | 2.0 | 0.1 | 0.80 | 391 | -1.81 |
| 9 | plaice | 6.6 | 3.1 | 6 | NM | 3.1 | 6 | 30.0 | 0.0 | 0.73 | 388 | -1.25 |
| 10 | orangutan | 18.3 | 3.1 | 6 | 45.9 | 3 | 4 | 29.7 | 0.6 | 0.77 | 401 | -2.06 |
| 11 | human P35K | 94.5 | 29.2 | 6 | 44.6 | 40.9 | 6 | 86.7 | 0.1 | 0.81 | 396 | -1.29 |

FIG. 17

| | | Stability and solubility properties | | | | | | Functional Properties | | | |
|---|---|---|---|---|---|---|---|---|---|---|---|
| | | Aggregation at 0.1mM | | | Thermo-stability DSF | Shearing stability at 0.1mM | | Aggregation at 1mM PAGE | Free Thiols | Binding of heme | Reduction of heme | Reduction of ABTS |
| No | Name | PAGE Aggregates (%) | DLS Average radius (nm) | DLS Measurements used (# of 6) | $T_m$ | DLS Average radius (nm) | DLS Measurements used (# of 6) | Aggregates (%) | nmol L-cystein/ nmol A1M | μM bound / μM added | Peak λ (380-420nm) | Average Max Net AUC |
| 12 | human M41K | 20.5 | 3.2 | 3 | 47.9 | 3.2 | 5 | 27.5 | 0.4 | 0.92 | 414 | -1.87 |
| 13 | human R66H | 13.6 | 3.1 | 4 | 47.8 | 19 | 6 | 37.0 | 0.7 | 0.79 | 405 | -2.19 |
| 14 | human T75K | 60.0 | 42.3 | 6 | 43.3 | 82 | 6 | 96.3 | 0.3 | 0.76 | 393 | -1.28 |
| 15 | human T75Y | 36.1 | 35.7 | 6 | 49.8 | 32.4 | 6 | 45.7 | 0.4 | 0.87 | 392 | -2.08 |
| 16 | human M99K | 37.7 | 65.8 | 6 | 45.9 | 56.4 | 6 | 44.8 | 0.4 | 0.69 | 397 | -1.71 |
| 17 | human S101Y | 36.8 | 2.7 | 6 | 46.1 | 3 | 3 | 70.7 | 0.4 | 0.79 | 403 | -1.63 |
| 60 | human, wt | 4.8 | 3.2 | 6 | 46.6 | 3.8 | 4 | 22.3 | 0.6 | 0.81 | 405 | -1.84 to -2.04 |
| 19 | coelacanth | 4.1 | 3.7 | 6 | NM | 3.8 | 6 | 38.2 | 0.2 | 0.68 | 396 | -2.00 |
| 21 | human L89T | 42.1 | 2.9 | 1 | 46.1 | 25.7 | 6 | 51.6 | 0.5 | 0.96 | 403 | -1.69 |
| 22 | human N17.96D | 2.9 | 3.1 | 6 | 49.6 | 3.7 | 4 | 9.9 | 0.6 | 0.80 | 409 | -2.48 |
| 23 | human T45K | 91.2 | 48.5 | 6 | 42.8 | 86.9 | 6 | 89.9 | 0.3 | 0.94 | 394 | -1.29 |
| 24 | human A135E | 54.6 | 23.9 | 6 | 46.1 | 17.5 | 6 | 90.7 | 0.3 | 0.70 | 400 | -1.47 |

FIG. 17, cont.

| 25 | human V170S | 40.1 | 3 | 6 | 46 | 23.7 | 6 | 58.8 | 0.4 | 0.90 | 399 | -2.04 |
| 26 | human V148D | 35.8 | 3 | 6 | 46 | 3 | 2 | 44.9 | 0.6 | 0.86 | 402 | -2.16 |
| 27 | human G172Q | 93.4 | 36.1 | 6 | 44.1 | 34.2 | 6 | 89.5 | 0.2 | 0.81 | 396 | -1.95 |

Properties regarded to be better for variant compared to human wt A1M are presented. Properties regarded to be inferior of variant compared to human wt A1M are presented. All other properties are regarded as similar to human wt A1M.
In PAGE, variants with a significantly higher percentage of large aggregates are judged as inferior to human wt A1M.
In DLS, an average radius >> 3nm is regarded as indication of aggregates as well as difficulties in recording of measurements (seen as lower number of measurements used for calculations).
In DSF a $T_m$ >3 S.D of human wt A1M is regarded as higher or lower.
Free thiols of human wt A1M is typically in the range 0.6-0.8 anything significantly below this is regarded as inferior.
In heme binding assay, human wt A1M binds to ≈80% in this assay. Binding of other variants below 75% and above 85% is regarded as different.
In heme reduction assay a Soret band peak maximum <400nm is regarded as inferior of human wt A1M and a shift ≥409nm is regarded as better than human wt A1M.
In ABTS assay, a T-test p-value of <0.2 is regarded to indicate an inferior ABTS reduction capacity.

FIG. 17, cont.

| | | Stability and solubility properties | | | | | | | |
|---|---|---|---|---|---|---|---|---|---|
| | | Aggregation at 0.1mM | | | | Thermo-stability | Shearing stability at 0.1mM | | Aggregation at 1mM |
| | | PAGE | DLS | | SEC-FPLC | DSF | DLS | | PAGE | SEC-FPLC |
| No | Name | Aggregates (%) | Average radius (nm) | Measurements used (# of 6) | Monomer (%) | Tm | Average radius (nm) | Measurements used (# of 6) | Aggregates (%) | Monomer (%) |
| 60 | M8H4DK-wt | 1-2 | 3.0 | 6 | 87-94 | 46.6 | 3.0 | 2 | 8 | 80-87 |
| 12 | M8H5GIEGR-M41K | 34 | 6.0 | 3 | ND | 51.8 | 4.1 | 2 | 33 | ND |
| 13 | M8H5GIEGR-R66H | 25 | 3.2 | 6 | ND | 47.3 | 10.3 | 1 | 51 | ND |
| 22 | M8H5GIEGR-N1796D | 1 | 3.0 | 4 | 94 | 49.9 | 6.5 | 2 | 4.2 | 82 |
| 33 | M8H4DK-M41K+R66H | 19 | 3.4 | 1 | ND | 34.3 | 13.7 | 5 | 42.9 | ND |
| 34 | M8H4DK-M41K+N1796D | 1 | 3.4 | 6 | 96 | 52.7 | 3.2 | 5 | 1.0 | 77 |
| 35 | M8H4DK-R66H+N1796D | 0.4 | 3.3 | 6 | 93 | 51.6 | 3.1 | 6 | 0.4 | 89 |
| 36 | M8H4DK-M41K+R66H+N1796D | 0.8 | 3.3 | 5 | 82 | 37.4 | 3.6 | 6 | 1.1 | 63 |

Table 6a. Solubility, Stability and functional properties of phase II variants:
Properties regarded to be better for variant compared to human wt A1M are presented. Properties regarded to be inferior of variant compared to human wt A1M are presented. All other properties are regarded as similar to human wt A1M.
In PAGE, variants with a significantly higher percentage of large aggregates are judged as inferior to human wt A1M.
In DLS an average radius >> 3nm is regarded as indication of aggregates as well as difficulties in recording of measurements (seen as lower number of measurements used for calculations).
In DSF a $T_m$ >3 S.D of human wt A1M is regarded as higher or lower.

FIG. 18

| | | Functional Properties | | | |
|---|---|---|---|---|---|
| | | Binding to heme-agarose | Red-shift of heme-binding peak | Reduction of ABTS | Rescue from heme induced cell death |
| No | Name | µM bound /µM added | Peak λ (nm) | Average Max Net AUC | Ocular observation of graph in two separate experiments |
| 60 | M8H4DK-wt | 0.85 | 415 | -2.1 | |
| 12 | M8H5GIEGR-M41K | 0.81 | 408 | -1.2 | Similar as wt |
| 13 | M8H5GIEGR-R66H | 0.84 | ND | -1.5 | Similar as wt |
| 22 | M8H5GIEGR-N1796D | 0.82 | 415 | -2.2 | Similar as wt |
| 33 | M8H4DK-M41K+R66H | 0.68 | 417 | -1.8 | Similar as wt |
| 34 | M8H4DK-M41K+N1796D | 0.74 | 419 | -2.2 | Weaker than wt |
| 35 | M8H4DK-R66H+N1796D | 1.07 | 413 | -2.1 | Similar as wt |
| 36 | M8H4DK-M41K+R66H+N1796D | 1.13 | 412 | -2.0 | Similar as wt |

Table 6b. Functional properties of phase II variants.
Human wt A1M binds to ≈80% in the heme-agarose binding assay. Binding of other variants below 75% and above 85% is regarded as dif-ferent.
In heme-binding absorbance assay, a redshift to <400nm is regarded as inferior of human wt A1M and a shift ≥417nm is regarded as better than human wt A1M.
In ABTS assay, a T-test p-value of <0.2 is regarded to indicate an inferior ABTS reduction capacity.

FIG. 19

ALPHA-1-MICROGLOBULIN DERIVED PROTEINS AND THEIR USE

CROSS-REFERENCE TO RELATED APPLICATIONS

The present application is the U.S. National Stage of International Application PCT/EP2017/056436, filed Mar. 17, 2017, and claims priority to Denmark Patent Application No. PA 2016 70158, filed Mar. 18, 2016.

SEQUENCE LISTING

The present application contains a Sequence Listing which has been submitted electronically in ASCII format and is hereby incorporated by reference in its entirety. Said ASCII copy, created on Jan. 15, 2019, is named 105454-0110_SL.txt and is 158,170 bytes in size.

FIELD OF THE INVENTION

The present invention relates to modified variants of human alpha-1-microglobulin protein with improved properties and the use of such variants in medical treatment and diagnostics. The inventors have surprisingly found that introduction of specific amino acid substitutions and/or addition of specific N-terminal extensions confer improved properties to alpha-1-microglobulin with regard to stability, solubility, and binding of heme.

BACKGROUND OF THE INVENTION

A1 M ($a_1$-microglobulin) is a low molecular weight protein with an extracellular tissue-cleaning function (Ekström et al., 1977; Akerström and Gram, 2014). It is present in all tissues and organs in fish, birds, rodents, mammals and other vertebrates. A1M is synthesized mainly in the liver but also at a lower rate in most other cells in the body. It is encoded by the $\alpha_1$-microglobulin-bikunin precursor gene (AMBP) and translated in all cells and species as a continuous peptide precursor together with another protein, bikunin (Kaumeyer et al., 1986). However, the two proteins are separated by protease cleavage, processed and secreted into the blood as two different proteins with different functions (Lindqvist et al., 1992; Bratt et al., 1993). The reason for the ubiquitous cosynthesis of A1M and bikunin is still unknown. In the blood, about 50% of A1M is found in free, monomeric form, and the remaining 50% as high-molecular weight complexes covalently bound with immunoglobulin A, albumin and prothrombin (Berggård et al., 1997).

A1M is a one-domain, 183-amino acid, glycosylated protein. The crystal structure of a large fragment of A1M expressed in E. coli was recently published (Meining and Skerra, 2012). Based on its structure, A1M belongs to a protein family, Lipocalins, with 50 or more members from animals, plants and bacteria (Flower, 1996; Akerström et al., 2006). The lipocalins have a common three-dimensional structure which consists of eight antiparallel β-strands forming a barrel with one closed end (bottom) and an open end (top). The barrel functions as a pocket for hydrophobic ligands in most lipocalins. Four loops (loop 1-4), which make up the rim of the open end of the barrel, vary highly in length and composition between the various lipocalins. In A1M, a handful of amino acid side-groups located on these loops, or on the inside of the pocket, have been shown to be important for the identified functions of the protein. Thus, a free cysteine, C34, located on a short helix on loop 1, has a negative reduction potential and gives A1M reductase properties (Allhorn et al., 2005). Two tyrosine residues, Y22 and 132, were shown to be covalently modified by radical oxidation products in vitro (Åkerström et al., 2007). Four lysine residues, K69, 92, 118 and 130, regulate the reductase activity (Allhorn et al., 2005), influence the binding of free heme groups (Rutardottir et al., 2015), and are covalently modified on A1M purified from human urine and amniotic fluid with low molecular weight yellow-brown, heterogeneous substances (Berggård et al., 1999; Sala et al., 2004).

Employing the reductase activity, radical scavenging and heme-binding properties, A1M acts an antioxidant that protects cells and tissues from oxidative damage. A1M was shown to protect in vitro blood cell cultures, placenta tissue and skin against oxidative damage from hemoglobin, heme and reactive oxygen species (ROS) (Olsson et al., 2008; May et al., 2011; Olsson et al., PloS One 2011; Olsson et al., ARS 2012). A1M also showed in vivo protective effects in rats and rabbits against placenta and kidney tissue damage after hemoglobin infusion (Sverrison et al., 2014; Nääv et al., 2015). In a series of reports, hemoglobin and oxidative stress were shown to be involved in the pathogenesis of preeclampsia, a serious complication of pregnancy (Centlow et al., 2008; Hansson et al., 2013), and the levels of A1M-mRNA and protein in liver, placenta and plasma were elevated in pregnant women with preeclampsia (Olsson et al., 2010; Anderson et al., 2011). Therefore, it was suggested that A1M may be employed as a therapeutic agent to treat pregnant women with preeclampsia to ameliorate the oxidative damage and thus the clinical symptoms of the disease (Olsson et al., 2010).

A production process of recombinant human A1M was developed in E. coli and shown to possess the reductase, radical-binding and heme-binding properties (Kwasek et al., Allhorn et al., 2002; 2005; Åkerström et al., 2007). Indeed, this recombinant A1M variant showed in vivo therapeutic effects in a sheep model of preeclampsia (Wester-Rosenlöf et al., 2014). However, although functional, E. coli-expressed recombinant A1M lacks glycosylation, and has poor solubility and stability compared to human A1M purified from urine or plasma. The lack of stability and solubility of the protein limits its use as a drug for human use, mainly due to difficulties to obtain highly concentrated solutions and long-term storage conditions in buffers at physiological pH and salt conditions.

Accordingly, there is a need for developing a protein with structural similarities with human A1M, but with improved properties regarding stability and solubility. Moreover, the protein should be relatively easy to prepare in amounts suitable for therapeutic use.

DETAILED DESCRIPTION OF THE INVENTION

The present invention relates to novel alpha-1-microglobulin proteins with improved stability and solubility profiles.

Site-directed and additive mutagenesis was used to engineer A1M-species with retained, or possibly enhanced functional properties, but with improved protein stability and solubility that allow long-term storage at high concentrations in physiological buffers.

As it appears from the Examples herein, four lines of reasoning were followed when selecting the positions and identities of mutated amino acid side-groups:

1) Animal homologues from a variety of species with different expected environmental pressure in terms of oxidative stress, temperature, oxygen pressure were expressed (N=12);

2) Single amino acid substitutions that occur frequently among the 56 sequenced A1M-homologues at positions located in loops 1-4 or the interior surface of the hydrophobic pocket, were introduced into the human gene construct and expressed (N=3); and 3) Addition or removal of favourably located lysyl or tyrosyl residues, based on the hypothesis that these may infuence pKa of the C35 thiolyl (Allhorn et al., 2005) or serve as radical-trapping sites (Berggård et al., 1999; Sala et al., 2004; Akerström et al. 2007) (N=5; −4).

In addition, the influence of N-terminal, charged and hydrophilic extensions were tested on some A1M-variants. The rationale behind the design of the tested N-terminal extensions was to add 1) a tag for purification (e.g. His-tag), 2) a linker to separate the tag from the core of the A1M protein, 3) several (1-5) charged amino acid side-groups conferring hydrophilic properties to the protein in order to gain maximal stability and solubility in water-solutions, 4) without compromising the physiological functions of A1M.

The project was divided into three major phases:

Phase I) Expression of the 27 A1M-variants described above followed by analysis of solubility, stability and function;

Phase II) Design, expression and analysis of a few A1M-variants with expected optimal properties based on the outcome of phase 1; and Phase III) Design, expression and analysis of non-mutated wildtype (wt)-A1M and the most successful mutated A1M-variant equipped with or without N-terminal, charged and hydrophilic extensions.

As will be explained in more details herein, the present invention provides an A1M-derived protein having the amino acid sequence of formula I:

(SEQ ID NO: 10)
$X^1-X^2-X^3-X^4-X^5-X^6-X^7-X^8-X^9-X^{10}-X^{11}-X^{12}-X^{13}-X^{14}-$

GPVPTPPDN IQVQENF-$X^{15}$-IS RIYGKWYNLA IGSTCPWLKK I-

$X^{16}$-DRMTVSTL VLGEGATEAE ISMTST-$X^{17}$-WRK GVCEETSGAY

EKTDTDGKFL YHKSKW-$X^{18}$-ITM ESYVVHTNYD EY-AIFLTKKF

SRHHGPTITA KLYGRAPQLR ETLLQDFRVV AQGVGIPEDS IFT-

MADRGEC VPGEQEPEPI LIPR (formula I)

wherein at least one X is present and (in parentheses are suggestions for further substitutions)
$X^1$ is absent or represents Met or N-formyl Met;
$X^2$ is absent or represents His;
$X^3$ is absent or represents His;
$X^4$ is absent or represents His;
$X^5$ is absent or represents His;
$X^6$ is absent or represents His;
$X^7$ is absent or represents His;
$X^8$ is absent or represents His;
$X^9$ is absent or represents His;
$X^{10}$ is absent or selected from Asp and Glu, Lys and Arg;
$X^{11}$ is absent or selected from Asp and Glu, Lys and Arg;
$X^{12}$ is absent or selected from Asp and Glu, Lys and Arg;
$X^{13}$ is absent or selected from Asp and Glu, Lys and Arg;
$X^{14}$ is absent or represents Lys Glu, Asp or Arg or Met or N-formyl Met;
$X^{15}$ represents Asp or Asn or Glu;
$X^{16}$ represents Met or Lys or Arg;
$X^{17}$ represents Arg or His or Lys;
$X^{18}$ represents Asp or Asn or Glu;
or a pharmaceutically acceptable salt thereof,
with the proviso that when all $X^1$-$X^{14}$ are absent, $X^{15}$ represents Asn, $X^{16}$ represents Met, and $X^{17}$ represents Arg, then $X^{18}$ cannot represent Asn.

The invention also provides a derivative of A1M, i.e. $X^1$-$X^{14}$-A1M, wherein A1M may be any A1M obtained from the species mentioned in Table 2 (i.e. human, mouse, naked mole-rat, frog, chicken, rabbit, squirrel monkey, walrus, manatee, plaice and orangutan). The present inventors have found that inclusion of $X^1$-$X^{14}$ imparts improved properties at least to human A1M, and accordingly, it is contemplated that this start sequence also can impart important improved properties to A1M from other species or to species-recombinant A1M.

The present invention also provides an A1M-derived protein having the amino acid sequence of formula II:

(SEQ ID NO: 17)
$X^1-X^2-X^3-X^4-X^5-X^6-X^7-X^8-X^9-X^{10}-X^{11}-X^{12}-X^{13}-X^{14}-$

GPVPTPPDN IQVQENF-$X^{15}$-IS RIYGKWYNLA IGSTCPWLKK I-

$X^{16}$-DRMTVSTL VLGEGATEAE ISMTST-$X^{17}$-WRK GVCEETSGAY

EKTDTDGKFL YHKSKW-$X^{18}$-ITM ESYVVHTNYD EY-AIFLTKKF

SRHHGPTITA KLYGRAPQLR ETLLQDFRVV AQGVGIPEDS IFT-

MADRGEC VPGEQEPEPI (formula II)

wherein at least one X is present and (in parentheses are suggestions for further substitutions)
$X^1$ is absent or represents Met or N-formyl Met;
$X^2$ is absent or represents His;
$X^3$ is absent or represents His;
$X^4$ is absent or represents His;
$X^5$ is absent or represents His;
$X^6$ is absent or represents His;
$X^7$ is absent or represents His;
$X^8$ is absent or represents His;
$X^9$ is absent or represents His;
$X^{10}$ is absent or selected from Asp and Glu, Lys and Arg;
$X^{11}$ is absent or selected from Asp and Glu, Lys and Arg;
$X^{12}$ is absent or selected from Asp and Glu, Lys and Arg;
$X^{13}$ is absent or selected from Asp and Glu, Lys and Arg;
$X^{14}$ is absent or represents Lys or Glu, Asp or Arg or Met or N-formyl Met;
$X^{15}$ represents Asp or Asn or Glu;
$X^{16}$ represents Met or Lys or Arg;
$X^{17}$ represents Arg or His or Lys;
$X^{18}$ represents Asp or Asn or Glu;
or a pharmaceutically acceptable salt thereof,
with the proviso that when all $X^1$-$X^{14}$ are absent, $X^{15}$ represents Asn, $X^{16}$ represents Met, and $X^{17}$ represents Arg, then $X^{18}$ cannot represent Asn.

The invention also provides a derivative of A1M, i.e. $X^1$-$X^{14}$-A1M, wherein A1M may be any A1M obtained from the species mentioned in Table 2 (i.e. human, mouse, naked mole-rat, frog, chicken, rabbit, squirrel monkey, walrus, manatee, plaice and orangutan), wherein A1M is truncated C-terminally, so that the C-terminal tetrapeptide sequence LIPR does not form part of the protein.

As it appears from the Examples herein, the present inventors have found that:

i) The initial sequence $X^1$-$X^{14}$ seems to impart improved properties to A1M,
ii) Point mutation M41K, R66H or N17,96D of the A1M molecule imparts improved stability with maintained function of A1M,
iii) Mutations (M41K+R66H), (M41K+N17,96D), (R66H+N17,96D), and/or (M41K+R66H+N17,96D) show increased solubility and/or stability with maintained function,
iv) Mutation (R66H+N17,96D) had best overall performance in the experiments performed,
v) A1M with mutations (R66H+N17,96D) and initial sequences MHHHHHHHHGGGGGIEGR (M8H5-GIEGR) (SEQ ID NO: 96); MHHHHHHHHDDDDK (M8H4DK) (SEQ ID NO: 97), MHHHHHHDDDDK (M6H4DK) (SEQ ID NO: 98) or MHHHHHHHH (M8H) (SEQ ID NO: 99) as N-terminal sequences have been tested, and the protein variants with M8H4DK as N-terminal sequence showed higher solubility and/or stability compared with the other N-terminal extensions.
vi) Truncation of the C-terminal of A1M seems to impart improved heme binding and degradation.

It is interesting to note that this N-terminal extension sequence resembles a His-tag with an enterokinase cleavage site, but it is without the ability to cleave the His-tag from A1M as the amino acid Ala is not included. The presence of Ala in a DDDKA (SEQ ID NO: 100) indicate the enterokinase cleavage site. Thus, it is contemplated that the N-terminal sequence itself imparts improved protein stability and solubility properties to A1M when the repeated His-residues are followed by five charged amino acids.

Based on these observations, it is contemplated that variation of an A1M protein along the lines indicated above will provide proteins with A1M functionality, but with improved characteristics regarding stability and/or solubility.

Thus, the present invention relates to all possible combinations of A1M containing $X^1$-$X^{18}$ as described above.

More specifically, the following A1M derived proteins are within the scope of the present invention, such that the all proteins may be full-length corresponding to human wild type A1M; or may be truncated C-terminally, i.e. without LIPR (SEQ ID NO: 101) ("6-His" disclosed as SEQ ID NO: 102 and "8-His" disclosed as SEQ ID NO: 103):

| Tag | Position in hA1M Mutations | Compound | X1 | X2 | X3 | X4 |
|---|---|---|---|---|---|---|
|  | Broadest claim | 1 | Met/Absent | His/absent | His/absent | His/absent |
| 6-His | 'in sequence' mutations can be any | 2 | (f)Met | His | His | His |
| 8-His | in sequence' mutations can be any | 3 | (f)Met | His | His | His |
| No tag; | in sequence' mutations can be any | 4 | Absent | Absent | Absent | Absent |
| Any tag | M41K | 5 | Met/Absent | His/absent | His/absent | His/absent |
| Any tag | N17, 96D | 6 | Met/Absent | His/absent | His/absent | His/absent |
| No tag | N17D | 7 | Absent | Absent | Absent | Absent |
| No tag | N17, 96D | 8 | Absent | Absent | Absent | Absent |
| No tag | N96D | 9 | Absent | Absent | Absent | Absent |
| No tag | N17, 96D, R66H | 10 | Absent | Absent | Absent | Absent |
| No tag | M41K | 11 | Absent | Absent | Absent | Absent |
| No tag | R66H | 12 | Absent | Absent | Absent | Absent |
| No tag | N17, 96D, M41K, R66H | 13 | Absent | Absent | Absent | Absent |
| No tag | N17D, R66H | 14 | Absent | Absent | Absent | Absent |
| No tag | R66H, N96D | 15 | Absent | Absent | Absent | Absent |
| No tag | M41K, R66H | 16 | Absent | Absent | Absent | Absent |
| No tag | N17, 96D, M41K | 17 | Absent | Absent | Absent | Absent |
| No tag | N17D, M41K | 18 | Absent | Absent | Absent | Absent |
| No tag | M41K, N96D | 19 | Absent | Absent | Absent | Absent |
| Any tag | N17, 96D, R66H | 20 | Met/Absent | His/absent | His/absent | His/absent |
| No tag | N17D, M41K, R66H | 21 | Absent | Absent | Absent | Absent |
| No tag | M41K, R66H, N96D | 22 | Absent | Absent | Absent | Absent |
| 6His | N17D | 23 | (f)Met | His | His | His |
| 6His | N17, 96D | 24 | (f)Met | His | His | His |
| 6His | N96D | 25 | (f)Met | His | His | His |
| 6His | N17, 96D, R66H | 26 | (f)Met | His | His | His |
| 6His | M41K | 27 | (f)Met | His | His | His |
| 6His | R66H | 28 | (f)Met | His | His | His |
| 6His | N17, 96D, M41K, R66H | 29 | (f)Met | His | His | His |
| 6His | N17D, R66H | 30 | (f)Met | His | His | His |
| 6His | R66H, N96D | 31 | (f)Met | His | His | His |
| 6His | M41K, R66H | 32 | (f)Met | His | His | His |
| 6His | N17, 96D, M41K | 33 | (f)Met | His | His | His |
| 6His | N17D, M41K | 34 | (f)Met | His | His | His |
| 6His | M41K, N96D | 35 | (f)Met | His | His | His |
| 6His | N17D, M41K, R66H | 36 | (f)Met | His | His | His |
| 6His | M41K, R66H, N96D | 37 | (f)Met | His | His | His |
| 8His | N17D | 38 | (f)Met | His | His | His |
| 8His | N17, 96D | 39 | (f)Met | His | His | His |
| 8His | N96D | 40 | (f)Met | His | His | His |
| 8His | N17, 96D, R66H | 41 | (f)Met | His | His | His |
| 8His | M41K | 42 | (f)Met | His | His | His |
| 8His | R66H | 43 | (f)Met | His | His | His |
| 8His | N17, 96D, M41K, R66H | 44 | (f)Met | His | His | His |
| 8His | N17D, R66H | 45 | (f)Met | His | His | His |
| 8His | R66H, N96D | 46 | (f)Met | His | His | His |
| 8His | M41K, R66H | 47 | (f)Met | His | His | His |
| 8His | N17, 96D, M41K | 48 | (f)Met | His | His | His |
| 8His | N17D, M41K | 49 | (f)Met | His | His | His |

-continued

| Tag | Mutations | Compound | | | | |
|---|---|---|---|---|---|---|
| 8His | M41K, N96D | 50 | (f)Met | His | His | His |
| 8His | N17D, M41K, R66H | 51 | (f)Met | His | His | His |
| 8His | M41K, R66H, N96D | 52 | (f)Met | His | His | His |

| | Position in hA1M | Con'd | N-terminal 'tag' | | | | | |
|---|---|---|---|---|---|---|---|---|
| Tag | Mutations | Compound | X5 | X6 | X7 | X8 | X9 | X10 |
| | Broadest claim | 1 | His/absent | His/absent | His/absent | His/absent | His/absent | Asp/absent/Glu/Lys/Arg |
| 6-His | 'in sequence' mutations can be any | 2 | His | His | His | Absent | Absent | Asp |
| 8-His | in sequence' mutations can be any | 3 | His | His | His | His | His | Asp |
| No tag; | in sequence' mutations can be any | 4 | Absent | Absent | Absent | Absent | Absent | Absent |
| Any tag | M41K | 5 | His/absent | His/absent | His/absent | His/absent | His/absent | Asp/absent/Glu/Lys/Arg |
| Any tag | N17, 96D | 6 | His/absent | His/absent | His/absent | His/absent | His/absent | Asp/absent/Glu/Lys/Arg |
| No tag | N17D | 7 | Absent | Absent | Absent | Absent | Absent | Absent |
| No tag | N17, 96D | 8 | Absent | Absent | Absent | Absent | Absent | Absent |
| No tag | N96D | 9 | Absent | Absent | Absent | Absent | Absent | Absent |
| No tag | N17, 96D, R66H | 10 | Absent | Absent | Absent | Absent | Absent | Absent |
| No tag | M41K | 11 | Absent | Absent | Absent | Absent | Absent | Absent |
| No tag | R66H | 12 | Absent | Absent | Absent | Absent | Absent | Absent |
| No tag | N17, 96D, M41K, R66H | 13 | Absent | Absent | Absent | Absent | Absent | Absent |
| No tag | N17D, R66H | 14 | Absent | Absent | Absent | Absent | Absent | Absent |
| No tag | R66H, N96D | 15 | Absent | Absent | Absent | Absent | Absent | Absent |
| No tag | M41K, R66H | 16 | Absent | Absent | Absent | Absent | Absent | Absent |
| No tag | N17, 96D, M41K | 17 | Absent | Absent | Absent | Absent | Absent | Absent |
| No tag | N17D, M41K | 18 | Absent | Absent | Absent | Absent | Absent | Absent |
| No tag | M41K, N96D | 19 | Absent | Absent | Absent | Absent | Absent | Absent |
| Any tag | N17, 96D, R66H | 20 | His/absent | His/absent | His/absent | His/absent | His/absent | Asp/absent/Glu/Lys/Arg |
| No tag | N17D, M41K, R66H | 21 | Absent | Absent | Absent | Absent | Absent | Absent |
| No tag | M41K, R66H, N96D | 22 | Absent | Absent | Absent | Absent | Absent | Absent |
| 6His | N17D | 23 | His | His | His | Absent | Absent | Asp |
| 6His | N17, 96D | 24 | His | His | His | Absent | Absent | Asp |
| 6His | N96D | 25 | His | His | His | Absent | Absent | Asp |
| 6His | N17, 96D, R66H | 26 | His | His | His | Absent | Absent | Asp |
| 6His | M41K | 27 | His | His | His | Absent | Absent | Asp |
| 6His | R66H | 28 | His | His | His | Absent | Absent | Asp |
| 6His | N17, 96D, M41K, R66H | 29 | His | His | His | Absent | Absent | Asp |
| 6His | N17D, R66H | 30 | His | His | His | Absent | Absent | Asp |
| 6His | R66H, N96D | 31 | His | His | His | Absent | Absent | Asp |
| 6His | M41K, R66H | 32 | His | His | His | Absent | Absent | Asp |
| 6His | N17, 96D, M41K | 33 | His | His | His | Absent | Absent | Asp |
| 6His | N17D, M41K | 34 | His | His | His | Absent | Absent | Asp |
| 6His | M41K, N96D | 35 | His | His | His | Absent | Absent | Asp |
| 6His | N17D, M41K, R66H | 36 | His | His | His | Absent | Absent | Asp |
| 6His | M41K, R66H, N96D | 37 | His | His | His | Absent | Absent | Asp |
| 8His | N17D | 38 | His | His | His | His | His | Asp |
| 8His | N17, 96D | 39 | His | His | His | His | His | Asp |
| 8His | N96D | 40 | His | His | His | His | His | Asp |
| 8His | N17, 96D, R66H | 41 | His | His | His | His | His | Asp |
| 8His | M41K | 42 | His | His | His | His | His | Asp |
| 8His | R66H | 43 | His | His | His | His | His | Asp |
| 8His | N17, 96D, M41K, R66H | 44 | His | His | His | His | His | Asp |
| 8His | N17D, R66H | 45 | His | His | His | His | His | Asp |
| 8His | R66H, N96D | 46 | His | His | His | His | His | Asp |
| 8His | M41K, R66H | 47 | His | His | His | His | His | Asp |
| 8His | N17, 96D, M41K | 48 | His | His | His | His | His | Asp |
| 8His | N17D, M41K | 49 | His | His | His | His | His | Asp |
| 8His | M41K, N96D | 50 | His | His | His | His | His | Asp |
| 8His | N17D, M41K, R66H | 51 | His | His | His | His | His | Asp |
| 8His | M41K, R66H, N96D | 52 | His | His | His | His | His | Asp |

| | Position in hA1M | Con'd | | | |
|---|---|---|---|---|---|
| Tag | Mutations | Compound | X11 | X12 | X13 |
| | Broadest claim | 1 | Asp/absent/Glu/Lys/Arg | Asp/absent/Glu/Lys/Arg | Asp/absent/Glu/Lys/Arg |
| 6-His | 'in sequence' mutations can be any | 2 | Asp | Asp | Asp |
| 8-His | in sequence' mutations can be any | 3 | Asp | Asp | Asp |
| No tag; | in sequence' mutations can be any | 4 | Absent | Absent | Absent |
| Any tag | M41K | 5 | Asp/absent/Glu/Lys/Arg | Asp/absent/Glu/Lys/Arg | Asp/absent/Glu/Lys/Arg |
| Any tag | N17, 96D | 6 | Asp/absent/Glu/Lys/Arg | Asp/absent/Glu/Lys/Arg | Asp/absent/Glu/Lys/Arg |
| No tag | N17D | 7 | Absent | Absent | Absent |
| No tag | N17, 96D | 8 | Absent | Absent | Absent |
| No tag | N96D | 9 | Absent | Absent | Absent |
| No tag | N17, 96D, R66H | 10 | Absent | Absent | Absent |
| No tag | M41K | 11 | Absent | Absent | Absent |

-continued

| Tag | Mutations | Compound | | | |
|---|---|---|---|---|---|
| No tag | R66H | 12 | Absent | Absent | Absent |
| No tag | N17, 96D, M41K, R66H | 13 | Absent | Absent | Absent |
| No tag | N17D, R66H | 14 | Absent | Absent | Absent |
| No tag | R66H, N96D | 15 | Absent | Absent | Absent |
| No tag | M41K, R66H | 16 | Absent | Absent | Absent |
| No tag | N17, 96D, M41K | 17 | Absent | Absent | Absent |
| No tag | N17D, M41K | 18 | Absent | Absent | Absent |
| No tag | M41K, N96D | 19 | Absent | Absent | Absent |
| Any tag | N17, 96D, R66H | 20 | Asp/absent/Glu/Lys/Arg | Asp/absent/Glu/Lys/Arg | Asp/absent/Glu/Lys/Arg |
| No tag | N17D, M41K, R66H | 21 | Absent | Absent | Absent |
| No tag | M41K, R66H, N96D | 22 | Absent | Absent | Absent |
| 6His | N17D | 23 | Asp | Asp | Asp |
| 6His | N17, 96D | 24 | Asp | Asp | Asp |
| 6His | N96D | 25 | Asp | Asp | Asp |
| 6His | N17, 96D, R66H | 26 | Asp | Asp | Asp |
| 6His | M41K | 27 | Asp | Asp | Asp |
| 6His | R66H | 28 | Asp | Asp | Asp |
| 6His | N17, 96D, M41K, R66H | 29 | Asp | Asp | Asp |
| 6His | N17D, R66H | 30 | Asp | Asp | Asp |
| 6His | R66H, N96D | 31 | Asp | Asp | Asp |
| 6His | M41K, R66H | 32 | Asp | Asp | Asp |
| 6His | N17, 96D, M41K | 33 | Asp | Asp | Asp |
| 6His | N17D, M41K | 34 | Asp | Asp | Asp |
| 6His | M41K, N96D | 35 | Asp | Asp | Asp |
| 6His | N17D, M41K, R66H | 36 | Asp | Asp | Asp |
| 6His | M41K, R66H, N96D | 37 | Asp | Asp | Asp |
| 8His | N17D | 38 | Asp | Asp | Asp |
| 8His | N17, 96D | 39 | Asp | Asp | Asp |
| 8His | N96D | 40 | Asp | Asp | Asp |
| 8His | N17, 96D, R66H | 41 | Asp | Asp | Asp |
| 8His | M41K | 42 | Asp | Asp | Asp |
| 8His | R66H | 43 | Asp | Asp | Asp |
| 8His | N17, 96D, M41K, R66H | 44 | Asp | Asp | Asp |
| 8His | N17D, R66H | 45 | Asp | Asp | Asp |
| 8His | R66H, N96D | 46 | Asp | Asp | Asp |
| 8His | M41K, R66H | 47 | Asp | Asp | Asp |
| 8His | N17, 96D, M41K | 48 | Asp | Asp | Asp |
| 8His | N17D, M41K | 49 | Asp | Asp | Asp |
| 8His | M41K, N96D | 50 | Asp | Asp | Asp |
| 8His | N17D, M41K, R66H | 51 | Asp | Asp | Asp |
| 8His | M41K, R66H, N96D | 52 | Asp | Asp | Asp |

| Tag | Position in hA1M Mutations | Con'd Compound | tag'/first AA X14 | 17 X15 | 41 X16 | 66 X17 | 96 X18 |
|---|---|---|---|---|---|---|---|
| | Broadest claim | 1 | Lys/(f)Met/Absent/Glu/Asp/Arg | Asp/Asn | Met/Lys/Arg | Arg/His/Lys | Asp/Asn |
| 6-His | 'in sequence' mutations can be any | 2 | Lys | Asp/Asn | Met/Lys/Arg | Arg/His/Lys | Asp/Asn |
| 8-His | in sequence' mutations can be any | 3 | Lys | Asp/Asn | Met/Lys/Arg | Arg/His/Lys | Asp/Asn |
| No tag; | in sequence' mutations can be any | 4 | Absent | Asp/Asn | Met/Lys/Arg | Arg/His/Lys | Asp/Asn |
| Any tag | M41K | 5 | Lys/(f)Met/Absent/Glu/Asp/Arg | Asn | Lys | Arg | Asn |
| Any tag | N17, 96D | 6 | Lys/(f)Met/Absent Glu/Asp/Arg | Asp | Met | Arg | Asp |
| No tag | N17D | 7 | (f)Met | Asp | Met | Arg | Asn |
| No tag | N17, 96D | 8 | (f)Met | Asp | Met | Arg | Asp |
| No tag | N96D | 9 | (f)Met | Asn | Met | Arg | Asp |
| No tag | N17, 96D, R66H | 10 | (f)Met | Asp | Met | His | Asp |
| No tag | M41K | 11 | (f)Met | Asn | Lys | Arg | Asn |
| No tag | R66H | 12 | (f)Met | Asp | Met | His | Asn |
| No tag | N17, 96D, M41K, R66H | 13 | (f)Met | Asp | Lys | His | Asp |
| No tag | N17D, R66H | 14 | (f)Met | Asp | Met | His | Asn |
| No tag | R66H, N96D | 15 | (f)Met | Asn | Met | His | Asp |
| No tag | M41K, R66H | 16 | (f)Met | Asn | Lys | His | Asn |
| No tag | N17, 96D, M41K | 17 | (f)Met | Asp | Lys | Arg | Asp |
| No tag | N17D, M41K | 18 | (f)Met | Asp | Lys | Arg | Asn |
| No tag | M41K, N96D | 19 | (f)Met | Asn | Lys | Arg | Asp |
| Any tag | N17, 96D, R66H | 20 | Lys/(f)Met/Absent Glu/Asp/Arg | Asp | Met | His | Asp |
| No tag | N17D, M41K, R66H | 21 | (f)Met | Asp | Lys | His | Asn |
| No tag | M41K, R66H, N96D | 22 | (f)Met | Asn | Lys | His | Asp |
| 6His | N17D | 23 | Lys | Asp | Met | Arg | Asn |
| 6His | N17, 96D | 24 | Lys | Asp | Met | Arg | Asp |
| 6His | N96D | 25 | Lys | Asn | Met | Arg | Asp |
| 6His | N17, 96D, R66H | 26 | Lys | Asp | Met | His | Asp |
| 6His | M41K | 27 | Lys | Asn | Lys | Arg | Asn |
| 6His | R66H | 28 | Lys | Asn | Met | His | Asn |
| 6His | N17, 96D, M41K, R66H | 29 | Lys | Asp | Lys | His | Asp |
| 6His | N17D, R66H | 30 | Lys | Asp | Met | His | Asn |

-continued

| Tag | Mutations | Compound | | | | | |
|---|---|---|---|---|---|---|---|
| 6His | R66H, N96D | 31 | Lys | Asn | Met | His | Asp |
| 6His | M41K, R66H | 32 | Lys | Asn | Lys | His | Asn |
| 6His | N17, 96D, M41K | 33 | Lys | Asp | Lys | Arg | Asp |
| 6His | N17D, M41K | 34 | Lys | Asp | Lys | Arg | Asn |
| 6His | M41K, N96D | 35 | Lys | Asn | Lys | Arg | Asp |
| 6His | N17D, M41K, R66H | 36 | Lys | Asp | Lys | His | Asn |
| 6His | M41K, R66H, N96D | 37 | Lys | Asn | Lys | His | Asp |
| 8His | N17D | 38 | Lys | Asp | Met | Arg | Asn |
| 8His | N17, 96D | 39 | Lys | Asp | Met | Arg | Asp |
| 8His | N96D | 40 | Lys | Asn | Met | Arg | Asp |
| 8His | N17, 96D, R66H | 41 | Lys | Asp | Met | His | Asp |
| 8His | M41K | 42 | Lys | Asn | Lys | Arg | Asn |
| 8His | R66H | 43 | Lys | Asn | Met | His | Asn |
| 8His | N17, 96D, M41K, R66H | 44 | Lys | Asp | Lys | His | Asp |
| 8His | N17D, R66H | 45 | Lys | Asp | Met | His | Asn |
| 8His | R66H, N96D | 46 | Lys | Asn | Met | His | Asp |
| 8His | M41K, R66H | 47 | Lys | Asn | Lys | His | Asn |
| 8His | N17, 96D, M41K | 48 | Lys | Asp | Lys | Arg | Asp |
| 8His | N17D, M41K | 49 | Lys | Asp | Lys | Arg | Asn |
| 8His | M41K, N96D | 50 | Lys | Asn | Lys | Arg | Asp |
| 8His | N17D, M41K, R66H | 51 | Lys | Asp | Lys | His | Asn |
| 8His | M41K, R66H, N96D | 52 | Lys | Asn | Lys | His | Asp |

| Tag | Position in hA1M Mutations | Con'd Compound | Comment |
|---|---|---|---|
|  | Broadest claim | 1 | Proviso: when all X1-X14 are absent, X15 represents Asn, X16 represents |
| 6-His | 'in sequence' mutations can be any | 2 | Met, and X17 represents Arg, then X18 cannot represent Asn. |
| 8-His | in sequence' mutations can be any | 3 |  |
| No tag; | in sequence' mutations can be any | 4 | Proviso: when X15 represents Asn, X16 represents Met, |
| Any tag | M41K | 5 | and X17 represents Arg, then X18 cannot represent Asn |
| Any tag | N17, 96D | 6 |  |
| No tag | N17D | 7 |  |
| No tag | N17, 96D | 8 |  |
| No tag | N96D | 9 |  |
| No tag | N17, 96D, R66H | 10 | Preferred mutation without tag |
| No tag | M41K | 11 |  |
| No tag | R66H | 12 |  |
| No tag | N17, 96D, M41K, R66H | 13 | All mutations |
| No tag | N17D, R66H | 14 |  |
| No tag | R66H, N96D | 15 |  |
| No tag | M41K, R66H | 16 |  |
| No tag | N17, 96D, M41K | 17 |  |
| No tag | N17D, M41K | 18 |  |
| No tag | M41K, N96D | 19 |  |
| Any tag | N17, 96D, R66H | 20 |  |
| No tag | N17D, M41K, R66H | 21 |  |
| No tag | M41K, R66H, N96D | 22 |  |
| 6His | N17D | 23 |  |
| 6His | N17, 96D | 24 |  |
| 6His | N96D | 25 |  |
| 6His | N17, 96D, R66H | 26 | Preferred mutation with 6His |
| 6His | M41K | 27 |  |
| 6His | R66H | 28 |  |
| 6His | N17, 96D, M41K, R66H | 29 |  |
| 6His | N17D, R66H | 30 |  |
| 6His | R66H, N96D | 31 |  |
| 6His | M41K, R66H | 32 |  |
| 6His | N17, 96D, M41K | 33 |  |
| 6His | N17D, M41K | 34 |  |
| 6His | M41K, N96D | 35 |  |
| 6His | N17D, M41K, R66H | 36 |  |
| 6His | M41K, R66H, N96D | 37 |  |
| 8His | N17D | 38 |  |
| 8His | N17, 96D | 39 |  |
| 8His | N96D | 40 |  |
| 8His | N17, 96D, R66H | 41 | Preferred mutation with 8His |
| 8His | M41K | 42 |  |
| 8His | R66H | 43 |  |
| 8His | N17, 96D, M41K, R66H | 44 |  |
| 8His | N17D, R66H | 45 |  |
| 8His | R66H, N96D | 46 |  |
| 8His | M41K, R66H | 47 |  |
| 8His | N17, 96D, M41K | 48 |  |
| 8His | N17D, M41K | 49 |  |
| 8His | M41K, N96D | 50 |  |
| 8His | N17D, M41K, R66H | 51 |  |
| 8His | M41K, R66H, N96D | 52 |  |

Alpha-1-Microglobulin—a General Background

A1M is synthesized in the liver at a high rate, secreted into the blood stream and transported across the vessel walls to the extravascular compartment of all organs. The protein is also synthesized in other tissues (blood cells, brain, kidney, skin) but at a lower rate. Due to the small size, free A1M is rapidly filtered from blood in the kidneys.

Figure 10:
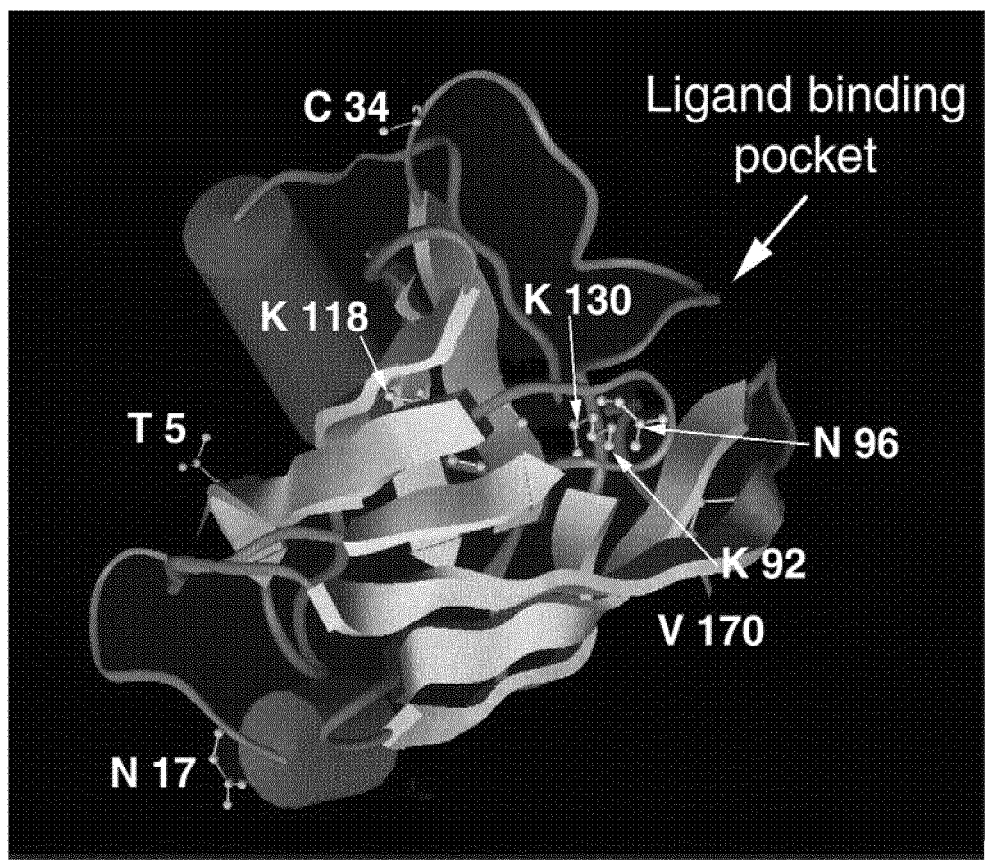

A1M is a member of the lipocalin superfamily, a group of proteins from animals, plants and bacteria with a conserved three-dimensional structure but very diverse functions. Each lipocalin consists of a 160-190-amino acid chain that is folded into a β-barrel pocket with a hydrophobic interior. At least twelve human lipocalin genes are known. A1M is a 26 kDa plasma and tissue protein that so far has been identified in mammals, birds, fish and frogs. The three-dimensional structure of A1M determined by X-ray crystallography is shown in FIG. 10. A1M is synthesized in the liver at a high rate, secreted into the blood stream and rapidly (T½=2-3 min) transported across the vessel walls to the extravascular compartment of all organs. A1M is found both in a free, monomeric form and as covalent complexes with larger molecules (IgA, albumin, prothrombin) in blood and interstitial tissues. Due to the small size, free A1M is rapidly filtered from blood in the kidneys. The major portion is then readsorbed, but significant amounts are excreted to the urine.

Antioxidants are protective factors that eliminate oxidants or prevent harmful oxidation reactions. The human organism can produce antioxidants in response to oxidative stress. Such endogenous antioxidants include the superoxide-degrading enzyme superoxide dismutase (SOD), the hydrogen peroxide-degrading enzymes catalase and glutathione peroxidase, and the heme-degrading enzyme heme oxygenase-1 (HO-1). A1M was recently shown to be involved in protecting against oxidative tissue damage by functioning both as a scavenger of radicals and heme as well as a reductase and inhibitor of oxidation. Several recent papers demonstrate that A1M protects cell cultures and organ explants against oxidative damage, partly by accumulating in mitochondria and protecting mitochondrial function. Indeed, infusion of human recombinant A1M has been successfully employed for in vivo treatment of the oxidative stress-related diseases preeclampsia and hemoglobin-induced glomerular injuries in animal models.

Sequence and Structural Properties of A1M

The full sequence of human A1M is known. The protein consists of a polypeptide with 183 amino acid residues. Many additional A1M cDNAs and/or proteins have been detected, isolated and/or sequenced from other mammals, birds, amphibians, and fish. The length of the peptide chain of A1M differs slightly among species, due mainly to variations in the C-terminus. Alignment comparisons of the different deduced amino acid sequences show that the percentage of identity varies from approximately 75-80% between rodents or ferungulates and man, down to approximately 45% between fish and mammals. A free cysteine side-chain at position 34 is conserved. This group has been shown to be involved in redox reactions (see below), in complex formation with other plasma proteins and in binding to a yellow-brown chromophore. The three-dimensional structure of A1M shows that C34 is solvent exposed and located near the opening of the lipocalin pocket (see FIG. 10).

In the present context the term "$\alpha_1$-microglobulin" intends to cover $\alpha_1$-microglobulin as identified in SEQ ID NO: 1 (human A1M), SEQ ID NO: 2 (human recombinant A1M) and A1M from other species, including homologues, fragments or variants thereof having similar therapeutic activities. Thus, A1M as used herein is intended to mean a protein having at least 80% sequence identity with SEQ ID NO:1 or SEQ ID NO:2. It is preferred that A1M as used herein has at least 90% sequence identity with SEQ ID NO:1 or SEQ ID NO:2. It is even more preferred that A1M as used herein has at least 95% such as 99% or 100% sequence identity with SEQ ID NO:1 or SEQ ID NO:2. In a preferred aspect, the $\alpha_1$-microglobulin is in accordance with SEQ ID NO: 1 or 2 as identified herein. In the sequence listing the amino acid sequences of human A1M and human recombinant A1M (SEQ ID NOs 1 and 2, respectively) are given. However, homologues, variants and fragments of A1M having the important parts of the proteins as identified in the following are also comprised in the term A1M as used herein. Regarding alignments/identity see the following paragraph.

Details on Alignment/Identity

Positions of amino acid residues herein refer to the positions in human wt A1M as it is found in human blood plasma (SEQ ID NO:1). When referring to amino acid residues in recombinant A1M, which harbors a methionine or N-formyl methionine residue N-terminally linked to the glycine residue that is the initial residue in wt-A1M (SEQ ID NO: 2), or in mutated human A1M or A1M from other species a person skilled in the art will understand how to identify residues corresponding to residues in human wt-A1M (SEQ ID NO:1) even when positions are shifted due to e.g. deletions or insertions.

When recombinant proteins are produced they most often start with an initial Met residue, which may be removed using e.g. a methionine aminopeptidase or another enzyme with a similar activity. The A1M variants presented here may be with or without an initial Met residue.

Homologues of A1M

As mentioned above homologues of A1M can also be used in accordance with the description herein. In theory A1M from all species can be used for the purposes described herein including the most primitive found so far, which is from fish (plaice). A1M is also available in isolated form from human, orangutan, squirrel monkey, rat, naked mole rat, mouse, rabbit, guinea pig, cow, frog, chicken, walrus, manatee and plaice.

Considering homologues, variants and fragments of A1M, the following has been identified as important parts of the protein for the anti-oxidative effect:

Y22 (Tyrosine, pos 22, basepairs 64-66)
C34 (Cystein, position 34, basepairs 100-102)
K69 (Lysine, pos 69, basepairs 205-207)
K92 (Lysine, pos 92, basepairs 274-276)
K118 (Lysine, pos 118, basepairs 352-354)
K130 (Lysine, pos 130, basepairs 388-390)
Y132 (Tyrosine, pos 132, basepairs 394-396)
L180 (Leucine, pos 180, basepairs 538-540)
I181 (Isoleucine, pos 181, basepairs 541-543)
P182 (Proline, pos 182, basepairs 544-546)
R183 (Arginine, pos 183, basepairs 547-549)

Numbering of amino acids and nucleotides throughout the document refers to SEQ ID 1; if other A1M from other species, A1M analogs or recombinant sequences thereof are employed, a person skilled in the art will know how to identify the amino acids corresponding to the amino acids in SEQ ID NO: 1.

Thus, in those cases, where A1M eg has 80% (or 90% or 95%) sequence identity with one of SEQ ID NO: 1 or 2, it is preferred that the amino acids mentioned above are present at the appropriate places in the molecule.

Human A1M—is substituted with oligosaccharides in three positions, two sialylated complex-type, probably diantennary carbohydrated linked to N17 and N96 and one more simple oligosaccharide linked to T5. The carbohydrate content of A1M proteins from different species varies greatly, though, ranging from no glycosylation at all in *Xenopus leavis* over a spectrum of different glycosylation patterns. However, one glycosylation site, corresponding to N96 in man, is conserved in mammals, suggesting that this specific carbohydrate may be a more important constituent of the protein than the other two oligosaccharides.

A1M is yellow-brown-coloured when purified from plasma or urine. The colour is caused by heterogeneous compounds covalently bound to various amino acid side groups mainly located at the entrance to the pocket. These modifications represent the oxidized degradation products of organic oxidants covalently trapped by A1M in vivo, for example heme, kynurenine and tyrosyl radicals.

A1M is also charge- and size-heterogeneous and more highly brown-coloured A1M-molecules are more negatively charged. The probable explanation for the heterogeneity is that different side-groups are modified to a varying degree with different radicals, and that the modifications alter the net charge of the protein. Covalently linked coloured substances have been localized to C34, and K92, K118 and K130, the latter with molecular masses between 100 and 300 Da. The tryptophan metabolite kynurenine was found covalently attached to lysyl residues in A1M from urine of haemodialysis patients and appears to be the source of the brown colour of the protein in this case [6]. Oxidized fragments of the synthetic radical ABTS (2,2'-azino-di-(3-ethylbenzothiazoline)-6-sulfonic acid) was bound to the side-chains of Y22 and Y132.

C34 is the reactive center of A1M. It becomes very electronegative, meaning that it has a high potential to give away electrons, by the proximity of the positively charged side-chains of K69, K92, K118 and K130, which induce a deprotonization of the C34 thiol group which is a prerequisite of oxidation of the sulphur atom. Preliminary data shows that C34 is one of the most electronegative groups known.

Theoretically, the amino acids that characterize the properties of A1M (C34, Y22, K92, K118, K130, Y132, L180, 1181, P182, R183), which will be described in more detail below, can be arranged in a similar three-dimensional configuration on another framework, for instance a protein with the same global folding (another lipocalin) or a completely artificial organic or inorganic molecule such as a plastic polymer, a nanoparticle or metal polymer.

The three-dimensional arrangement of some of these amino acids (ovals, the lysines are depicted by a "+"), the A1M-framework (barrel), the electron-flow and the radical-trapping, are illustrated in FIG. 10.

Accordingly, homologues, fragments or variants comprising a structure including the reactive centre and its surroundings as depicted above, are preferred.

Modifications and changes have been made in the structure of the polypeptides of this disclosure and still resulted in a molecule having similar functional characteristics as the original polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like functional properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biologically functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamnine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids the hydrophilicity values of which are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take one or more of the foregoing characteristics into consideration are well known to those of skill in the art and include, but are not limited to (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Trp: Tyr), (Tyr: Trp, Phe), and (Val: Lle, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of in-terest.

In the present context, the homology between two amino acid sequences or between two nucleic acid sequences is described by the parameter "identity" (see also above). Alignments of sequences and calculation of homology scores may be done using a full Smith-Waterman alignment, useful for both protein and DNA alignments. The default scoring matrices BLOSUM50 and the identity matrix are used for protein and DNA alignments respectively. The penalty for the first residue in a gap is −12 for proteins and −16 for DNA, while the penalty for additional residues in a gap is −2 for proteins and −4 for DNA. Alignment may be made with the FASTA package version v20u6.

Multiple alignments of protein sequences may be made using "ClustalW". Multiple alignments of DNA sequences may be done using the protein alignment as a template, replacing the amino acids with the corresponding codon from the DNA sequence.

Alternatively different software can be used for aligning amino acid sequences and DNA sequences. The alignment of two amino acid sequences is e.g. determined by using the Needle program from the EMBOSS package (http://emboss.org) version 2.8.0. The Needle program implements the global alignment algorithm described in. The substitution matrix used is BLOSUM62, gap opening penalty is 10, and gap extension penalty is 0.5.

The degree of identity between an amino acid sequence; e.g. SEQ ID NO: 1 and a different amino acid sequence (e.g. SEQ ID NO: 2) is calculated as the number of exact matches in an alignment of the two sequences, divided by the length of the "SEQ ID NO: 1" or the length of the "SEQ ID NO: 2", whichever is the shortest. The result is expressed in percent identity. See above regarding alignment and identity.

An exact match occurs when the two sequences have identical amino acid residues in the same positions of the overlap.

If relevant, the degree of identity between two nucleotide sequences can be determined by the Wilbur-Lipman method using the LASER-GENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

The percentage of identity of an amino acid sequence of a polypeptide with, or to, amino acids of SEQ ID NO: 1 may be determined by i) aligning the two amino acid sequences using the Needle program, with the BLOSUM62 substitution matrix, a gap opening penalty of 10, and a gap extension penalty of 0.5; ii) counting the number of exact matches in the alignment; iii) dividing the number of exact matches by the length of the shortest of the two amino acid sequences, and iv) converting the result of the division of iii) into percentage. The percentage of identity to, or with, other sequences of the invention is calculated in an analogous way.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution (including conservative and non-conservative substitution), or insertion, and wherein said alterations may occur at the amino- or carboxy-terminus positions of the reference polypeptide sequence or anywhere between those terminal positions, interspersed either individually among the amino acids in the reference sequence, or in one or more contiguous groups within the reference sequence.

Conservative amino acid variants can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxy-ethylcysteine, hydroxyethyl-homo-cysteine, nitro-glutamine, homoglutamine, pipecolic acid, thiazolidine carboxylic acid, dehydroproline, 3- and 4-methylproline, 3,3-dimethylproline, tert-leucine, norvaline, 2-azaphenyl-alanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an E. coli S30 extract and commercially available enzymes and other reagents. Proteins are purified by chromatography. In a second method, translation is carried out in Xenopus oocytes by microinjection of mutated mRNA and chemically aminoacylated suppressor tRNAs. Within a third method, E. coli cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. Naturally occurring amino acid residues can be converted to non-naturally occurring species by in vitro chemical modification. Chemical modification can be combined with site-directed mutagenesis to further expand the range of substitutions. Alternative chemical structures providing a 3-dimensional structure sufficient to support the antioxidative properties of A1M may be provided by other technologies e.g. artificial scaffolds, amino-acid substitutions and the like. Furthermore, structures mimicking the active sites of A1M as listed above are contemplated as having the same therapeutic or physiologic function as A1M.

Pharmaceutical Compositions and Dosage

The present invention also provides a kit comprising:

i) a pharmaceutical composition comprising a contrast medium, and ii) a pharmaceutical composition comprising A1M, any of the SEQ ID Nos: 1-10 and 17, or any of the A1M derived proteins mentioned herein (or a mutant, analogue, fragment or variant as defined herein).

In the following a listing of the sequences are given. The invention encompass all possible variations eg such as those illustrated herein.

SEQ ID NO: 1: wt hA1M

SEQ ID NO: 2: rhA1M (i.e. Met-A1M)

SEQ ID NO: 3: Preferred mutation without "extension"—N17,96D, R66H

SEQ ID NO: 4: No extension, M41K

SEQ ID NO: 5: Preferred mutation with 6 His (SEQ ID NO: 102), N17,96D, R66H

SEQ ID NO: 6: 6His (SEQ ID NO: 102), M41K

SEQ ID NO: 7: preferred mutation with 8 His extension (SEQ ID NO: 103), N17,96D, R66H SEQ ID NO: 8: 8 His (SEQ ID NO: 103), M41K SEQ ID NO:9: Extension+wt hA1M SEQ ID NO: 10: Omnibus A1M with possible extensions.

SEQ ID NO: 11-16: segments of wt hA1M

SEQ ID NO: 17: Omnibus C-terminally truncated A1M with possible extensions

SEQ ID NO: 18: Preferred mutation without "extension"—N17,96D, R66; C-terminally truncated.

SEQ ID NO: 19: No extension, M41K; C-terminally truncated.

SEQ ID NO: 20: Preferred mutation with 6 His (SEQ ID NO: 102), N17,96D, R66H; C-terminally truncated.

SEQ ID NO: 21: 6His (SEQ ID NO: 102), M41K; C-terminally truncated.

SEQ ID NO: 22: preferred mutation with 8 His extension (SEQ ID NO: 103), N17,96D, R66H; C-terminally truncated.

SEQ ID NO: 23: 8 His (SEQ ID NO: 103), M41K; C-terminally truncated.

The kit is in the form of one package containing the above-mentioned two compositions.

The pharmaceutical composition comprising a contrast medium is typically a composition already on the market.

The pharmaceutical composition comprising A1M (or an analogue, fragment or variant thereof as defined herein) is intended for i.v. administration. Accordingly, A1M can be formulated in a liquid, e.g. in a solution, a dispersion, an emulsion, a suspension etc.

For parenteral use suitable solvents include water, vegetable oils, propylene glycol and organic solvents generally approved for such purposes. In general, a person skilled in the art can find guidance in "Remington's Pharmaceutical Science" edited by Gennaro et al. (Mack Publishing Company), in "Handbook of Pharmaceutical Excipients" edited by Rowe et al. (PhP Press) and in official Monographs (e.g. Ph.Eur. or USP) relating to relevant excipients for specific formulation types and to methods for preparing a specific formulation.

A1M will be administrated in one or several doses in connection to the administration of contrast medium. Preferably, each dose will be administrated i.v. either as a single dose, as a single dose followed by slow infusion during a short time-period up to 60 minutes, or only as a slow infusion during a short time-period up to 60 minutes. The first dose may be administrated at the same time as the contrast medium, or within a period of 0-60 minutes before to 0-30 minutes after injection of the contrast medium. Additional A1M-doses can be added, but may not be necessary, after injection of the contrast medium. Each dose contains an amount of A1M which is related to the body-weight of the patient: 1-15 mg A1M/kg of the patient.

| Sequence Listing Free Text |
|---|
| SEQ ID NO: 1<br><223> Wildtype human A1M, no mutations |
| SEQ ID NO: 2<br><223> rhA1M, ie N-terminal Met |
| SEQ ID NO: 3<br><223> hA1M, No tag, N-terminal Met, N17, 96D; R66H |
| SEQ ID NO: 4<br><223> hA1M, not tag, N-terminal Met, M41K |
| SEQ ID NO: 5<br><223> 6His, N17, 96D; R66H |
| SEQ ID NO: 6<br><223> hA1M, 6His, M41K |

| Sequence Listing Free Text |
|---|
| SEQ ID NO: 7<br><223> 8His, N17, 96D; R66H |
| SEQ ID NO: 8<br><223> hA1M, 8His, M41K |
| SEQ ID NO: 9<br><223> hA1M, 8His, no mut |
| SEQ ID NO: 10<br><211> 193<br><212> PRT<br><213> Homo sapiens |
| <220><br><221> VARIANT<br><222> 1<br><223> Xaa = Met or absent |
| <220><br><221> VARIANT<br><222> 1<br><223> Xaa = Met or absent |
| <220><br><221> VARIANT<br><222> 2<br><223> Xaa = His or absent |
| <220><br><221> VARIANT<br><222> 2<br><223> Xaa = His or absent |
| <220><br><221> VARIANT<br><222> 3<br><223> Xaa = His or absent |
| <220><br><221> VARIANT<br><222> 3<br><223> Xaa = His or absent |
| <220><br><221> VARIANT<br><222> 4<br><223> Xaa = His or absent |
| <220><br><221> VARIANT<br><222> 4<br><223> Xaa = His or absent |
| <220><br><221> VARIANT<br><222> 5<br><223> Xaa = His or absent |
| <220><br><221> VARIANT<br><222> 5<br><223> Xaa = His or absent |
| <220><br><221> VARIANT<br><222> 6<br><223> Xaa = His or absent |
| <220><br><221> VARIANT<br><222> 6<br><223> Xaa = His or absent |
| <220><br><221> VARIANT |

Sequence Listing Free Text

```
<222> 7
<223> Xaa = His or absent

<220>
<221> VARIANT
<222> 7
<223> Xaa = His or absent

<220>
<221> VARIANT
<222> 8
<223> Xaa = His or absent

<220>
<221> VARIANT
<222> 8
<223> Xaa = His or absent

<220>
<221> VARIANT
<222> 9
<223> Xaa = His or absent

<220>
<221> VARIANT
<222> 9
<223> Xaa = His or absent

<220>
<221> VARIANT
<222> 10
<223> Xaa = Asp, Glu, Lys, Arg, or absent

<220>
<221> VARIANT
<222> 10
<223> Xaa = Asp, Glu, Lys, Arg, or absent

<220>
<221> VARIANT
<222> 11
<223> Xaa = Asp, Glu, Lys, Arg, or absent

<220>
<221> VARIANT
<222> 11
<223> Xaa = Asp, Glu, Lys, Arg, or absent

<220>
<221> VARIANT
<222> 12
<223> Xaa = Asp, Glu, Lys, Arg, or absent

<220>
<221> VARIANT
<222> 12
<223> Xaa = Asp, Glu, Lys, Arg, or absent

<220>
<221> VARIANT
<222> 13
<223> Xaa = Asp, Glu, Lys, Arg, or absent

<220>
<221> VARIANT
<222> 13
<223> Xaa = Asp, Glu, Lys, Arg, or absent

<220>
<221> VARIANT
<222> 14
<223> Xaa = Asp, Glu, Lys, Arg, or absent

<220>
<221> VARIANT
<222> 14
<223> Xaa = Asp, Glu, Lys, Arg, or absent

<220>
<221> VARIANT
<222> 31
<223> Xaa = Asn or Asp

<220>
<221> VARIANT
<222> 55
<223> Xaa = Met or Lys

<220>
<221> VARIANT
<222> 80
<223> Xaa = Arg or His

<220>
<221> VARIANT
<222> 110
<223> Xaa = Asn or Asp

SEQ ID NO: 11
<223> Y1

SEQ ID NO: 12
<223> Y2

SEQ ID NO: 13
<223> Y3

SEQ ID NO: 14
<223> Y4

SEQ ID NO: 15
<223> Y5

SEQ ID NO: 16
<223> Y5

SEQ ID NO: 17
<211> 197
<212> PRT
<213> Homo sapiens

<220>
<221> VARIANT
<222> 1
<223> Xaa = Met or absent

<220>
<221> VARIANT
<222> 1
<223> Xaa = Met or absent

<220>
<221> VARIANT
<222> 2
<223> Xaa = His or absent

<220>
<221> VARIANT
<222> 2
<223> Xaa = His or absent

<220>
<221> VARIANT
<222> 3
<223> Xaa = His or absent

<220>
<221> VARIANT
<222> 3
<223> Xaa = His or absent

<220>
<221> VARIANT
```

| Sequence Listing Free Text |
|---|
| <222> 4
<223> Xaa = His or absent

<220>
<221> VARIANT
<222> 4
<223> Xaa = His or absent

<220>
<221> VARIANT
<222> 5
<223> Xaa = His or absent

<220>
<221> VARIANT
<222> 5
<223> Xaa = His or absent

<220>
<221> VARIANT
<222> 6
<223> Xaa = His or absent

<220>
<221> VARIANT
<222> 6
<223> Xaa = His or absent

<220>
<221> VARIANT
<222> 7
<223> Xaa = His or absent

<220>
<221> VARIANT
<222> 7
<223> Xaa = His or absent

<220>
<221> VARIANT
<222> 8
<223> Xaa = His or absent

<220>
<221> VARIANT
<222> 8
<223> Xaa = His or absent

<220>
<221> VARIANT
<222> 9
<223> Xaa = His or absent

<220>
<221> VARIANT
<222> 9
<223> Xaa = His or absent

<220>
<221> VARIANT
<222> 10
<223> Xaa = Asp, Glu, Lys, Arg, or absent

<220>
<221> VARIANT
<222> 10
<223> Xaa = Asp, Glu, Lys, Arg, or absent

<220>
<221> VARIANT
<222> 11
<223> Xaa = Asp, Glu, Lys, Arg, or absent

<220>
<221> VARIANT
<222> 11
<223> Xaa = Asp, Glu, Lys, Arg, or absent |

| Sequence Listing Free Text |
|---|
| <220>
<221> VARIANT
<222> 12
<223> Xaa = Asp, Glu, Lys, Arg, or absent <220>
<221> VARIANT
<222> 12
<223> Xaa = Asp, Glu, Lys, Arg, or absent <220>
<221> VARIANT
<222> 13
<223> Xaa = Asp, Glu, Lys, Arg, or absent <220>
<221> VARIANT
<222> 13
<223> Xaa = Asp, Glu, Lys, Arg, or absent <220>
<221> VARIANT
<222> 14
<223> Xaa = Asp, Glu, Lys, Arg, or absent <220>
<221> VARIANT
<222> 14
<223> Xaa = Asp, Glu, Lys, Arg, or absent <220>
<221> VARIANT
<222> 31
<223> Xaa = Asn or Asp <220>
<221> VARIANT
<222> 55
<223> Xaa = Met or Lys <220>
<221> VARIANT
<222> 80
<223> Xaa = Arg or His <220>
<221> VARIANT
<222> 110
<223> Xaa = Asn or Asp SEQ ID NO: 18
<223> hA1M, No tag, N-terminal Met, N17, 96D; R66H; truncated SEQ ID NO: 19
<223> hA1M, not tag, N-terminal Met, M41K; truncated SEQ ID NO: 20
<223> 6His (SEQ ID NO: 102), N17, 96D; R66H; truncated SEQ ID NO: 21
<223> hA1M, 6His (SEQ ID NO: 102), M41K; truncated SEQ ID NO: 22
<223> 8His (SEQ ID NO: 103), N17, 96D; R66H; truncated SEQ ID NO: 23
<223> hA1M, 8His (SEQ ID NO: 103), M41K; truncated |

| Sequence Listing Free Text |
|---|
| SEQ ID NO: 24<br><223> 1.M8H5GIEGR-Mouse |
| SEQ ID NO: 25<br><223> 2.M8H5GIEGR-Naked Mole rat |
| SEQ ID NO: 26<br><223> 3.M8H5GIEGR-Frog |
| SEQ ID NO: 27<br><223> 4.M8H5GIEGR-Chicken |
| SEQ ID NO: 28<br><223> 5.M8H5GIEGR-Rabbit |
| SEQ ID NO: 29<br><223> 6.M8H5GIEGR-SQ Monkey |
| SEQ ID NO: 30<br><223> 7.M8H5GIEGR-Walrus |
| SEQ ID NO: 31<br><223> 8.M8H5GIEGR-Manatee |
| SEQ ID NO: 32<br><223> 9. M8H5GIEGR-Plaice |
| SEQ ID NO: 33<br><223> 10.M8H5GIEGR-Orangutan |
| SEQ ID NO: 34<br><223> 11.M8H5GIEGR-Human P35K |
| SEQ ID NO: 35<br><223> 12.M8H5GIEGR-Human M41K |
| SEQ ID NO: 36<br>.M8H5GIEGR-Human R66H |
| SEQ ID NO: 37<br>.M8H5GIEGR-Human T75K |
| SEQ ID NO: 38<br><223> 15.M8H5GIEGR-Human T75Y |
| SEQ ID NO: 39<br><223> 16.M8H5GIEGR-Human M99K |
| SEQ ID NO: 40<br><223> 17.M8H5GIEGR-Human S101Y |
| SEQ ID NO: 41<br><223> 18.M8H5GIEGR-Human K69.92.118.130R |
| SEQ ID NO: 42<br><223> 19.M8H5GIEGR-Coelacanth |
| SEQ ID NO: 43<br><223> 21.M8H5GIEGR-Human L89T |
| SEQ ID NO: 44<br><223> 22.M8H5GIEGR-Human N1796D |
| SEQ ID NO: 45<br><223> 23.M8H5GIEGR-Human T45K |
| SEQ ID NO: 46<br><223> 24.M8H5GIEGR-Human A135E |
| SEQ ID NO: 47<br><223> 25.M8H5GIEGR-Human V170S |
| SEQ ID NO: 48<br><223> 26.M8H5GIEGR-Human |
| SEQ ID NO: 49<br><223> 27.M8H5GIEGR-Human G172Q |

| Sequence Listing Free Text |
|---|
| SEQ ID NO: 50<br><223> 33.M8H4DK-Human M41K+ |
| SEQ ID NO: 51<br><223> 34.M8H4DK-Human M41K + N1796D 34 |
| SEQ ID NO: 52<br><223> 35.M8H4DK-Human R66H + N1796D |
| SEQ ID NO: 53<br><223> 36.M8H4DK-Human M41K + R66H + N1796D |
| SEQ ID NO: 54<br><223> 38.M8H4DK-Human R66H |
| SEQ ID NO: 55<br><223> 39.M8H4DK-Human |
| SEQ ID NO: 56<br><223> 40.M8H-Human wt |
| SEQ ID NO: 57<br><223> 41.M8H-Human R66H + N1796D |
| SEQ ID NO: 58<br><223> 60.M8H4DK-Human wt |
| SEQ ID NO: 59<br><223> 1.M8H5GIEGR-Mouse |
| SEQ ID NO: 60<br><223> 2.M8H5GIEGR-Naked Mole |
| SEQ ID NO: 61<br><223> 3.M8H5GIEGR-Frog |
| SEQ ID NO: 62<br><223> 4.M8H5GIEGR-Chicken |
| SEQ ID NO: 63<br><223> 5.M8H5GIEGR-Rabbit |
| SEQ ID NO: 64<br><223> 6.M8H5GIEGR-SQ Monkey |
| SEQ ID NO: 65<br><223> 7.M8H5GIEGR-Walrus |
| SEQ ID NO: 66<br><223> 8.M8H5GIEGR-Manatee |
| SEQ ID NO: 67<br><223> 9.M8H5GIEGR-Plaice |
| SEQ ID NO: 68<br><223> 10.M8H5GIEGR-Orangutan |
| SEQ ID NO: 69<br><223> 11.M8H5GIEGR-Human P35K |
| SEQ ID NO: 70<br><223> 12.M8H5GIEGR-Human M41K |
| SEQ ID NO: 71<br><223> 13.M8H5GIEGR-Human R66H |
| SEQ ID NO: 72<br><223> 14.M8H5GIEGR-Human T75K |
| SEQ ID NO: 73<br><223> 15.M8H5GIEGR-Human T75Y |
| SEQ ID NO: 74<br><223> 16.M8H5GIEGR-Human M99K |

-continued

Sequence Listing Free Text

SEQ ID NO: 75
<223> 17.M8H5GIEGR-Human S101Y

SEQ ID NO: 76
<223> 18.M8H5GIEGR-Human K69.92.118.

SEQ ID NO: 77
<223> 19.M8H5GIEGR-Coelacanth

SEQ ID NO: 78
<223> 21.M8H5GIEGR-Human L89T

SEQ ID NO: 79
<223> 22.M8H5GIEGR-Human N1796D

SEQ ID NO: 80
<223> 23.M8H5GIEGR-Human T45K

SEQ ID NO: 81
<223> 24.M8H5GIEGR-Human A135E

SEQ ID NO: 82
<223> 25.M8H5GIEGR-Human V170S

SEQ ID NO: 83
<223> 26.M8H5GIEGR-Human V148D

SEQ ID NO: 84
<223> 27.M8H5GIEGR-Human G172Q

SEQ ID NO: 85
<223> 33.M8H4DK-Human M41K + R66H

SEQ ID NO: 86
<223> 34.M8H4DK-Human M41K + N1796D

SEQ ID NO: 87
<223> 35.M8H4DK-Human R66H + N1796D

SEQ ID NO: 88
<223> 36.M8H4DK-Human M41K + R66H + N1796D

SEQ ID NO: 89
<223> 37.M8H4DK-Human M41K

SEQ ID NO: 90
<223> 38.M8H4DK-Human R66H

SEQ ID NO: 91
<223> 39.M8H4DK-Human N1796D

SEQ ID NO: 92
<223> 40.M8H-Human wt

SEQ ID NO: 93
<223> 41.M8H-Human R66H + N1796D

SEQ ID NO: 94
<223> 42.untagged-Human R66H + N1796D

SEQ ID NO: 95
<223> 61.untagged-Human wt

Abbreviations

A1M: alpha-1-microglobulin, IB: inclusion bodies, wt: wildtype, R66H: point mutation in A1M-gene leading to expression of His instead of Arg at position 66, N17,96D: point mutations in A1M-gene leading to expression of Asp instead of Asn at positions 17 and 96, M8H4DK: peptide with amino acid sequence MHHHHHHHHDDDDK (SEQ ID NO: 97), M6H4DK: peptide with amino acid sequence MHHHHHHDDDDK (SEQ ID NO: 98), MBH: peptide with amino acid sequence MHHHHHHHH (SEQ ID NO: 99), M8H5GIEGR: peptide with amino acid sequence MHHHHHHHHGGGGIEGR (SEQ ID NO: 96), CV: col- umn volume, SEC: size-exclusion chromatography, DLS: dynamic light scattering, DSF: differential scanning fluorimetry, Gu-HCl: guanidine hydrochloride, ORAC: oxygen radical antioxidant capacity, SD: standard deviation, PAGE: polyacrylamide gel electrophoresis.

Definitions

In describing and claiming the disclosed subject matter, the following terminology will be used in accordance with the definitions set forth below. Unless defined otherwise, all technical and scientific terms used herein have the same meaning as commonly understood by one, of ordinary skill in the art to which this disclosure belongs. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art. As appropriate, procedures involving the use of commercially available kits and reagents are generally carried out in accordance with manufacturer defined protocols and/or parameters unless otherwise noted. Although any methods and materials similar or equivalent to those described herein can also be used in the practice or testing of the present disclosure, the preferred methods and materials are described herein.

In this specification, unless otherwise specified, "a" or "an" means "one or more".

The terms "treatment or prophylaxis" in their various grammatical forms in relation to the present invention refer to preventing, curing, reversing, attenuating, alleviating, ameliorating, inhibiting, minimizing, suppressing, or halting (1) the deleterious effects of a disorder, (2) disorder progression, or (3) disorder causative agent.

The term "effective amount" in relation to the present invention refers to that amount which provides a therapeutic effect for a given condition and administration regimen. This is a predetermined quantity of active material calculated to produce a desired therapeutic effect in association with the required additives and diluents; i.e., a carrier, or administration vehicle. Further, it is intended to mean an amount sufficient to reduce and most preferably prevent a clinically significant deficit in the activity and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluents; i.e., carrier, or additive. Further, the dosage to be administered will vary depending on the active principle or principles to be used, the age, weight etc. of the patient to be treated but will generally be within the range from 0.001 to 1000 mg/kg body weight/day. Moreover, the dose depends on the administration route.

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall (homologous) and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

The invention is further illustrated in—but not limited to—the figures.

LEGEND TO FIGURES

Figure 1:
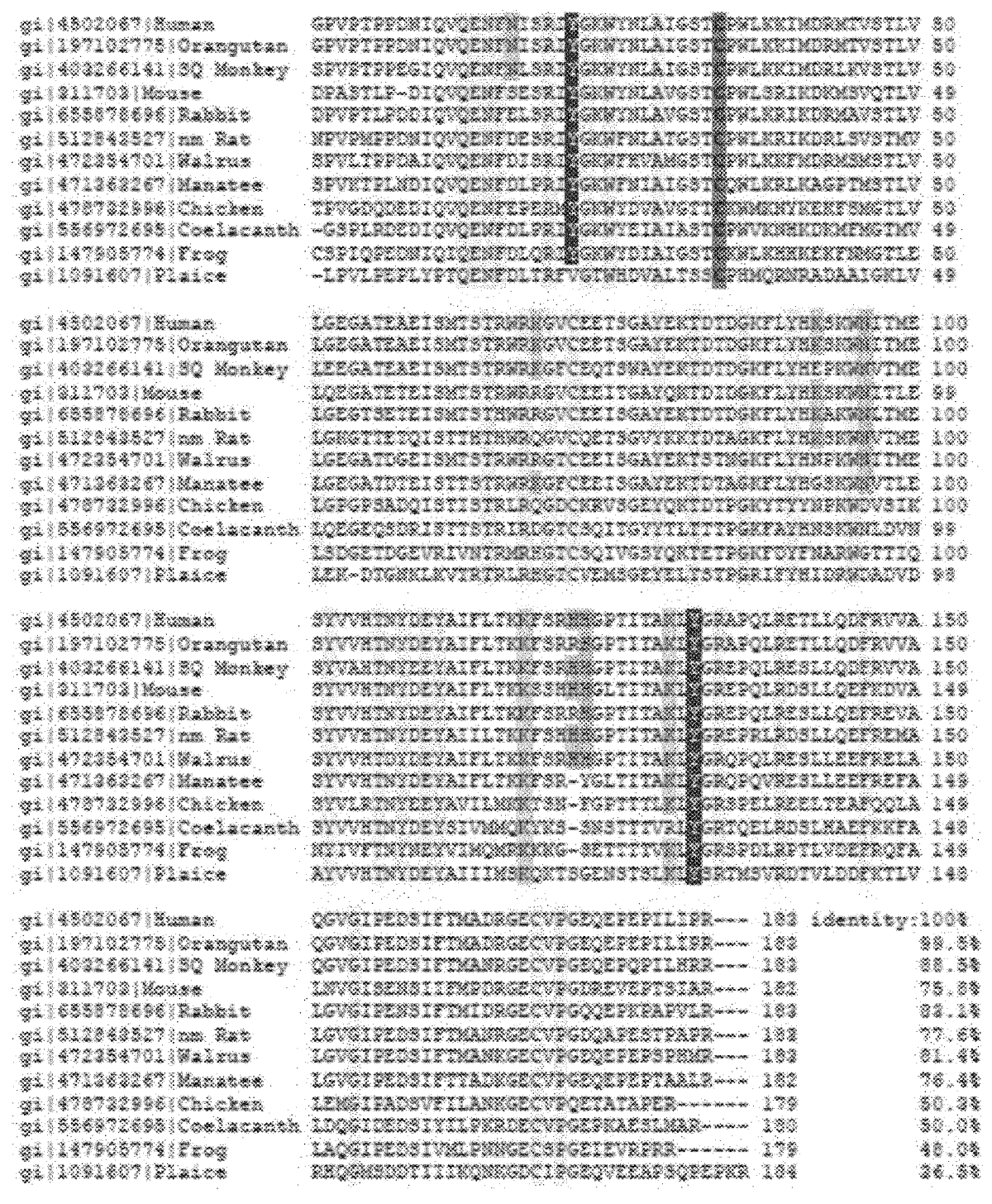

FIG. 1. Amino acid sequence alignment of A1M from 12 different species.

The amino acid sequence of human wt A1M and 11 additional species (SEQ ID NOS 1 and 104-114, respectively, in order of appearance) investigated in project phase I were aligned using the http://www.ebi.ac.uk/Tools/msa/clustalw2/software. The identity of the different sequences to the human sequence is presented as percent. Amino acids identical between all species in the set are marked with yellow. Additionally, amino acids believed to be important in human A1M are marked: the unpaired cysteine residue (C34) important for reduction and antioxidant properties (Allhorn et al., 2005) as well as heme binding is marked with pink (Mening and Skerra, 2012). The asparagines known to be glycosylated (N17 and 96) are marked with green (Escribano et al, 1990). The four lysines (K69, 92, 118 and 130) that have been found modified in urine A1M (Åkerström et al., 1995; Berggård et al., 1999) and are believed to be important for the reductase activity (Allhorn et al., 2005) are marked. The H123 suggested to take part in the heme-binding (Meining and Skerra, 2012) is marked with grey and finally the tyrosines (Y22 and 132) shown to be involved in radical scavenging (Åkerström et al., 2007) are marked.

Figure 2:
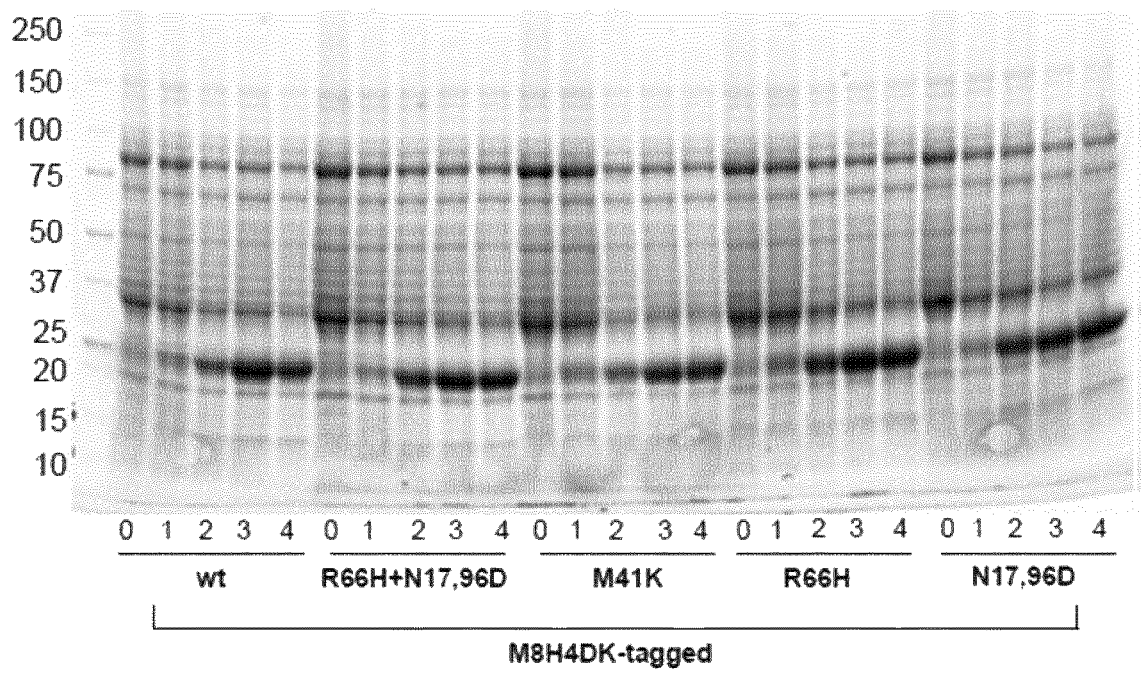
Figure 2:
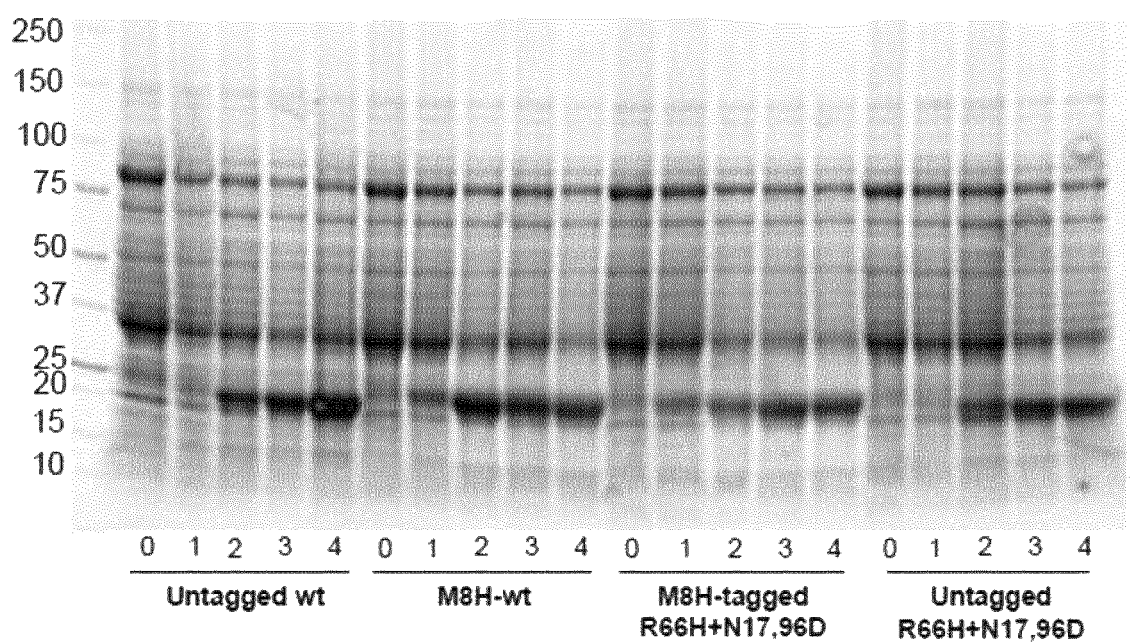

FIG. 2. SDS-PAGE of expressed proteins in phase III.

Equal amount of bacterial lysate from uninduced samples (marked 0) and samples taken one to four hours after induction (marked 1, 2, 3, 4) were separated by SDS-PAGE. In these samples a band slightly below 25 kDa is expressed at increasing amounts by time. The intensity of the bands culminates after 3 hours of induction. M8H-tagged wt-A1M and R66K+N17,96D-A1M are expressed with molecular weights slightly smaller than for the M8H4DK bands, but also here the expression level culminates around 3 hours. Untagged wt-A1M and R66H+N17,96D-A1M appear as even smaller bands, but here the intensity of the bands is stronger at 4 hours than 3 hours indicating a slightly delayed expression, in particular for wt A1M.

Figure 3:
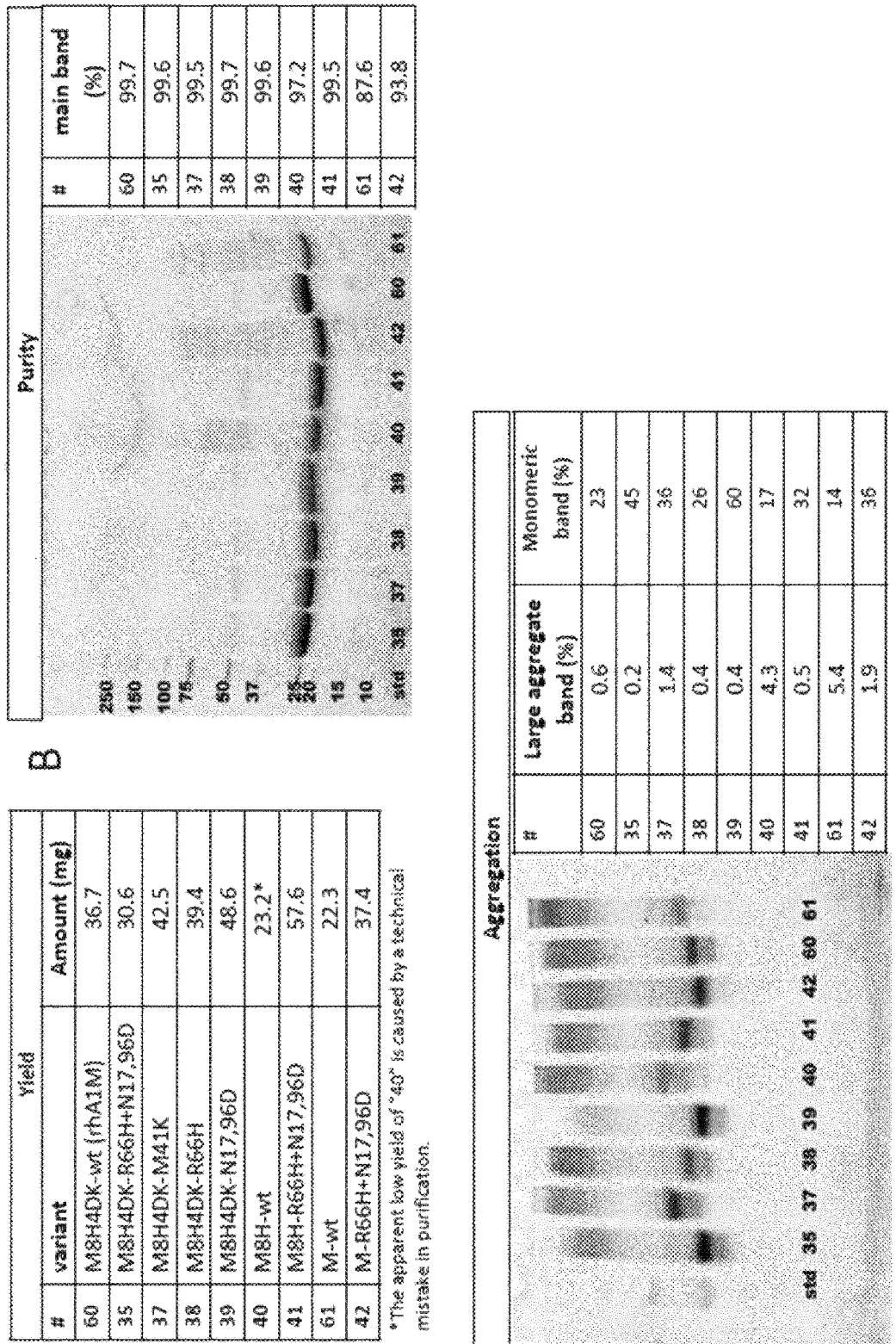

FIG. 3. Yield, purity and aggregation of phase Ill variants.

A. The yields of purified A1M of all phase III variants were compared. All variants resulted in good yields, with a slightly lower yield of the untagged wt-A1M. B. The purity was investigated by separation of 10 μg of all variants on SDS-PAGE. The purity was determined by densiometric analysis of the main monomeric band compared to all bands using the Image software from Bio-Rad. All histidine-tagged variants showed very high purity while the purities of the untagged variants were a little bit lower (around 90%). C. The presence of large aggregates were analysed by separating 20 μg of each variant by native PAGE. The intensity of the main monomeric band and the material remaining in the application slit (very large aggregated) were determined by densiometry. Most variants showed low amounts of large aggregates with exception of M8H-wt-A1M and the untagged variants, which show a slightly higher percentage. All variants are coded by a number given in panel A.

Figure 4:
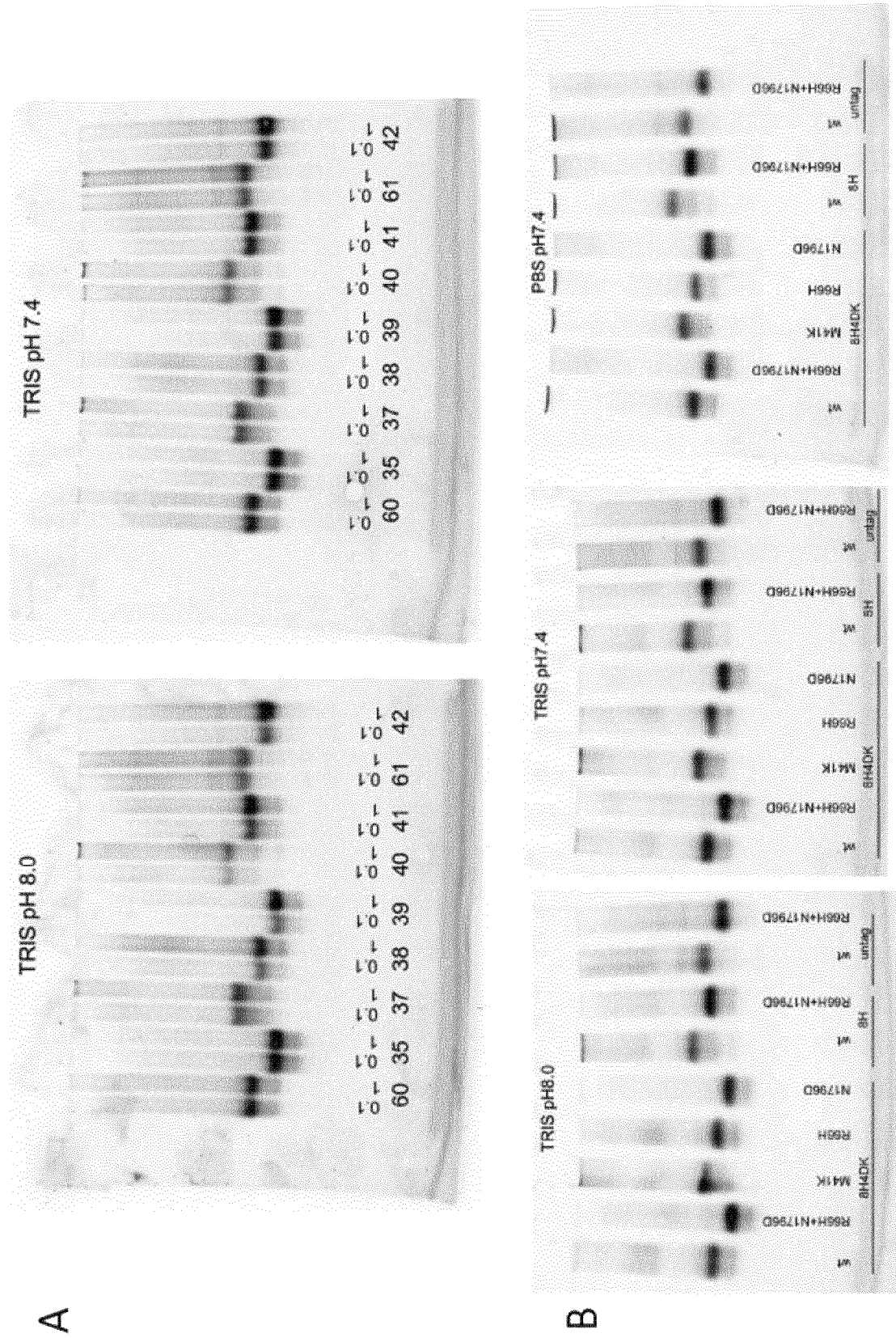

FIG. 4. Aggregation analysis of 100 μM and 1 mM solutions of phase Ill variants in various buffers.

The tendency to aggregate after concentration from 100 μM to 1 mM in different buffers was investigated by native PAGE analysis. 20 μg of protein were separated in each lane. The percent large aggregates were calculated using densiometry analysis of the individual band intensities.

A. All variants were concentrated from 100 μM to 1 mM in Tris-buffer pH 8.0 or 7.4 and separated by PAGE. The M8H4DK-wt, R66H+N1796D, M41K, R66H, N1796D are labelled 60, 35, 37, 38 and 39 respectively, the M8H-wt and M8H-R66H+N1796D are labeled 40 and 41 and the untagged wt and R66H+N1796D are labelled 61 and 42.

B. The variants were concentrated to 1 mM in TRIS-buffer pH 8.0 and 7.4 and in PBS pH7.4, subjected to one freeze-thaw cycle, and then separated by PAGE and analysed as described:

FIG. 5. Analysis of reductase and antioxidant capacity of phase III variants.

A. The reductase activity was analysed as the reduction of the ABTS radical. 0-2 μM A1M were added in duplicates to 56 μM ABTS radical. The reduction was followed as decrease of absorbance at 405 nm during 95 seconds. The area under the curve (AUC) for each concentration was calculated and the Net AUC was calculated by subtracting the AUC of buffer only. The average Net AUC+/−SEM of the duplicates was plotted against concentration. All M8H4DK-variants have about the same activity as wt A1M with a tendency to lower activity for M41K and R66H. The M8H and untagged variants also show full activity with a small tendency of higher activity of the R66H+N1796D variants compared to wt A1M.

B. The antioxidation ability was investigated in the ORAC assay. The activities of the A1M-variants were compared to a Trolox standard and expressed as number of Trolox equivalents. Each assay was done in triplicates and the result of M84DK-wt was set to 100%. The antioxidation capacities of all other variants were expressed in relation. The M8H4DK-R66H+N17,96D variant showed significantly higher capacity than the M8H4DK-wt A1M. When the tags were shortened or removed the difference was smaller. Data presented are the combined results of two independent experiments.

FIG. 6. Analysis of reductase activity and heme binding of phase III variants.

A. The ability of A1M-variants to reduce cytochrome c was investigated by mixing dilution series (0-10 μM) of A1M with 100 μM cytochrome c+100 μM NADH and following the increase in absorbance at 550 nm for 20 minutes. The assay was done in duplicates. The AUC was calculated for each concentration and the Net AUC was calculated by subtraction of the AUC of buffer only. Data are presented as the Net AUC+/−SEM of two independent experiments. Ovalbumin was used as a negative control. Most A1M variants showed a slightly lower reduction capacity compared to wt at the lower concentrations. For N17,96D-A1M and R66H+N17,96D-A1M it is significant (at 0.3-0.6 μM). Shortening and removal of the tag had no influence of this property.

B. The incorporation of heme into the A1M-variants was analysed by the appearance of an absorbance peak between 410-420 nm, and the magnitude of the red-shift of the peak (Karnaukhova et al., 2014; Rutardottir et al., 2016). 44 μM protein solutions were mixed with 40 μM heme in duplicates and incubated for 2 hours at RT. The mixtures were analysed by wavelength scan between 270-450 nm. The position of the maximal peak and the 413:386 ratio were calculated. All M8H4DK-variants have about the same red-shift and ratio as wt-A1M, while the M8H-tagged variants have significantly higher ratio. The untagged variants lack red-shift activity, confirming previous results (Karnaukhova et al., 2014).

C. The binding of A1M to heme agarose. The specific binding of A1M was analysed by mixing dilution series of A1M, or the control ovalbumin, with heme-agarose or control agarose. The assay was made in duplicates. Protein quantification of the starting material and the flow-throughs from heme-agarose and control agarose incubations was determined using BCA. From these data the amount of protein specifically bound to heme agarose could be determined for each sample. Bound protein was plotted against added protein, and a linear correlation was seen for all variants. The slope of the line was calculated with linear regression and the average between the duplicates is shown. All variants bind heme in this method to about the same extent.

Figure 7:
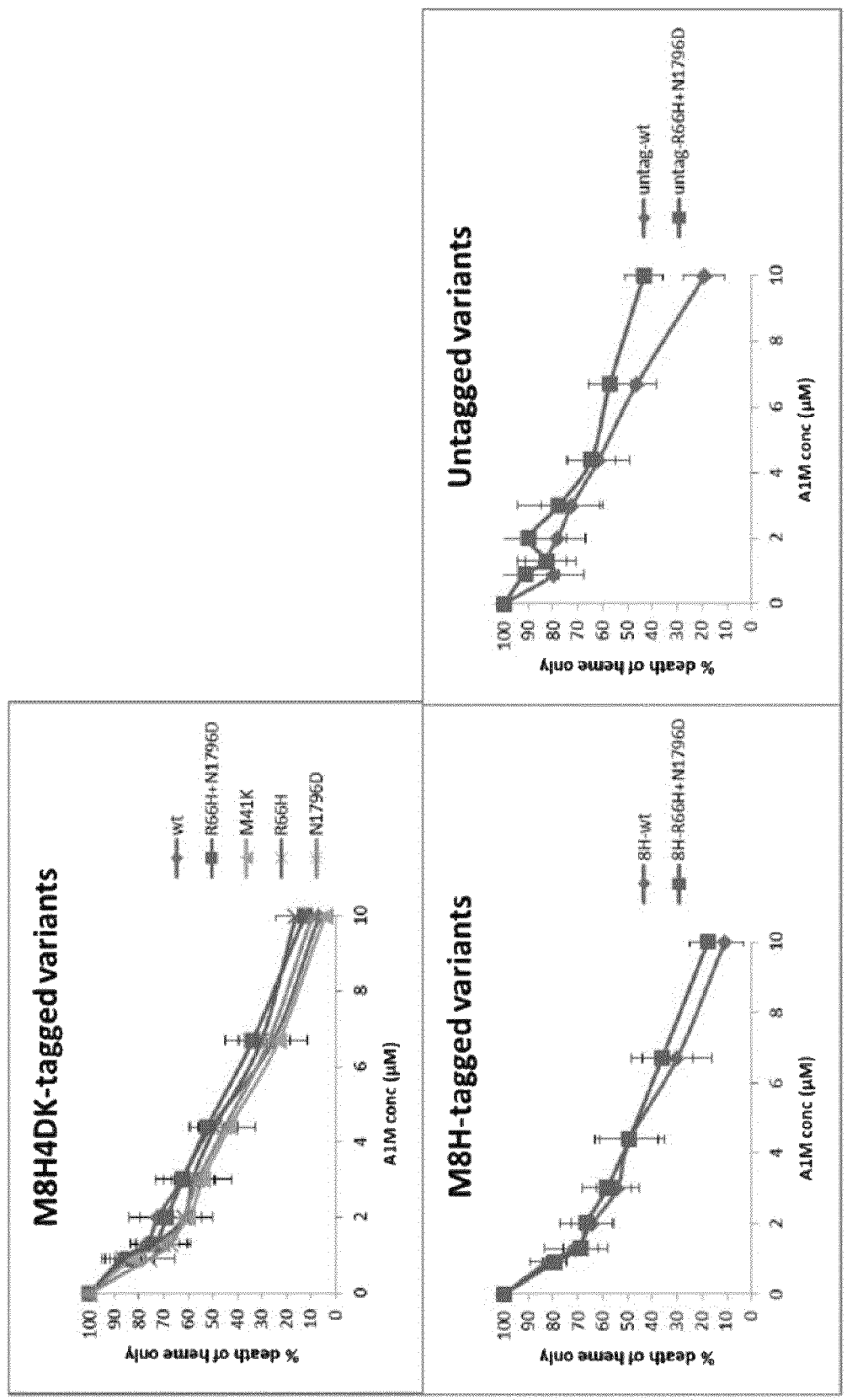

FIG. 7. Rescue of K562 cells from heme-induced cell death.

K562 cells were exposed to 100 μM heme in the presence of a dilution series of A1M (0-10 μM) for 1 hour. Then, cell death was monitored as release of LDH into the medium. The absorbance value from live cells was subtracted and the signal of heme-incubated cells without A1M was set to 100%. The values of the A1M incubations were calculated in-relation to this. The assay was made in duplicates. The average result from three independent experiments (mean+/−SEM) is shown in the figure. No significant difference could be seen between any of the variants except for untagged R66H+N17,96D-A1M that has lower activity than untagged wt-A1M.

FIG. 8. Size-distribution and reductase activity of M8H4DK-R66H+N17,96D-A1M and M8H4DK-wt-A1M after storage at +4° C. and room-temperature.

M8H4DK-Wt-A1M and M8H4DK-R66H+N17,96D-A1M are depicted as "wt" and "variant 35" and shown in the upper and lower panels, respectively. Aggregation was analysed by SEC-FPLC. Monomeric A1M and large aggregates were eluted around 15 ml and 8 ml, respectively. The small shoulder seen around 13-14 ml most likely is dimeric A1M. The percentage of large aggregates was calculated from the area under the 8 ml peak compared to the total peak area. The recovery of protein (%; shown in italic) after stress exposure was calculated from the total peak areas compared to the total peak area of the starting material. The reduction activity of ABTS was analysed in 2 μM A1M solutions. Data are shown as average of duplicates. Freshly thawed 100 μM A1M solutions are shown in (A), 100 μM A1M exposed to five freeze-thaw cycles (B), 1 mM A1M stored at +4° C. over-night (C), 1 mM A1M stored at +4° C. for a week (D), 100 μM A1M stored at RT for a week (E), and 1 mM A1M stored at RT for a week (F). Data show that M8H4DK-R66H+N1796D better tolerates concentration to 1 mM (C & D) and storage at RT (E and F).

FIG. 9. Size-distribution and reductase activity of 1 mM M8H4DK-wt-A1M and M8H4DK-R66H+N17,96D-A1M after storage at +37° C.

Wt-A1M and R66H+N17,96D-A1M are depicted as "ht2014" and "35" and shown in the upper and lower panels, respectively. Aggregation was analysed by SEC-FPLC. Monomeric A1M and large aggregates are eluted around 20 min and 12 min, respectively. The small shoulder seen around 18-19 min most likely is dimeric A1M. The percentage of large aggregates was calculated from the area under the 12 min peak compared to the total peak area. The recovery of protein (%; shown in italic) after stress exposure was calculated from the total peak areas compared to the total peak area of the starting material. The reduction activity of ABTS was analysed in 2 μM A1M solutions. Data are shown as average of duplicates. 1 mM A1M solutions stored for 1.5 hours (B), 2.5 hours (C) and 4.5 hours (D) were compared to 1 mM A1M start material (A). The M8H4DK-wt at 4.5 hours was completely precipitated and could not be analysed. Data show that M8H4DH-R66H+N1796D better tolerates storage at +37° C. than M8H4DK-wt.

FIG. 10. Model of the structure of A1M. The model was prepared as described (ref 29). The eight β-strands, shown as ribbons, form a slightly cone-shaped cylinder with a hydrophobic interior: the "lipocalin pocket". One side of the lipocalin pocket is open (shown by the arrow), i.e. it permits entrance of small molecules. The opposite side is closed. Two α-helices are shown as cylinders. The positions of three carbohydrate groups (T5; N17; N96) and four side-chains involved in reductase activity (C34; K92; K118; K130) are shown.

FIG. 11

Heme-binding analysed by migration shift/fluorescence quenching on native PAGE (A and B), and UV-absorbance spectrophotometry (C). A. Fifteen μg M8H4DK-wt A1M (wt-A1M) or M8H4DK-35-A1M (35-A1M) were incubated with different amounts of heme for 30 min at 20° C., separated by native PAGE, and the gel analysed by tryptophan fluorescence (Flourescence) and densitometry scanning after Coommassie staining (Stain). B. The images were digitalized by using Image Lab™ Software (Bio-Rad). Heme binding, measured as flourescence quenching and migration distance were plotted against the molar ratio A1M:heme. Mean values of duplicate experiments are shown, wt-A1M (filled symbols), 35-A1M (open symbols). C. A1M and heme were mixed (32 and 19 μM, respectively), incubated for 2h at 20° C. and scanned. The absorbance of the proteins alone at 32 μM are shown as comparison. The absorbance of the buffer (20 mM Tris-HCl, pH 8.0+0.15M NaCl) was subtracted from all scans as blank.

FIG. 12

Comparison of the enzymatic properties of M8H4DK-wt A1M (wt-A1M) and M8H4DK-35-A1M (35-A1M). A. Freshly purified wt-A1M (■) or 35-A1M (○) at various concentrations were mixed with ABTS-radical at 56 μM in 25 mM sodium phosphate buffer pH 8.0 in microtiter plate wells, and the rate of reduction was followed by reading the absorbance at 405 nm during 95 seconds. The absorbance for each concentration was plotted against time and the area under the curve (AUC) between 0 and 95 s was calculated for each concentration. The net AUC was calculated by subtracting the AUC of buffer only. Mean of triplicates+/−SEM are shown. B. The ABTS-reduction rate was determined as described in A, but using wt-A1M (■) or 35-A1M (○) after storage for 7 days at 4° C. or room-temperature and 0.1 or 1 mM. Single experiments are shown. C. The reduction of cytochrome c was investigated by mixing dilution series (0-10 μM) of wt-A1M (■) or 35-A1M (○) with 100 μM cytochrome c+100 μM NADH and following the increase in absorbance at 550 nm for 20 minutes. The assay was done in duplicates. The AUC was calculated for each concentration and the Net AUC was calculated by subtraction of the AUC of buffer only. Data are presented as the Net AUC+/−SEM of two independent experiments. Ovalbumin was used as a negative control. D. The antioxidation ability was investigated in the ORAC assay. The activities of the A1M-variants at 5 μM were compared to a Trolox standard and expressed as number of Trolox equivalents. Each assay was done in triplicates and the result of wt-A1M was set to 100%. Data presented are the mean of two independent experiments+/−SEM.

FIG. 13

K562 cells cultured at $10^5$ cells per well in a 96-well microtiter plate, were exposed to 100 μM heme in the presence of a dilution series of M8H4DK-wt A1M (wt-A1M) or M8H4DK-35-A1M (35-A1M) (0-10 μM) for 1 hour. Cell death was monitored as release of LDH into the medium. The LDH-value from live cells was subtracted and the signal of heme-incubated cells without A1M was set to 100% and the values of the A1M incubations were calculated in relation to this. The assay was made in duplicates. The average result from three independent experiments (mean+/−SEM) is shown. Wt-A1M (■) or 35-A1M (○).

FIG. 14

HK-2 cells were exposed to a mixture of 200 μM $(NH_4)Fe(SO_4)_2$, 400 μM hydrogen peroxide, and 2 mM ascorbate (the Fenton reaction, displayed in A and B) or 0-30 μM heme (displayed in C and D) with or without the simultaneous addition of 0-20 μM M8H4DK-wt A1M (wt-A1M) (displayed as ■ and black columns) or M8H4DK-35-A1M (35-A1M) (displayed as ○ and columns) for 6 hours. After incubation, cells were analyzed for cell viability using WST-1 (displayed in A and C) or mRNA expression of HO-1 and Hsp70 (displayed in B and D) as described in materials and methods. The cell viability (A and C) was normalized against control samples from untreated cells. Results are from triplicate experiments and presented as mean±SEM. The mRNA expression of HO-1 and Hsp70 (B and D) was normalized against GAPDH and is given as fold change. The fold-change values were calculated by normalizing against control samples from untreated cells. Results are from triplicate experiments and presented as mean±SEM. Differences between the respective exposures and control conditions were analyzed using One way ANOVA with post hoc Bonferroni correction. * indicates statistical comparison vs. Fenton (displayed in B) or heme (displayed in D). *P<0.05, P<0.01, *P<0.001. No significant difference was observed when comparing wt-A1M vs. 35-A1M.

FIG. 15

Plasma clearance (pharmacokinetics, displayed in A) and biodistribution (displayed in B) of M8H4DK-wt A1M (wt-A1M) and M8H4DK-35-A1M (35-A1M) injected intravenously in animals. A. Wt-A1M (■) or 35-A1M (○) was injected (5 mg/kg) in Wistar rats and blood was collected at regular intervals. A1M-concentrations were determined by RIA using the particular A1M-variant as standard. Each point are from three animals and presented as mean±SEM. B. Wt- or 35-A1M, 5 mg/kg, was injected intravenously in C57BL/6NRj-mice which were sacrificed 10 and 30 min post-injection. Organs were sampled, weighed and homogenized. Concentrations of injected (human) A1M were determined by sandwich-ELISA. Each bar are from three animals and presented as mean±SD. Wt-A1M, 10 min (black) and 30 min (dark gray); 35-A1M, 10 min (white) and 30 min (light gray).

FIG. 16

Female C57BL/6 mice were exposed to Glycerol (2.0 ml/kg, i.m.) followed by i.v. administration of either M8H4DK-wt A1M (wt-A1M) (dark grey bars, n=10), M8H4DK-35-A1M (35-A1M) (white bars, n=10) or vehicle buffer (sham control, grey bars, n=6) 30 minutes post-glycerol injections. At 4 hours (post-glycerol administration) animals were euthanized and kidneys excised, snap frozen and subsequently analyzed for mRNA expression of HO-1 (A) and Hsp70 (B) using real-time PCR as described in materials and methods. mRNA expression were normalized against those of GAPDH and fold change values were calculated by normalizing against control samples from untreated animals (controls). Results are presented as box plots, displaying medians and 25th and 75th percentiles. Statistical comparison between groups were performed by ANOVA with post hoc Bonferroni correction. * indicates statistical comparison vs. Glycerol. *P<0.05, **P<0.01. No significant difference was observed when comparing wt-A1M vs. 35-A1M.

FIG. 17

FIG. 17 illustrates Table 4.

FIG. 18

FIG. 18 illustrates Table 6a.

FIG. 19

FIG. 19 illustrated Table 6b.

The invention is further illustrated in the following examples. The examples are illustrative and do not limit the scope of the invention in any manner.

EXPERIMENTAL

The experimental work was divided into three major phases:

Phase I) Expression of the 27 A1M-variants described above followed by analysis of solubility, stability and function;

Phase II) Design, expression and analysis of a few A1M-variants with expected optimal properties based on the outcome of phase 1;

Phase III) Design, expression and analysis of wt-A1M and the most successful mutated A1M-variant equipped with or without N-terminal tags.

In Phase I, four lines of reasoning were used, when selecting the positions and identities of mutated amino acid side-groups: 1) Animal homologues from a variety of species with different expected environmental pressure in terms of oxidative stress, temperature, oxygen pressure were expressed (N=12); 2) Single amino acid substitutions that occur frequently among the 56 sequenced A1M-homologues at positions located in loops 1-4 or the interior surface of the hydrophobic pocket, were introduced into the human gene construct and expressed (N=3); 3) Addition or removal of favourably located lysyl or tyrosyl residues, based on the hypothesis that these may influence pKa of the C35 thiolyl (Allhorn et al., 2005) or serve as radical-trapping sites (Berggård et al., 1999; Sala et al., 2004; Åkerström et al. 2007) (N=5); 4) Hydrophobic→hydrophilic substitutions on the surface of the protein, with no predicted influence on function or folding (N=7).

Materials and Methods

Expression

The sequences of the A1M variants were provided to DNA2.0, Inc. (USA) which synthesized the genes and cloned them into their PJ401Express vector (T5 promoter, kanamycin resistance). The DNA sequence was confirmed by sequencing. The vectors were transformed into competent E. coli (BL21 Star(DE3) (Invitrogen, Life technologies corp, USA)) according to the manufacturer's instructions and four individual clones of each variants were tested for micro-expression. The clone with highest expression of each variant was prepared as a glycerol stock which was used for production expression.

A1M variant expression clones were grown in complete NYAT (15 mM $(NH_4)_2SO_4$, 84 mM $K_2HPO_4$, 23 mM $NaH_2PO_4 \times H_2O$, 2.2 mM $(NH_4)_2$Hcitrate, 1% (w/v) glucose, 2 mM $MgSO_4$, 9 µM $CaCl_2 \times 2H_2O$, 85 µM $FeCl_3 \times 6\ H_2O$, 1.3 µM $ZnSO_4 \times 7\ H_2O$, 1.3 µM $CuSO_4 \times 5H_2O$, 1.8 µM $MnSO_4 \times H2O$, 1.5 µM $CoCl_2 \times 6\ H_2O$, 108 µM EDTA, 50 µg/ml kanamycin) to an $OD_{600}$ of 1.5. Then protein expression was induced by addition of 1 mM IPTG. The production went on for 4 hours. Samples for SDS-PAGE analysis were taken before induction, and 1, 2, 3 and 4 hours after induction.

Purification

Bacteria from the cultures were collected by centrifugation at 5000 rpm, 15 minutes. The bacterial pellets were lysed by five freeze-thaw cycles, diluted 3 times in 20 mM Tris-HCl pH 8.0 and sonicated. The inclusion bodies (IB's) were collected by centrifugation at 6000 rpm, 30 minutes, and washed by three more cycles of resuspension and centrifugation. For extraction, the IB's were resuspended in 6M guanidine-hydrochloride, 20 mM Tris-HCl pH 8.0 (6M Gu-HCl) and incubated with stirring overnight at +4° C. The extract was clarified by high-speed centrifugation at 26000 g, 60 minutes. The supernatant was saved for further clarification, while the pellet went through another cycle of extraction. The supernatants of the extractions were combined and further clarified by depth filter filtration (K700P filter laid on top of KS50P filter, Pall Corp., USA). A1M in the clarified extract was purified, using a Ni-agarose resin (Sigma-Aldrich, USA). Briefly, the resin was packed into a 10-ml disposable chromatography column (Bio-Rad, USA) and equilibrated in 6M Gu-HCl. The A1M extract was applied onto the column using free-flow and the flow-through collected. The column was washed with five column volumes of 6M Gu-HCl and then eluted with four volumes of 6M Gu-HCl+0.5 M imidazole. Starting material, flow-through and eluted fractions were precipitated with ethanol, resolved in 1×SDS-PAGE loading buffer and separated by SDS-PAGE. The purification procedure was repeated if the flow through contained significant amounts of A1M. The protein content of the extract was determined by absorbance 280 nm.

The Ni-agarose eluates were diluted to an approximate A280 of 5.0 and cooled to +4° C. before refolding. The eluate was then mixed with ⅔ volumes of 0.275 M L-cystein in 20 mM Tris-HCl pH 9.5+0.1M NaCl. Then 16.7 volumes refolding buffer were quickly added. The final buffer concentration was: (0.2 mg/ml A1M, 0.1M Tris, 0.6 M NaCl, 0.45 M L-arginine, 2 mM EDTA, 10 mM L-cystein and 1 mM L-cystein, pH 9.5). The mixture was then stirred for 1 hour at +4° C., and the solution concentrated to the initial volume of the A1M solution using Centricon plus 70, 10K ultrafiltration devices (Merck Millipore; USA). After concentration, the A1M solution was diafiltrated to 20 mM Tris-HCl pH 8.0 using the same devices, by 10 consecutive 2.5× dilution/concentration cycles. After diafiltration the solution was clarified by centrifugation at 15000 g for 15 minutes and then run through a 0.2 µm filter.

The refolded A1M was immediately applied to a 5 ml Bio-Scale Mini UNOsphere Q Cartridge (Bio-Rad), equilibrated with 20 mM Tris-HCl pH 8.0. The column was run on an ÄKTA purifier 10 instrument (GE Healthcare, USA) according to Bio-Rad's instruction for the cartridges. After sample application the column was washed with five column volumes (CV) of 20 mM Tris-HCl pH 8.0 before elution with a 20 CV linear gradient from 0-0.35M NaCl. Finally, the column was washed with three CVs of 1 M NaCl. The flow-though and selected fractions collected during the linear gradient were analysed by SDS-PAGE. Flow-through with remaining A1M was immediately re-run on a new column and the A1M containing fractions were pooled, concentrated to 100 µM, sterile filtered and frozen at −20° C. in aliqoutes.

Gel Electrophoresis

SDS-PAGE was run according to Laemmli (Laemmli, 1970) using standard protocols. Proteins were separated on stain-free 4-20% TGX gels (Bio-Rad) at 300V for 17 minutes. Native PAGE was run without SDS and without reducing agents on stain-free 4-20% TGX gels at 200V for 40 minutes. The gels were analysed on a Chemidoc MP instrument (Bio-Rad).

Circular Dichroism

The circular dichroism spectra were recorded on a Jasco-J180 spectrofluorimeter instrument (JASCO Inc., Japan) of 10 µM solutions in 20 mM Tris-HCl pH 8.0+0.15 M NaCl in a 2-mm cuvette. The solutions were scanned at +22° C. between 190-260 nm. Three runs were overlayed for each sample. The percentage of α-helix and β-sheet structure was calculated using the http://k2d3.ogic.ca software.

SEC-FPL C

Proteins were analysed by size exclusion on an ÄKTA purifier 10 instrument using a 24-ml Superose 12 10/30 GL column (GE Healthcare). The column was equilibrated with 20 mM Tris-HCl pH 8.0+0.15 M NaCl using a flow-rate of 1 ml/min. 100-200 µg of protein were loaded onto the column in a volume of 100 µl and eluted with 20 mM Tris-HCl pH 8.0+0.15 M NaCl using a flow-rate of 0.75 ml/min. Typically, monomeric A1M was eluted after 15 ml/20 min, dimeric after 13-14 ml/18-19 min, and large aggregates were eluted after 8 ml/12 min. The percentage of large aggregates was calculated from the area under the 8-ml peak compared to the total peak area. The percentage of total protein retrieved on the column after stress treatments (see below) was calculated by comparing the total peak areas of treated vs. non-treated samples.

RP-HPLC

Reversed phase HPLC was run on an Agilent 1260 Infinity Binary LC system using an Aeris Wildpore 3.6 µM XP-C8 column (Phenomenex Inc., USA). The column was run at +25° C. using a flow rate of 1 ml/min and equilibrated with a mixture of 70% $H_2O$+0.1% TFA and 30% Acetonitrile+0.1% TFA. 10 µl (=10 µg of protein) were loaded and eluted with a linear gradient of 30-50% acetonitrile over 20 minutes. The column was regenerated by washing with 95% acetonitrile for 10 minutes.

Dynamic Light Scattering

Dynamic light scattering (DLS) analysis of non-stressed and shearing-stressed sam-pies was done using the service of SARomics Biostructure AB, Lund. A1M samples, diluted to 10 µM in 10 mM Tris-HCl pH 8.0+0.125 M NaCl, were analysed on a Malvern APS instrument at +20° C. Samples were prepared in duplicates and each sample was monitored three times.

Differential Scanning Fluorimetry

Thermostability of the A1M variants was analysed by differential scanning fluorimetry (DSF) using the service of SARomics Biostructure AB, Lund. A1M diluted to 4.4 µM in 10 mM HEPES pH 8.0+0.125 M NaCl was mixed with SYPRO orange (1000× dilution of SYPRO orange in total). The analysis was made in duplicates and the average melting temperature (Tm) was calculated.

Introduction of Stress by Shearing Forces

10 µl of 100-µM A1M solutions were exposed to shearing force stress by 80 pipettings with a multiple channel pipett using 0-10 µl pipett tips. The stress-treatment was performed in duplicates. After pipetting, the duplicates were combined and diluted 10 times before analysis with DLS as described.

High Concentration-Induced Stress

Solubility and stability of A1M was analysed at high concentration. 500 µl of 100 µM A1M solutions were concentrated tenfold to 50 µl using Amicon Ultra-0.5, 10K devices (Merck Millipore) by centrifugation at 14000 g for 10 min. After concentration the volumes were corrected to exactly 50 µl using the respective flowthroughs. Concentrated and non-concentrated samples (10 µg) were compared side-by-side on native PAGE. The influence of different buffers were examined by diafiltration of the samples before concentration. This was done by five cycles 10-time dilution/concentration in Amicon Ultra-15, 10K devices.

Quantification of Free Thiol Groups

The free thiol groups of the A1M variants were determined with the "Thiol and sulfide quantification kit" from Molecular probes. The assay was performed in 96-well plates according to the kit manual. A volume of 3 µl standard or A1M (100 µM) was mixed with 3 µl cystamine work solution, 100 µl papain-SSCH, 100 µl L-BAPNA. The assay was read as absorbance 405 nm.

ABTS Reduction Assay

The assay is a modification of (Åkerström et al 2007). 7 mM of 2,2 Azino-bis (3-etylbenzothiazoline-6-sulfonic acid) di-ammonium salt (Sigma-Aldrich) was oxidized with 2.45 mM $K_2S_2O_8$ overnight, and then diluted to 56 µM in 25 mM sodium phosphate buffer pH 8.0. 100 µl of the ABTS working solution was added per well in a 96-well plate. A time-point zero measurement was done at A405 using a Perkin Elmer Plate reader. 2 µl of an A1M solution (0-100 µM) were quickly added by a multiple channel pipett. The kinetics of the decrease in absorbance at 405 nm was quickly followed for 95s. For practical reasons only 8 wells were analysed at the time. The A1M dilution series was run in duplicate or triplicates. If the number of samples to be analysed required several plates, new ABTS stock was diluted into working stock for each plate and an wt-A1M reference sample was included in all plates. The absorbance for each concentration was plotted against time and the area under the curve (AUC) was calculated for each concentration. The net AUC was calculated by subtracting the AUC of buffer only.

Oxygen Radical Antioxidant Capacity (ORAC) Assay

The commercial kit OxySelect™ Oxygen radical antioxidant capacity (ORAC) activity assay (Cell Biolabs, Inc. USA) is based on the oxidation and destruction of a fluorescent probe by peroxyl radicals. When an antioxidant is present this destruction is inhibited. As standard the water soluble vitamin E derivate, Trolox is used. Performance, analysis and calculations followed the kit manual and an A1M concentrations of 2.5-5 µM fitted nicely in to the standard curve. Ovalbumin (Sigma-Aldrich) was used as a negative protein control.

Cytochrome c Reduction Assay

The assay is modified from (Allhorn el al. 2005). A working solution was made by mixing 100 µM cytochrome c (Sigma-Aldrich) and 100 µM NADH in 10 mM Tris-HCl pH 8.0+0.125M NaCl. 11 µl of an A1M solution (0-100 µM) were added to a 96-well plate in duplicates. 100 µl of the cytochrome c working solution was quickly added per well using a multichannel pipett. The kinetics of the increase in absorbance at 550 nm was followed for 20 minutes. One plate was analysed at the time. No biases over time could be observed. If several plates were to be analysed the same working solution was used for all without any observable artefacts caused by this procedure. After measurements the results were analysed as described for the ABTS assay.

The Red-Shift Assay

The incorporation of free heme in A1M yields a red-shift of the Soret band absorbance peak (Karnaukhova et al., 2014; Rutardottir et al., 2016), and was evaluated in the A1M-mutants as the $A_{413}/A_{386}$ ratio. 44 µM A1M in 20 mM Tris-HCl pH 8.0+0.25M NaCl was mixed with 40 µM free heme (Applichem). The incubations were done in duplicates and incubated for 2 hours at room temperature. The red-shift was analysed in four times diluted samples by wavelength scan in a Beckman Spectrophotometer. The average maximal peak of the duplicates as well as the average ratio between the absorbances at 413 and 386 nm was calculated. Ovalbumin and buffer only were used as negative controls.

Specific Binding of A1M to Heme-Agarose

Binding of A1M to heme-agarose was analysed by the method of (Larsson et al., 2004), modified as described (Rutardottir et al., 2016). Heme-agarose (Sigma-Aldrich) and control Sepharose 4B (Sigma-Aldrich) were equilibrated with 20 mM Tris-HCl pH 8.0+0.25M NaCl and prepared as 50% slurries. 75 µl of an A1M dilution series (0-13.3 µM) were added to duplicate 96-well plates (one plate for heme agarose and one for control Sepharose). 20 µl of heme-agarose och control Sepharose slurry were added to the wells by careful pipetting to assure transfer of similar amounts, and incubated for 30 minutes at RT during rotational stirring. The mixtures were carefully transferred to an AcroPrep Advance 96-well filter plate, 1.2 µm Supor membrane (Pall Corp). The plates were centrifuged for 2 min at 1000 g collecting the flow-through in a low-binding microplate. 25 µl of each flow-through, as well as the non-incubated starting material, were assayed for protein content using Pierce BCA Protein Assay kit (Thermo Scientific Inc., USA). Protein amounts were recalculated as amount bound (added minus amount in flow-through) for both the heme- and control Sepharose-incubated samples. After subtraction of the amount bound to the control Sepharose, the amount specifically bound to heme agarose was plotted against the added amount. The slope of the curve was calculated with linear regression. The SD of the duplicates were used to evaluate the significance of the differences between the A1M variants.

Heme Binding of M8H4DK-wt A1M (Wt-A1M) and M8H4DK-35-A1M (35-A1M)

Heme binding was analysed as previously described by native PAGE (Karnaukhova et al., 2014) and UV-spectrophotometry (Ruttarsdottir et al., 2016). Briefly, for native PAGE, A1M and various concentrations of heme were incubated in Tris-buffer, pH 8.0 for 30 min at room temperature, separated by native PAGE on stain-free 12% Criterion TGX gels at 200V for 40 minutes. The gel bands were analysed on a Chemidoc MP instrument (Bio-Rad) for tryptophan fluorescence using the Stain-free setting, stained with Coommassie Brilliant Blue, destained and imaged again on the Chemidoc using the Coommassie setting. Both sets of bands were then quantified using Image Lab™ Software (Bio-Rad). Heme binding was then estimated as the amount of quenching of the tryptophan fluorescence relative to total protein amounts after Coommassie staining. Absorbance spectra were measured on a Beckman (Beckman Instruments, Fullerton, Calif.) DU 800 spectrophotometer using a scan rate of 600 nm/min in the UV-VIS region between 250 and 700 nm at 22° C. Concentrations of A1M and heme were 32 and 19 µM, respectively, in 20 mM Tris-HCl, pH 8.0, 0.15 M NaCl. Heme was added from a stock solution of 10 mM in DMSO. Protein solutions were scanned 2 h after mixing.

Plasma Clearance and Biodistribution

For the plasma clearance studies, each A1M-variant was injected intravenously (i.v) in six male Wistar rats (5.0 mg/kg; stock-solutions in 20 mM Tris-HCl, pH 8.0) and blood samples were taken in EDTA-tubes at 1, 5, 15, 30 min, and 1, 3, 6, 16 and 24 h post-injection, using different sampling intervals in groups of three rats to avoid oversampling. Plasma was aspirated after centrifugation 140×g for 10 min, and the concentration of A1M was determined by radioimmunoassay (RIA) as described (Gram et al. 2015) using the specific A1M-variant as standard. For the biodistribution studies, the A1M-variants were injected i.v. in C57BL/6NRj mice (5.0 mg/kg; stock-solutions in 20 mM Tris-HCl, pH 8.0). The mice were sacrificed 10 min post-injection (n=3), and after 30 min (n=3). Organs were sampled, weighed and homogenized in 5:1 (vol:weight) Cell Extraction Buffer (Invitrogen, cat. No. FNN0011), containing 50 µl/ml complete Mini, EDTA-free proteinase inhibitor cocktail tablets (Roche, cat. no. 11836170001). A1M-concentrations were determined by an in-house sandwich ELISA. Briefly, 96-well microtiter plates were coated overnight at 4° C. with mouse monoclonal anti-A1M (clone 35.14, 5 µg/ml in PBS), washed, and then incubated with A1M-standards (human urinary A1M, purified as described at our laboratory (Åkerström et al., 1995) or homogenised tissue samples, diluted in incubation buffer (PBS+0.05% Tween 20+0.5% bovine serum albumin), for 60 min at RT. After washing, the wells were incubated with horseradish peroxidase-conjugated mouse monoclonal anti-A1M (clone 57.10, 5 ng/ml in incubation buffer) for 60 min at RT. The plates were washed and developed by incu-bating with SureBlue TMB Microwell Peroxidase Substrate (KPL) in the dark for 20 min, and finally stopped with 1M sulfuric acid. Absorbance was read at 450 nm in a Wallac 1420 Multilabel Counter. The two mouse monoclonal antibodies were raised by AgriSera AB. (Vännäs, Sweden) against human urinary A1M. The ELISA was specific for human A1M, did not cross-react with endogenous mouse plasma A1M, and reacted with human urinary A1M, M8H4DK-wt A1M (wt-A1M) and M8H4DK-35-A1M (35-A1M) equally well.

Rhabdomyolysis Induced Kidney Damage

This study was approved by the ethical committee for animal studies in Malmö-Lund, no. M21-15. Female C57BL/6 mice with a body weight of 20.5±0.7 g were obtained from Taconic (Denmark), housed in Type III cages with wire lids, at a constant room temperature with 12 hour light dark cycles. Temperature (20±0.5° C.) and relative moist (50±5%) was maintained throughout the studies. All animals had free access to food (RM1(E) SQC, SDS, England), tap water and cage enrichment. After overnight water deprivation (15 hours) animals were weighed and anaesthetized using isoflurane and then allocated to the following four groups: 1) Control (n=6), received no intramuscular (i.m.) or intravenous (i.v.) administration; 2) Glycerol (n=10), received 50% sterile glycerol (Teknova, Hollister, Calif., USA) i.m. (2.0 ml/kg body weight, single dose, divided into both hind limbs); 3) Glycerol+M8H4DK-wt A1M (wt-A1M) (n=10), received wt-A1M i.v. (7 mg/kg body weight, single dose) 30 minutes after glycerol i.m. (2.0 ml/kg body weight) administration; and 4) Glycerol+ M8H4DK-35-A1M (35-A1M) (n=10), received 35-A1M i.v. (7 mg/kg body weight, single dose) 30 minutes after glycerol i.m. (2.0 ml/kg body weight)-administration. Following i.m. administration animals were placed on a heat pad during awakening and then put back to their cages and supplied with free access to food and water. After 4 hours (post-glycerol injection) animals were anaesthetized using isoflurane and kidney collected for RNA extraction followed by mRNA evaluation as described below.

RNA Isolation and Real-Time PCR

Total RNA was isolated from HK-2 cells, using Direct-zol™ RNA MiniPrep supplied by Zymo Research (Irvine, Calif., USA), or mouse kidneys, using NucleoSpin RNA/ Protein (Machery-Nagel, Duren, Germany) followed by RNeasy® Mini Kit (QIAGEN, Germantown, Md., USA). The OD ratio (optical density at 260 nm/280 nm) of RNA was always higher than 1.9. Reverse transcription was performed according to the manufacturer on 1.0 µg total RNA using iScript™ cDNA Synthesis Kit (Bio-Rad, CA, USA). $RT^2$ qPCR Primer Assay (human (HK-2 cells) and mouse (kidneys) primers from QIAGEN) were used to quantify the mRNA expression of heme oxygenase 1 (HO-1) and heat shock protein 70 (Hsp70). Data were normalized to glyceraldehyde-3-phosphate dehydrogenase (human (HK-2 cells) and mouse (kidney) GAPDH, $RT^2$ qPCR Primer Assay from QIAGEN). Data are presented as as columns, displaying mean±SEM, for in vitro data and box plots, displaying medians and $25^{th}$ and $75^{th}$ percentiles, for in vivo data. The fold change values were calculated by normalizing against control samples from untreated cells or animals (controls). Expression was analyzed using iTaq™ Universal SYBR® Green Supermix (Bio-Rad). Amplification was performed as described by the manufacturer (Bio-Rad) for 40 cycles in an iCycler Thermal Cycler (Bio-Rad) and data analyzed using iCycler iQ Optical System Software (Bio-Rad).

Rescue of K562 Cells from Heme Induced Cell Death

A1M was previously shown to inhibit heme-induced cell-death of human erythroid K562 cells (Olsson et al., 2008). The cells were cultured in DMEM with glutamax+ 10% FCS and antibiotics (Gibco, Life Technologies Corp., USA) according to the instructions at ATCC. Cells were washed and resuspended in DMEM without phenol red and FCS but supplemented with glutamax I and antibiotics (Gibco). Cells were seeded into 96-well plates, $10^5$ cells per well, and exposed to 100 µM heme in the presence of a 0-10 µM A1M dilution series. As a positive control for cell death, 10 µl of lysis solution from the LDH detection kit (see below) was added. The cells were incubated in a 37° C. $CO_2$-incubator for 1 hour. The plates were quickly centrifuged at 350 g for 4 minutes before 50 µl of the medium was transferred to a 96-well microplate for analysis of LDH release using the cytoTox 96® Non-Radio. Cytotoxicity Assay (Promega Biotech AB, Sweden) according to the manufacturer's instructions. Heme-induced cells typically gave 7 times higher signal compared to live cells and 70% of the signal of completely lysed cells. The average signal of cells incubated without heme- or A1M-addition was subtracted from all and the signal of heme only-incubated cells was set to 100%. All other signals were related to this value. This procedure enabled comparison of several independent experiments.

Protection of HK-2 Cells

Human kidney cortex proximal tubule epithelial cells (HK-2, ATCC® CRL-2190, ATCC, Teddington, UK) were cultured in keratinocyte serum free medium (K-SFM) supplemented with bovine pituitary extract (BPE, 0.05 mg/ml) and epidermal growth factor (5 ng/mL)(all from Invitrogen, Paisley, UK). When cells reached approximately 80-90% confluence, heme (0-30 µM, from a freshly prepared 10 mM stock solution) or a mixture of $(NH_4)Fe(SO_4)_2$, hydrogen peroxide, and ascorbate (0-200 µM, the Fenton reaction), with or without the simultaneous addition of A1M (0-20 µM, M8H4DK-wt A1M (wt-A1M) and M8H4DK-35-A1M (35-A1M)), were added and cells were incubated for 6 hours. After incubation, cells were analyzed for cell viability using WST-1 (the measured metabolic activity of cells, e.g. measurement of cellular cleavage of the WST-1 stable tetrazolium salt to the soluble formazan dye, is a direct correlate to the number of viable cells)(Roche Diagnostics GmbH, Mannheim, Germany) according to the instructions from the manufacturer. The cell viability was normalized against control samples from untreated cells. Parallel cultures were harvested using Qiazol™ Lysis reagent (for RNA extraction, QIAGEN, Germantown, Md., USA). Total RNA was extracted from cells to evaluate mRNA expression as described below.

Statistics

Comparisons between unrelated groups were performed by ANOVA with post hoc Bonferroni correction. P-values <0.05 were considered significant.

Results and Discussion

Project Overview

The purpose of this investigation is to identify more stable and soluble variants of A1M with preserved functional properties. The project was performed in three phases. In phase I, A1M of different species and point mutations of human A1M were screened to identify individual amino acids that had a positive effect on stability without compromising function. In phase II, amino acids shown to have positive effect in phase I, were combined to find even better combinations. Finally in phase III, data from phase I and II were confirmed and the effect of different N-terminal tags was investigated. In all three phases, the proteins were expressed in the same *E coli* system, using the same vector and purification protocol. All variants were expressed, purified and analysed in parallel, using similar protocols and procedure, within each phase. The analysis panel of each phase is summarized in Table 1. Amino acid and DNA sequence of all constructs can be found below.

TABLE 1

Analyses performed in the different phases of the A1M variant project

| | Analysis | phase I | phase II | phase III |
|---|---|---|---|---|
| 1 | SDS-PAGE (identifty, purity) | x | x | x |
| 2 | Absorbance 280 nm (quantity) | x | x | x |
| 3 | Circular Dichroism (identity) | x | | |
| 4 | PAGE (aggregation analysis) | x | x | x |
| 5 | SEC-FPLC (aggregation analysis) | | x | |
| 6 | DLS (aggregation analysis) | x | | x |
| 7 | RP-HPLC (purity, aggregation analysis) | | | x |
| 8 | DSF (thermostability) | x | | x |
| 9 | Shearing stability (DLS analysis) | x | | x |
| 10 | Concentration stability (PAGE analysis) | x | x | x |
| 11 | Concentration stability other buffers (PAGE analysis) | | | x |
| 12 | Stability freeze thaw, prolonged storage in fridge, RT, +37° C. (SEC-FPLC, ABTS reduction)* | | x | |
| 13 | Quantification of free thiol groups | x | | |
| 14 | Reduction capacity of the ABTS radical | x | x | x |
| 15 | Oxygen radical anti-oxidant capacity (ORAC) | | | x |
| 16 | Reduction capacity of cytochrome c | | | x |
| 17 | Reduction/binding capacity of free heme | x | x | x |
| 18 | Binding capacity of heme-agarose | x | x | x |
| 19 | Rescue of K562 cells from heme-induced cell death | | x | x |

*Only performed on human wt and the M8H4DK-R66H + N1796D variant.

```
Amino acid sequence of all constructs:

60. M8H4DK-Human wt (rhA1M)
                                                            (SEQ ID NO: 9)
MHHHHHHHHDDDDKGPVPTPPDNIQVQENFNISRIYGKWYNLAIGSTCPWLKKIM-DRMTVSTLVLGEGATEAEISMT
STRWRKGVCEETSGAYEKTDTDGKFLYHKSKWNITMESYVVHTNYDEYAIFLTKKFSRHHGPTITAKLYGRAPQLRET
LLQDFRVVAQGVGI-PEDSIFTMADRGECVPGEQEPEPILIPR 1. M8H5GIEGR-Mouse
                                                            (SEQ ID NO: 24)
MHHHHHHHGGGGGIEGRDPASTLPDIQVQENFSESRI-YGKWYNLAVGSTCPWLSRIK-DKMSVQTLVLQEGATETE
ISMTSTRWRRGVCEEITGAYQKTDIDGKFLYHKSKWNITLESYVVHTNYDEYAIFLTKKSSHHHGLTI-TAKLYGREP
QLRDSLLQEFKDVALNVGISENSIIFMPDRGECVPGDREVEPTSIAR 2. M8H5GIEGR-Naked Mole rat
                                                            (SEQ ID NO: 25)
MHHHHHHHHGGGGGIEGRNPVPMPPDNIQVQENFDESRI-YGKWFNLATGSTCPWLKRIK-DRLSVSTMVLGKGTTET
QISTTHTHWRQGVCQETSGVYKKTDTAGKFLYHKSKWNVTMESYVVHTNYDEYAIILTKKFSHHHGPTITAKLYGREP
RLRDSLLQEFREMALGVGI-PEDSIFTMANRGECVPGDQAPESTPAPR 3. M8H5GIEGR-Frog
                                                            (SEQ ID NO: 26)
MHHHHHHHHGGGGGIEGRCSPIQPEDNIQIQENFDLQRIYGKWYDIAIGSTCK-WLKHH-KEKFNMGTLELSDGETDG
EVRIVNTRMRHGTCSQIVGSYQKTETPGKFDYFNARWGTTIQNYIVFTNYNEYVIMQMRKKKGSETTTTVKLYGRSPD
LRPTLVDEFRQFALAQGI-PEDSIVMLPNNGECSPGEIEVRPRR 4. M8H5GIEGR-Chicken
                                                            (SEQ ID NO: 27)
MHHHHHHHGGGGGIEGRTPVGDQDEDIQVQENFEPERMYGKWYDVAVGTTCK-WMKNYKEKFSMGTLVLGPGPSADQ
ISTISTRLRQGDCKRVSGEYQKTDTPGKYTYYNPKWDVSIKSYVLRTNYEEYAVILMKKTSNFGPTTTLKLYGRSPEL
REEL-TEAFQQLALEMGIPADSVFILANKGECVPQETATAPER
```

-continued

5. M8H5GIEGR-Rabbit (SEQ ID NO: 28)

MHHHHHHHHGGGGIEGRDPVPTLPDDIQVQENFELSRI-YGKWYNLAVGSTCPWLKRIK-DRMAVSTLVLGEGTSET
EISMTSTHWRRGVCEEISGAYEKTDTDGKFLYHKAKWNLTMESYVVHTNYDEYAIFLTKKFSRRHGPTITAKLYGREP
QLRESLLQE-FREVALGVGIPENSIFTMIDRGECVPGQQEPKPAPVLR

6. M8H5GIEGR-SQ Monkey (SEQ ID NO: 29)

MHHHHHHHHGGGGIEGRSPVPTPPEGIQVQENFNLSRIYGKWYNLAIGSTCPWLK-KIMDRL-KVSTLVLEEGATEA
EISMTSTRWRKGFCEQTSWAYEKTDTDGKFLYHEPKWNVTMESYVAHTNYEEYAIFLTKKFSRHHGPTITAKLYGREP
QLRESLLQDFRVVAQGVGI-PEDSIFTMANRGECVPGEQEPQPILHRR

7. M8H5GIEGR-Walrus (SEQ ID NO: 30)

MHHHHHHHHGGGGIEGRSPVLTPPDAIQVQENFDISRIYGKWFH-VAMGSTCPWLKKFMDRMSMSTLVLGEGATDGE
ISMTSTRWRRGTCEEISGAYEKTSTNGKFLYHNPKWNITMESYVVHTDYDEYAIFLTKKFSRHHGPTI-TAKLYGRQP
QLRESLLEEFRELALGVGIPEDSIFTMANKGECVPGEQEPEPSPHMR

8. M8H5GIEGR-Manatee (SEQ ID NO: 31)

MHHHHHHHHGGGGIEGRSPVKTPLNDIQVQENFDLPRIYGKWFNIAIG-STCQWLKRLKAG-PTMSTLVLGEGATDT
EISTTSTRWRKGFCEEISGAYEKTDTAGKFLYHGSKWNVTLESYVVHTNYDEYAIFLIKKFSRYGLTITAKLYGRQPQ
VRESLLEEFREFALGVGI-PEDSIFTTADKGECVPGEQEPEPTAALR

9. M8H5GIEGR-Plaice (SEQ ID NO: 32)

MHHHHHHHHGGGGIEGRLPVLPEP-LYPTQENFDLTRFVGTWHDVALTSSCPHMQRN-RADAAIGKLVLEKDTGNKL
KVTRTRLRHGTCVEMSGEYELTSTPGRIFYHIDRWDADVDAYVVHTNYDEYAIIIMSKQKTSGENSTSLKLYSRTMSV
RDTVLDDFKTLVRHQGMSDDTIIIKQNKGDCIPGEQVEEAPSQPEPKR

10. M8H5GIEGR-Orangutan (SEQ ID NO: 33)

MHHHHHHHHGGGGIEGRGPVPTPPDNIQVQENFNISRIYGKWYNLAIGSTCPWLK-KIM-DRMTVSTLVLGEGATEA
EISMTSTRWRKGVCEETSGAYEKTDTDGKFLYHKSKWNITMESYVVHTNYDEYAIFLTKKFSRRHGPTITAKLYGRAP
QLRETLLQDFRVVAQGVGI-PEDSIFTMADRGECVPGEQEPEPILIPR

11. M8H5GIEGR-Human P35K (SEQ ID NO: 34)

MHHHHHHHHGGGGIEGRGPVPTPPDNIQVQENFNISRIYGKWYNLAIGSTCKWLK-KIM-DRMTVSTLVLGEGATEA
EISMTSTRWRKGVCEETSGAYEKTDTDGKFLYHKSKWNITMESYVVHTNYDEYAIFLTKKFSRHHGPTITAKLYGRAP
QLRETLLQDFRVVAQGVGI-PEDSIFTMADRGECVPGEQEPEPILIPR

12. M8H5GIEGR-Human M41K (SEQ ID NO: 35)

MHHHHHHHHGGGGIEGRGPVPTPPDNIQVQENFNISRIYGKWYNLAIGSTCPWLK-KIK-DRMTVSTLVLGEGATEA
EISMTSTRWRKGVCEETSGAYEKTDTDGKFLYHKSKWNITMESYVVHTNYDEYAIFLTKKFSRHHGPTITAKLYGRAP
QLRETLLQDFRVVAQGVGI-PEDSIFTMADRGECVPGEQEPEPILIPR

13. M8H5GIEGR-Human R66H (SEQ ID NO: 36)

MHHHHHHHHGGGGIEGRGPVPTPPDNIQVQENFNISRIYGKWYNLAIGSTCPWLK-KIM-DRMTVSTLVLGEGATEA
EISMTSTHWRKGVCEETSGAYEKTDTDGKFLYHKSKWNITMESYVVHTNYDEYAIFLTKKFSRHHGPTITAKLYGRAP
QLRETLLQDFRVVAQGVGI-PEDSIFTMADRGECVPGEQEPEPILIPR

14. M8H5GIEGR-Human T75K (SEQ ID NO: 37)

MHHHHHHHHGGGGIEGRGPVPTPPDNIQVQENFNISRIYGKWYNLAIGSTCPWLK-KIM-DRMTVSTLVLGEGATEA
EISMTSTRWRKGVCEEKSGAYEKTDTDGKFLYHKSKWNITMESYVVHTNYDEYAIFLTKKFSRHHGPTITAKLYGRAP
QLRETLLQDFRVVAQGVGI-PEDSIFTMADRGECVPGEQEPEPILIPR

15. M8H5GIEGR-Human T75Y (SEQ ID NO: 38)

MHHHHHHHHGGGGIEGRGPVPTPPDNIQVQENFNISRIYGKWYNLAIGSTCPWLK-KIM-DRMTVSTLVLGEGATEA
EISMTSTRWRKGVCEEYSGAYEKTDTDGKFLYHKSKWNITMESYVVHTNYDEYAIFLTKKFSRHHGPTITAKLYGRAP
QLRETLLQDFRVVAQGVGI-PEDSIFTMADRGECVPGEQEPEPILIPR

16. M8H5GIEGR-Human M99K (SEQ ID NO: 39)

MHHHHHHHHGGGGIEGRGPVPTPPDNIQVQENFNISRIYGKWYNLAIGSTCPWLK-KIM-DRMTVSTLVLGEGATEA
EISMTSTRWRKGVCEETSGAYEKTDTDGKFLYHKSKWNITKESYVVHTNYDEYAIFLTKKFSRHHGPTITAKLYGRAP
QLRETLLQDFRVVAQGVGI-PEDSIFTMADRGECVPGEQEPEPILIPR

17. M8H5GIEGR-Human S101Y (SEQ ID NO: 40)

MHHHHHHHHGGGGIEGRGPVPTPPDNIQVQENFNISRIYGKWYNLAIGSTCPWLK-KIM-DRMTVSTLVLGEGATEA
EISMTSTRWRKGVCEETSGAYEKTDTDGKFLYHKSKWNITMEYYVVHTNYDEYAIFLTKKFSRHHGPTITAKLYGRAP
QLRETLLQDFRVVAQGVGI-PEDSIFTMADRGECVPGEQEPEPILIPR

18. M8H5GIEGR-Human K69.92.118.130R (SEQ ID NO: 41)

MHHHHHHHHGGGGIEGRGPVPTPPDNIQVQENFNISRIYGKWYNLAIGSTCPWLK-KIM-DRMTVSTLVLGEGATEA
EISMTSTRWRRGVCEETSGAYEKTDTDGKFLYHRSKWNITMESYVVHTNYDEYAIFLTKRFSRHHGPTITARLYGRAP
QLRETLLQDFRVVAQGVGI-PEDSIFTMADRGECVPGEQEPEPILIPR

19. M8H5GIEGR-Coelacanth (SEQ ID NO: 42)

MHHHHHHHHGGGGIEGRGSPLRDEDIQVQENFDLPRIYGKWYEIAI-ASTCPWVKNHKDKFMGTMVLQEGEQSDRI
STTSTRIRDGTCSQITGYYTLTTTPGKFAYHNSKWNLDVNSYVVHTNYDEYSIVMMQKYKSS-NSTTTVRLYGRTQEL
RDSLHAEFKKFALDQGIDEDSIYILPKRDECVPGEPKAESLMAR

21. M8H5GIEGR-Human L89T (SEQ ID NO: 43)

MHHHHHHHHGGGGIEGRGPVPTPPDNIQVQENFNISRIYGKWYNLAIGSTCPWLK-KIM-DRMTVSTLVLGEGATEA
EISMTSTRWRKGVCEETSGAYEKTDTDGKFTYHKSKWNITMESYVVHTNYDEYAIFLTKKFSRHHGPTITAKLYGRAP
QLRETLLQDFRVVAQGVGI-PEDSIFTMADRGECVPGEQEPEPILIPR

22. M8H5GIEGR-Human N1796D (SEQ ID NO: 44)

MHHHHHHHHGGGGIEGRGPVPTPPDNIQVQENFDISRIYGKWYNLAIGSTCPWLK-KIM-DRMTVSTLVLGEGATEA
EISMTSTRWRKGVCEETSGAYEKTDTDGKFLYHKSKWDITMESYVVHTNYDEYAIFLTKKFSRHHGPTITAKLYGRAP
QLRETLLQDFRVVAQGVGI-PEDSIFTMADRGECVPGEQEPEPILIPR

23. M8H5GIEGR-Human T45K (SEQ ID NO: 45)

MHHHHHHHHGGGGIEGRGPVPTPPDNIQVQENFNISRIYGKWYNLAIGSTCPWLK-KIM-DRMKVSTLVLGEGATEA
EISMTSTRWRKGVCEETSGAYEKTDTDGKFLYHKSKWNITMESYVVHTNYDEYAIFLTKKFSRHHGPTITAKLYGRAP
QLRETLLQDFRVVAQGVGI-PEDSIFTMADRGECVPGEQEPEPILIPR

24. M8H5GIEGR-Human A135E (SEQ ID NO: 46)

MHHHHHHHHGGGGIEGRGPVPTPPDNIQVQENFNISRIYGKWYNLAIGSTCPWLK-KIM-DRMTVSTLVLGEGATEA
EISMTSTRWRKGVCEETSGAYEKTDTDGKFLYHKSKWNITMESYVVHTNYDEYAIFLTKKFSRHHGPTITAKLYGREP
QLRETLLQDFRVVAQGVGI-PEDSIFTMADRGECVPGEQEPEPILIPR

25. M8H5GIEGR-Human V170S (SEQ ID NO: 47)

MHHHHHHHHGGGGIEGRGPVPTPPDNIQVQENFNISRIYGKWYNLAIGSTCPWLK-KIM-DRMTVSTLVLGEGATEA
EISMTSTRWRKGVCEETSGAYEKTDTDGKFLYHKSKWNITMESYVVHTNYDEYAIFLTKKFSRHHGPTITAKLYGRAP
QLRETLLQDFRVVAQGVGI-PEDSIFTMADRGECSPGEQEPEPILIPR

26. M8H5GIEGR-Human V148D (SEQ ID NO: 48)

MHHHHHHHHGGGGIEGRGPVPTPPDNIQVQENFNISRIYGKWYNLAIGSTCPWLK-KIM-DRMTVSTLVLGEGATEA
EISMTSTRWRKGVCEETSGAYEKTDTDGKFLYHKSKWNITMESYVVHTNYDEYAIFLTKKFSRHHGPTITAKLYGRAP
QLRETLLQDFRDVAQGVGI-PEDSIFTMADRGECVPGEQEPEPILIPR

27. M8H5GIEGR-Human G172Q (SEQ ID NO: 49)

MHHHHHHHHGGGGIEGRGPVPTPPDNIQVQENFNISRIYGKWYNLAIGSTCPWLK-KIM-DRMTVSTLVLGEGATEA
EISMTSTRWRKGVCEETSGAYEKTDTDGKFLYHKSKWNITMESYVVHTNYDEYAIFLTKKFSRHHGPTITAKLYGRAP
QLRETLLQDFRVVAQGVGI-PEDSIFTMADRGECVPQEQEPEPILIPR

33. M8H4DK-Human M41K + R66H (SEQ ID NO: 50)

MHHHHHHHHDDDDKGPVPTPPDNIQVQENFNISRIYGKWYNLAIGSTCPWLKKIK-DRMTVSTLVLGEGATEAEISMT
STHWRKGVCEETSGAYEKTDTDGKFLYHKSKWNITMESYVVHTNYDEYAIFLTKKFSRHHGPTITAKLYGRAPQLRET
LLQDFRVVAQGVGI-PEDSIFTMADRGECVPGEQEPEPILIPR

34. M8H4DK-Human M41K + N1796D (SEQ ID NO: 51)

MHHHHHHHHDDDDKGPVPTPPDNIQVQENFDISRIYGKWYNLAIGSTCPWLKKIK-DRMTVSTLVLGEGATEAEISMT
STRWRKGVCEETSGAYEKTDTDGKFLYHKSKWDITMESYVVHTNYDEYAIFLTKKFSRHHGPTITAKLYGRAPQLRET
LLQDFRVVAQGVGI-PEDSIFTMADRGECVPGEQEPEPILIPR

35. M8H4DK-Human R66H + N1796D (SEQ ID NO: 52)

MHHHHHHHHDDDDKGPVPTPPDNIQVQENFDISRIYGKWYNLAIGSTCPWLKKIM-DRMTVSTLVLGEGATEAEISMT
STHWRKGVCEETSGAYEKTDTDGKFLYHKSKWDITMESYVVHTNYDEYAIFLTKKFSRHHGPTITAKLYGRAPQLRET
LLQDFRVVAQGVGI-PEDSIFTMADRGECVPGEQEPEPILIPR

36. M8H4DK-Human M41K + R66H + N1796D (SEQ ID NO: 53)

MHHHHHHHHDDDDKGPVPTPPDNIQVQENFDISRIYGKWYNLAIGSTCPWLKKIK-DRMTVSTLVLGEGATEAEISMT
STHWRKGVCEETSGAYEKTDTDGKFLYHKSKWDITMESYVVHTNYDEYAIFLTKKFSRHHGPTITAKLYGRAPQLRET
LLQDFRVVAQGVGI-PEDSIFTMADRGECVPGEQEPEPILIPR

37. M8H4DK-Human M41K
(SEQ ID NO: 8)
MHHHHHHHHDDDDKGPVPTPPDNIQVQENFNISRIYGKWYNLAIGSTCPWLKKIK-DRMTVSTLVLGEGATEAEISMT
STRWRKGVCEETSGAYEKTDTDGKFLYHKSKWNITMESYVVHTNYDEYAIFLTKKFSRHHGPTITAKLYGRAPQLRET
LLQDFRVVAQGVGI-PEDSIFTMADRGECVPGEQEPEPILIPR 38. M8H4DK-Human R66H
(SEQ ID NO: 54)
MHHHHHHHHDDDDKGPVPTPPDNIQVQENFNISRIYGKWYNLAIGSTCPWLKKIM-DRMTVSTLVLGEGATEAEISMT
STHWRKGVCEETSGAYEKTDTDGKFLYHKSKWNITMESYVVHTNYDEYAIFLTKKFSRHHGPTITAKLYGRAPQLRET
LLQDFRVVAQGVGI-PEDSIFTMADRGECVPGEQEPEPILIPR 39. M8H4DK-Human N1796D
(SEQ ID NO: 55)
MHHHHHHHHDDDDKGPVPTPPDNIQVQENFDISRIYGKWYNLAIGSTCPWLKKIM-DRMTVSTLVLGEGATEAEISMT
STRWRKGVCEETSGAYEKTDTDGKFLYHKSKWDITMESYVVHTNYDEYAIFLTKKFSRHHGPTITAKLYGRAPQLRET
LLQDFRVVAQGVGI-PEDSIFTMADRGECVPGEQEPEPILIPR 40. M8H-Human wt
(SEQ ID NO: 56)
MHHHHHHHHGPVPTPPDNIQVQENFNISRIYGKWYNLAIGSTCPWLKKIM-DRMTVSTLVLGEGATEAEISMTSTRWR
KGVCEETSGAYEKTDTDGKFLYHKSKWNITMESYVVHTNYDEYAIFLTKKFSRHHGPTITAKLYGRAPQLRETLLQDF
RVVAQGVGI-PEDSIFTMADRGECVPGEQEPEPILIPR 41. M8H-Human R66H + N1796D
(SEQ ID NO: 57)
MHHHHHHHHGPVPTPPDNIQVQENFDISRIYGKWYNLAIGSTCPWLKKIM-DRMTVSTLVLGEGATEAEISMTSTHWR
KGVCEETSGAYEKTDTDGKFLYHKSKWDITMESYVVHTNYDEYAIFLTKKFSRHHGPTITAKLYGRAPQLRETLLQDF
RVVAQGVGI-PEDSIFTMADRGECVPGEQEPEPILIPR 42. untagged-Human R66H + N1796D
(SEQ ID NO: 3)
MGPVPTPPDNIQVQENFDISRIYGKWYNLAIGSTCPWLKKIMDRMTVSTLVLGEGA-TEAEISMTSTHWRKGVCEETS
GAYEKTDTDGKFLYHKSKWDITMESYVVHTNYDEYAIFLTKKFSRHHGPTITAKLYGRAPQLRETLLQDFRVVAQGVG
IPEDSIFT-MADRGECVPGEQEPEPILIPR 61 untagged-Human wt
(SEQ ID NO: 2)
MGPVPTPPDNIQVQENFNISRIYGKWYNLAIGSTCPWLKKIMDRMTVSTLVLGEGA-TEAEISMTSTRWRKGVCEETS
GAYEKTDTDGKFLYHKSKWNITMESYVVHTNYDEYAIFLTKKFSRHHGPTITAKLYGRAPQLRETLLQDFRVVAQGVG
IPEDSIFT-MADRGECVPGEQEPEPILIPR DNA sequence of all constructs:

60. M8H4DK-Human wt
(SEQ ID NO: 58)
ATGCATCACCATCACCATCACCATCACGATGACGATGACAAGGGCCCTGTGCCAACGCCGCCCGACAACATCCAAGTG
CAGGAAAACTTCAATATCTCTCGGATCTATGGGAAGTGGTACAACCTGGCCATCGGTTCCACCTGCCCCTGGCTGAAG
AAGATCATGGACAGGATGACAGTGAGCACGCTGGTGCTGGGAGAGGGCGCTACAGAGGCGGAGATCAGCATGACCAGC
ACTCGTTGGCGGAAAGGTGTCTGTGAGGAGACGTCTGGAGCTTATGAGAAAACAGATACTGATGGGAAGTTTCTCTAT
CACAAATCCAAATGGAACATAACCATGGAGTCCTATGTGGTCCACACCAACTATGACGAGTATGCGCATTTTCCTGACC
AAGAAATTCAGCCGCCATCATGGACCCACCATTACTGCCAAGCTCTACGGGCGGGCGCCGCAGCTGAGGGAAACTCTC
CTGCAGGACTTCAGAGTGGTTGCCCAGGGTGTGGGCATCCCTGAGGACTCCATCTTCACCATGGCTGACCGAGGTGAA
TGTGTCCCTGGGGAGCAGGAACCAGAGCCCATCTTAATCCCGAGATGA 1. M8H5GIEGR-Mouse
(SEQ ID NO: 59)
ATGCATCACCATCACCATCACCATCACGGTGGAGGAGGGGGTATCGAGGGCCGCGACCCTGCGTCAACACTGCCAGAT
ATCCAGGTTCAGGAGAACTTCAGTGAGTCCCGGATCTATGGAAAATGGTACAACCTGGCGGTGGGATCCACCTGCCCG
TGGCTGAGCCGCATTAAGGACAAGATGAGCGTGAGCACGCTGGTGCTGCAGGAGGGGCGACAGAAACAGAGATCAGC
ATGACCAGTACTCGATGGCGGAGAGGTGTCTGTGAGGAGATCACTGGGGCGTACCAGAAGACGGACATCGATGGAAAG
TTCCTCTACCACAAATCCAAATGGAACATAACCTTGGAATCCTATGTGGTCCACACCAACTATGACGAATATGCCATT
TTCCTTACCAAGAAGTCCAGCCACCACCACGGGCTCACCATCACTGCCAAGCTCTATGGTCGGGAGCCACAGCTGAGG
GACAGCCTTCTGCAGGAGTTCAAGGATGTGGCCCTGAATGTGGGCATCTCTGAGAACTCCATCATTTTTATGCCTGAC
AGAGGGGAATGTGTCCCTGGGGATCGGGAGGTGGAGCCCACATCAATTGCCAGATGA 2. M8H5GIEGR-Naked Mole rat
(SEQ ID NO: 60)
ATGCATCACCATCACCATCACCATCACGGTGGAGGAGGGGGTATCGAGGGCCGCAATCCTGTGCCGATGCCGCCAGAC
AACATCCAAGTGCAGGAGAACTTTGATGAATCCCGGATCTATGGGAAATGGTTCAACCTGGCTACGGGCTCCACGTGC
CCGTGGCTGAAGAGGATCAAAGACAGGCTGAGTGTGAGCACAATGGTGCTGGGCAAGGGGACCACGGAGACAGATC
AGCACAACCCACACCCACTGGCGGCAAGGGGTGTGCCAGGAGACCTCAGGGGTTTACAAGAAACAGACACGGCTGGG
AAGTTCCTCTACCACAAGTCCAAATGGAATGTAACCATGGAGTCCTATGTGGTCCACACCAACTATGATGAGTATGCC
ATCATTCTAACTAAGAAGTTCAGCCACCACCATGGACCGACCATTACTGCCAAGCTCTATGGGAGAGCCGCGGCTG
AGAGACAGCCTCCTGCAGGAATTCAGGGAGATGGCCCTGGGCGTAGGCATCCCCGAGGATTCCATCTTCACAATGGCC
AACAGAGGGGAATGTGTCCCTGGTGACCAGGCACCAGAGTCCACCCCAGCCCCGAGGTGA -continued 3. M8H5GIEGR-Frog
(SEQ ID NO: 61)
ATGCATCACCATCACCATCACCATCACGGTGGAGGAGGGGGTATCGAGGGCCGCTGCAGCCCAATCCAGCCAGAGGAC
AATATCCAGATCCAGGAGAACTTTGATCTCCAGAGGATTTATGGCAAATGGTACGACATTGCCATCGGCTCCACCTGC
AAATGGCTGAAGCACCACAAGGAAAAGTTCAACATGGGGACACTGGAGCTTAGCGATGGGGAGACCGACGGGGAGGTG
CGGATTGTGAACACAAGGATGAGGCACGGAACCTGCTCTCAGATTGTTGGGTCCTATCAGAAGACAGAGACCCCAGGG
AAGTTCGACTATTTCAACGCACGGTGGGGAACCACGATCCAAAACTACATTGTCTTCACTAACTACAATGAGTATGTC
ATCATGCAGATGAGGAAGAAGAAGGGATCGGAGACCACCACGACCGTCAAGCTGTATGGGCGGAGCCCAGACTTGCGT
CCGACCCTCGTTGATGAATTCAGGCAGTTTGCCTTGGCTCAGGGCATTCCTGAAGACTCCATCGTGATGCTACCTAAC
AATGGTGAGTGCTCTCCAGGGGAAATAGAAGTGAGACCACGGAGATGA 4. M8H5GIEGR-Chicken
(SEQ ID NO: 62)
ATGCATCACCATCACCATCACCATCACGGTGGAGGAGGGGGTATCGAGGGCCGCACGCCTGTTGGGGACCAGGATGAG
GACATTCAAGTGCAAGAGAATTTTGAGCCTGAGCGGATGTATGGGAAATGGTATGACGTAGCTGTTGGCACCACCTGC
AAGTGGATGAAGAACTACAAGGAGAAGTTCAGCATGGGCACACTGGTGCTGGGCCCCGGCCCCAGCGCTGACCAGATC
AGTACCATCAGCACCAGGCTGCGCAAGGTGACTGCAAACGTGTCTCAGGAGAGTACCAGAAAACTGACACCCCTGGC
AAATACACCTACTATAACCCCAAGTGGGATGTGTCTATCAAGTCCTACGTGCTTCGCACCAACTATGAAGAATACGCA
GTCATTCTGATGAAGAAGACAAGTAATTTTGGCCCAACCACCACACTGAAGCTGTATGGGAGAAGCCCAGAGCTGCGG
GAAGAGCTCACCGAGGCTTTCCAGCAGCTGGCTCTGGAGATGGGCATCCCTGCAGATTCCGTCTTCATCCTGGCCAAC
AAAGGTGAATGTGTCCCACAGGAGACTGCCACTGCCCCTGAGAGGTGA 5. M8H5GIEGR-Rabbit
(SEQ ID NO: 63)
ATGCATCACCATCACCATCACCATCACGGTGGAGGAGGGGGTATCGAGGGCCGCGACCCCGTGCCCACCCTGCCGGAC
GACATCCAAGTGCAGGAGAACTTCGAGCTCTCTCGGATCTACGGGAAATGGTACAACCTGGCTGTGGGGTCCACCTGC
CCGTGGCTGAAGAGGATCAAGGACAGGATGGCCGTGAGCACGCTGGTGCTGGGAGAGGGGACGAGCGAGACGGAGATC
AGCATGACCAGCACGCACTGGCGGAGGGGCGTCTGTGAGGAGATCTCCGGGGCCTATGAGAAACGGACACTGACGGG
AAGTTCCTGTACCACAAAGCCAATGGAACTTAACCATGGAGTCCTACGTGGTGCACACCAACTACGATGAGTATGCC
ATTTTTCTCACCAAGAAATTCAGCCGCCGCCACGGCCCCACCATCACCGCCAAGCTCTATGGGCGGGAGCCGCAGCTG
AGGGAGAGCCTCCTGCAGGAGTTCAGGGAGGTGGCTCTCGGGGTGGGGATCCCCGAGAACTCCATCTTCACCATGATC
GACAGAGGGGAATGTGTGCCCGGGCAGCAGGAACCAAAGCCTGCCCCCGTGTTGAGATGA 6. M8H5GIEGR-SQ Monkey
(SEQ ID NO: 64)
ATGCATCACCATCACCATCACCATCACGGTGGAGGAGGGGGTATCGAGGGCCGCAGCCCAGTGCCGACGCCGCCCGAA
GGCATTCAAGTGCAGGAAAACTTCAATCTCTCTCGGATCTACGGCAAGTGGTACAACCTGGCCATCGGTTCCACCTGC
CCCTGGCTAAAGAAGATCATGGACAGGTTGAAAGTGAGCACGCTGGTGCTGGAAGAGGGCGCCACGGAGGCGGAGATC
AGCATGACCAGCACTCGCTGGCGGAAAGGTTTCTGTGAGCAGACCTCTTGGGCTTATGAGAAAACAGATACTGATGGG
AAGTTTCTCTATCACGAACCCAAATGGAACGTAACCATGGAGTCCTATGTGGCCCACACCAACTATGAGGAGTATGCC
ATTTTCCTGACCAAGAAATTCAGCCGCCATCATGGACCCACCATTACTGCCAAGCTCTATGGGCGGGAGCCACAGCTG
AGGGAAAGCCTCCTGCAGGACTTCAGAGTGGTTGCCCAGGGTGTGGGCATCCCTGAGGATTCCATCTTCACCATGGCT
AACCGAGGTGAATGCGTCCCTGGGGAGCAGGAACCACAGCCCATCCTACACCGGAGATGA 7. M8H5GIEGR-Walrus
(SEQ ID NO: 65)
ATGCATCACCATCACCATCACCATCACGGTGGAGGAGGGGGTATCGAGGGCCGCAGTCCCGTGCTGACGCCGCCTGAC
GCCATCCAAGTGCAAGAGAACTTCGACATCTCTCGGATCTACGGGAAGTGGTTTCATGTGGCCATGGGCTCCACCTGC
CCGTGGCTGAAGAAGTTCATGGACAGGATGTCCATGAGCACGCTGGTGCTGGGCGAGGGGGCGACGGATGGGGAGATC
AGCATGACCAGCACACGTTGGCGGAGAGGCCACCTGTGAGGAGATCTCTGGGGCTTATGAGAAAACCAGCACTAACGGA
AAGTTCCTCTATCATAATCCCAAATGGAACATCACCATGGAGTCCTATGTGGTCCACACCGACTATGATGAGTACGCC
ATCTTTCTGACCAAGAAATTCAGCCGCCACCATGGGCCCACCATTACTGCCAAGCTCTATGGGCGACAGCCGCAGCTT
CGAGAAAGCCTGCTGGAGGAGTTCAGGGAGCTTGCCTTGGGTGTGGGCATCCCCGAGGACTCCATCTTCACCATGGCC
AACAAAGGTGAGTGTGTCCCTGGGGAGCAGGAACCAGAGCCCTCTCCACACATGAGGTGA 8. M8H5GIEGR-Manatee
(SEQ ID NO: 66)
ATGCATCACCATCACCATCACCATCACGGTGGAGGAGGGGGTATCGAGGGCCGCAGCCCAGTGAAAACACCACTCAAC
GACATCCAAGTGCAGGAGAACTTTGACCTCCCTCGGATCTACGGGAAATGGTTCAACATAGCCATTGGCTCCACCTGC
CAATGGCTGAAGAGGTTGAAGGCCGGGCCGACCATGAGCACCCTGGTCCTGGGAGAGGGAGCTACAGACACAGAGATC
AGCACAACCAGCACTCGTTGGCGGAAAGGCTTCTGTGAGGAGATCTCTGGGGCATATGAGAAAACAGACACAGCTGGG
AAGTTCCTTTATCACGGATCCAAATGGAATGTAACCTTGGAGTCCTATGTGGTCCACACCAACTATGATGAGTACGCC
ATTTTTCTGACCAAGAAATTCAGCCGCTATGACTCACCATTACTGCTAAGCTCTATGGGCGGCAGCCTCAGGTGAGG
GAGAGCCTCCTGGAGGAGTTCAGGGAATTTGCCCTGGGTGTGGGCATCCCTGAGGATTCCATCTTCACCACGGCCGAC
AAAGGTGAGTGTGTCCCTGGAGAGCAGGAGCCAGAACCCACCGCAGCCCTGAGATGA 9. M8H5GIEGR-Plaice
(SEQ ID NO: 67)
ATGCATCACCATCACCATCACCATCACGGTGGAGGAGGGGGTATCGAGGGCCGCCTCCCTGTGCTCCCTGAACCTCTT
TACCCGACACAGGAGAACTTTGATCTGACCCGGTTTGTGGGGACATGGCACGATGTTGCCTTGACGAGCAGCTGCCCC
CATATGCAGCGTAACAGGGCGGATGCAGCCATTGGTAAACTGGTTCTGGAGAAGACACTGGAAACAAACTCAAGGTG
ACACGAACTAGACTCAGACATGGAACATGTGTGGAGATGTCTGGAGAATATGAGTTAACCAGCACACCAGGACGAATC
TTCTACCATATTGACAGGTGGGATGCAGACGTGGACGCCTACGTGGTTCACACCAACTACGACGAGTACGCAATTATA
ATAATGAGCAAACAGAAACATCGGGGGAGACAGCCACCTCACTCAAGCTGTACAGTCGGACGATGTCTGTGAGAGAC
ACTGTGCTGGATGACTTCAAAACTCTGGTCAGACATCAGGGAATGAGTGACGACACCATTATCATCAAGCAGAACAAA
GGTGACTGTATTCCTGGAGAGCAGGTGGAAGAAGCACCATCTCAGCCAGAGCCCAAGCGGTGA -continued 10. M8H5GIEGR-Orangutan (SEQ ID NO: 68)
ATGCATCACCATCACCATCACCATCACGGTGGAGGAGGGGGTATCGAGGGCCGCGGCCCTGTGCCGACGCCGCCCGAC
AACATCCAAGTGCAGGAAAACTTCAATATCTCTCGGATCTATGGGAAGTGGTACAACCTGGCCATCGGTTCCACCTGC
CCCTGGCTGAAGAAGATCATGGACAGGATGACAGTGAGCACCCTGGTGCTGGGAGAGGGCGCTACAGAGGCGGAGATC
AGCATGACCAGCACTCGTTGGCGGAAAGGTGTCTGTGAGGAGACATCTGGAGCTTATGAGAAAACAGATACTGATGGG
AAGTTTCTCTATCACAAATCCAATGGAACATAACCATGGAGTCCTATGTGGTCCACACCAACTATGATGAGTATGCC
ATTTTCCTGACCAAGAAATTCAGCCGCCGTCATGGACCCACCATTACTGCCAAGCTCTACGGGCGGGCGCCGCAGCTG
AGGGAAACCCTCCTGCAGGACTTCAGAGTGGTTGCCCAGGGTGTGGGCATCCCTGAGGACTCCATCTTCACCATGGCT
GACCGAGGTGAATGTGTCCCTGGGGAACAGGAACCAGAGCCCATCTTAATCCCGAGATGA 11. M8H5GIEGR-Human P35K (SEQ ID NO: 69)
ATGCATCACCATCACCATCACCATCACGGTGGAGGAGGGGGTATCGAGGGCCGCGGCCCTGTGCCAACGCCGCCCGAC
AACATCCAAGTGCAGGAAAACTTCAATATCTCTCGGATCTATGGGAAGTGGTACAACCTGGCCATCGGTTCCACCTGC
AAATGGCTGAAGAAGATCATGGACAGGATGACAGTGAGCACGCTGGTGCTGGGAGAGGGCGCTACAGAGGCGGAGATC
AGCATGACCAGCACTCGTTGGCGGAAAGGTGTCTGTGAGGAGACGTCTGGAGCTTATGAGAAAACAGATACTGATGGG
AAGTTTCTCTATCACAAATCCAATGGAACATAACCATGGAGTCCTATGTGGTCCACACCAACTATGATGAGTATGCC
ATTTTCCTGACCAAGAAATTCAGCCGCCATCATGGACCCACCATTACTGCCAAGCTCTACGGGCGGGCGCCGCAGCTG
AGGGAAACTCTCCTGCAGGACTTCAGAGTGGTTGCCCAGGGTGTGGGCATCCCTGAGGACTCCATCTTCACCATGGCT
GACCGAGGTGAATGTGTCCCTGGGGAGCAGGAACCAGAGCCCATCTTAATCCCGAGATGA 12. M8H5GIEGR-Human M41K (SEQ ID NO: 70)
ATGCATCACCATCACCATCACCATCACGGTGGAGGAGGGGGTATCGAGGGCCGCGGCCCTGTGCCAACGCCGCCCGAC
AACATCCAAGTGCAGGAAAACTTCAATATCTCTCGGATCTATGGGAAGTGGTACAACCTGGCCATCGGTTCCACCTGC
CCCTGGCTGAAGAAGATCAAAGACAGGATGACAGTGAGCACGCTGGTGCTGGGAGAGGGCGCTACAGAGGCGGAGATC
AGCATGACCAGCACTCGTTGGCGGAAAGGTGTCTGTGAGGAGACGTCTGGAGCTTATGAGAAAACAGATACTGATGGG
AAGTTTCTCTATCACAAATCCAATGGAACATAACCATGGAGTCCTATGTGGTCCACACCAACTATGATGAGTATGCC
ATTTTCCTGACCAAGAAATTCAGCCGCCATCATGGACCCACCATTACTGCCAAGCTCTACGGGCGGGCGCCGCAGCTG
AGGGAAACTCTCCTGCAGGACTTCAGAGTGGTTGCCCAGGGTGTGGGCATCCCTGAGGACTCCATCTTCACCATGGCT
GACCGAGGTGAATGTGTCCCTGGGGAGCAGGAACCAGAGCCCATCTTAATCCCGAGATGA 13. M8H5GIEGR-Human R66H (SEQ ID NO: 71)
ATGCATCACCATCACCATCACCATCACGGTGGAGGAGGGGGTATCGAGGGCCGCGGCCCTGTGCCAACGCCGCCCGAC
AACATCCAAGTGCAGGAAAACTTCAATATCTCTCGGATCTATGGGAAGTGGTACAACCTGGCCATCGGTTCCACCTGC
CCCTGGCTGAAGAAGATCATGGACAGGATGACAGTGAGCACGCTGGTGCTGGGAGAGGGCGCTACAGAGGCGGAGATC
AGCATGACCAGCACTCATTGGCGGAAAGGTGTCTGTGAGGAGACGTCTGGAGCTTATGAGAAAACAGATACTGATGGG
AAGTTTCTCTATCACAAATCCAATGGAACATAACCATGGAGTCCTATGTGGTCCACACCAACTATGATGAGTATGCC
ATTTTCCTGACCAAGAAATTCAGCCGCCATCATGGACCCACCATTACTGCCAAGCTCTACGGGCGGGCGCCGCAGCTG
AGGGAAACTCTCCTGCAGGACTTCAGAGTGGTTGCCCAGGGTGTGGGCATCCCTGAGGACTCCATCTTCACCATGGCT
GACCGAGGTGAATGTGTCCCTGGGGAGCAGGAACCAGAGCCCATCTTAATCCCGAGATGA 14. M8H5GIEGR-Human T75K (SEQ ID NO: 72)
ATGCATCACCATCACCATCACCATCACGGTGGAGGAGGGGGTATCGAGGGCCGCGGCCCTGTGCCAACGCCGCCCGAC
AACATCCAAGTGCAGGAAAACTTCAATATCTCTCGGATCTATGGGAAGTGGTACAACCTGGCCATCGGTTCCACCTGC
CCCTGGCTGAAGAAGATCATGGACAGGATGACAGTGAGCACGCTGGTGCTGGGAGAGGGCGCTACAGAGGCGGAGATC
AGCATGACCAGCACTCGTTGGCGGAAAGGTGTCTGTGAGGAGAAATCTGGAGCTTATGAGAAAACAGATACTGATGGG
AAGTTTCTCTATCACAAATCCAATGGAACATAACCATGGAGTCCTATGTGGTCCACACCAACTATGATGAGTATGCC
ATTTTCCTGACCAAGAAATTCAGCCGCCATCATGGACCCACCATTACTGCCAAGCTCTACGGGCGGGCGCCGCAGCTG
AGGGAAACTCTCCTGCAGGACTTCAGAGTGGTTGCCCAGGGTGTGGGCATCCCTGAGGACTCCATCTTCACCATGGCT
GACCGAGGTGAATGTGTCCCTGGGGAGCAGGAACCAGAGCCCATCTTAATCCCGAGATGA 15. M8H5GIEGR-Human T75Y (SEQ ID NO: 73)
ATGCATCACCATCACCATCACCATCACGGTGGAGGAGGGGGTATCGAGGGCCGCGGCCCTGTGCCAACGCCGCCCGAC
AACATCCAAGTGCAGGAAAACTTCAATATCTCTCGGATCTATGGGAAGTGGTACAACCTGGCCATCGGTTCCACCTGC
CCCTGGCTGAAGAAGATCATGGACAGGATGACAGTGAGCACGCTGGTGCTGGGAGAGGGCGCTACAGAGGCGGAGATC
AGCATGACCAGCACTCGTTGGCGGAAAGGTGTCTGTGAGGAGTATTCTGGAGCTTATGAGAAAACAGATACTGATGGG
AAGTTTCTCTATCACAAATCCAATGGAACATAACCATGGAGTCCTATGTGGTCCACACCAACTATGATGAGTATGCC
ATTTTCCTGACCAAGAAATTCAGCCGCCATCATGGACCCACCATTACTGCCAAGCTCTACGGGCGGGCGCCGCAGCTG
AGGGAAACTCTCCTGCAGGACTTCAGAGTGGTTGCCCAGGGTGTGGGCATCCCTGAGGACTCCATCTTCACCATGGCT
GACCGAGGTGAATGTGTCCCTGGGGAGCAGGAACCAGAGCCCATCTTAATCCCGAGATGA 16. M8H5GIEGR-Human M99K (SEQ ID NO: 74)
ATGCATCACCATCACCATCACCATCACGGTGGAGGAGGGGGTATCGAGGGCCGCGGCCCTGTGCCAACGCCGCCCGAC
AACATCCAAGTGCAGGAAAACTTCAATATCTCTCGGATCTATGGGAAGTGGTACAACCTGGCCATCGGTTCCACCTGC
CCCTGGCTGAAGAAGATCATGGACAGGATGACAGTGAGCACGCTGGTGCTGGGAGAGGGCGCTACAGAGGCGGAGATC
AGCATGACCAGCACTCGTTGGCGGAAAGGTGTCTGTGAGGAGACGTCTGGAGCTTATGAGAAAACAGATACTGATGGG
AAGTTTCTCTATCACAAATCCAATGGAACATAACCAAAGAGTCCTATGTGGTCCACACCAACTATGATGAGTATGCC
ATTTTCCTGACCAAGAAATTCAGCCGCCATCATGGACCCACCATTACTGCCAAGCTCTACGGGCGGGCGCCGCAGCTG
AGGGAAACTCTCCTGCAGGACTTCAGAGTGGTTGCCCAGGGTGTGGGCATCCCTGAGGACTCCATCTTCACCATGGCT
GACCGAGGTGAATGTGTCCCTGGGGAGCAGGAACCAGAGCCCATCTTAATCCCGAGATGA 17. M8H5GIEGR-Human S101Y (SEQ ID NO: 75)

ATGCATCACCATCACCATCACCATCACGGTGGAGGAGGGGGTATCGAGGGCCGCGGCCCTGTGCCAACGCCGCCCGAC
AACATCCAAGTGCAGGAAAACTTCAATATCTCTCGGATCTATGGGAAGTGGTACAACCTGGCCATCGGTTCCACCTGC
CCCTGGCTGAAGAAGATCATGGACAGGATGACAGTGAGCACGCTGGTGCTGGGAGAGGGCGCTACAGAGGCGGAGATC
AGCATGACCAGCACTCGTTGGCGGAAAGGTGTCTGTGAGGAGACGTCTGGAGCTTATGAGAAAACAGATACTGATGGG
AAGTTTCTCTATCACAAATCCAATGGAACATAACCATGGAGTATTATGTGGTCCACACCAACTATGATGAGTATGCC
ATTTTCCTGACCAAGAAATTCAGCCGCCATCATGGACCCACCATTACTGCCAAGCTCTACGGGCGGGCGCCGCAGCTG
AGGGAAACTCTCCTGCAGGACTTCAGAGTGGTTGCCCAGGGTGTGGGCATCCCTGAGGACTCCATCTTCACCATGGCT
GACCGAGGTGAATGTGTCCCTGGGGAGCAGGAACCAGAGCCCATCTTAATCCCGAGATGA

18. M8H5GIEGR-Human K69.92.118.130R (SEQ ID NO: 76)

ATGCATCACCATCACCATCACCATCACGGTGGAGGAGGGGGTATCGAGGGCCGCGGCCCTGTGCCAACGCCGCCCGAC
AACATCCAAGTGCAGGAAAACTTCAATATCTCTCGGATCTATGGGAAGTGGTACAACCTGGCCATCGGTTCCACCTGC
CCCTGGCTGAAGAAGATCATGGACAGGATGACAGTGAGCACGCTGGTGCTGGGAGAGGGCGCTACAGAGGCGGAGATC
AGCATGACCAGCACTCGTTGGCGGCGTGGTGTCTGTGAGGAGACGTCTGGAGCTTATGAGAAAACAGATACTGATGGG
AAGTTTCTCTATCACCGTTCCAATGGAACATAACCATGGAGTCCTATGTGGTCCACACCAACTATGATGAGTATGCC
ATTTTCCTGACCAAGCGTTTCAGCCGCCATCATGGACCCACCATTACTGCCCGTCTCTACGGGCGGGCGCCGCAGCTG
AGGGAAACTCTCCTGCAGGACTTCAGAGTGGTTGCCCAGGGTGTGGGCATCCCTGAGGACTCCATCTTCACCATGGCT
GACCGAGGTGAATGTGTCCCTGGGGAGCAGGAACCAGAGCCCATCTTAATCCCGAGATGA

19. M8H5GIEGR-Coelacanth (SEQ ID NO: 77)

ATGCATCACCATCACCATCACCATCACGGTGGAGGAGGGGGTATCGAGGGCCGCGGAAGTCCCCTTCGAGATGAAGAC
ATCCAAGTGCAGGAGAACTTTGACCTTCCCAGGATTTATGGAAAATGGTACGAAATTGCAATCGCTTCGACCTGTCCC
TGGGTGAAGAATCACAAGGATAAGATGTTCATGGGAACTATGGTGCTACAAGAGGGAGAGCAGAGTGACCGGATCAGT
ACCACCTCCACCCGAATCAGGGATGGAACCTGCTCACAGATCACTGGATATTACACGTTAACCACAACACCTGGGAAG
TTCGCTTATCACAATTCTAAATGGAACTTGGATGTCAACAGTTATGTTGTTCACACTAACTATGACGAATACTCGATT
GTGATGATGCAGAAATACAAAAGCTCTAACTCTACCACTACAGTCCGACTCTATGGAAACTCAAGAGCTACGAGAC
AGCTTGCATGCCGAGTTCAAAAAGTTTGCTCTGGATCAGGGAATAGATGAGGACTCCATTTACATTCTGCCAAAAAGA
GATGAATGTGTACCTGGTGAACCTAAAGCAGAATCTCTCATGGCACGTTGA

21. M8H5GIEGR-Human L89T (SEQ ID NO: 78)

ATGCATCACCATCACCATCACCATCACGGTGGAGGAGGGGGTATCGAGGGCCGCGGCCCTGTGCCAACGCCGCCCGAC
AACATCCAAGTGCAGGAAAACTTCAATATCTCTCGGATCTATGGGAAGTGGTACAACCTGGCCATCGGTTCCACCTGC
CCCTGGCTGAAGAAGATCATGGACAGGATGACAGTGAGCACGCTGGTGCTGGGAGAGGGCGCTACAGAGGCGGAGATC
AGCATGACCAGCACTCGTTGGCGGAAAGGTGTCTGTGAGGAGACGTCTGGAGCTTATGAGAAAACAGATACTGATGGG
AAGTTTACCTATCACAAATCCAATGGAACATAACCATGGAGTCCTATGTGGTCCACACCAACTATGATGAGTATGCC
ATTTTCCTGACCAAGAAATTCAGCCGCCATCATGGACCCACCATTACTGCCAAGCTCTACGGGCGGGCGCCGCAGCTG
AGGGAAACTCTCCTGCAGGACTTCAGAGTGGTTGCCCAGGGTGTGGGCATCCCTGAGGACTCCATCTTCACCATGGCT
GACCGAGGTGAATGTGTCCCTGGGGAGCAGGAACCAGAGCCCATCTTAATCCCGAGATGA

22. M8H5GIEGR-Human N1796D (SEQ ID NO: 79)

ATGCATCACCATCACCATCACCATCACGGTGGAGGAGGGGGTATCGAGGGCCGCGGCCCTGTGCCAACGCCGCCCGAC
AACATCCAAGTGCAGGAAAACTTCAATATCTCTCGGATCTATGGGAAGTGGTACAACCTGGCCATCGGTTCCACCTGC
CCCTGGCTGAAGAAGATCATGGACAGGATGACAGTGAGCACGCTGGTGCTGGGAGAGGGCGCTACAGAGGCGGAGATC
AGCATGACCAGCACTCGTTGGCGGAAAGGTGTCTGTGAGGAGACGTCTGGAGCTTATGAGAAAACAGATACTGATGGG
AAGTTTCTCTATCACAAATCCAATGGGATATAACCATGGAGTCCTATGTGGTCCACACCAACTATGATGAGTATGCC
ATTTTCCTGACCAAGAAATTCAGCCGCCATCATGGACCCACCATTACTGCCAAGCTCTACGGGCGGGCGCCGCAGCTG
AGGGAAACTCTCCTGCAGGACTTCAGAGTGGTTGCCCAGGGTGTGGGCATCCCTGAGGACTCCATCTTCACCATGGCT
GACCGAGGTGAATGTGTCCCTGGGGAGCAGGAACCAGAGCCCATCTTAATCCCGAGATGA

23. M8H5GIEGR-Human T45K (SEQ ID NO: 80)

ATGCATCACCATCACCATCACCATCACGGTGGAGGAGGGGGTATCGAGGGCCGCGGCCCTGTGCCAACGCCGCCCGAC
AACATCCAAGTGCAGGAAAACTTCAATATCTCTCGGATCTATGGGAAGTGGTACAACCTGGCCATCGGTTCCACCTGC
CCCTGGCTGAAGAAGATCATGGACAGGATGAAAGTGAGCACGCTGGTGCTGGGAGAGGGCGCTACAGAGGCGGAGATC
AGCATGACCAGCACTCGTTGGCGGAAAGGTGTCTGTGAGGAGACGTCTGGAGCTTATGAGAAAACAGATACTGATGGG
AAGTTTCTCTATCACAAATCCAATGGAACATAACCATGGAGTCCTATGTGGTCCACACCAACTATGATGAGTATGCC
ATTTTCCTGACCAAGAAATTCAGCCGCCATCATGGACCCACCATTACTGCCAAGCTCTACGGGCGGGCGCCGCAGCTG
AGGGAAACTCTCCTGCAGGACTTCAGAGTGGTTGCCCAGGGTGTGGGCATCCCTGAGGACTCCATCTTCACCATGGCT
GACCGAGGTGAATGTGTCCCTGGGGAGCAGGAACCAGAGCCCATCTTAATCCCGAGATGA

24. M8H5GIEGR-Human A135E (SEQ ID NO: 81)

ATGCATCACCATCACCATCACCATCACGGTGGAGGAGGGGGTATCGAGGGCCGCGGCCCTGTGCCAACGCCGCCCGAC
AACATCCAAGTGCAGGAAAACTTCAATATCTCTCGGATCTATGGGAAGTGGTACAACCTGGCCATCGGTTCCACCTGC
CCCTGGCTGAAGAAGATCATGGACAGGATGACAGTGAGCACGCTGGTGCTGGGAGAGGGCGCTACAGAGGCGGAGATC
AGCATGACCAGCACTCGTTGGCGGAAAGGTGTCTGTGAGGAGACGTCTGGAGCTTATGAGAAAACAGATACTGATGGG
AAGTTTCTCTATCACAAATCCAATGGAACATAACCATGGAGTCCTATGTGGTCCACACCAACTATGATGAGTATGCC
ATTTTCCTGACCAAGAAATTCAGCCGCCATCATGGACCCACCATTACTGCCAAGCTCTACGGGCGGGAACCGCAGCTG
AGGGAAACTCTCCTGCAGGACTTCAGAGTGGTTGCCCAGGGTGTGGGCATCCCTGAGGACTCCATCTTCACCATGGCT
GACCGAGGTGAATGTGTCCCTGGGGAGCAGGAACCAGAGCCCATCTTAATCCCGAGATGA

-continued

25. M8H5GIEGR-Human V170S (SEQ ID NO: 82)
ATGCATCACCATCACCATCACCATCACGGTGGAGGAGGGGGTATCGAGGGCCGCGGCCCTGTGCCAACGCCGCCCGAC
AACATCCAAGTGCAGGAAAACTTCAATATCTCTCGGATCTATGGGAAGTGGTACAACCTGGCCATCGGTTCCACCTGC
CCCTGGCTGAAGAAGATCATGGACAGGATGACAGTGAGCACGCTGGTGCTGGGAGAGGGCGCTACAGAGGCGGAGATC
AGCATGACCAGCACTCGTTGGCGGAAAGGTGTCTGTGAGGAGACGTCTGGAGCTTATGAGAAAACAGATACTGATGGG
AAGTTTCTCTATCACAAATCCAATGGAACATAACCATGGAGTCCTATGTGGTCCACACCAACTATGATGAGTATGCC
ATTTTCCTGACCAAGAAATTCAGCCGCCATCATGGACCCACCATTACTGCCAAGCTCTACGGGCGGGCGCCGCAGCTG
AGGGAAACTCTCCTGCAGGACTTCAGAGTGGTTGCCCAGGGTGTGGGCATCCCTGAGGACTCCATCTTCACCATGGCT
GACCGAGGTGAATGTTCTCCTGGGGAGCAGGAACCAGAGCCCATCTTAATCCCGAGATGA 26. M8H5GIEGR-Human V148D (SEQ ID NO: 83)
ATGCATCACCATCACCATCACCATCACGGTGGAGGAGGGGGTATCGAGGGCCGCGGCCCTGTGCCAACGCCGCCCGAC
AACATCCAAGTGCAGGAAAACTTCAATATCTCTCGGATCTATGGGAAGTGGTACAACCTGGCCATCGGTTCCACCTGC
CCCTGGCTGAAGAAGATCATGGACAGGATGACAGTGAGCACGCTGGTGCTGGGAGAGGGCGCTACAGAGGCGGAGATC
AGCATGACCAGCACTCGTTGGCGGAAAGGTGTCTGTGAGGAGACGTCTGGAGCTTATGAGAAAACAGATACTGATGGG
AAGTTTCTCTATCACAAATCCAATGGAACATAACCATGGAGTCCTATGGTCCACACCAACTATGATGAGTATGCC
ATTTTCCTGACCAAGAAATTCAGCCGCCATCATGGACCCACCATTACTGCCAAGCTCTACGGGCGGGCGCCGCAGCTG
AGGGAAACTCTCCTGCAGGACTTCAGAGATGTTGCCCAGGGTGTGGGCATCCCTGAGGACTCCATCTTCACCATGGCT
GACCGAGGTGAATGTGTCCCTGGGGAGCAGGAACCAGAGCCCATCTTAATCCCGAGATGA 27. M8H5GIEGR-Human G172Q (SEQ ID NO: 84)
ATGCATCACCATCACCATCACCATCACGGTGGAGGAGGGGGTATCGAGGGCCGCGGCCCTGTGCCAACGCCGCCCGAC
AACATCCAAGTGCAGGAAAACTTCAATATCTCTCGGATCTATGGGAAGTGGTACAACCTGGCCATCGGTTCCACCTGC
CCCTGGCTGAAGAAGATCATGGACAGGATGACAGTGAGCACGCTGGTGCTGGGAGAGGGCGCTACAGAGGCGGAGATC
AGCATGACCAGCACTCGTTGGCGGAAAGGTGTCTGTGAGGAGACGTCTGGAGCTTATGAGAAAACAGATACTGATGGG
AAGTTTCTCTATCACAAATCCAATGGAACATAACCATGGAGTCCTATGTGGTCCACACCAACTATGATGAGTATGCC
ATTTTCCTGACCAAGAAATTCAGCCGCCATCATGACCCACCATTACTGCCAAGCTCTACGGGCGGGCGCCGCAGCTG
AGGGAAACTCTCCTGCAGGACTTCAGAGTGGTTGCCCAGGGTGTGGGCATCCCTGAGGACTCCATCTTCACCATGGCT
GACCGAGGTGAATGTGTCCCTCAGGAGCAGGAACCAGAGCCCATCTTAATCCCGAGATGA 33. M8H4DK-Human M41K + R66H (SEQ ID NO: 85)
ATGCATCACCATCACCATCACCATCACGATGACGATGACAAGGGCCCTGTGCCAACGCCGCCCGACAACATCCAAGTG
CAGGAAAACTTCAATATCTCTCGGATCTATGGGAAGTGGTACAACCTGGCCATCGGTTCCACCTGCCCCTGGCTGAAG
AAGATCAAAGACAGGATGACAGTGAGCACGCTGGTGCTGGGAGAGGGCGCTACAGAGGCGGAGATCAGCATGACCAGC
ACTCATTGGCGGAAAGGTGTCTGTGAGGAGACGTCTGGAGCTTATGAGAAAACAGATACTGATGGGAAGTTTCTCTAT
CACAAATCCAATGGAACATAACCATGGAGTCCTATGTGGTCCACACCAACTATGATGAGTATGCCATTTTCCTGACC
AAGAAATTCAGCCGCCATCATGGACCCACCATTACTGCCAAGCTCTACGGGCGGGCGCCGCAGCTGAGGGAAACTCTC
CTGCAGGACTTCAGAGTGGTTGCCCAGGGTGTGGGCATCCCTGAGGACTCCATCTTCACCATGGCTGACCGAGGTGAA
TGTGTCCCTGGGGAGCAGGAACCAGAGCCCATCTTAATCCCGAGATGA 34. M8H4DK-Human M41K + N1796D (SEQ ID NO: 86)
ATGCATCACCATCACCATCACCATCACGATGACGATGACAAGGGCCCTGTGCCAACGCCGCCCGACAACATCCAAGTG
CAGGAAAACTTCGATATCTCTCGGATCTATGGGAAGTGGTACAACCTGGCCATCGGTTCCACCTGCCCCTGGCTGAAG
AAGATCAAAGACAGGATGACAGTGAGCACGCTGGTGCTGGGAGAGGGCGCTACAGAGGCGGAGATCAGCATGACCAGC
ACTCGTTGGCGGAAAGGTGTCTGTGAGGAGACGTCTGGAGCTTATGAGAAAACAGATACTGATGGGAAGTTTCTCTAT
CACAAATCCAAATGGATATAACCATGGAGTCCTATGTGGTCCACACCAACTATGATGAGTATGCCATTTTCCTGACC
AAGAAATTCAGCCGCCATCATGGACCCACCATTACTGCCAAGCTCTACGGGCGGGCGCCGCAGCTGAGGGAAACTCTC
CTGCAGGACTTCAGAGTGGTTGCCCAGGGTGTGGGCATCCCTGAGGACTCCATCTTCACCATGGCTGACCGAGGTGAA
TGTGTCCCTGGGGAGCAGGAACCAGAGCCCATCTTAATCCCGAGATGA 35. M8H4DK-Human R66H + N1796D (SEQ ID NO: 87)
ATGCATCACCATCACCATCACCATCACGATGACGATGACAAGGGCCCTGTGCCAACGCCGCCCGACAACATCCAAGTG
CAGGAAAACTTCGATATCTCTCGGATCTATGGGAAGTGGTACAACCTGGCCATCGGTTCCACCTGCCCCTGGCTGAAG
AAGATCATGGACAGGATGACAGTGAGCACGCTGGTGCTGGGAGAGGGCGCTACAGAGGCGGAGATCAGCATGACCAGC
ACTCATTGGCGGAAAGGTGTCTGTGAGGAGACGTCTGGAGCTTATGAGAAAACAGATACTGATGGGAAGTTTCTCTAT
CACAAATCCAAATGGATATAACCATGGAGTCCTATGTGGTCCACACCAACTATGATGAGTATGCCATTTTCCTGACC
AAGAAATTCAGCCGCCATCATGGACCCACCATTACTGCCAAGCTCTACGGGCGGGCGCCGCAGCTGAGGGAAACTCTC
CTGCAGGACTTCAGAGTGGTTGCCCAGGGTGTGGGCATCCCTGAGGACTCCATCTTCACCATGGCTGACCGAGGTGAA
TGTGTCCCTGGGGAGCAGGAACCAGAGCCCATCTTAATCCCGAGATGA 36. M8H4DK-Human M41K + R66H + N1796D (SEQ ID NO: 88)
ATGCATCACCATCACCATCACCATCACGATGACGATGACAAGGGCCCTGTGCCAACGCCGCCCGACAACATCCAAGTG
CAGGAAAACTTCGATATCTCTCGGATCTATGGGAAGTGGTACAACCTGGCCATCGGTTCCACCTGCCCCTGGCTGAAG
AAGATCAAAGACAGGATGACAGTGAGCACGCTGGTGCTGGGAGAGGGCGCTACAGAGGCGGAGATCAGCATGACCAGC
ACTCATTGGCGGAAAGGTGTCTGTGAGGAGACGTCTGGAGCTTATGAGAAAACAGATACTGATGGGAAGTTTCTCTAT
CACAAATCCAAATGGATATAACCATGGAGTCCTATGTGGTCCACACCAACTATGATGAGTATGCCATTTTCCTGACC
AAGAAATTCAGCCGCCATCATGGACCCACCATTACTGCCAAGCTCTACGGGCGGGCGCCGCAGCTGAGGGAAACTCTC
CTGCAGGACTTCAGAGTGGTTGCCCAGGGTGTGGGCATCCCTGAGGACTCCATCTTCACCATGGCTGACCGAGGTGAA
TGTGTCCCTGGGGAGCAGGAACCAGAGCCCATCTTAATCCCGAGATGA 37. M8H4DK-Human M41K (SEQ ID NO: 89)

ATGCATCACCATCACCATCACCATCACGATGACGATGACAAGGGCCCTGTGCCAACGCCGCCCGACAACATCCAAGTG
CAGGAAAACTTCAATATCTCTCGGATCTATGGGAAGTGGTACAACCTGGCCATCGGTTCCACCTGCCCCTGGCTGAAG
AAGATCAAAGACAGGATGACAGTGAGCACGCTGGTGCTGGGAGAGGGCGCTACAGAGGCGGAGATCAGCATGACCAGC
ACTCGTTGGCGGAAAGGTGTCTGTGAGGAGACGTCTGGAGCTTATGAGAAAACAGATACTGATGGGAAGTTTCTCTAT
CACAAATCCAAATGGAACATAACCATGGAGTCCTATGTGGTCCACACCAACTATGATGAGTATGCCATTTTCCTGACC
AAGAAATTCAGCCGCCATCATGGACCCACCATTACTGCCAAGCTCTACGGGCGGGCGCCGCAGCTGAGGGAAACTCTC
CTGCAGGACTTCAGAGTGGTTGCCCAGGGTGTGGGCATCCCTGAGGACTCCATCTTCACCATGGCTGACCGAGGTGAA
TGTGTCCCTGGGGAGCAGGAACCAGAGCCCATCTTAATCCCGAGATGA

38. M8H4DK-Human R66H (SEQ ID NO: 90)

ATGCATCACCATCACCATCACCATCACGATGACGATGACAAGGGCCCTGTGCCAACGCCGCCCGACAACATCCAAGTG
CAGGAAAACTTCAATATCTCTCGGATCTATGGGAAGTGGTACAACCTGGCCATCGGTTCCACCTGCCCCTGGCTGAAG
AAGATCATGGACAGGATGACAGTGAGCACGCTGGTGCTGGGAGAGGGCGCTACAGAGGCGGAGATCAGCATGACCAGC
ACTCATTGGCGGAAAGGTGTCTGTGAGGAGACGTCTGGAGCTTATGAGAAAACAGATACTGATGGGAAGTTTCTCTAT
CACAAATCCAAATGGAACATAACCATGGAGTCCTATGTGGTCCACACCAACTATGATGAGTATGCCATTTTCCTGACC
AAGAAATTCAGCCGCCATCATGGACCCACCATTACTGCCAAGCTCTACGGGCGGGCGCCGCAGCTGAGGGAAACTCTC
CTGCAGGACTTCAGAGTGGTTGCCCAGGGTGTGGGCATCCCTGAGGACTCCATCTTCACCATGGCTGACCGAGGTGAA
TGTGTCCCTGGGGAGCAGGAACCAGAGCCCATCTTAATCCCGAGATGA

39. M8H4DK-Human N1796D (SEQ ID NO: 91)

ATGCATCACCATCACCATCACCATCACGATGACGATGACAAGGGCCCTGTGCCAACGCCGCCCGACAACATCCAAGTG
CAGGAAAACTTCGATATCTCTCGGATCTATGGGAAGTGGTACAACCTGGCCATCGGTTCCACCTGCCCCTGGCTGAAG
AAGATCATGGACAGGATGACAGTGAGCACGCTGGTGCTGGGAGAGGGCGCTACAGAGGCGGAGATCAGCATGACCAGC
ACTCGTTGGCGGAAAGGTGTCTGTGAGGAGACGTCTGGAGCTTATGAGAAAACAGATACTGATGGGAAGTTTCTCTAT
CACAAATCCAAATGGGATATAACCATGGAGTCCTATGTGGTCCACACCAACTATGATGAGTATGCCATTTTCCTGACC
AAGAAATTCAGCCGCCATCATGGACCCACCATTACTGCCAAGCTCTACGGGCGGGCGCCGCAGCTGAGGGAAACTCTC
CTGCAGGACTTCAGAGTGGTTGCCCAGGGTGTGGGCATCCCTGAGGACTCCATCTTCACCATGGCTGACCGAGGTGAA
TGTGTCCCTGGGGAGCAGGAACCAGAGCCCATCTTAATCCCGAGATGA

40. M8H-Human wt (SEQ ID NO: 92)

ATGCATCACCATCACCATCACCATCACGGCCCTGTGCCAACGCCGCCCGACAACATCCAAGTGCAGGAAAACTTCAAT
ATCTCTCGGATCTATGGGAAGTGGTACAACCTGGCCATCGGTTCCACCTGCCCCTGGCTGAAGAAGATCATGGACAGG
ATGACAGTGAGCACGCTGGTGCTGGGAGAGGGCGCTACAGAGGCGGAGATCAGCATGACCAGCACTCGTTGGCGGAAA
GGTGTCTGTGAGGAGACGTCTGGAGCTTATGAGAAAACAGATACTGATGGGAAGTTTCTCTATCACAAATCCAAATGG
AACATAACCATGGAGTCCTATGTGGTCCACACCAACTATGATGAGTATGCCATTTTCCTGACCAAGAAATTCAGCCGC
CATCATGGACCCACCATTACTGCCAAGCTCTACGGGCGGGCGCCGCAGCTGAGGGAAACTCTCCTGCAGGACTTCAGA
GTGGTTGCCCAGGGTGTGGGCATCCCTGAGGACTCCATCTTCACCATGGCTGACCGAGGTGAATGTGTCCCTGGGGAG
CAGGAACCAGAGCCCATCTTAATCCCGAGATGA

41. M8H-Human R66H + N1796D (SEQ ID NO: 93)

ATGCATCACCATCACCATCACCATCACGGCCCTGTGCCAACGCCGCCCGACAACATCCAAGTGCAGGAAAACTTCGAT
ATCTCTCGGATCTATGGGAAGTGGTACAACCTGGCCATCGGTTCCACCTGCCCCTGGCTGAAGAAGATCATGGACAGG
ATGACAGTGAGCACGCTGGTGCTGGGAGAGGGCGCTACAGAGGCGGAGATCAGCATGACCAGCACTCATTGGCGGAAA
GGTGTCTGTGAGGAGACGTCTGGAGCTTATGAGAAAACAGATACTGATGGGAAGTTTCTCTATCACAAATCCAAATGG
GATATAACCATGGAGTCCTATGTGGTCCACACCAACTATGATGAGTATGCCATTTTCCTGACCAAGAAATTCAGCCGC
CATCATGGACCCACCATTACTGCCAAGCTCTACGGGCGGGCGCCGCAGCTGAGGGAAACTCTCCTGCAGGACTTCAGA
GTGGTTGCCCAGGGTGTGGGCATCCCTGAGGACTCCATCTTCACCATGGCTGACCGAGGTGAATGTGTCCCTGGGGAG
CAGGAACCAGAGCCCATCTTAATCCCGAGATGA 42. untagged-Human R66H + N1796D (SEQ ID NO: 94)

ATGGGCCCTGTGCCAACGCCGCCCGACAACATCCAAGTGCAGGAAAACTTCGATATCTCTCGGATCTATGGGAAGTGG
TACAACCTGGCCATCGGTTCCACCTGCCCCTGGCTGAAGAAGATCATGGACAGGATGACAGTGAGCACGCTGGTGCTG
GGAGAGGGCGCTACAGAGGCGGAGATCAGCATGACCAGCACTCATTGGCGGAAAGGTGTCTGTGAGGAGACGTCTGGA
GCTTATGAGAAAACAGATACTGATGGGAAGTTTCTCTATCACAAATCCAAATGGGATATAACCATGGAGTCCTATGTG
GTCCACACCAACTATGATGAGTATGCCATTTTCCTGACCAAGAAATTCAGCCGCCATCATGGACCCACCATTACTGCC
AAGCTCTACGGGCGGGCGCCGCAGCTGAGGGAAACTCTCCTGCAGGACTTCAGAGTGGTTGCCCAGGGTGTGGGCATC
CCTGAGGACTCCATCTTCACCATGGCTGACCGAGGTGAATGTGTCCCTGGGGAGCAGGAACCAGAGCCCATCTTAATC
CCGAGATGA 61. untagged-Human wt (SEQ ID NO: 95)

ATGGGCCCTGTGCCAACGCCGCCCGACAACATCCAAGTGCAGGAAAACTTCAATATCTCTCGGATCTATGGGAAGTGG
TACAACCTGGCCATCGGTTCCACCTGCCCCTGGCTGAAGAAGATCATGGACAGGATGACAGTGAGCACGCTGGTGCTG
GGAGAGGGCGCTACAGAGGCGGAGATCAGCATGACCAGCACTCGTTGGCGGAAAGGTGTCTGTGAGGAGACGTCTGGA
GCTTATGAGAAAACAGATACTGATGGGAAGTTTCTCTATCACAAATCCAAATGGAACATAACCATGGAGTCCTATGTG
GTCCACACCAACTATGATGAGTATGCCATTTTCCTGACCAAGAAATTCAGCCGCCATCATGGACCCACCATTACTGCC
AAGCTCTACGGGCGGGCGCCGCAGCTGAGGGAAACTCTCCTGCAGGACTTCAGAGTGGTTGCCCAGGGTGTGGGCATC
CCTGAGGACTCCATCTTCACCATGGCTGACCGAGGTGAATGTGTCCCTGGGGAGCAGGAACCAGAGCCCATCTTAATC
CCGAGATGA

Rationale of A1M Variant Constructions

Human wt-A1M, 11 A1M-homologues from various species, and 15 A1M-variants with point mutations were constructed, expressed, purified and analysed in phase I, i.e. a total of 27 A1M-variants (Table 2). The 11 A1M-homologues were selected as follows. A1M is well conserved between species. A1M sequences of different species were searched for in data bases (www.ncbi.nlm.nih.gov and www.uniprot.orq). AMBP sequences from 67 different species were found. The sequences were investigated for presence of A1M-specific functional groups (K69, K92, K118, K130, Y22; Y132, H122 and H123), lipocalin motifs (SCR1, 2, 3) (see refs in Introduction) and predicted carbohydrate binding sites (Escribano et al., 1990). Five were classified as non-A1M and dismissed because they lacked cystein 34, three were dismissed because they lacked cystein 169, four because they were incomplete, and two because they had long, questionable, inserts. The amino acid sequences of the remaining 53 homologues were aligned and their suggested 3D structure were modelled by projecting their amino acid sequences on the crystal structure of human A1M (Meining and Skerra, 2012) to identify the location of individual amino acid side chains in the lipocalin loops or on the inside or outside of the pocket. The result of this was used for construction of point mutations affecting A1M-function as described below. The rationale for selection of the final 11 homologues (see Table 2) was a combination of wide-spread evolutionary representation, methodological feasibility, potentially increased environmental oxidative stress in the living habitat of the species, presence or absence of A1M-specific functional groups, and lack of glycosylation. The 15 A1M-variants with point mutations were selected as follows. Eight of the variants were mutated in strategic amino acids for functional properties and seven variants in exposed positions to improve stability/solubility (Table 2). The eight functional mutations were selected as they 1) occurred in other species in positions in the 3D-structural model (see above) that could potentially influence the function of A1M and/or 2) theoretically would lower the pKa of cystein 34 and/or 3) theoretically would provide an extra radical trapping site. Predicted data for all variants was calculated using the www.alphalyse.com/gpmaw_lite.html tool (Table 3).

TABLE 2

Variants expressed and analysed in A1M variants project phase I.

| No* | Name | Systematic name | Protein sequence | Gene Info Identifier | Aim of mutation | Rationale | N-terminal tag |
|---|---|---|---|---|---|---|---|
| 60 | human wt | Homo sapiens | NP_001624 | gi: 4502067 | | | M8H4DK |
| 1 | mouse | Mus musculus | NP_031469 | gi: 311703 | Species | only rodent, lab animal, we have antibodies | M8H5GIEGR |
| 2 | naked mole-rat | Heterocephalus glaber | XP_004885260 | gi: 512843527 | Species | long-lived, low tumor frequency suggests good endogeneous antioxidation | M8H5GIEGR |
| 3 | frog | Xenopus laevis | NP_001080820 | gi: 147905774 | Species | no predicted carbohydrate suggests high solubility of polypeptide, 1 extra Cys, high pI | M8H5GIEGR |
| 4 | chicken | Gallus gallus | NP_001264627 | gi: 478732996 | Species | only bird | M8H5GIEGR |
| 5 | rabbit | Oryctolagus cuniculus | XP_008271622 | gi: 655878696 | Species | lab animal, we have antibodies | M8H5GIEGR |
| 6 | squirrel monkey | Saimiri boliviensis | XP_0039252551 | gi: 403266141 | Species | two primates, less substitutions compared to human, easier readout | M8H5GIEGR |
| 7 | walrus | Odobenus rosmarus | XP_004397010 | gi: 472354701 | Species | uneven oxygenation due to diving | M8H5GIEGR |
| 8 | manatee | Trichechus manatus | XP_004372191 | gi: 0471363267 | Species | uneven oxygenation due to diving | M8H5GIEGR |
| 9 | plaice | Pleuronectes platessa | 2021284A | gi: 1091607 | Species | uneven oxygenation due to diving | M8H5GIEGR |
| 10 | orangutan | Pongo abelii | NP_001127069 | gi: 197102775 | Species | one substitution - H122R - in an interesting position: reductase and heme-binding | M8H5GIEGR |
| 11 | human P35K | | | | Functional | a) occurs in birds and frogs, b) may lower pKa of C34, c) may be radical trapping site | M8H5GIEGR |
| 12 | human M41K | | | | Functional | a) occurs in many species, b) may lower pKa of C34, c) may be radical trapping site | M8H5GIEGR |
| 13 | human R66H | | | | Functional | occurs in many species, c.f. rodents and rabbits | M8H5GIEGR |
| 14 | human I75K | | | | Functional | a) may lower pKa of C34, b) may be radical trapping site | M8H5GIEGR |
| 15 | human T75Y | | | | Functional | may be radical trapping site | M8H5GIEGR |
| 16 | human M99K | | | | Functional | a) may lower pKa of C34, b) may be radical trapping site | M8H5GIEGR |
| 17 | human S101Y | | | | Functional | may be radical trapping site | M8H5GIEGR |
| 18 | human K69, 92, 118, 130R | | | | Functional | may be radical trapping sites | M8H5GIEGR |
| 19 | coelacanth | Latimeria chalumnae | XP_005994505.1 | gi: 556972695 | Species | most primitive A1M-sequence identified | M8H5GIEGR |
| 21 | human L89T | | | | Solubility | exposed position, increased hydrophilicity, occurs in many species | M8H5GIEGR |
| 22 | human N17, 96D | | | | Solubility | carbohydrate sites, increased hydrophilicity | M8H5GIEGR |
| 23 | human T45K | | | | Solubility | exposed position, increased charge, occurs in many species | M8H5GIEGR |

TABLE 2-continued

Variants expressed and analysed in A1M variants project phase I.

| No* | Name | Systematic name | Protein sequence | Gene Info Identifier | Aim of mutation | Rationale | N-terminal tag |
|---|---|---|---|---|---|---|---|
| 24 | human A135E | | | | Solubility | exposed position, increased charge, occurs in many species | M8H5GIEGR |
| 25 | human V170S | | | | Solubility | exposed position, increased hydrophilicity, occurs in many species | M8H5GIEGR |
| 26 | human V148D | | | | Solubility | exposed position, increased hydrophilicity, occurs in many species | M8H5GIEGR |
| 27 | human G172Q | | | | Solubility | exposed position, increased hydrophilicity, occurs in birds | M8H5GIEGR |

TABLE 3

Predicted data for phase I variants

| # | Variant | # amino acids | mw (Da) | pI | Net charge (D + E) − (R + K) | ext. Coeff 280 nm (cm⁻¹) | Hydrophob. index |
|---|---|---|---|---|---|---|---|
| 60 | human wt | 197 | 22561 | 6.4 | −5 | 1.47 | −0.64 |
| 1 | mouse | 200 | 22732 | 6.6 | −4 | 1.46 | −0.60 |
| 2 | naked mole rat | 201 | 22741 | 9.2 | 2 | 1.40 | −0.73 |
| 3 | frog | 197 | 22660 | 8.0 | 0 | 1.22 | −0.79 |
| 4 | chicken | 197 | 22302 | 6.5 | −3 | 1.40 | −0.76 |
| 5 | rabbit | 201 | 22911 | 6.9 | −2 | 1.45 | −0.61 |
| 6 | Sq. monkey | 201 | 23066 | 7.3 | −1 | 1.68 | −0.69 |
| 7 | walrus | 201 | 22837 | 6.6 | −4 | 1.39 | −0.63 |
| 8 | manatee | 200 | 22469 | 6.6 | −3 | 1.47 | −0.54 |
| 9 | plaice | 202 | 22896 | 6.6 | −4 | 0.89 | −0.71 |
| 10 | orangutan | 201 | 22733 | 7.2 | −1 | 1.46 | −0.58 |
| 11 | human P35K | 201 | 22745 | 7.2 | −1 | 1.46 | −0.58 |
| 12 | human M41K | 201 | 22711 | 7.2 | −1 | 1.46 | −0.60 |
| 13 | human R66H | 201 | 22695 | 6.7 | −3 | 1.46 | −0.57 |
| 14 | human T75K | 201 | 22741 | 7.2 | −1 | 1.46 | −0.59 |
| 15 | human T75Y | 201 | 22776 | 6.9 | −2 | 1.51 | −0.58 |
| 16 | human M99K | 201 | 22711 | 7.2 | −1 | 1.46 | −0.60 |
| 17 | human S101Y | 201 | 22790 | 6.9 | −2 | 1.51 | −0.57 |
| 18 | human K69.92.118.130R | 201 | 22826 | 6.9 | −2 | 1.45 | −0.58 |
| 19 | coelacanth | 198 | 22741 | 6.7 | −3 | 1.38 | −0.78 |
| 21 | human L89T | 201 | 22702 | 6.9 | −2 | 1.46 | −0.59 |
| 22 | human N17.96D | 201 | 22716 | 6.5 | −4 | 1.46 | −0.57 |
| 23 | human T45K | 201 | 22741 | 7.2 | −1 | 1.46 | −0.59 |
| 24 | human A135E | 201 | 22772 | 6.7 | −3 | 1.45 | −0.60 |
| 25 | human V170S | 201 | 22702 | 6.9 | −2 | 1.46 | −0.60 |
| 26 | human V148D | 201 | 22730 | 6.7 | −3 | 1.46 | −0.61 |
| 27 | human G172Q | 201 | 22785 | 6.9 | −2 | 1.45 | −0.59 |

Phase I

The variants were expressed in parallel shake-flasks. There was a variation in expression levels and for a few A1M-variants expression had to be repeated several times to obtain reasonable protein amounts. Good expression and relatively large amounts after purification (>10 mg/L culture) were obtained for mouse, squirrel monkey, walrus, orangutan, M41K, R66H, T75Y, M99K, N17,96D, T45K and V148D. The expression and amount of purified protein was similar to previous yields for human wt A1M (12 mg/L) expressed and purified under similar conditions. Variants with lower expression levels resulting in lower yields (1-10 mg/L) were naked mole rat, frog, rabbit, manatee, P35K, T75K, S101Y, L89T, V170S and G172Q. Chicken, plaice and coelacanth A1M displayed suboptimal expression levels resulting in a purification yield of <1 mg/L culture. The quadruple human mutant K69,92,118,130R expressed well, but was impossible to refold successfully. Also T75K-A1M showed increased precipitation tendencies during purification.

All variants were purified to >99% purity according to SDS-PAGE except chicken and coelacanth A1M, which were purified to 95% purity. According to SDS-PAGE all variants contained a maximum of 0.5% covalent dimers with no major differences between the variants. Circular dichroism revealed about 2% alpha helix and 40% β-sheet structure for all variants without major differences, the expected values for A1M (Kwasek et al., 2007). After purification, all variants were analysed as summarized in Table 4. Firstly, stability and solubility was analysed. The aggregation tendency and thermostability of freshly thawed, unstressed 0.1 mM protein solutions were analysed by dynamic light scattering (DLS), PAGE (aggregation) and differential scanning fluorimetry (DSF) (thermostability). In addition, the tendency to aggregate in response to shearing forces or concentration to 1 mM was investigated. Human wt A1M performed relatively well in these assays (Table 4), but some variants performed even better in the stability/solubility properties: chicken A1M, manatee A1M and N17,96D-A1M. The chicken and manatee A1M differed from human wt A1M in too many positions to enable assumptions on individual amino acids beneficial for human A1M and was not used in further studies. When functional properties were investigated, M41K and R66H were found to have the same (R66H) or improved (M41K) functions. As these variants also had higher thermostability and only slightly higher tendency to aggregate than most other variants, they were selected for further investigation. Hence, N17,96D-A1M, M41K-A1M and R66H-A1M were continued to phase II of the project.

Phase II

The aim of phase II of the project was to combine the beneficial mutations (M41K, R66H and N17,96D) to investigate if even more stable variants with similar or improved function could be constructed. In addition, the same N-terminal tag (M8H4DK) which is used for human wt A1M was introduced (Table 5). Thus, the new combined M8H4DK-variants were compared to M8H4DK-human wt.

TABLE 5

Variants expressed in phase II with predicted data

| # | Variant | # amino acids | mw (Da) | pI | Net charge (D + E) − (R + K) | ext. coeff 280 nm (cm⁻¹) | hydrophob. index |
|---|---|---|---|---|---|---|---|
| 12 | M8H5GIEGR-M41K | 201 | 22711 | 7.2 | −1 | 1.46 | −0.60 |
| 13 | M8H5GIEGR-R66H | 201 | 22695 | 6.7 | −3 | 1.46 | −0.57 |
| 22 | M8H5GIEGR-N17, 96D | 201 | 22716 | 6.5 | −4 | 1.46 | −0.57 |
| 60 | M8H4DK-wt | 197 | 22561 | 6.4 | −5 | 1.47 | −0.64 |

TABLE 5-continued

Variants expressed in phase II with predicted data

| # | Variant | # amino acids | mw (Da) | pI | Net charge (D + E) − (R + K) | ext. coeff 280 nm (cm$^{-1}$) | hydro- phob. index |
|---|---|---|---|---|---|---|---|
| 33 | M8H4DK-M41K + R66H | 197 | 22539 | 6.4 | −5 | 1.47 | −0.67 |
| 34 | M8H4DK-M41K + N17, 96D | 197 | 22560 | 6.2 | −6 | 1.47 | −0.67 |
| 35 | M8H4DK-R66H + N17, 96D | 197 | 22544 | 6.1 | −8 | 1.47 | −0.64 |
| 36 | M8H4DK-M41K-R66H + N1796D | 197 | 22541 | 6.2 | −7 | 1.47 | −0.67 |

All four new variants (M8H4DK-M41K+R66H, M8H4DK-M41K+N17,96D, M8H4DK-R66H+N17,96D and M8H4DK-M41K+R66H+N17,96D) expressed very well and yields of 29, 13, 37 and 15 mg pure protein/L were achieved. The four new variants were purified to >99% purity according to SDS-PAGE and showed the same or lower percentage of covalent dimers except M8H4DK-M41K+R66H that showed approximately 2% covalent dimers.

Solubilization/stability properties were analysed (Table 6a). Data revealed that the combination of M41K and R66H was suboptimal for thermostability. The N17,96D mutation, on the other hand, was generally beneficial for solubilization and stability, and the combination with R66H (i.e. the M8H4DK-R66H+N17,96D-A1M) yielded even better solubilization and stability.

Functional properties were analysed (Table 6b). Data showed that the M41K mutation had increased heme reduction capacity, but decreased heme binding. When the M41K mutation was combined with N17,96D, however, it showed less potential to rescue cells from heme-induced cell death. The R66H+N17,96D combination yielded similar results compared to wt-A1M in all functional aspects investigated. Therefore, the M8H4DK-tagged R66H+N17,96D A1M is a promising candidate after phase II, while the M41K-mutation is less useful.

Phase III

The first aim of phase III was to compare M8H4DK-tagged R66H+N17,96D-A1M with wt-A1M and promising M8H4DK-tagged single mutations of phase I and II, when expressed in parallel under identical conditions. The second aim was to investigate the influence of the tag on stability, solubility and function. The N-terminal tag of human wt A1M (M8H4DK) consist of 8 histidines tag (SEQ ID NO: 103) followed by an enterokinase cleavage site. The cleavage site enables cleavage of the histidine tag after expression and purification. Therefore, wt-A1M and R66H+N17,96D-A1M were expressed with N-terminal M8H4DK- and M8H-tags and without a tag. The third aim was to compare in more detail the properties of M8H4DK-wt A1M (Wt-A1M) and M8H4DK-R66H+N17,96D-A1M (35-A1M). All expressed variants of phase III with predictive data are shown in Table 7.

TABLE 7

Variants expressed in phase III with predicted data

| # | Variant | # amino acids | mw (Da) | pI | Net charge (D + E) − (R + K) | ext. coeff 280 nm (cm$^{-1}$) | hydro- phob. index |
|---|---|---|---|---|---|---|---|
| 60 | M8H4DK-wt | 197 | 22561 | 6.4 | −5 | 1.47 | −0.64 |
| 35 | M8H4DK-R66H + N1796D | 197 | 22544 | 6.1 | −8 | 1.47 | −0.64 |
| 37 | M8H4DK-M41K | 197 | 22558 | 6.5 | −4 | 1.47 | −0.67 |
| 38 | M8H4DK-R66H | 197 | 22542 | 6.3 | −8 | 1.47 | −0.64 |
| 39 | M8H4DK-N17.96D | 197 | 22563 | 6.1 | −7 | 1.47 | −0.64 |
| 40 | M8H-wt | 192 | 21973 | 6.9 | −2 | 1.51 | −0.57 |
| 41 | M8H-R66H + N1796D | 192 | 21956 | 6.4 | −5 | 1.51 | −0.56 |
| 42 | M-R66H + N1796D | 184 | 20859 | 5.6 | −5 | 1.59 | −0.45 |
| 61 | M-wt | 184 | 20876 | 6.3 | −2 | 1.59 | −0.45 |

The parallel expression and purification allowed more accurate comparison of expression levels and purification yields. It was found that all A1M variants expressing bacteria grow with the same rate (not shown) and the same relatively good yield (FIG. 2). The only difference was a slower expression of the untagged variants (#60 and #42) compared to the others. From the 2×750 ml expressions it was possible to purify 20-60 mg of each variant (FIG. 3a). All histidine-tagged variants were purified to >99% purity, while the untagged variants (#61 and #42) showed a somewhat lower purity (around 90%) (FIG. 3b). All displayed a low amounts of covalent dimers. PAGE analysis showed less than 1-2% large aggregates of all variants except M8H-wt (40) and untagged wt-A1M (#61) (FIG. 3c). Thus, all single and multiple M8H4DK-tagged, M8H-tagged and untagged A1M variants could be produced.

The aggregation and thermostability of 100 μM solutions were analysed by reversed-phase HPLC, dynamic light scattering and differential scanning fluorimetry (Table 8). The M8H4DK-tagged variants were eluted in RP-HPLC at approximately 12 min, with 87-90% of the protein in the main peak. The only exception was M8H4DK-M41K that appeared at a retentation time of 9.8 minutes and only 80% of the protein in the main peak. The data once more indicate that the M41K mutation yields unexpected protein properties of A1M, and is suboptimal. Changing the tag to M8H or completely removing the tag, resulted in increased retentation times to 12.2 and 12.9 min, respectively, indicating more hydrophobic molecules, as expected. Less protein appeared in the main peak for M8H-wt and both untagged variants, possibly reflecting the slightly lower purity seen in SDS-PAGE of these variants. DLS-data indicated an average radius around 3 of all variants, and the possibility to collect data from all 6 recordings. All variants had the same or higher thermostability as M8H4DK-wt A1M. Higher stability was seen for all variants carrying the N17,96D mutation.

TABLE 8

Aggregation and thermostability of non-stressed phase III variants.

| # | variant | RP-HPLC RT [min] | RP-HPLC Main peak (% of total) | DLS Average radius (nm) | DLS Measurements used (# of 6) | DSF Tm |
|---|---|---|---|---|---|---|
| 60 | M8H4DK-wt | 12.1 | 87 | 2.9 | 6 | 46.6 |
| 35 | M8H4DK-R66H + N1796D | 12.1 | 89 | 3.2 | 6 | 49.8 |
| 37 | M8H4DK-M41K | 9.8 | 80 | 3.3 | 6 | 46.8 |
| 38 | M8H4DK-R66H | 12.1 | 89 | 2.9 | 6 | 46.4 |
| 39 | M8H4DK-N1796D | 12.1 | 90 | 3.0 | 6 | 49.7 |
| 40 | M8H-wt | 12.2 | 78 | 3.2 | 6 | 47.1 |
| 41 | M8H-R66H + N1796D | 12.2 | 88 | 3.2 | 6 | 50.2 |
| 61 | M-wt | 12.9 | 81 | 3.8 | 6 | 46.3 |
| 42 | M-R66H + N1796D | 12.9 | 82 | 3.4 | 6 | 50.2 |

TABLE 9

Shearing stability of phase III variants.

| # | variant | Average radius (nm) | Measurements used (#of 6) |
|---|---|---|---|
| 60 | M8H4DK-wt | 2.9 | 3 |
| 35 | M8H4DK-R66H + N1796D | 3.0 | 6 |
| 37 | M8H4DK-M41K | | 0 |
| 38 | M8H4DK-R66H | | 0 |
| 39 | M8H4DK-N1796D | 3.1 | 6 |
| 40 | M8H-wt | 3.1 | 1 |
| 41 | M8H-R66H + N1796D | | 0 |
| 61 | M-wt | 3.9 | 5 |
| 42 | M-R66H + N1796D | 3.4 | 6 |

TABLE 10

Concentration and freeze-thaw stability of phase III variants in different buffers.

| # | variant | 0.1 mM pH 8.0 | 1 mM pH 8.0 | 1 mM pH 8.0, 1x freeze-thaw | 0.1 mM pH 7.4 | 1 mM pH 7.4 | 1 mM pH 7.4, 1x freeze-thaw | 1 mM PBS pH 7.4, 1x freeze-thaw |
|---|---|---|---|---|---|---|---|---|
| | | | | Large aggregates (%) | | | | |
| 60 | M8H4DK-wt | 0.3 | 1.1 | 2.0 | 0.4 | 1.2 | 3.1 | 13.2 |
| 35 | M8H4DK-R66H + N1796D | 0.2 | 0.3 | 0.1 | 0.4 | 0.2 | 0.3 | 1.3 |
| 37 | M8H4DK-M41K | 1.3 | 4.1 | 4.8 | 0.8 | 7.9 | 11.9 | 15.6 |
| 38 | M8H4DK-R66H | 0.6 | 0.5 | 1.0 | 0.2 | 0.7 | 2.4 | 16.0 |
| 39 | M8H4DK-N1796D | 0.7 | 1.1 | 0.1 | 0.2 | 0.1 | 0.7 | 2.5 |
| 40 | M8H-wt | 0.8 | 7.2 | 3.6 | 8.4 | 10.2 | 11.4 | 14.0 |
| 41 | M8H-R66H + N1796D | 0.3 | 0.4 | 0.4 | 0.3 | 0.4 | 1.2 | 7.6 |
| 61 | M-wt | 0.4 | 2.0 | 2.3 | 9.1 | 1.6 | 3.9 | 17.9 |
| 42 | M-R66H + N1796D | 0.4 | 0.3 | 0.5 | 0.4 | 0.5 | 0.5 | 1.6 |

The variants of phase III were exposed to shearing forces by pipetting 80 times in a narrow pipett tip. The shearing-stress induced aggregation was the analysed with DLS. In general, all variants with the N17,96D mutation showed high tolerance towards shearing stress (Table 9), with the exception of M8H-tagged R66H+N1796D variant (#41). Also, the tolerance towards stress induced by concentration to 1 mM in different buffers was investigated. All variants were concentrated to 1 mM in 20 mM Tris-HCl+0.125M NaCl pH 8.0 or 7.4, and were immediately analysed by PAGE (FIG. 4a, Table 10). The 0.1 mM and 1 mM samples were also analysed with PAGE after a single freeze-thaw cycle in the Tris-buffers or PBS (FIG. 4b, Table 10). Among the M8H4DK-tagged variants all the N17,96D-carrying mutations displayed an increased tolerance to concentration, freeze-thawing, decreased pH and buffer-change (to PBS) compared to wt A1M. The addition of the R66H mutation improved the stability and solubility even further. The R66H mutation alone had approximately the same tolerance as wt A1M, while the M41K mutation had significantly lower tolerance. Shortening or removal of the N-terminal tag had a negative effect on the tolerance, which was more pronounced for wt A1M compared to corresponding R66H+N17,96D variants.

The functional activities of all phase III variants were investigated in an extended program to cover all possible aspects of known A1M functions. Non-heme related reduction capacity was investigated on the synthetic ABTS radical and in the commercially available oxygen radical antioxidant capacity (ORAC) assay (FIG. 5). M8H4DK-tagged N17,96D-A1M and R66H+N17,96D-A1M showed a similar reduction capacity as wt A1M, while M8H4DK-tagged M41K-A1M and R66H-A1M showed a slightly lower ABTS reduction capacity (FIG. 5A). Shortening or removal of the tag had little effect, but the R66H-N17,96D variants show a tendency to higher reduction capacity than wt A1M when M8H-tagged and untagged. The performance of M8H4DK-tagged wt A1M in the ORAC assay was set to 100% and the other variants were compared in relation to this. All M8H4DK-variants showed the same results in ORAC as M8H4DK-wt except M8H4DK-R66H+N17,96D which had significantly higher capacity (FIG. 5b). Also the M8H-tagged and untagged R66H+N17,96D-A1M showed a slightly higher ORAC capacity than wt-A1M. The reduction capacity was also investigated in a cytochrome c reduction assay (FIG. 6). Most variants showed a slightly lower reduction capacity at the lower concentrations, compared to wt-A1M, and for N17,96D and R66H+N17,96D this was significant (at 0.3-0.6 µM) (FIG. 6A). The importance of this is not understood. Shortening and removal of the tag had no influence of this property.

Heme-binding was investigated in a free heme incorporation assay and in a heme-agarose binding assay (FIG. 6). The incorporation and coordination of free heme is seen as the appearance of an absorbance peak around 410-415 nm, the so-called Soret band (Karnaukhova et al., 2014; Rutardottir et al, 2016). Heme normally has an absorbance peak around 380-390 nm and this can be seen when it is dissolved alone or mixed and incubated with a non-binding control protein like ovalbumin. However, when heme is mixed with wt A1M, an absorbance peak is formed between 410-415 nm, yielding a so-called red-shift (i.e. a shift of the peak towards higher wave-lengths), and an increased Abs(413/386) ratio. It was shown that the degree of red-shift and the Abs(413/386) ratio are related to the heme-binding function of A1M (Rutardottir et al, 2016). These properties were therefore compared for all variants in phase III (FIG. 6b). Among the M8H4DK-tagged variants all showed about the same red-shift as wt A1M except the M41K variants which had a stronger shift. Interestingly, shortening the tag to M8H increased the red-shift, while removal of the tag decreased the red-shift. Clearly, the tag had a strong influence of this property. The binding of heme to A1M was investigated as binding of a dilution series of A1M to heme-agarose in comparison to binding to a control agarose. Typically, a control protein like ovalbumin shows no binding to heme-agarose above the background binding to the control agarose (FIG. 6C). Typically, 70-80% of added M8H4DK-wt A1M (35-A1M) was bound to the heme agarose, whereas no-binding was seen to control agarose. The binding was compared for all variants in phase III. All showed similar degree of binding to the heme-agarose (66-72%), while ovalbumin showed no binding.

Figure 11:
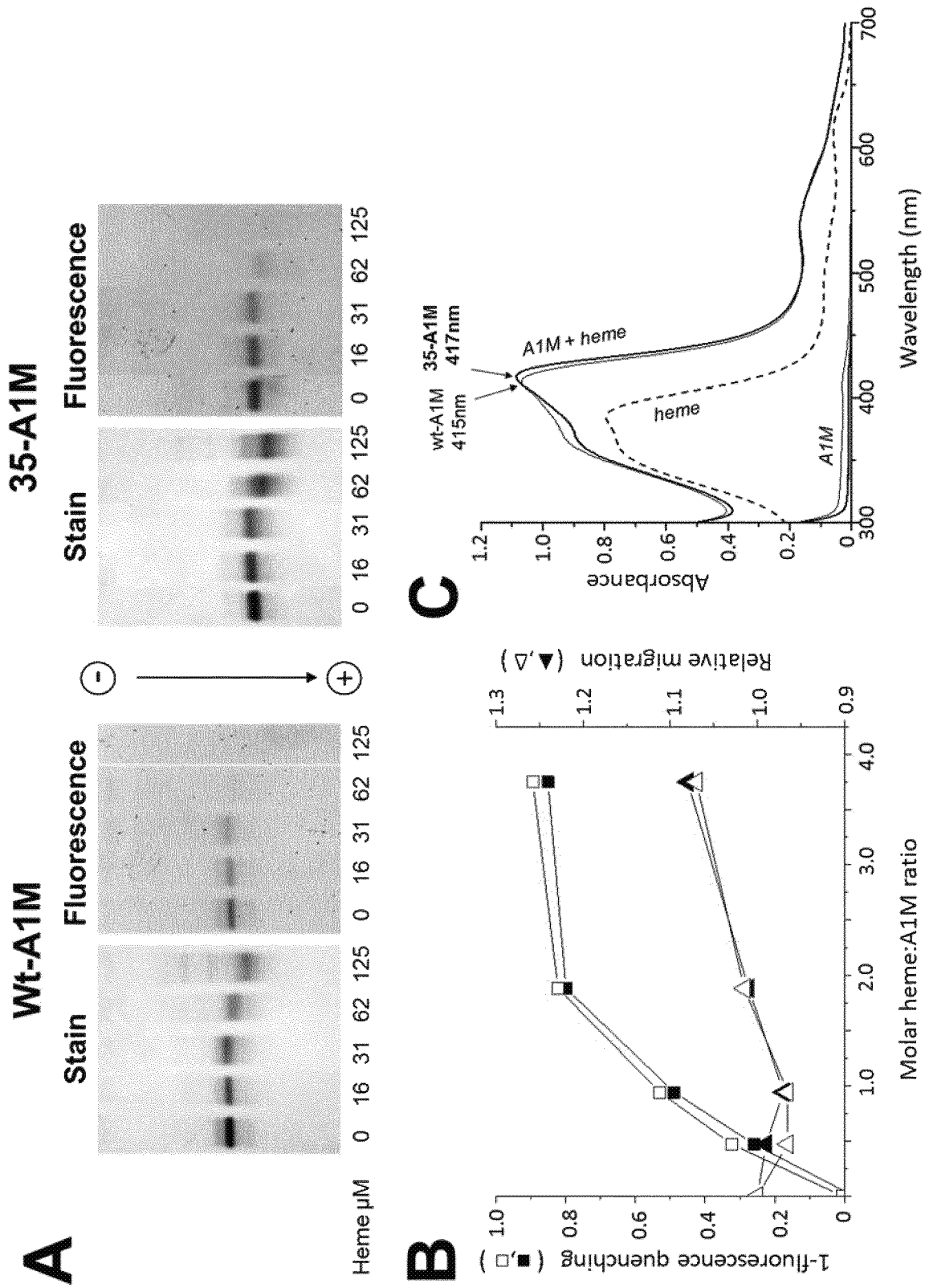

Heme binding of M8H4DK-wt A1M (wt-A1M) and M8H4DK-35-A1M (35-A1M) was further analysed (FIG. 11) using a combination of migration shift and fluorescence analysis (Karnaukhova et al. 2014). As a result of heme-incorporation, the migration of wt-A1M and 35-A1M in native PAGE analysis was slower at heme:protein ratio <1, and faster at heme:protein ratio >1, showing the same dependence upon heme-concentration (FIGS. 11A and B). At high heme concentrations, both variants showed a tendency towards oligomerization, supporting previous findings for wt-A1M (Karanaukhova et al. 2014). Likewise, heme-incorporation induced quenching of tryptophan fluorescence in both wt-A1M and 35-A1M, with similar kinetics (FIG. 11B). The coordination of heme in A1M was previously shown to induce formation of a UV-absorbance peak at 415 nm (Ruttarsdottir et al., 2016; karnaukhova et al., 2014). Similar UV-absorbance patterns of wt-A1M- and 35-A1M/heme complexes were seen (FIG. 11C), with only a small red-shift of the 35-A1M peak (4154417 nm).

The rate of reduction of ABTS-radicals of wt-A1M and 35-A1M was investigated [10] and was similar for wt-A1M and 35-A1M using unstressed, freshly prepared proteins (FIG. 12A). After storage for 7 days, wt-A1M displayed a slower reduction rate after concentration to 1 mM and at 22° C. (FIG. 12B), suggesting a loss of protein activity in addition to the aggregation shown at these conditions (Table 11). The cytochrome c-reduction (Allhorn et al., 2005) was slightly slower for 35-A1M (FIG. 12C), whereas the anti-oxidation capacity measured by the ORAC assay was somewhat higher for 35-A1M (FIG. 12D).

TABLE 11

Physicochemical properties of M8H4DK-wt A1M (wt-A1M) and M8H4DK-35-A1M (35-A1M).

| Conditions[1] | Concentration | Method | Parameter | wt-A1M | 35-A1M |
|---|---|---|---|---|---|
| Unstressed[2] | 0.1 mM | HPLC | Elution time (min) | 12.1 | 12.1 |
| | | | Monomer (%) | 87 | 89 |
| | | DLS | Radius (nm) | 2.9 | 3.2 |
| | | PAGE | Aggregates (%) | 1.5 | 0.4 |
| | | SEC | Monomer (%) | 87 | 93 |
| Stressed | | | | | |
| Heat | 0.1 mM | DSF | $T_m$ (° C.) | 46.6 | 51.6 |
| High conc | 1 mM | PAGE | Aggregates (%) | 1.1 | 0.4 |
| pH 7.4[3] | 1 mM | PAGE | Aggregates (%) | 1.2 | 0.4 |
| Freeze-thaw[2] | 1 mM | PAGE | Aggregates (%) | 2.0 | 0.4 |
| Freeze-thaw/PBS | 1 mM | PAGE | Aggregates (%) | 13.2 | 7.6 |
| Prolonged storage[4] | | | | | |
| 4° C.-1 day | 1 mM | SEC | Recovery[5] (%) | 100 | 100 |
| | | | Aggregates (%) | 17.9 | 3.9 |
| 4° C.-7 days | 1 mM | SEC | Recovery (%) | 100 | 100 |
| | | | Aggregates (%) | 12.1 | 3.7 |
| RT-7 days | 1 mM | SEC | Recovery (%) | 44 | 100 |
| | | | Aggregates (%) | 0.2 | 0.1 |
| 37° C.-1.5 h | 1 mM | SEC | Recovery (%) | 67 | 100 |
| | | | Aggregates (%) | 53 | 28 |
| 37° C.-4.5 h | 1 mM | SEC | Recovery (%) | 0 | 44 |
| | | | Aggregates (%) | ND[6] | 15 |

Footnotes:
[1]Room temperature unless otherwise stated.
[2]20 mM Tris-HCl, 0.125M NaCl, pH 8.0
[3]20 mM Tris-HCl, 0.125M NaCl, pH 7.4
[4]PBS
[5]Calculated after centrifugation 10,000 × g, from total peak area compared to starting material.
[6]Not determined A biologic assay where the ability of the A1M variants to rescue K562 cells from heme-induced cell death was investigated (FIG. 7). The degree of cell death, according to lactate dehydrogenase release, was set to 100% for cells incubated with heme without A1M. All M8H4DK-tagged variants, including wt-A1M, showed almost 100% rescue at 10 μM (FIG. 7), with no significant differences between the variants. The M8H-tagged variants showed almost the same rescuing potential, while a slightly lower potential was observed for the untagged variants.

Figure 12:
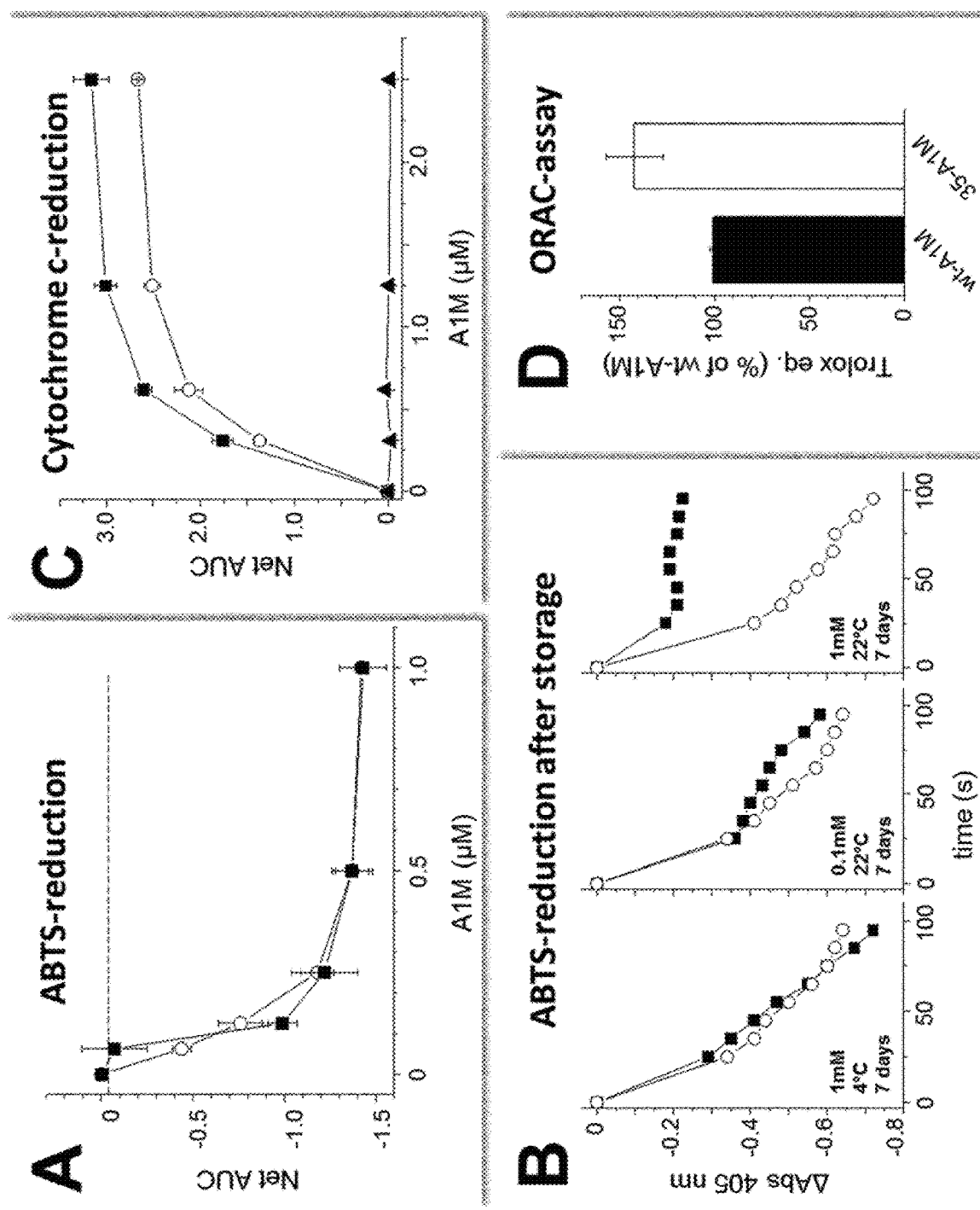
Figure 13:
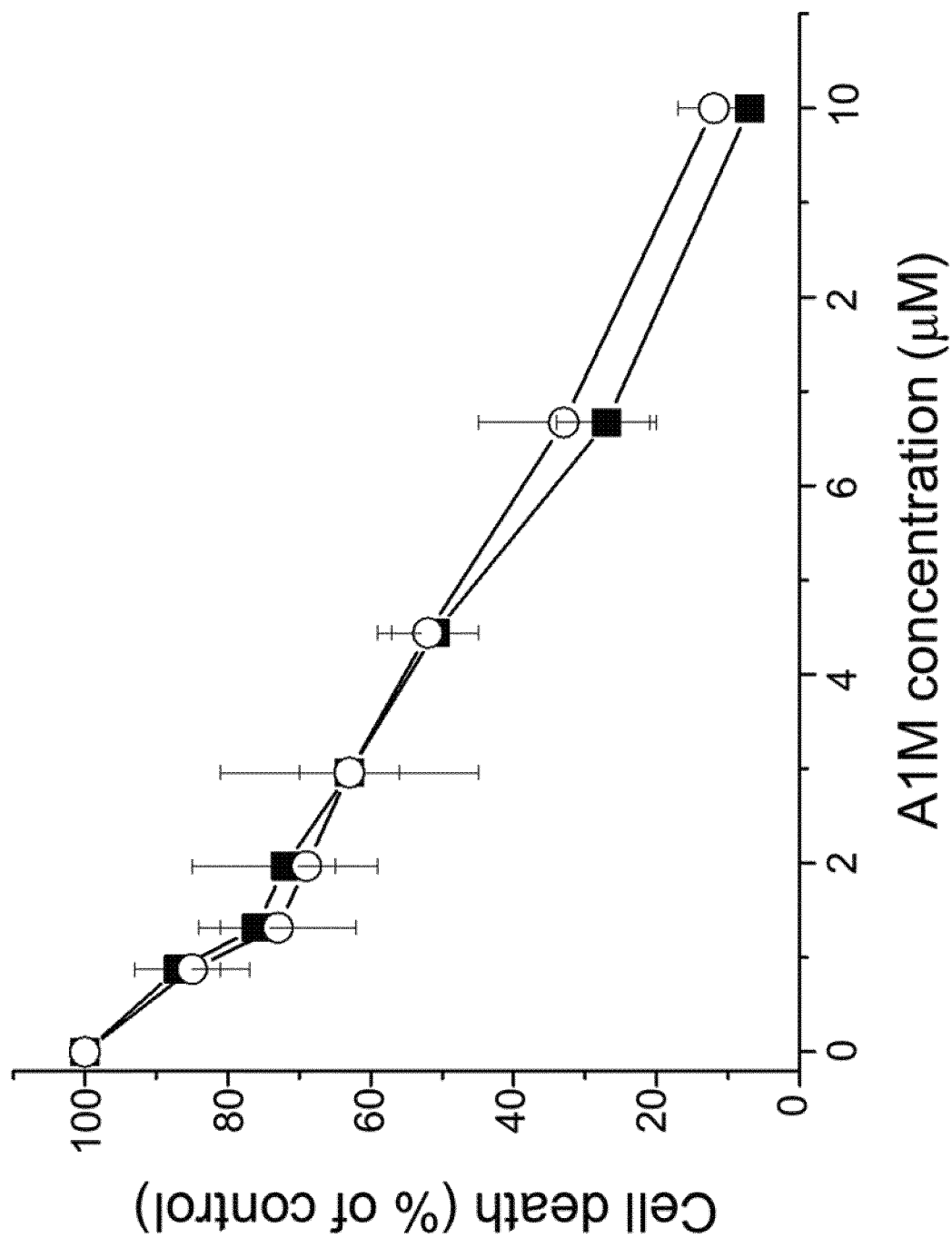

Cell protection capacity of M8H4DK-wt A1M (35-A1M) and M8H4DK-35-A1M (wt-A1M) The cell protection properties of the two A1M-variants were tested in K562 cells and a human kidney proximal tubule epithelial cell line (HK-2), exposed to free heme and free iron. FIG. 12 shows that both A1M-variants completely inhibited the cell-death, measured by extracellular release of the cytosolic marker LDH, of K562-cells exposed to 0.1 mM heme. The dose-response curves of wt-A1M and 35-A1M overlaps almost completely, suggesting similar cell-protection capacities.

Figure 14:
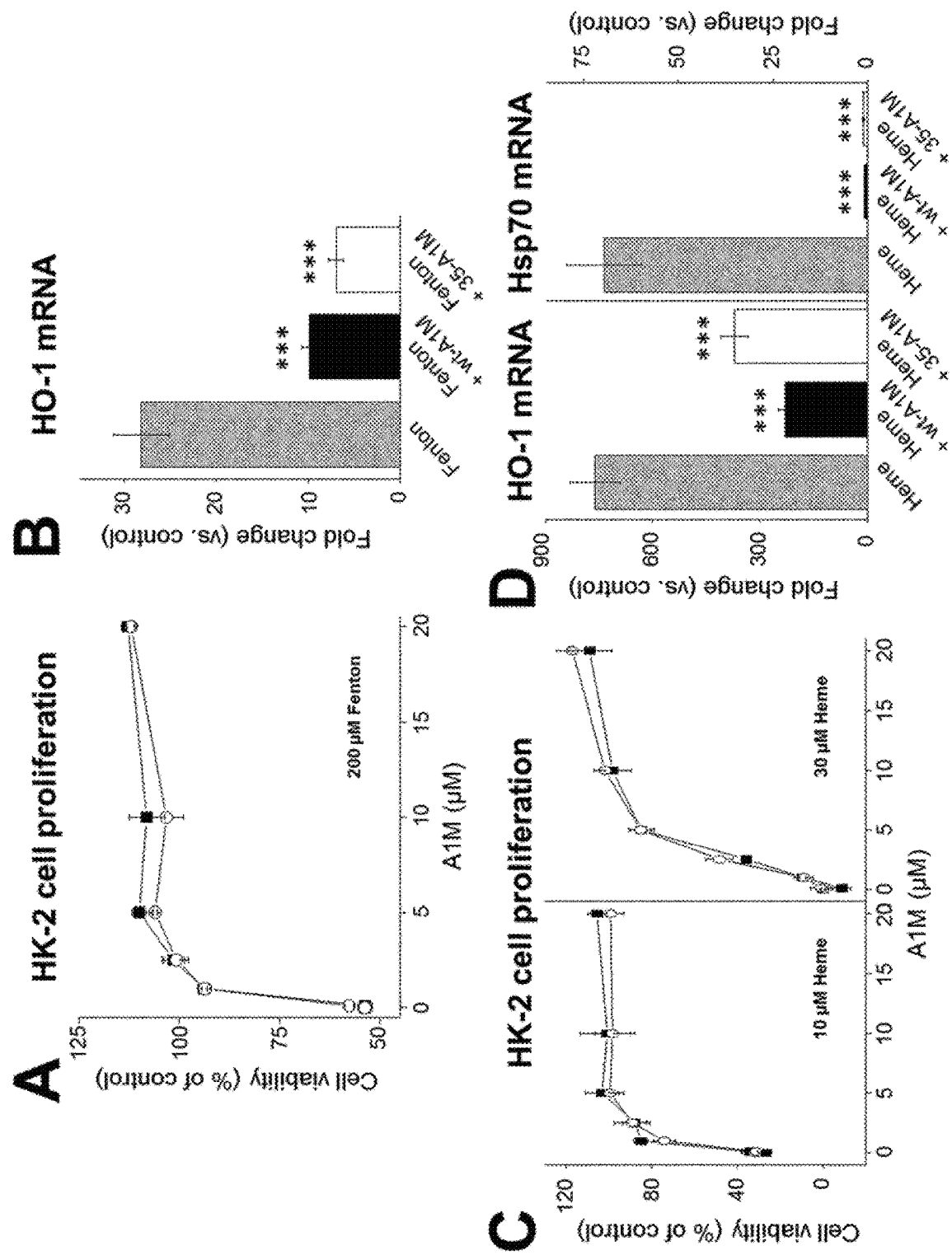

Protection of HK-2 cells are shown in FIG. 14. First, cell damage was induced by the Fenton reaction, a mixture of free iron, ascorbate and hydrogen peroxide which generates hydroxyl radicals. Cell viability, measured by the WST-1 assay, was restored by both A1M-variants, following overlapping dose-response curves (FIG. 14A). The upregulation of heme oxygenase-1 (HO-1), a well-documented biomarker of oxidative stress-response (Alam et al., 1999), was significantly suppressed by wt-A1M and 35-A1M to similar degrees (FIG. 14B). Cell damage of HK-2 cells was also induced by incubation with heme, and could be inhibited by both A1M-variants (FIGS. 14C and D). Again, cell viability measured by the WST-1 assay was restored by both proteins to a similar degree, using two heme concentrations, 10 and 30 μM (FIG. 14C). The upregulation of HO-1 and another cellular stress response gene, Hsp70, was inhibited to a similar degree by both A1M-variants (FIG. 14D).

Figure 15:
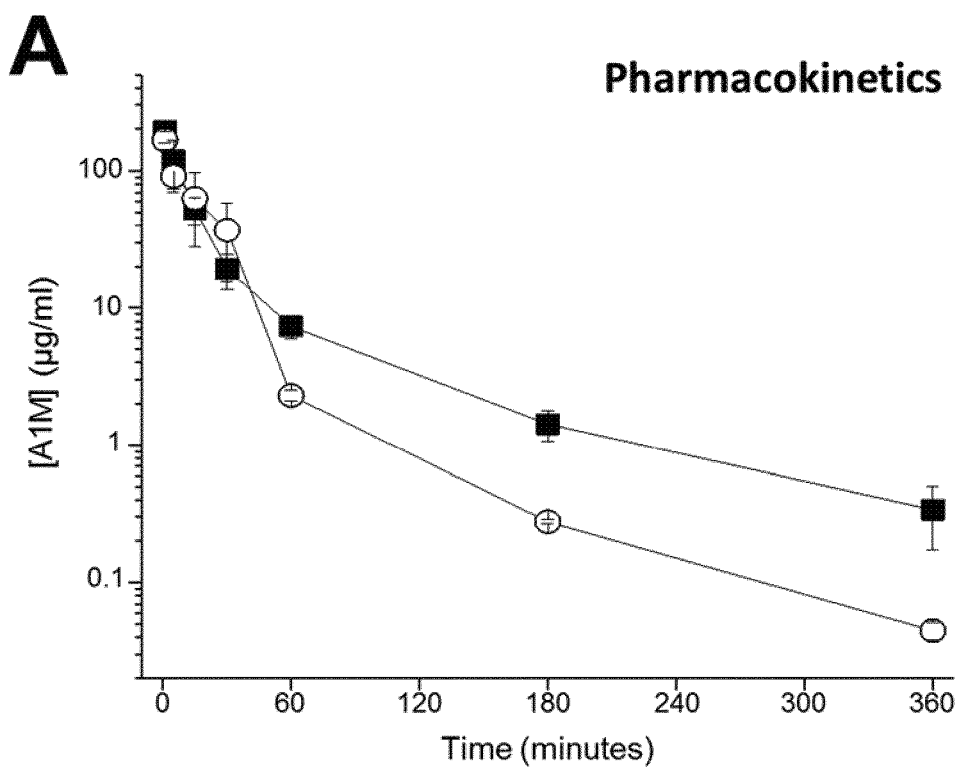
Figure 15:
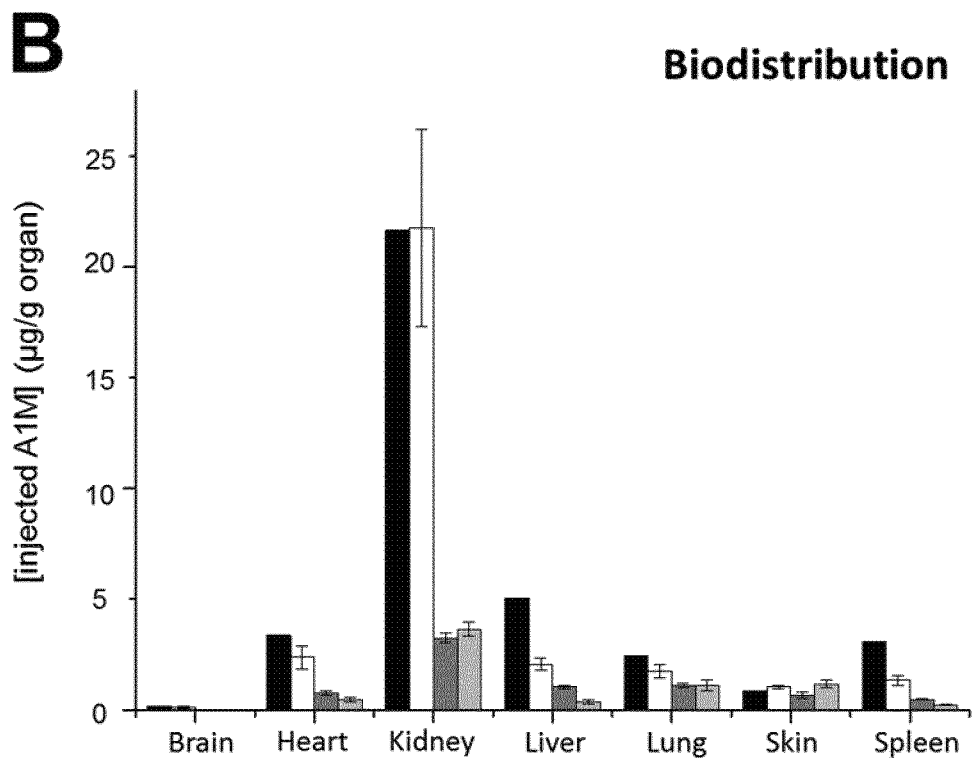

In Vivo Distribution of M8H4DK-wt A1M (wt-A1M) and M8H4DK-35-1M (35-A1M) in Mice Intravenously injected A1M was previously shown to be rapidly cleared from blood and predominantly localized to kidneys and liver in rats and mice (Larsson et al., 2001; Ahlstedt et al., 2015). We compared the clearance rates in blood and distribution in organs of wt-A1M and 35-A1M (FIG. 15). Similar turnover rates were seen during the first 60 min, whereas 35-A1M was cleared more rapidly after 1h. The distribution of A1M in the investigated organs after 10 and 30 min did not show any significant differences between the two proteins. Both wt-A1M and 35-A1M were found predominantly in kidneys, and smaller amounts were seen in heart, liver, lung, skin and spleen, while neglible amounts were found in brain.

In Vivo Protection of Kidneys by M8H4DK-Wt A1M (Wt-A1M) and M8H4DK-35-A1M (35-A1M)

Figure 16:
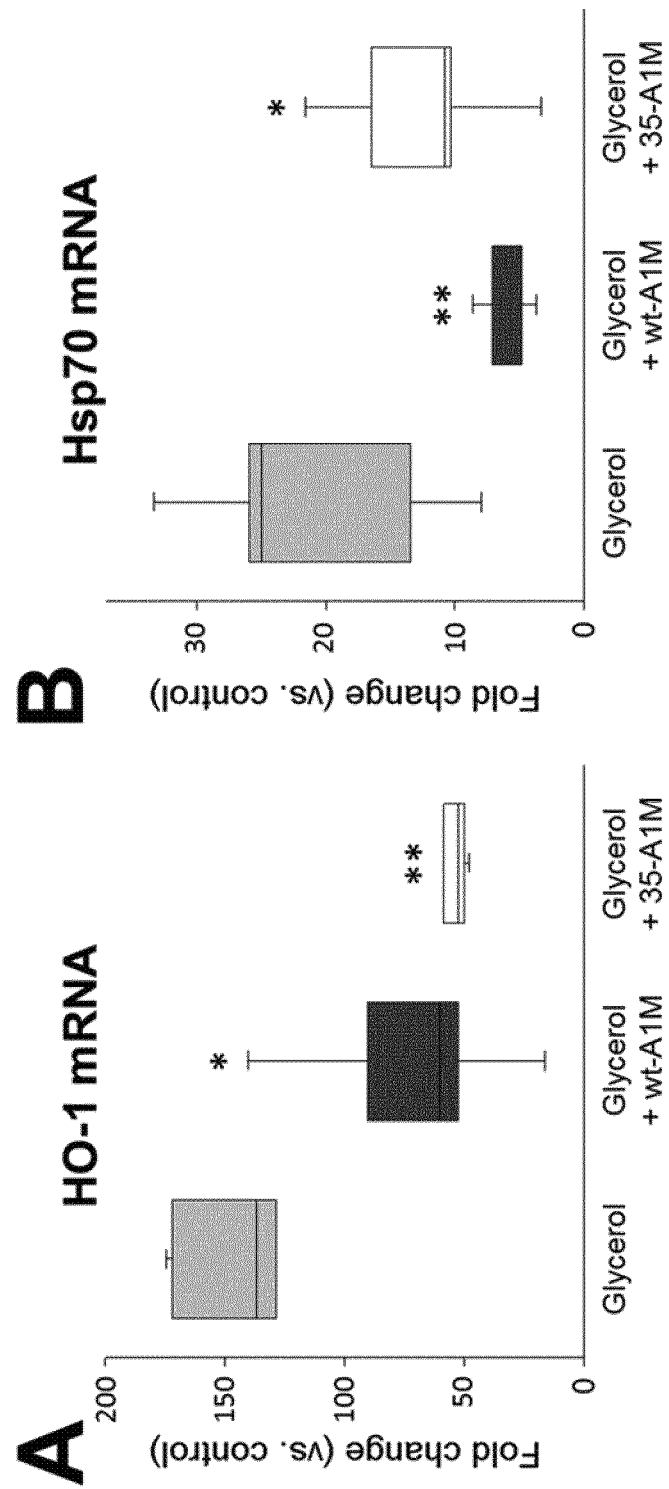

Previously, A1M has shown in vivo therapeutic effects in animal models where heme- and oxidative stress-related kidney injuries are induced (Wester-Rosenlöf et al., 2014; Nääv et al., 2015; Sverrison et al., 2014). Here, we investigated the in vivo protective effects of the two A1M-variants in a glycerol-injection rhabdomyolysis mouse model where acute kidney injuries (AKI) develops as a result of muscle rupture with release of myoglobin, free heme, radicals and other tissue components. The glycerol-injection resulted in a massive upregulation of the HO-1 and Hsp70 genes, two biomarkers of cellular stress (FIGS. 16A and B), and most of the upregulation was inhibited by simultaneous injection of wt-A1M or 35-A1M. No significant difference between the two A1M-variants were seen at the applied doses (7 mg/kg animal weight).

In summary, the investigations in phase III showed that the N17,96D-containing A1M-mutations significantly added stability to the A1M molecule, which was further improved when the R66H mutation was added. Furthermore, M8H4DK-tagged A1M variants were more stable than variants with a shorter tag or no tag. Therefore, the tag does not only serve as a purification tool but also provide A1M with increased stability and stability and does not interfere with function. The M8H4DK-R66H+N1796D (35-A1M) molecule show the same or better functional properties, possibly with the exception of the cytochrome c reduction. In conclusion, stability/solubility and functional studies suggest that M8H4DK-R66H+N17,96D (35-A1M) has improved molecular properties compared to M8H4DK-wt A1M (wt-A1M), and both Wt-A1M and 35-A1M show in vivo protective effects on kidneys using a rhabdomyolysis glycerol-injection model of acute kidney in-jury.

Further Stability Studies on M8H4DK-R66H+N1796D Vs M8H4DK-wt.

To further compare M8H4DK-R66H+N17,96D-A1M and wt-A1M, aggregation and function were tested with SEC-FPLC and the ABTS reduction assay after freeze-thaw cycles and storage at +4° C. and room temperature (FIG. 8). Samples (100 μM) of wt-A1M and R66H+N17,96D-A1M both tolerated 5× freeze-thaw cycles very well. As previously shown wt-A1M showed more aggregation after concentration to 1 mM than R66H+N17,96D-A1M, and similar results were seen after storage for 1 week compared to overnight. The increased aggregation of wt-A1M did not affect the ABTS reduction activity of 2 μM-samples. Ocular inspections show completely clear solutions of both variants after freeze-thaw, concentration and storage for 1 week at +4° C. To stress the A1M solutions further, 100 μM and 1 mM solutions were stored in room temperature for 1 week. Ocular inspection of the 100 μM solutions showed a slight cloudiness of wt-A1M, but the R66H+N17,96D-A1M solution remained clear. SEC-FPLC showed a decreased area under the curve of wt-A1M to 80% of the starting material, indicating loss of wt-A1M, although no increase in large aggregates was seen. The loss was most likely caused by precipitation of protein and removal by the filtration before the FPLC-run. For R66H+N17,96D-A1M, some increased aggregation could be seen, but no loss of protein after the storage at room-temperature for one week at 100 μM. In the ABTS assay, R66H+N17,96D-A1M still showed full activity, while a small decrease was seen for wt-A1M. Ocular inspection of 1 mM solutions stored for 1 week showed cloudiness of both variants, but the wt-A1M solution appeared thicker. When the solutions were diluted 10 times for loading onto the SEC, the precipitate of the R66H+N17,96D-A1M, but not wt-A1M, was resolved. In the SEC, very little aggregates were seen, but only 44% of the wt-A1M starting material remained. In contrast, 100% of R66H+N17,96D-A1M remained. In the ABTS assay wt-A1M had seriously decreased activity while the activity of R66H+N17,96D-A1M stayed the same. This study shows that M8H4DK-R66H+N17,96D-A1M can tolerate storage at high concentrations at room temperature, whereas wt-A1M cannot.

The stability of 1 mM solutions at 37° C. was investigated. The samples were incubated for 1.5, 2.5 and 4.5 h and then ocularly inspected, analysed by SEC-FPLC and the ABTS reduction assay (FIG. 9). After 1.5 h incubation, both solutions were still clear when ocularly inspected, but the SEC-FPLC revealed more aggregates in the wt-A1M solution (53%) compared to the R66H+N17,96D-A1M solution (28%). Only 67% of the starting material was eluted on the SEC of wt-A1M, while 100% was eluted of R66H+N17, 96D-A1M, estimated by the area under the curve. Both variants showed full activity in the ABTS assay. After 2.5 h of incubation the wt-A1M solution had become cloudy with precipitates impossible to resolve. 40% of the starting material was found on the SEC and the ABTS activity was significantly decreased. The R66H+N17,96D-A1M solution was still clear and showed full activity in the ABTS assay, but large aggregates had increased from 28 to 38% in the SEC-FPLC. After 4.5 h, the wt-A1M had developed into a thick substance, impossible to pipett. Therefore, it was not further analysed. The R66H+N17,96D-A1M had become cloudy, but was still possible to pipette. Some precipitation remained after dilution. The amount of protein eluted on the SEC was 44% of the starting material and a decreased activity in the ABTS assay was seen. The study suggest that following incubation at +37° C., A1M first forms resolvable aggregates, then it forms irreversible aggregates and loss of activity in the ABTS assay. Complete irreversible precipitation of wt-A1M was seen after 2.5 hours of incubation, and partial irreversible precipitation was seen only after 4.5 hours for M8H4DK-R66H+N17,96D-A1M. Hence, M8H4DK-R66H+N17,96D-A1M is more resistant to storage at +37° C. than M8H4DK-wt-A1M.

REFERENCES

Ahlstedt J, Tran TA, Strand F, Holmqvist B, Strand S-E, Gram M, and Åkerström B. Biodistribution and pharmacokinetics of recombinant $\alpha_1$-microglobulin and its potential use in radioprotection of kidneys. Am J Nucl Med Mol Imaging 5(4): 333-347, 2015. Alam J, Stewart D, Touchard C, Boinapally S, Choi AM, and Cook JL. Nrf2, a Cap'n'Collar transcription factor, regulates induction of the heme-oxygenase gene. J Biol Chem 274: 26071-26078, 1999.

Allhorn M, Berggård T, Nordberg J, Olsson M L, Åkerström B. Processing of the lipocalin $\alpha_1$-microglobulin by hemoglobin induces heme-binding and heme-degradation properties. Blood 99; 2002: 1894-1901.

Allhorn M, Klapyta A, Åkerström B. Redox properties of the lipocalin $\alpha_1$-microglobulin reduction of cytochrome c, hemoglobin, and free iron. Free Radic Biol Med 38; 2005: 557-567.

Anderson U D, Rutardottir S, Centlow M, Olsson MG, Kristensen, K, lsberg PE, Thilaganatan B, Akerström B, Hansson SR. Fetal hemoglobin and $\alpha_1$-microglobulin as first and early second trimester predictive biomarkers of preeclampsia. Am J Obst Gynecol 204; 2011: 520.e1-520.e5

Berggård T, Cohen A, Persson P, Lindqvist A, Cedervall T, Silow M, Thøgersen I B, Jönsson J-A, Enghild J J, Åkerstrom B. $\alpha_1$-Microglobulin chromophores are located to three lysine residues semiburied in the lipocalin pocket and associated with a novel lipophilic compound. Protein Sci. 8; 1999: 2611-2620.

Bergård T, Thelin N, Falkenberg C, Enghild J J, Åkerström B. Prothrombin, albumin and immunoglobulin A form covalent complexes with $\alpha_1$-microglobulin in human plasma. Eur J Biochem 245; 1997: 676-683.

Bratt T, Olsson H, Sjöberg E M, Jergil B, Åkerström B. Cleavage of the $\alpha_1$-microglobulin-bikunin precursor is localized to the Golgi apparatus of rat liver cells. Biochim Biophys Acta 1157; 1993: 147-154.

Centlow M, Carninci P, Nemeth K, Mezey E, Brownstein M, Hansson S R. Placental expression profiling in preeclampsia: local overproduction of hemoglobin may drive pathological changes. Fertility and sterility 90; 2008: 1834-1843.

Ekström B., Berggård I. Human $\alpha_1$-microglobulin: Purification procedure, chemical and physicochemical properties. J Biol Chem 252(22); 1977: 8048-8057.

Escribano J, Lopez-Otin C, Hjerpe A, Grubb A, Mendez E. Location and characterization of the three carbohydrate prosthetic groups of human protein HC. FEBS Lett 266 (1-2); 1990: 167-170.

Flower D R. The lipocalin family. Biochem J 318; 1996: 1-14.

Gram M, Anderson U D, Johansson M E, Edström-Hägerwall A, Larsson I, Jälmby M, Hansson S R, and Åkerström B. The human endogenous protection system against cell-free hemoglobin and heme is overwhelmed in preeclampsia and provides potential biomarkers and clinical indicators. *PloS One* 10(9): e0138111, 2015.

Hansson S R, Gram M and Åkerström B. Fetal hemoglobin in preeclampsia: a new etiological tool for prediction/diagnosis and a potential target for therapy. Curr Opin Obstet Gynecol. 25(6); 2013: 448-455.

Karnaukhova E, Rutardottir S, Majabi M, Wester Rosenlöf L, Alayash Al, Åkerström B. Characterization of heme binding to recombinant $\alpha_1$-microglobulin. Front Physiol 5; 2014: 465. doi: 10.3389/fphys.2014.00465.

Kaumeyer J F, Polazzi J O, Kotick M P. The mRNA for a proteinase inhibitor related to the HI-30 domain of inter-alpha-trypsin inhibitor also encodes $\alpha_1$-microglobulin (protein H C). Nucleic Acids Res 14(20); 1986: 7839-7850.

Kwasek A, Osmark P, Allhorn M, Lindqvist A, Åkerström B, Wasylewski Z. Production of recombinant human $\alpha_1$-microglobulin and mutated forms involved in chromophore formation. Prot. Expr. Purif. 53; 2007: 145-152.

Laemmli U K. Cleavage of structural proteins during the assembly of the head of bacteriophage T4. Nature 227; 1970: 680-685.

Larsson J, Wingårdh K, Berggård T, Davies J R, Lögdberg L, Strand S-E, Åkerström B. Distribution of $^{125}$I-labelled $\alpha_1$-microglobulin in rats after intravenous injection. J Lab Clin Med 137: 165-175, 2001

Lindqvist A, Bratt T, Altieri M, Kastern W, Åkerström B. Rat $\alpha_1$-microglobulin: co-expression in liver with the light chain of inter-alpha-trypsin inhibitor. Biochim Biophys Acta 1130; 1992: 63-67.

May K, Rosenlöf L, Olsson M G, Centlow M, Mörgelin M, Larsson I, Cederlund M, Rutardottir S, Schneider H, Siegmund W, Åkerström B, Hansson S R. Perfusion of human placenta with haemoglobin introduces preeclampsia-like injuries that are prevented by $\alpha_1$-microglobulin. Placenta 32(4); 2011: 323-332.

Meining W, Skerra A. The crystal structure of human $\alpha_1$-microglobulin reveals a potential haem-binding site. Biochem J. 445(2); 2012: 175-82.

Nääv A, Erlandsson L, Axelsson J, Larsson I, Johansson M, Wester Rosenlof L, Mörgelin M, Casslén V, Gram M, Åkerström B, Hansson S R. A1M ameliorates preeclampsia-like symptoms in placenta and kidney induced by cell-free fetal hemoglobin in rabbit. PloS One, 10(5); 2015: e0125499.

Olsson M G, Allhorn M, Larsson J, Cederlund M, Lundqvist, K, Schmidtchen A, Sorensen O E, Mörgelin M, Åkerström B. Up-regulation of A1M/$\alpha_1$-microglobulin in skin by heme and reactive oxygen species gives protection from oxidative damage. PLoS One 6(11); 2011: e27505.

Olsson M G, Centlow M, Rutardottir S, Stenfors I, Larsson J, Hosseini-Maaf B, Olsson M L, Hansson S R, Åkerström B. Increased levels of free hemoglobin, oxidation mark-ers, and the antioxidative heme scavenger $\alpha_1$-microglobulin in preeclampsia. Free Rad. Biol. Med. 48; 2010: 284-291.

Olsson M G, Olofsson T, Tapper H, Åkerström B. The lipocalin $\alpha_1$-microglobulin protects erythroid K562 cells against oxidative damage induced by heme and reactive oxygen species. Free Rad Res. 42; 2008: 725-736.

Olsson M G, Rosenlöf L W, Kotarsky H, Olofsson T, Leanderson T, Morgelin M, Fellman V, Åkerström B. The radical-binding lipocalin A1M binds to a Complex I subunit and protects mitochondrial structure and function. Antiox Redox Signal. 18(16); 2013: 2017-2028.

Rutardottir S, Karnaukhova E, Nantasenamat C, Songtawee N, Prachayasittikul V, Rajabi M, Wester Rosenlof L, Alayash A I, Åkerström B. Studies of two heme binding sites in A1M/$\alpha_1$-microglobulin using site-directed mutagenesis and molecular simulation. Biochim Biophys Acta 1864(1); 2016: 29-41.

Sala A, Campagnoli M, Perani E, Romano A, Labó S, Monzani E, Minchiotti L, Galliano M. Human $\alpha_1$-microglobulin is covalently bound to kynurenine-derived chromophores. J Biol Chem 279(49); 2004: 51033-51044.

Sverrisson K, Axelsson J, Rippe A, Gram M, Åkerström B, Hansson S R. Rippe B. Extracellular fetal hemoglobin (HbF) induces increases in glomerular permeability. Inhibi-tion with $\alpha_1$-microglobulin (A1M) and Tempol. Am J Physiol Renal Physiol 306(4); 2014: F442-448.

Wester-Rosenlöf L, Casslén V, Axelsson J, Edström-Hägerwall A, Gram M, Holmquist M, Johansson M E, Larsson I, Ley D, Marsal K, Morgelin M, Rippe B, Rutardottir S, Shohani B, Åkerström B, Hansson S R. A1M/$\alpha_1$-microglobulin protects from heme-induced placental and renal damage in a pregnant sheep model of preeclampsia. PLoS One 9(1); 2014: e86353.

Åkerström B, Borregaard N, Flower D, Salier J P. Lipocalins, an introduction. In Lipocalins. Eds. Åkerström B, Borregaard N, Flower D, Salier J P, Landes Bioscience, Georgetown Tex.

Åkerström B, Gram M. A1M, an extravascular tissue cleaning and house-keeping protein. Free Rad Biol Med 74; 2014: 274-282.

Åkerström B, Maghzal G J, Winterbourn C C, Kettle A J. The lipocalin a$_1$-microglobulin has radical scavenging activity. J Biol Chem 282; 2007: 31493-31503.

Åkerström B, Bratt T, Enghild J J. Formation of the $\alpha_1$-microglobulin chromophore in mammalian and insect cells: a novel post-translational mechanism? FEBS Lett 362, 50-54, 1995.

The invention claimed is:

1. An alpha-1-microglobulin protein variant selected from the group of amino acid sequences consisting of:

formula I:

(SEQ ID NO: 10)
$X^1-X^2-X^3-X^4-X^5-X^6-X^7-X^8-X^9-X^{10}-X^{11}-X^{12}-X^{13}-X^{14}$-GPVPTPPD

NIQVQENF-$X^{15}$-ISRIYGKWYNLAIGSTCPWLKKI-$X^{16}$-DRMTVSTLV

LGEGATEAEISMTST-$X^{17}$-WRKGVCEETSGAYEKTDTDGKFLYHKSKW- $X^{18}$-ITMESYVVHTNYDEYAIFLTKKFSRHHGPTITAKLYGRAPQLRETL

LQDFRVVAQGVGIPEDSIFTMADRGECVPGEQEPEPILIPR, and formula II:

(SEQ ID NO: 17)
$X^1-X^2-X^3-X^4-X^5-X^6-X^7-X^8-X^9-X^{10}-X^{11}-X^{12}-X^{13}-X^{14}$-GPVPTPPDN

IQVQENF-$X^{15}$-ISRIYGKWYNLAIGSTCPWLKKI-$X^{16}$-DRMTVSTLVLG

EGATEAEISMTST-$X^{17}$-WRKGVCEETSGAYEKTDTDGKFLYHKSKW-$X^{18}$-

ITMESYVVHTNYDEYAIFLTKKFSRHHGPTITAKLYGRAPQLRETLLQDF

RVVAQGVGIPEDSIFTMADRGECVPGEQEPEPI, wherein
at least one of $X^1$-$X^{14}$ is present,
$X^1$ is absent or represents Met or N-formyl Met;
$X^2$ is absent or represents His;
$X^3$ is absent or represents His;
$X^4$ is absent or represents His;
$X^5$ is absent or represents His;
$X^6$ is absent or represents His;
$X^7$ is absent or represents His;
$X^8$ is absent or represents His;
$X^9$ is absent or represents His;
$X^{10}$ is absent or selected from Asp, Glu, Lys, or Arg;
$X^{11}$ is absent or selected from Asp, Glu, Lys, or Arg;
$X^{12}$ is absent or selected from Asp, Glu, Lys, or Arg;
$X^{13}$ is absent or selected from Asp, Glu, Lys, or Arg;
$X^{14}$ is absent or selected from Asp, Glu, Lys, or Arg;
$X^{15}$ represents Asp;
$X^{16}$ represents Met;
$X^{17}$ represents His;
$X^{18}$ represents Asp;
or a pharmaceutically acceptable salt thereof.

2. The alpha-1-microglobulin protein variant according to claim 1,
wherein
$X^1$ is Met,
$X^2$-$X^{14}$ are absent,
$X^{15}$ is Asp,
$X^{16}$ is Met,
$X^{17}$ is His, and
$X^{18}$ is Asp.

3. The alpha-1-microglobulin protein variant according to claim 2, having the amino acid sequence of SEQ ID NO: 3 or SEQ ID NO: 18.

4. The alpha-1-microglobulin protein variant according to claim 1,
wherein
$X^1$ is Met or N-formyl Met,
$X^2$-$X^7$ are His
$X^8$ and $X^9$ are absent,
$X^{10}$-$X^{13}$ are Asp,
$X^{14}$ is Lys,
$X^{15}$ is Asp,
$X^{16}$ is Met,
$X^{17}$ is His, and
$X^{18}$ is Asp.

5. The alpha-1-microglobulin protein variant according to claim 4, having the amino acid sequence of SEQ ID NO: 5 or SEQ ID NO: 20.

6. The alpha-1-microglobulin protein variant according to claim 1, wherein
$X^1$ is Met or N-formyl Met,
$X^2$-$X^9$ are His
$X^{10}$-$X^{13}$ are Asp,
$X^{14}$ is Lys,
$X^{15}$ is Asp,
$X^{16}$ is Met,
$X^{17}$ is His, and
$X^{18}$ is Asp.

7. The alpha-1-microglobulin protein variant according to claim 6, having the amino acid sequence of SEQ ID NO: 7 or SEQ ID NO: 22.

8. The alpha-1-microglobulin protein variant according to claim 1, wherein the protein variant is an antioxidant.

9. The alpha-1-microglobulin protein variant according to claim 1, wherein the protein variant binds heme.

10. A pharmaceutical composition comprising an alpha-1-microglobulin protein variant according to claim 1 and one or more pharmaceutically acceptable excipients.

* * * * *

SEQUENCE LISTING

```
<160> NUMBER OF SEQ ID NOS: 114

<210> SEQ ID NO 1
<211> LENGTH: 183
<212> TYPE: PRT
<213> ORGANISM: Homo sapiens
<220> FEATURE:
<223> OTHER INFORMATION: Wildtype human A1M, no mutations

<400> SEQUENCE: 1

Gly Pro Val Pro Thr Pro Pro Asp Asn Ile Gln Val Gln Glu Asn Phe
1               5                   10                  15

Asn Ile Ser Arg Ile Tyr Gly Lys Trp Tyr Asn Leu Ala Ile Gly Ser
            20                  25                  30

Thr Cys Pro Trp Leu Lys Lys Ile Met Asp Arg Met Thr Val Ser Thr
        35                  40                  45

Leu Val Leu Gly Glu Gly Ala Thr Glu Ala Glu Ile Ser Met Thr Ser
    50                  55                  60

Thr Arg Trp Arg Lys Gly Val Cys Glu Glu Thr Ser Gly Ala Tyr Glu
65                  70                  75                  80

Lys Thr Asp Thr Asp Gly Lys Phe Leu Tyr His Lys Ser Lys Trp Asn
                85                  90                  95

Ile Thr Met Glu Ser Tyr Val Val His Thr Asn Tyr Asp Glu Tyr Ala
            100                 105                 110

Ile Phe Leu Thr Lys Lys Phe Ser Arg His His Gly Pro Thr Ile Thr
        115                 120                 125

Ala Lys Leu Tyr Gly Arg Ala Pro Gln Leu Arg Glu Thr Leu Leu Gln
    130                 135                 140

Asp Phe Arg Val Val Ala Gln Gly Val Gly Ile Pro Glu Asp Ser Ile
145                 150                 155                 160

Phe Thr Met Ala Asp Arg Gly Glu Cys Val Pro Gly Glu Gln Glu Pro
                165                 170                 175
```

```
Glu Pro Ile Leu Ile Pro Arg
            180

<210> SEQ ID NO 2
<211> LENGTH: 184
<212> TYPE: PRT
<213> ORGANISM: Homo sapiens
<220> FEATURE:
<223> OTHER INFORMATION: rhA1M, ie N-terminal Met

<400> SEQUENCE: 2

Met Gly Pro Val Pro Thr Pro Pro Asp Asn Ile Gln Val Gln Glu Asn
1               5                   10                  15

Phe Asn Ile Ser Arg Ile Tyr Gly Lys Trp Tyr Asn Leu Ala Ile Gly
            20                  25                  30

Ser Thr Cys Pro Trp Leu Lys Lys Ile Met Asp Arg Met Thr Val Ser
        35                  40                  45

Thr Leu Val Leu Gly Glu Gly Ala Thr Glu Ala Glu Ile Ser Met Thr
    50                  55                  60

Ser Thr Arg Trp Arg Lys Gly Val Cys Glu Glu Thr Ser Gly Ala Tyr
65                  70                  75                  80

Glu Lys Thr Asp Thr Asp Gly Lys Phe Leu Tyr His Lys Ser Lys Trp
                85                  90                  95

Asn Ile Thr Met Glu Ser Tyr Val Val His Thr Asn Tyr Asp Glu Tyr
            100                 105                 110

Ala Ile Phe Leu Thr Lys Lys Phe Ser Arg His His Gly Pro Thr Ile
        115                 120                 125

Thr Ala Lys Leu Tyr Gly Arg Ala Pro Gln Leu Arg Glu Thr Leu Leu
    130                 135                 140

Gln Asp Phe Arg Val Val Ala Gln Gly Val Gly Ile Pro Glu Asp Ser
145                 150                 155                 160

Ile Phe Thr Met Ala Asp Arg Gly Glu Cys Val Pro Gly Glu Gln Glu
                165                 170                 175

Pro Glu Pro Ile Leu Ile Pro Arg
            180

<210> SEQ ID NO 3
<211> LENGTH: 184
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: hA1M, No tag, N-terminal Met, N17,96D; R66H

<400> SEQUENCE: 3

Met Gly Pro Val Pro Thr Pro Pro Asp Asn Ile Gln Val Gln Glu Asn
1               5                   10                  15

Phe Asp Ile Ser Arg Ile Tyr Gly Lys Trp Tyr Asn Leu Ala Ile Gly
            20                  25                  30

Ser Thr Cys Pro Trp Leu Lys Lys Ile Met Asp Arg Met Thr Val Ser
        35                  40                  45

Thr Leu Val Leu Gly Glu Gly Ala Thr Glu Ala Glu Ile Ser Met Thr
    50                  55                  60

Ser Thr His Trp Arg Lys Gly Val Cys Glu Glu Thr Ser Gly Ala Tyr
65                  70                  75                  80

Glu Lys Thr Asp Thr Asp Gly Lys Phe Leu Tyr His Lys Ser Lys Trp
```

```
                    85                  90                  95
Asp Ile Thr Met Glu Ser Tyr Val Val His Thr Asn Tyr Asp Glu Tyr
                100                 105                 110

Ala Ile Phe Leu Thr Lys Lys Phe Ser Arg His His Gly Pro Thr Ile
            115                 120                 125

Thr Ala Lys Leu Tyr Gly Arg Ala Pro Gln Leu Arg Glu Thr Leu Leu
        130                 135                 140

Gln Asp Phe Arg Val Val Ala Gln Gly Val Gly Ile Pro Glu Asp Ser
145                 150                 155                 160

Ile Phe Thr Met Ala Asp Arg Gly Glu Cys Val Pro Gly Glu Gln Glu
                165                 170                 175

Pro Glu Pro Ile Leu Ile Pro Arg
            180

<210> SEQ ID NO 4
<211> LENGTH: 184
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: hA1M, not tag, N-terminal Met, M41K

<400> SEQUENCE: 4

Met Gly Pro Val Pro Thr Pro Pro Asp Asn Ile Gln Val Gln Glu Asn
1               5                   10                  15

Phe Asn Ile Ser Arg Ile Tyr Gly Lys Trp Tyr Asn Leu Ala Ile Gly
            20                  25                  30

Ser Thr Cys Pro Trp Leu Lys Lys Ile Lys Asp Arg Met Thr Val Ser
        35                  40                  45

Thr Leu Val Leu Gly Glu Gly Ala Thr Glu Ala Glu Ile Ser Met Thr
    50                  55                  60

Ser Thr Arg Trp Arg Lys Gly Val Cys Glu Glu Thr Ser Gly Ala Tyr
65                  70                  75                  80

Glu Lys Thr Asp Thr Asp Gly Lys Phe Leu Tyr His Lys Ser Lys Trp
                85                  90                  95

Asn Ile Thr Met Glu Ser Tyr Val Val His Thr Asn Tyr Asp Glu Tyr
                100                 105                 110

Ala Ile Phe Leu Thr Lys Lys Phe Ser Arg His His Gly Pro Thr Ile
            115                 120                 125

Thr Ala Lys Leu Tyr Gly Arg Ala Pro Gln Leu Arg Glu Thr Leu Leu
        130                 135                 140

Gln Asp Phe Arg Val Val Ala Gln Gly Val Gly Ile Pro Glu Asp Ser
145                 150                 155                 160

Ile Phe Thr Met Ala Asp Arg Gly Glu Cys Val Pro Gly Glu Gln Glu
                165                 170                 175

Pro Glu Pro Ile Leu Ile Pro Arg
            180

<210> SEQ ID NO 5
<211> LENGTH: 195
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 6His, N17,96D; R66H
```

<400> SEQUENCE: 5

```
Met His His His His His Asp Asp Asp Lys Gly Pro Val Pro
1               5                   10                  15

Thr Pro Pro Asp Asn Ile Gln Val Gln Glu Asn Phe Asp Ile Ser Arg
            20                  25                  30

Ile Tyr Gly Lys Trp Tyr Asn Leu Ala Ile Gly Ser Thr Cys Pro Trp
        35                  40                  45

Leu Lys Lys Ile Met Asp Arg Met Thr Val Ser Thr Leu Val Leu Gly
    50                  55                  60

Glu Gly Ala Thr Glu Ala Glu Ile Ser Met Thr Ser Thr His Trp Arg
65                  70                  75                  80

Lys Gly Val Cys Glu Glu Thr Ser Gly Ala Tyr Glu Lys Thr Asp Thr
                85                  90                  95

Asp Gly Lys Phe Leu Tyr His Lys Ser Lys Trp Asp Ile Thr Met Glu
            100                 105                 110

Ser Tyr Val Val His Thr Asn Tyr Asp Glu Tyr Ala Ile Phe Leu Thr
        115                 120                 125

Lys Lys Phe Ser Arg His His Gly Pro Thr Ile Thr Ala Lys Leu Tyr
    130                 135                 140

Gly Arg Ala Pro Gln Leu Arg Glu Thr Leu Leu Gln Asp Phe Arg Val
145                 150                 155                 160

Val Ala Gln Gly Val Gly Ile Pro Glu Asp Ser Ile Phe Thr Met Ala
                165                 170                 175

Asp Arg Gly Glu Cys Val Pro Gly Glu Gln Glu Pro Glu Pro Ile Leu
            180                 185                 190

Ile Pro Arg
        195
```

<210> SEQ ID NO 6
<211> LENGTH: 195
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: hA1M, 6His, M41K

<400> SEQUENCE: 6

```
Met His His His His His Asp Asp Asp Lys Gly Pro Val Pro
1               5                   10                  15

Thr Pro Pro Asp Asn Ile Gln Val Gln Glu Asn Phe Asn Ile Ser Arg
            20                  25                  30

Ile Tyr Gly Lys Trp Tyr Asn Leu Ala Ile Gly Ser Thr Cys Pro Trp
        35                  40                  45

Leu Lys Lys Ile Lys Asp Arg Met Thr Val Ser Thr Leu Val Leu Gly
    50                  55                  60

Glu Gly Ala Thr Glu Ala Glu Ile Ser Met Thr Ser Thr Arg Trp Arg
65                  70                  75                  80

Lys Gly Val Cys Glu Glu Thr Ser Gly Ala Tyr Glu Lys Thr Asp Thr
                85                  90                  95

Asp Gly Lys Phe Leu Tyr His Lys Ser Lys Trp Asn Ile Thr Met Glu
            100                 105                 110

Ser Tyr Val Val His Thr Asn Tyr Asp Glu Tyr Ala Ile Phe Leu Thr
        115                 120                 125
```

```
Lys Lys Phe Ser Arg His His Gly Pro Thr Ile Thr Ala Lys Leu Tyr
        130                 135                 140
Gly Arg Ala Pro Gln Leu Arg Glu Thr Leu Leu Gln Asp Phe Arg Val
145                 150                 155                 160
Val Ala Gln Gly Val Gly Ile Pro Glu Asp Ser Ile Phe Thr Met Ala
                165                 170                 175
Asp Arg Gly Glu Cys Val Pro Gly Glu Gln Glu Pro Glu Pro Ile Leu
                180                 185                 190
Ile Pro Arg
        195

<210> SEQ ID NO 7
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8His, N17,96D; R66H

<400> SEQUENCE: 7

Met His His His His His His His Asp Asp Asp Lys Gly Pro
1               5                   10                  15
Val Pro Thr Pro Pro Asp Asn Ile Gln Val Gln Glu Asn Phe Asp Ile
                20                  25                  30
Ser Arg Ile Tyr Gly Lys Trp Tyr Asn Leu Ala Ile Gly Ser Thr Cys
            35                  40                  45
Pro Trp Leu Lys Lys Ile Met Asp Arg Met Thr Val Ser Thr Leu Val
    50                  55                  60
Leu Gly Glu Gly Ala Thr Glu Ala Glu Ile Ser Met Thr Ser Thr His
65                  70                  75                  80
Trp Arg Lys Gly Val Cys Glu Glu Thr Ser Gly Ala Tyr Glu Lys Thr
                85                  90                  95
Asp Thr Asp Gly Lys Phe Leu Tyr His Lys Ser Lys Trp Asp Ile Thr
                100                 105                 110
Met Glu Ser Tyr Val Val His Thr Asn Tyr Asp Glu Tyr Ala Ile Phe
            115                 120                 125
Leu Thr Lys Lys Phe Ser Arg His His Gly Pro Thr Ile Thr Ala Lys
    130                 135                 140
Leu Tyr Gly Arg Ala Pro Gln Leu Arg Glu Thr Leu Leu Gln Asp Phe
145                 150                 155                 160
Arg Val Val Ala Gln Gly Val Gly Ile Pro Glu Asp Ser Ile Phe Thr
                165                 170                 175
Met Ala Asp Arg Gly Glu Cys Val Pro Gly Glu Gln Glu Pro Glu Pro
                180                 185                 190
Ile Leu Ile Pro Arg
        195

<210> SEQ ID NO 8
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: hA1M, 8His, M41K

<400> SEQUENCE: 8
```

Met His His His His His His His Asp Asp Asp Lys Gly Pro
1               5                       10                      15

Val Pro Thr Pro Pro Asp Asn Ile Gln Val Gln Glu Asn Phe Asn Ile
            20                      25                      30

Ser Arg Ile Tyr Gly Lys Trp Tyr Asn Leu Ala Ile Gly Ser Thr Cys
        35                      40                      45

Pro Trp Leu Lys Lys Ile Lys Asp Arg Met Thr Val Ser Thr Leu Val
    50                      55                      60

Leu Gly Glu Gly Ala Thr Glu Ala Glu Ile Ser Met Thr Ser Thr Arg
65                      70                      75                      80

Trp Arg Lys Gly Val Cys Glu Glu Thr Ser Gly Ala Tyr Glu Lys Thr
                85                      90                      95

Asp Thr Asp Gly Lys Phe Leu Tyr His Lys Ser Lys Trp Asn Ile Thr
                100                     105                     110

Met Glu Ser Tyr Val Val His Thr Asn Tyr Asp Glu Tyr Ala Ile Phe
            115                     120                     125

Leu Thr Lys Lys Phe Ser Arg His His Gly Pro Thr Ile Thr Ala Lys
    130                     135                     140

Leu Tyr Gly Arg Ala Pro Gln Leu Arg Glu Thr Leu Leu Gln Asp Phe
145                     150                     155                     160

Arg Val Val Ala Gln Gly Val Gly Ile Pro Glu Asp Ser Ile Phe Thr
                165                     170                     175

Met Ala Asp Arg Gly Glu Cys Val Pro Gly Glu Gln Glu Pro Glu Pro
            180                     185                     190

Ile Leu Ile Pro Arg
        195

<210> SEQ ID NO 9
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: hA1M, 8His, no mut

<400> SEQUENCE: 9

Met His His His His His His His Asp Asp Asp Lys Gly Pro
1               5                       10                      15

Val Pro Thr Pro Pro Asp Asn Ile Gln Val Gln Glu Asn Phe Asn Ile
            20                      25                      30

Ser Arg Ile Tyr Gly Lys Trp Tyr Asn Leu Ala Ile Gly Ser Thr Cys
        35                      40                      45

Pro Trp Leu Lys Lys Ile Met Asp Arg Met Thr Val Ser Thr Leu Val
    50                      55                      60

Leu Gly Glu Gly Ala Thr Glu Ala Glu Ile Ser Met Thr Ser Thr Arg
65                      70                      75                      80

Trp Arg Lys Gly Val Cys Glu Glu Thr Ser Gly Ala Tyr Glu Lys Thr
                85                      90                      95

Asp Thr Asp Gly Lys Phe Leu Tyr His Lys Ser Lys Trp Asn Ile Thr
                100                     105                     110

Met Glu Ser Tyr Val Val His Thr Asn Tyr Asp Glu Tyr Ala Ile Phe
            115                     120                     125

Leu Thr Lys Lys Phe Ser Arg His His Gly Pro Thr Ile Thr Ala Lys
    130                     135                     140

```
Leu Tyr Gly Arg Ala Pro Gln Leu Arg Glu Thr Leu Leu Gln Asp Phe
145                 150                 155                 160

Arg Val Val Ala Gln Gly Val Gly Ile Pro Glu Asp Ser Ile Phe Thr
                165                 170                 175

Met Ala Asp Arg Gly Glu Cys Val Pro Gly Gln Glu Pro Glu Pro
            180                 185                 190

Ile Leu Ile Pro Arg
        195

<210> SEQ ID NO 10
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met, N-formyl Met or not present
<220> FEATURE:
<221> NAME/KEY: MOD_RES
<222> LOCATION: (2)..(9)
<223> OTHER INFORMATION: May or may not be present
<220> FEATURE:
<221> NAME/KEY: MOD_RES
<222> LOCATION: (10)..(13)
<223> OTHER INFORMATION: Asp, Glu, Lys, Arg or not present
<220> FEATURE:
<221> NAME/KEY: MOD_RES
<222> LOCATION: (14)..(14)
<223> OTHER INFORMATION: Lys, Glu, Asp, Arg, Met, N-formyl Met or not
      present
<220> FEATURE:
<221> NAME/KEY: MOD_RES
<222> LOCATION: (31)..(31)
<223> OTHER INFORMATION: Asp, Asn or Glu
<220> FEATURE:
<221> NAME/KEY: MOD_RES
<222> LOCATION: (55)..(55)
<223> OTHER INFORMATION: Met, Lys or Arg
<220> FEATURE:
<221> NAME/KEY: MOD_RES
<222> LOCATION: (80)..(80)
<223> OTHER INFORMATION: Arg, His or Lys
<220> FEATURE:
<221> NAME/KEY: MOD_RES
<222> LOCATION: (110)..(110)
<223> OTHER INFORMATION: Asp, Asn or Glu
<220> FEATURE:
<223> OTHER INFORMATION: See specification as filed for detailed
      description of substitutions and preferred embodiments

<400> SEQUENCE: 10

Met His His His His His His His Xaa Xaa Xaa Xaa Xaa Gly Pro
1               5                   10                  15

Val Pro Thr Pro Pro Asp Asn Ile Gln Val Gln Glu Asn Phe Xaa Ile
                20                  25                  30

Ser Arg Ile Tyr Gly Lys Trp Tyr Asn Leu Ala Ile Gly Ser Thr Cys
            35                  40                  45

Pro Trp Leu Lys Lys Ile Xaa Asp Arg Met Thr Val Ser Thr Leu Val
        50                  55                  60

Leu Gly Glu Gly Ala Thr Glu Ala Glu Ile Ser Met Thr Ser Thr Xaa
65                  70                  75                  80

Trp Arg Lys Gly Val Cys Glu Glu Thr Ser Gly Ala Tyr Glu Lys Thr
                85                  90                  95

Asp Thr Asp Gly Lys Phe Leu Tyr His Lys Ser Lys Trp Xaa Ile Thr
```

```
                100             105             110
Met Glu Ser Tyr Val Val His Thr Asn Tyr Asp Glu Tyr Ala Ile Phe
        115                 120                 125

Leu Thr Lys Lys Phe Ser Arg His Gly Pro Thr Ile Thr Ala Lys
130                 135                 140

Leu Tyr Gly Arg Ala Pro Gln Leu Arg Glu Thr Leu Leu Gln Asp Phe
145                 150                 155                 160

Arg Val Val Ala Gln Gly Val Gly Ile Pro Glu Asp Ser Ile Phe Thr
                165                 170                 175

Met Ala Asp Arg Gly Glu Cys Val Pro Gly Glu Gln Glu Pro Glu Pro
            180                 185                 190

Ile Leu Ile Pro Arg
        195

<210> SEQ ID NO 11
<211> LENGTH: 16
<212> TYPE: PRT
<213> ORGANISM: Homo sapiens
<220> FEATURE:
<223> OTHER INFORMATION: Y1

<400> SEQUENCE: 11

Gly Pro Val Pro Thr Pro Pro Asp Asn Ile Gln Val Gln Glu Asn Phe
1               5                   10                  15

<210> SEQ ID NO 12
<211> LENGTH: 23
<212> TYPE: PRT
<213> ORGANISM: Homo sapiens
<220> FEATURE:
<223> OTHER INFORMATION: Y2

<400> SEQUENCE: 12

Ile Ser Arg Ile Tyr Gly Lys Trp Tyr Asn Leu Ala Ile Gly Ser Thr
1               5                   10                  15

Cys Pro Trp Leu Lys Lys Ile
            20

<210> SEQ ID NO 13
<211> LENGTH: 24
<212> TYPE: PRT
<213> ORGANISM: Homo sapiens
<220> FEATURE:
<223> OTHER INFORMATION: Y3

<400> SEQUENCE: 13

Asp Arg Met Thr Val Ser Thr Leu Val Leu Gly Glu Gly Ala Thr Glu
1               5                   10                  15

Ala Glu Ile Ser Met Thr Ser Thr
            20

<210> SEQ ID NO 14
<211> LENGTH: 29
<212> TYPE: PRT
<213> ORGANISM: Homo sapiens
<220> FEATURE:
<223> OTHER INFORMATION: Y4

<400> SEQUENCE: 14

Trp Arg Lys Gly Val Cys Glu Glu Thr Ser Gly Ala Tyr Glu Lys Thr
1               5                   10                  15

Asp Thr Asp Gly Lys Phe Leu Tyr His Lys Ser Lys Trp
```

```
                    20                  25

<210> SEQ ID NO 15
<211> LENGTH: 87
<212> TYPE: PRT
<213> ORGANISM: Homo sapiens
<220> FEATURE:
<223> OTHER INFORMATION: Y5

<400> SEQUENCE: 15

Ile Thr Met Glu Ser Tyr Val Val His Thr Asn Tyr Asp Glu Tyr Ala
1               5                   10                  15

Ile Phe Leu Thr Lys Lys Phe Ser Arg His His Gly Pro Thr Ile Thr
            20                  25                  30

Ala Lys Leu Tyr Gly Arg Ala Pro Gln Leu Arg Glu Thr Leu Leu Gln
        35                  40                  45

Asp Phe Arg Val Val Ala Gln Gly Val Gly Ile Pro Glu Asp Ser Ile
    50                  55                  60

Phe Thr Met Ala Asp Arg Gly Glu Cys Val Pro Gly Glu Gln Glu Pro
65                  70                  75                  80

Glu Pro Ile Leu Ile Pro Arg
                85

<210> SEQ ID NO 16
<211> LENGTH: 87
<212> TYPE: PRT
<213> ORGANISM: Homo sapiens
<220> FEATURE:
<223> OTHER INFORMATION: Y5

<400> SEQUENCE: 16

Ile Thr Met Glu Ser Tyr Val Val His Thr Asn Tyr Asp Glu Tyr Ala
1               5                   10                  15

Ile Phe Leu Thr Lys Lys Phe Ser Arg His His Gly Pro Thr Ile Thr
            20                  25                  30

Ala Lys Leu Tyr Gly Arg Ala Pro Gln Leu Arg Glu Thr Leu Leu Gln
        35                  40                  45

Asp Phe Arg Val Val Ala Gln Gly Val Gly Ile Pro Glu Asp Ser Ile
    50                  55                  60

Phe Thr Met Ala Asp Arg Gly Glu Cys Val Pro Gly Glu Gln Glu Pro
65                  70                  75                  80

Glu Pro Ile Leu Ile Pro Arg
                85

<210> SEQ ID NO 17
<211> LENGTH: 193
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met, N-formyl Met or not present
<220> FEATURE:
<221> NAME/KEY: MOD_RES
<222> LOCATION: (2)..(9)
<223> OTHER INFORMATION: May or may not be present
<220> FEATURE:
<221> NAME/KEY: MOD_RES
<222> LOCATION: (10)..(13)
<223> OTHER INFORMATION: Asp, Glu, Lys, Arg or not present
<220> FEATURE:
```

<221> NAME/KEY: MOD_RES
<222> LOCATION: (14)..(14)
<223> OTHER INFORMATION: Lys, Glu, Asp, Arg, Met, N-formyl Met or not
    present
<220> FEATURE:
<221> NAME/KEY: MOD_RES
<222> LOCATION: (31)..(31)
<223> OTHER INFORMATION: Asp, Asn or Glu
<220> FEATURE:
<221> NAME/KEY: MOD_RES
<222> LOCATION: (55)..(55)
<223> OTHER INFORMATION: Met, Lys or Arg
<220> FEATURE:
<221> NAME/KEY: MOD_RES
<222> LOCATION: (80)..(80)
<223> OTHER INFORMATION: Arg, His or Lys
<220> FEATURE:
<221> NAME/KEY: MOD_RES
<222> LOCATION: (110)..(110)
<223> OTHER INFORMATION: Asp, Asn or Glu
<220> FEATURE:
<223> OTHER INFORMATION: See specification as filed for detailed
    description of substitutions and preferred embodiments

<400> SEQUENCE: 17

Met His His His His His His His Xaa Xaa Xaa Xaa Xaa Gly Pro
1               5                   10                  15

Val Pro Thr Pro Pro Asp Asn Ile Gln Val Gln Glu Asn Phe Xaa Ile
            20                  25                  30

Ser Arg Ile Tyr Gly Lys Trp Tyr Asn Leu Ala Ile Gly Ser Thr Cys
        35                  40                  45

Pro Trp Leu Lys Lys Ile Xaa Asp Arg Met Thr Val Ser Thr Leu Val
    50                  55                  60

Leu Gly Glu Gly Ala Thr Glu Ala Glu Ile Ser Met Thr Ser Thr Xaa
65              70                  75                  80

Trp Arg Lys Gly Val Cys Glu Glu Thr Ser Gly Ala Tyr Glu Lys Thr
                85                  90                  95

Asp Thr Asp Gly Lys Phe Leu Tyr His Lys Ser Lys Trp Xaa Ile Thr
            100                 105                 110

Met Glu Ser Tyr Val Val His Thr Asn Tyr Asp Glu Tyr Ala Ile Phe
        115                 120                 125

Leu Thr Lys Lys Phe Ser Arg His His Gly Pro Thr Ile Thr Ala Lys
    130                 135                 140

Leu Tyr Gly Arg Ala Pro Gln Leu Arg Glu Thr Leu Leu Gln Asp Phe
145                 150                 155                 160

Arg Val Val Ala Gln Gly Val Gly Ile Pro Glu Asp Ser Ile Phe Thr
                165                 170                 175

Met Ala Asp Arg Gly Glu Cys Val Pro Gly Glu Gln Glu Pro Glu Pro
            180                 185                 190

Ile

<210> SEQ ID NO 18
<211> LENGTH: 180
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: hA1M, No tag, N-terminal Met, N17,96D; R66H;
    truncated

<400> SEQUENCE: 18

Met Gly Pro Val Pro Thr Pro Pro Asp Asn Ile Gln Val Gln Glu Asn

```
                1               5                   10                  15
        Phe Asp Ile Ser Arg Ile Tyr Gly Lys Trp Tyr Asn Leu Ala Ile Gly
                        20                  25                  30

Ser Thr Cys Pro Trp Leu Lys Lys Ile Met Asp Arg Met Thr Val Ser
                        35                  40                  45

Thr Leu Val Leu Gly Glu Gly Ala Thr Glu Ala Glu Ile Ser Met Thr
                        50                  55                  60

Ser Thr His Trp Arg Lys Gly Val Cys Glu Glu Thr Ser Gly Ala Tyr
        65                      70                  75                  80

Glu Lys Thr Asp Thr Asp Gly Lys Phe Leu Tyr His Lys Ser Lys Trp
                        85                  90                  95

Asp Ile Thr Met Glu Ser Tyr Val Val His Thr Asn Tyr Asp Glu Tyr
                        100                 105                 110

Ala Ile Phe Leu Thr Lys Lys Phe Ser Arg His His Gly Pro Thr Ile
                        115                 120                 125

Thr Ala Lys Leu Tyr Gly Arg Ala Pro Gln Leu Arg Glu Thr Leu Leu
                        130                 135                 140

Gln Asp Phe Arg Val Val Ala Gln Gly Val Gly Ile Pro Glu Asp Ser
        145                     150                 155                 160

Ile Phe Thr Met Ala Asp Arg Gly Glu Cys Val Pro Gly Glu Gln Glu
                        165                 170                 175

Pro Glu Pro Ile
                        180

<210> SEQ ID NO 19
<211> LENGTH: 184
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: hA1M, not tag, N-terminal Met, M41K; truncated

<400> SEQUENCE: 19

Met Gly Pro Val Pro Thr Pro Pro Asp Asn Ile Gln Val Gln Glu Asn
        1               5                   10                  15

Phe Asn Ile Ser Arg Ile Tyr Gly Lys Trp Tyr Asn Leu Ala Ile Gly
                        20                  25                  30

Ser Thr Cys Pro Trp Leu Lys Lys Ile Lys Asp Arg Met Thr Val Ser
                        35                  40                  45

Thr Leu Val Leu Gly Glu Gly Ala Thr Glu Ala Glu Ile Ser Met Thr
                        50                  55                  60

Ser Thr Arg Trp Arg Lys Gly Val Cys Glu Glu Thr Ser Gly Ala Tyr
        65                      70                  75                  80

Glu Lys Thr Asp Thr Asp Gly Lys Phe Leu Tyr His Lys Ser Lys Trp
                        85                  90                  95

Asn Ile Thr Met Glu Ser Tyr Val Val His Thr Asn Tyr Asp Glu Tyr
                        100                 105                 110

Ala Ile Phe Leu Thr Lys Lys Phe Ser Arg His His Gly Pro Thr Ile
                        115                 120                 125

Thr Ala Lys Leu Tyr Gly Arg Ala Pro Gln Leu Arg Glu Thr Leu Leu
                        130                 135                 140

Gln Asp Phe Arg Val Val Ala Gln Gly Val Gly Ile Pro Glu Asp Ser
        145                     150                 155                 160

Ile Phe Thr Met Ala Asp Arg Gly Glu Cys Val Pro Gly Glu Gln Glu
```

```
                        165                 170                 175

Pro Glu Pro Ile Leu Ile Pro Arg
            180

<210> SEQ ID NO 20
<211> LENGTH: 191
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 6His, N17,96D; R66H; truncated

<400> SEQUENCE: 20

Met His His His His His Asp Asp Asp Lys Gly Pro Val Pro
1               5                   10                  15

Thr Pro Pro Asp Asn Ile Gln Val Gln Glu Asn Phe Asp Ile Ser Arg
            20                  25                  30

Ile Tyr Gly Lys Trp Tyr Asn Leu Ala Ile Gly Ser Thr Cys Pro Trp
        35                  40                  45

Leu Lys Lys Ile Met Asp Arg Met Thr Val Ser Thr Leu Val Leu Gly
    50                  55                  60

Glu Gly Ala Thr Glu Ala Glu Ile Ser Met Thr Ser Thr His Trp Arg
65                  70                  75                  80

Lys Gly Val Cys Glu Glu Thr Ser Gly Ala Tyr Glu Lys Thr Asp Thr
                85                  90                  95

Asp Gly Lys Phe Leu Tyr His Lys Ser Lys Trp Asp Ile Thr Met Glu
            100                 105                 110

Ser Tyr Val Val His Thr Asn Tyr Asp Glu Tyr Ala Ile Phe Leu Thr
        115                 120                 125

Lys Lys Phe Ser Arg His His Gly Pro Thr Ile Thr Ala Lys Leu Tyr
    130                 135                 140

Gly Arg Ala Pro Gln Leu Arg Glu Thr Leu Leu Gln Asp Phe Arg Val
145                 150                 155                 160

Val Ala Gln Gly Val Gly Ile Pro Glu Asp Ser Ile Phe Thr Met Ala
                165                 170                 175

Asp Arg Gly Glu Cys Val Pro Gly Glu Gln Glu Pro Glu Pro Ile
            180                 185                 190

<210> SEQ ID NO 21
<211> LENGTH: 195
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: hA1M, 6His, M41K; truncated

<400> SEQUENCE: 21

Met His His His His His Asp Asp Asp Lys Gly Pro Val Pro
1               5                   10                  15

Thr Pro Pro Asp Asn Ile Gln Val Gln Glu Asn Phe Asn Ile Ser Arg
            20                  25                  30

Ile Tyr Gly Lys Trp Tyr Asn Leu Ala Ile Gly Ser Thr Cys Pro Trp
        35                  40                  45

Leu Lys Lys Ile Lys Asp Arg Met Thr Val Ser Thr Leu Val Leu Gly
    50                  55                  60
```

```
Glu Gly Ala Thr Glu Ala Glu Ile Ser Met Thr Ser Thr Arg Trp Arg
 65                  70                  75                  80

Lys Gly Val Cys Glu Glu Thr Ser Gly Ala Tyr Glu Lys Thr Asp Thr
                 85                  90                  95

Asp Gly Lys Phe Leu Tyr His Lys Ser Lys Trp Asn Ile Thr Met Glu
            100                 105                 110

Ser Tyr Val Val His Thr Asn Tyr Asp Glu Tyr Ala Ile Phe Leu Thr
            115                 120                 125

Lys Lys Phe Ser Arg His His Gly Pro Thr Ile Thr Ala Lys Leu Tyr
130                 135                 140

Gly Arg Ala Pro Gln Leu Arg Glu Thr Leu Leu Gln Asp Phe Arg Val
145                 150                 155                 160

Val Ala Gln Gly Val Gly Ile Pro Glu Asp Ser Ile Phe Thr Met Ala
                165                 170                 175

Asp Arg Gly Glu Cys Val Pro Gly Glu Gln Glu Pro Glu Pro Ile Leu
            180                 185                 190

Ile Pro Arg
        195

<210> SEQ ID NO 22
<211> LENGTH: 193
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8His, N17,96D; R66H; truncated

<400> SEQUENCE: 22

Met His His His His His His His Asp Asp Asp Lys Gly Pro
  1               5                  10                  15

Val Pro Thr Pro Pro Asp Asn Ile Gln Val Gln Glu Asn Phe Asp Ile
                 20                  25                  30

Ser Arg Ile Tyr Gly Lys Trp Tyr Asn Leu Ala Ile Gly Ser Thr Cys
            35                  40                  45

Pro Trp Leu Lys Lys Ile Met Asp Arg Met Thr Val Ser Thr Leu Val
 50                  55                  60

Leu Gly Glu Gly Ala Thr Glu Ala Glu Ile Ser Met Thr Ser Thr His
 65                  70                  75                  80

Trp Arg Lys Gly Val Cys Glu Glu Thr Ser Gly Ala Tyr Glu Lys Thr
                 85                  90                  95

Asp Thr Asp Gly Lys Phe Leu Tyr His Lys Ser Lys Trp Asp Ile Thr
            100                 105                 110

Met Glu Ser Tyr Val Val His Thr Asn Tyr Asp Glu Tyr Ala Ile Phe
            115                 120                 125

Leu Thr Lys Lys Phe Ser Arg His His Gly Pro Thr Ile Thr Ala Lys
130                 135                 140

Leu Tyr Gly Arg Ala Pro Gln Leu Arg Glu Thr Leu Leu Gln Asp Phe
145                 150                 155                 160

Arg Val Val Ala Gln Gly Val Gly Ile Pro Glu Asp Ser Ile Phe Thr
                165                 170                 175

Met Ala Asp Arg Gly Glu Cys Val Pro Gly Glu Gln Glu Pro Glu Pro
            180                 185                 190

Ile
```

```
<210> SEQ ID NO 23
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: hA1M, 8His, M41K; truncated

<400> SEQUENCE: 23

Met His His His His His His His Asp Asp Asp Lys Gly Pro
1               5                   10                  15

Val Pro Thr Pro Pro Asp Asn Ile Gln Val Gln Glu Asn Phe Asn Ile
            20                  25                  30

Ser Arg Ile Tyr Gly Lys Trp Tyr Asn Leu Ala Ile Gly Ser Thr Cys
        35                  40                  45

Pro Trp Leu Lys Lys Ile Lys Asp Arg Met Thr Val Ser Thr Leu Val
    50                  55                  60

Leu Gly Glu Gly Ala Thr Glu Ala Glu Ile Ser Met Thr Ser Thr Arg
65                  70                  75                  80

Trp Arg Lys Gly Val Cys Glu Glu Thr Ser Gly Ala Tyr Glu Lys Thr
                85                  90                  95

Asp Thr Asp Gly Lys Phe Leu Tyr His Lys Ser Lys Trp Asn Ile Thr
            100                 105                 110

Met Glu Ser Tyr Val Val His Thr Asn Tyr Asp Glu Tyr Ala Ile Phe
        115                 120                 125

Leu Thr Lys Lys Phe Ser Arg His His Gly Pro Thr Ile Thr Ala Lys
    130                 135                 140

Leu Tyr Gly Arg Ala Pro Gln Leu Arg Glu Thr Leu Leu Gln Asp Phe
145                 150                 155                 160

Arg Val Val Ala Gln Gly Val Gly Ile Pro Glu Asp Ser Ile Phe Thr
                165                 170                 175

Met Ala Asp Arg Gly Glu Cys Val Pro Gly Glu Gln Glu Pro Glu Pro
            180                 185                 190

Ile Leu Ile Pro Arg
        195

<210> SEQ ID NO 24
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 1.M8H5GIEGR-Mouse

<400> SEQUENCE: 24

Met His His His His His His His Gly Gly Gly Gly Ile Glu
1               5                   10                  15

Gly Arg Asp Pro Ala Ser Thr Leu Pro Asp Ile Gln Val Gln Glu Asn
            20                  25                  30

Phe Ser Glu Ser Arg Ile Tyr Gly Lys Trp Tyr Asn Leu Ala Val Gly
        35                  40                  45

Ser Thr Cys Pro Trp Leu Ser Arg Ile Lys Asp Lys Met Ser Val Gln
    50                  55                  60

Thr Leu Val Leu Gln Glu Gly Ala Thr Glu Thr Glu Ile Ser Met Thr
65                  70                  75                  80
```

```
Ser Thr Arg Trp Arg Arg Gly Val Cys Glu Glu Ile Thr Gly Ala Tyr
                85                  90                  95

Gln Lys Thr Asp Ile Asp Gly Lys Phe Leu Tyr His Lys Ser Lys Trp
            100                 105                 110

Asn Ile Thr Leu Glu Ser Tyr Val Val His Thr Asn Tyr Asp Glu Tyr
            115                 120                 125

Ala Ile Phe Leu Thr Lys Lys Ser His His Gly Leu Thr Ile
130                 135                 140

Thr Ala Lys Leu Tyr Gly Arg Glu Pro Gln Leu Arg Asp Ser Leu Leu
145                 150                 155                 160

Gln Glu Phe Lys Asp Val Ala Leu Asn Val Gly Ile Ser Glu Asn Ser
            165                 170                 175

Ile Ile Phe Met Pro Asp Arg Gly Glu Cys Val Pro Gly Asp Arg Glu
            180                 185                 190

Val Glu Pro Thr Ser Ile Ala Arg
            195                 200

<210> SEQ ID NO 25
<211> LENGTH: 201
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 2. M8H5GIEGR-Naked Mole rat

<400> SEQUENCE: 25

Met His His His His His His His Gly Gly Gly Gly Ile Glu
1               5                   10                  15

Gly Arg Asn Pro Val Pro Met Pro Pro Asp Asn Ile Gln Val Gln Glu
            20                  25                  30

Asn Phe Asp Glu Ser Arg Ile Tyr Gly Lys Trp Phe Asn Leu Ala Thr
            35                  40                  45

Gly Ser Thr Cys Pro Trp Leu Lys Arg Ile Lys Asp Arg Leu Ser Val
        50                  55                  60

Ser Thr Met Val Leu Gly Lys Gly Thr Thr Glu Thr Gln Ile Ser Thr
65                  70                  75                  80

Thr His Thr His Trp Arg Gln Gly Val Cys Gln Glu Thr Ser Gly Val
                85                  90                  95

Tyr Lys Lys Thr Asp Thr Ala Gly Lys Phe Leu Tyr His Lys Ser Lys
            100                 105                 110

Trp Asn Val Thr Met Glu Ser Tyr Val Val His Thr Asn Tyr Asp Glu
            115                 120                 125

Tyr Ala Ile Ile Leu Thr Lys Lys Phe Ser His His His Gly Pro Thr
130                 135                 140

Ile Thr Ala Lys Leu Tyr Gly Arg Glu Pro Arg Leu Arg Asp Ser Leu
145                 150                 155                 160

Leu Gln Glu Phe Arg Glu Met Ala Leu Gly Val Gly Ile Pro Glu Asp
            165                 170                 175

Ser Ile Phe Thr Met Ala Asn Arg Gly Glu Cys Val Pro Gly Asp Gln
            180                 185                 190

Ala Pro Glu Ser Thr Pro Ala Pro Arg
            195                 200

<210> SEQ ID NO 26
<211> LENGTH: 197
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 3. M8H5GIEGR-Frog

<400> SEQUENCE: 26

Met His His His His His His His Gly Gly Gly Gly Gly Ile Glu
1               5                   10                  15

Gly Arg Cys Ser Pro Ile Gln Pro Glu Asp Asn Ile Gln Ile Gln Glu
            20                  25                  30

Asn Phe Asp Leu Gln Arg Ile Tyr Gly Lys Trp Tyr Asp Ile Ala Ile
            35                  40                  45

Gly Ser Thr Cys Lys Trp Leu Lys His Lys Glu Lys Phe Asn Met
65              70                  75                  80
                               

Gly Ser Thr Cys Lys Trp Leu Lys His His Lys Glu Lys Phe Asn Met
50                  55                  60

Gly Thr Leu Glu Leu Ser Asp Gly Glu Thr Asp Gly Glu Val Arg Ile
65                  70                  75                  80

Val Asn Thr Arg Met Arg His Gly Thr Cys Ser Gln Ile Val Gly Ser
                85                  90                  95

Tyr Gln Lys Thr Glu Thr Pro Gly Lys Phe Asp Tyr Phe Asn Ala Arg
                100                 105                 110

Trp Gly Thr Thr Ile Gln Asn Tyr Ile Val Phe Thr Asn Tyr Asn Glu
            115                 120                 125

Tyr Val Ile Met Gln Met Arg Lys Lys Lys Gly Ser Glu Thr Thr Thr
130                 135                 140

Thr Val Lys Leu Tyr Gly Arg Ser Pro Asp Leu Arg Pro Thr Leu Val
145                 150                 155                 160

Asp Glu Phe Arg Gln Phe Ala Leu Ala Gln Gly Ile Pro Glu Asp Ser
                165                 170                 175

Ile Val Met Leu Pro Asn Asn Gly Glu Cys Ser Pro Gly Glu Ile Glu
                180                 185                 190

Val Arg Pro Arg Arg
            195

<210> SEQ ID NO 27
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4. M8H5GIEGR-Chicken

<400> SEQUENCE: 27

Met His His His His His His His Gly Gly Gly Gly Gly Ile Glu
1               5                   10                  15

Gly Arg Thr Pro Val Gly Asp Gln Asp Glu Asp Ile Gln Val Gln Glu
            20                  25                  30

Asn Phe Glu Pro Glu Arg Met Tyr Gly Lys Trp Tyr Asp Val Ala Val
            35                  40                  45

Gly Thr Thr Cys Lys Trp Met Lys Asn Tyr Lys Glu Lys Phe Ser Met
50                  55                  60

Gly Thr Leu Val Leu Gly Pro Gly Pro Ser Ala Asp Gln Ile Ser Thr
65                  70                  75                  80

Ile Ser Thr Arg Leu Arg Gln Gly Asp Cys Lys Arg Val Ser Gly Glu
                85                  90                  95
```

```
Tyr Gln Lys Thr Asp Thr Pro Gly Lys Tyr Thr Tyr Asn Pro Lys
            100                 105                 110

Trp Asp Val Ser Ile Lys Ser Tyr Val Leu Arg Thr Asn Tyr Glu Glu
            115                 120                 125

Tyr Ala Val Ile Leu Met Lys Lys Thr Ser Asn Phe Gly Pro Thr Thr
            130                 135                 140

Thr Leu Lys Leu Tyr Gly Arg Ser Pro Glu Leu Arg Glu Glu Leu Thr
145                 150                 155                 160

Glu Ala Phe Gln Gln Leu Ala Leu Glu Met Gly Ile Pro Ala Asp Ser
            165                 170                 175

Val Phe Ile Leu Ala Asn Lys Gly Glu Cys Val Pro Gln Glu Thr Ala
            180                 185                 190

Thr Ala Pro Glu Arg
            195

<210> SEQ ID NO 28
<211> LENGTH: 201
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 5. M8H5GIEGR-Rabbit

<400> SEQUENCE: 28

Met His His His His His His His Gly Gly Gly Gly Ile Glu
1               5                   10                  15

Gly Arg Asp Pro Val Pro Thr Leu Pro Asp Asp Ile Gln Val Gln Glu
            20                  25                  30

Asn Phe Glu Leu Ser Arg Ile Tyr Gly Lys Trp Tyr Asn Leu Ala Val
            35                  40                  45

Gly Ser Thr Cys Pro Trp Leu Lys Arg Ile Lys Asp Arg Met Ala Val
50                  55                  60

Ser Thr Leu Val Leu Gly Glu Gly Thr Ser Glu Thr Glu Ile Ser Met
65                  70                  75                  80

Thr Ser Thr His Trp Arg Arg Gly Val Cys Glu Glu Ile Ser Gly Ala
            85                  90                  95

Tyr Glu Lys Thr Asp Thr Asp Gly Lys Phe Leu Tyr His Lys Ala Lys
            100                 105                 110

Trp Asn Leu Thr Met Glu Ser Tyr Val Val His Thr Asn Tyr Asp Glu
            115                 120                 125

Tyr Ala Ile Phe Leu Thr Lys Lys Phe Ser Arg Arg His Gly Pro Thr
            130                 135                 140

Ile Thr Ala Lys Leu Tyr Gly Arg Glu Pro Gln Leu Arg Glu Ser Leu
145                 150                 155                 160

Leu Gln Glu Phe Arg Glu Val Ala Leu Gly Val Gly Ile Pro Glu Asn
            165                 170                 175

Ser Ile Phe Thr Met Ile Asp Arg Gly Glu Cys Val Pro Gly Gln Gln
            180                 185                 190

Glu Pro Lys Pro Ala Pro Val Leu Arg
            195                 200

<210> SEQ ID NO 29
<211> LENGTH: 201
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<223> OTHER INFORMATION: 6. M8H5GIEGR-SQ Monkey

<400> SEQUENCE: 29

Met His His His His His His His Gly Gly Gly Gly Gly Ile Glu
1               5                   10                  15

Gly Arg Ser Pro Val Pro Thr Pro Pro Glu Gly Ile Gln Val Gln Glu
            20                  25                  30

Asn Phe Asn Leu Ser Arg Ile Tyr Gly Lys Trp Tyr Asn Leu Ala Ile
        35                  40                  45

Gly Ser Thr Cys Pro Trp Leu Lys Lys Ile Met Asp Arg Leu Lys Val
50                  55                  60

Ser Thr Leu Val Leu Glu Glu Gly Ala Thr Glu Ala Glu Ile Ser Met
65                  70                  75                  80

Thr Ser Thr Arg Trp Arg Lys Gly Phe Cys Glu Gln Thr Ser Trp Ala
                85                  90                  95

Tyr Glu Lys Thr Asp Thr Asp Gly Lys Phe Leu Tyr His Glu Pro Lys
            100                 105                 110

Trp Asn Val Thr Met Glu Ser Tyr Val Ala His Thr Asn Tyr Glu Glu
        115                 120                 125

Tyr Ala Ile Phe Leu Thr Lys Lys Phe Ser Arg His His Gly Pro Thr
    130                 135                 140

Ile Thr Ala Lys Leu Tyr Gly Arg Glu Pro Gln Leu Arg Glu Ser Leu
145                 150                 155                 160

Leu Gln Asp Phe Arg Val Val Ala Gln Gly Val Gly Ile Pro Glu Asp
                165                 170                 175

Ser Ile Phe Thr Met Ala Asn Arg Gly Glu Cys Val Pro Gly Glu Gln
            180                 185                 190

Glu Pro Gln Pro Ile Leu His Arg Arg
        195                 200

<210> SEQ ID NO 30
<211> LENGTH: 201
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 7. M8H5GIEGR-Walrus

<400> SEQUENCE: 30

Met His His His His His His His Gly Gly Gly Gly Gly Ile Glu
1               5                   10                  15

Gly Arg Ser Pro Val Leu Thr Pro Pro Asp Ala Ile Gln Val Gln Glu
            20                  25                  30

Asn Phe Asp Ile Ser Arg Ile Tyr Gly Lys Trp Phe His Val Ala Met
        35                  40                  45

Gly Ser Thr Cys Pro Trp Leu Lys Lys Phe Met Asp Arg Met Ser Met
50                  55                  60

Ser Thr Leu Val Leu Gly Glu Gly Ala Thr Asp Gly Glu Ile Ser Met
65                  70                  75                  80

Thr Ser Thr Arg Trp Arg Arg Gly Thr Cys Glu Glu Ile Ser Gly Ala
                85                  90                  95

Tyr Glu Lys Thr Ser Thr Asn Gly Lys Phe Leu Tyr His Asn Pro Lys
```

```
                  100                 105                 110
Trp Asn Ile Thr Met Glu Ser Tyr Val Val His Thr Asp Tyr Asp Glu
            115                 120                 125

Tyr Ala Ile Phe Leu Thr Lys Lys Phe Ser Arg His His Gly Pro Thr
130                 135                 140

Ile Thr Ala Lys Leu Tyr Gly Arg Gln Pro Gln Leu Arg Glu Ser Leu
145                 150                 155                 160

Leu Glu Glu Phe Arg Glu Leu Ala Leu Gly Val Gly Ile Pro Glu Asp
                165                 170                 175

Ser Ile Phe Thr Met Ala Asn Lys Gly Glu Cys Val Pro Gly Glu Gln
                180                 185                 190

Glu Pro Glu Pro Ser Pro His Met Arg
                195                 200

<210> SEQ ID NO 31
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8. M8H5GIEGR-Manatee

<400> SEQUENCE: 31

Met His His His His His His Gly Gly Gly Gly Ile Glu
1               5                   10                  15

Gly Arg Ser Pro Val Lys Thr Pro Leu Asn Asp Ile Gln Val Gln Glu
            20                  25                  30

Asn Phe Asp Leu Pro Arg Ile Tyr Gly Lys Trp Phe Asn Ile Ala Ile
            35                  40                  45

Gly Ser Thr Cys Gln Trp Leu Lys Arg Leu Lys Ala Gly Pro Thr Met
        50                  55                  60

Ser Thr Leu Val Leu Gly Glu Gly Ala Thr Asp Thr Glu Ile Ser Thr
65                  70                  75                  80

Thr Ser Thr Arg Trp Arg Lys Gly Phe Cys Glu Glu Ile Ser Gly Ala
                85                  90                  95

Tyr Glu Lys Thr Asp Thr Ala Gly Lys Phe Leu Tyr His Gly Ser Lys
            100                 105                 110

Trp Asn Val Thr Leu Glu Ser Tyr Val Val His Thr Asn Tyr Asp Glu
            115                 120                 125

Tyr Ala Ile Phe Leu Thr Lys Lys Phe Ser Arg Tyr Gly Leu Thr Ile
130                 135                 140

Thr Ala Lys Leu Tyr Gly Arg Gln Pro Gln Val Arg Glu Ser Leu Leu
145                 150                 155                 160

Glu Glu Phe Arg Glu Phe Ala Leu Gly Val Gly Ile Pro Glu Asp Ser
                165                 170                 175

Ile Phe Thr Thr Ala Asp Lys Gly Glu Cys Val Pro Gly Glu Gln Glu
                180                 185                 190

Pro Glu Pro Thr Ala Ala Leu Arg
                195                 200

<210> SEQ ID NO 32
<211> LENGTH: 202
<212> TYPE: PRT
<213> ORGANISM: Artificial Sequence
<220> FEATURE:
<223> OTHER INFORMATION: Description of Artificial Sequence: Synthetic
```

```
            polypeptide
<220> FEATURE:
<223> OTHER INFORMATION: 9. M8H5GIEGR-Plaice

<400> SEQUENCE: 32

Met His His His His His His His Gly Gly Gly Gly Gly Ile Glu
1               5                   10                  15

Gly Arg Leu Pro Val Leu Pro Glu Pro Leu Tyr Pro Thr Gln Glu Asn
            20                  25                  30

Phe Asp Leu Thr Arg Phe Val Gly Thr Trp His Asp Val Ala Leu Thr
            35                  40                  45

Ser Ser Cys Pro His Met Gln Arg Asn Arg Ala Asp Ala Ile Gly
    50                  55                  60

Lys Leu Val Leu Glu Lys Asp Thr Gly Asn Lys Leu Lys Val Thr Arg
65                  70                  75                  80

Thr Arg Leu Arg His Gly Thr Cys Val Glu Met Ser Gly Glu Tyr Glu
                85                  90                  95

Leu Thr Ser Thr Pro Gly Arg Ile Phe Tyr His Ile Asp Arg Trp Asp
                100                 105                 110

Ala Asp Val Asp Ala Tyr Val Val His Thr Asn Tyr Asp Glu Tyr Ala
            115                 120                 125

Ile Ile Ile Met Ser Lys Gln Lys Thr Ser Gly Glu Asn Ser Thr Ser
    130                 135                 140

Leu Lys Leu Tyr Ser Arg Thr Met Ser Val Arg Asp Thr Val Leu Asp
145                 150                 155                 160

Asp Phe Lys Thr Leu Val Arg His Gln Gly Met Ser Asp Asp Thr Ile
                165                 170                 175

Ile Ile Lys Gln Asn Lys Gly Asp Cys Ile Pro Gly Glu Gln Val Glu
            180                 185                 190

Glu Ala Pro Ser Gln Pro Glu Pro Lys Arg
            195                 200

<210> SEQ ID NO 33
<211> LENGTH: 201
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 10. M8H5GIEGR-Orangutan

<400> SEQUENCE: 33

Met His His His His His His His Gly Gly Gly Gly Gly Ile Glu
1               5                   10                  15

Gly Arg Gly Pro Val Pro Thr Pro Pro Asp Asn Ile Gln Val Gln Glu
            20                  25                  30

Asn Phe Asn Ile Ser Arg Ile Tyr Gly Lys Trp Tyr Asn Leu Ala Ile
            35                  40                  45

Gly Ser Thr Cys Pro Trp Leu Lys Lys Ile Met Asp Arg Met Thr Val
    50                  55                  60

Ser Thr Leu Val Leu Gly Glu Gly Ala Thr Glu Ala Glu Ile Ser Met
65                  70                  75                  80

Thr Ser Thr Arg Trp Arg Lys Gly Val Cys Glu Glu Thr Ser Gly Ala
                85                  90                  95

Tyr Glu Lys Thr Asp Thr Asp Gly Lys Phe Leu Tyr His Lys Ser Lys
                100                 105                 110
```

```
Trp Asn Ile Thr Met Glu Ser Tyr Val Val His Thr Asn Tyr Asp Glu
            115                 120                 125

Tyr Ala Ile Phe Leu Thr Lys Lys Phe Ser Arg Arg His Gly Pro Thr
        130                 135                 140

Ile Thr Ala Lys Leu Tyr Gly Arg Ala Pro Gln Leu Arg Glu Thr Leu
145                 150                 155                 160

Leu Gln Asp Phe Arg Val Val Ala Gln Gly Val Gly Ile Pro Glu Asp
                165                 170                 175

Ser Ile Phe Thr Met Ala Asp Arg Gly Glu Cys Val Pro Gly Glu Gln
            180                 185                 190

Glu Pro Glu Pro Ile Leu Ile Pro Arg
        195                 200
```

<210> SEQ ID NO 34
<211> LENGTH: 201
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: 11. M8H5GIEGR-Human P35K

<400> SEQUENCE: 34

```
Met His His His His His His His Gly Gly Gly Gly Ile Glu
1               5                   10                  15

Gly Arg Gly Pro Val Pro Thr Pro Pro Asp Asn Ile Gln Val Gln Glu
                20                  25                  30

Asn Phe Asn Ile Ser Arg Ile Tyr Gly Lys Trp Tyr Asn Leu Ala Ile
            35                  40                  45

Gly Ser Thr Cys Lys Trp Leu Lys Lys Ile Met Asp Arg Met Thr Val
50                  55                  60

Ser Thr Leu Val Leu Gly Glu Gly Ala Thr Glu Ala Glu Ile Ser Met
65                  70                  75                  80

Thr Ser Thr Arg Trp Arg Lys Gly Val Cys Glu Glu Thr Ser Gly Ala
            85                  90                  95

Tyr Glu Lys Thr Asp Thr Asp Gly Lys Phe Leu Tyr His Lys Ser Lys
                100                 105                 110

Trp Asn Ile Thr Met Glu Ser Tyr Val Val His Thr Asn Tyr Asp Glu
            115                 120                 125

Tyr Ala Ile Phe Leu Thr Lys Lys Phe Ser Arg Arg His Gly Pro Thr
        130                 135                 140

Ile Thr Ala Lys Leu Tyr Gly Arg Ala Pro Gln Leu Arg Glu Thr Leu
145                 150                 155                 160

Leu Gln Asp Phe Arg Val Val Ala Gln Gly Val Gly Ile Pro Glu Asp
                165                 170                 175

Ser Ile Phe Thr Met Ala Asp Arg Gly Glu Cys Val Pro Gly Glu Gln
            180                 185                 190

Glu Pro Glu Pro Ile Leu Ile Pro Arg
        195                 200
```

<210> SEQ ID NO 35
<211> LENGTH: 201
<212> TYPE: PRT
<213> ORGANISM: Artificial Sequence
<220> FEATURE:
<223> OTHER INFORMATION: Description of Artificial Sequence: Synthetic polypeptide
<220> FEATURE:

<223> OTHER INFORMATION: 12. M8H5GIEGR-Human M41K

<400> SEQUENCE: 35

```
Met His His His His His His His Gly Gly Gly Gly Ile Glu
1               5                   10                  15

Gly Arg Gly Pro Val Pro Thr Pro Pro Asp Asn Ile Gln Val Gln Glu
            20                  25                  30

Asn Phe Asn Ile Ser Arg Ile Tyr Gly Lys Trp Tyr Asn Leu Ala Ile
        35                  40                  45

Gly Ser Thr Cys Pro Trp Leu Lys Lys Ile Lys Asp Arg Met Thr Val
    50                  55                  60

Ser Thr Leu Val Leu Gly Glu Gly Ala Thr Glu Ala Glu Ile Ser Met
65                  70                  75                  80

Thr Ser Thr Arg Trp Arg Lys Gly Val Cys Glu Glu Thr Ser Gly Ala
                85                  90                  95

Tyr Glu Lys Thr Asp Thr Asp Gly Lys Phe Leu Tyr His Lys Ser Lys
            100                 105                 110

Trp Asn Ile Thr Met Glu Ser Tyr Val Val His Thr Asn Tyr Asp Glu
        115                 120                 125

Tyr Ala Ile Phe Leu Thr Lys Lys Phe Ser Arg His His Gly Pro Thr
    130                 135                 140

Ile Thr Ala Lys Leu Tyr Gly Arg Ala Pro Gln Leu Arg Glu Thr Leu
145                 150                 155                 160

Leu Gln Asp Phe Arg Val Val Ala Gln Gly Val Gly Ile Pro Glu Asp
                165                 170                 175

Ser Ile Phe Thr Met Ala Asp Arg Gly Glu Cys Val Pro Gly Glu Gln
            180                 185                 190

Glu Pro Glu Pro Ile Leu Ile Pro Arg
            195                 200
```

<210> SEQ ID NO 36
<211> LENGTH: 201
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: 13. M8H5GIEGR-Human R66H

<400> SEQUENCE: 36

```
Met His His His His His His His Gly Gly Gly Gly Ile Glu
1               5                   10                  15

Gly Arg Gly Pro Val Pro Thr Pro Pro Asp Asn Ile Gln Val Gln Glu
            20                  25                  30

Asn Phe Asn Ile Ser Arg Ile Tyr Gly Lys Trp Tyr Asn Leu Ala Ile
        35                  40                  45

Gly Ser Thr Cys Pro Trp Leu Lys Lys Ile Met Asp Arg Met Thr Val
    50                  55                  60

Ser Thr Leu Val Leu Gly Glu Gly Ala Thr Glu Ala Glu Ile Ser Met
65                  70                  75                  80

Thr Ser Thr His Trp Arg Lys Gly Val Cys Glu Glu Thr Ser Gly Ala
                85                  90                  95

Tyr Glu Lys Thr Asp Thr Asp Gly Lys Phe Leu Tyr His Lys Ser Lys
            100                 105                 110

Trp Asn Ile Thr Met Glu Ser Tyr Val Val His Thr Asn Tyr Asp Glu
        115                 120                 125
```

Tyr Ala Ile Phe Leu Thr Lys Lys Phe Ser Arg His His Gly Pro Thr
            130                 135                 140

Ile Thr Ala Lys Leu Tyr Gly Arg Ala Pro Gln Leu Arg Glu Thr Leu
145                 150                 155                 160

Leu Gln Asp Phe Arg Val Val Ala Gln Gly Val Gly Ile Pro Glu Asp
                165                 170                 175

Ser Ile Phe Thr Met Ala Asp Arg Gly Glu Cys Val Pro Gly Glu Gln
            180                 185                 190

Glu Pro Glu Pro Ile Leu Ile Pro Arg
        195                 200

<210> SEQ ID NO 37
<211> LENGTH: 201
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 14. M8H5GIEGR-Human T75K

<400> SEQUENCE: 37

Met His His His His His His Gly Gly Gly Gly Ile Glu
1               5                   10                  15

Gly Arg Gly Pro Val Pro Thr Pro Pro Asp Asn Ile Gln Val Gln Glu
            20                  25                  30

Asn Phe Asn Ile Ser Arg Ile Tyr Gly Lys Trp Tyr Asn Leu Ala Ile
        35                  40                  45

Gly Ser Thr Cys Pro Trp Leu Lys Lys Ile Met Asp Arg Met Thr Val
    50                  55                  60

Ser Thr Leu Val Leu Gly Glu Gly Ala Thr Glu Ala Glu Ile Ser Met
65                  70                  75                  80

Thr Ser Thr Arg Trp Arg Lys Gly Val Cys Glu Glu Lys Ser Gly Ala
                85                  90                  95

Tyr Glu Lys Thr Asp Thr Asp Gly Lys Phe Leu Tyr His Lys Ser Lys
            100                 105                 110

Trp Asn Ile Thr Met Glu Ser Tyr Val Val His Thr Asn Tyr Asp Glu
        115                 120                 125

Tyr Ala Ile Phe Leu Thr Lys Lys Phe Ser Arg His His Gly Pro Thr
    130                 135                 140

Ile Thr Ala Lys Leu Tyr Gly Arg Ala Pro Gln Leu Arg Glu Thr Leu
145                 150                 155                 160

Leu Gln Asp Phe Arg Val Val Ala Gln Gly Val Gly Ile Pro Glu Asp
                165                 170                 175

Ser Ile Phe Thr Met Ala Asp Arg Gly Glu Cys Val Pro Gly Glu Gln
            180                 185                 190

Glu Pro Glu Pro Ile Leu Ile Pro Arg
        195                 200

<210> SEQ ID NO 38
<211> LENGTH: 201
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 15. M8H5GIEGR-Human T75Y

```
<400> SEQUENCE: 38

Met His His His His His His His Gly Gly Gly Gly Gly Ile Glu
1               5                   10                  15

Gly Arg Gly Pro Val Pro Thr Pro Pro Asp Asn Ile Gln Val Gln Glu
                20                  25                  30

Asn Phe Asn Ile Ser Arg Ile Tyr Gly Lys Trp Tyr Asn Leu Ala Ile
                35                  40                  45

Gly Ser Thr Cys Pro Trp Leu Lys Lys Ile Met Asp Arg Met Thr Val
50                  55                  60

Ser Thr Leu Val Leu Gly Glu Gly Ala Thr Glu Ala Glu Ile Ser Met
65                  70                  75                  80

Thr Ser Thr Arg Trp Arg Lys Gly Val Cys Glu Glu Tyr Ser Gly Ala
                85                  90                  95

Tyr Glu Lys Thr Asp Thr Asp Gly Lys Phe Leu Tyr His Lys Ser Lys
                100                 105                 110

Trp Asn Ile Thr Met Glu Ser Tyr Val Val His Thr Asn Tyr Asp Glu
                115                 120                 125

Tyr Ala Ile Phe Leu Thr Lys Lys Phe Ser Arg His His Gly Pro Thr
130                 135                 140

Ile Thr Ala Lys Leu Tyr Gly Arg Ala Pro Gln Leu Arg Glu Thr Leu
145                 150                 155                 160

Leu Gln Asp Phe Arg Val Val Ala Gln Gly Val Gly Ile Pro Glu Asp
                165                 170                 175

Ser Ile Phe Thr Met Ala Asp Arg Gly Glu Cys Val Pro Gly Glu Gln
                180                 185                 190

Glu Pro Glu Pro Ile Leu Ile Pro Arg
                195                 200

<210> SEQ ID NO 39
<211> LENGTH: 201
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 16. M8H5GIEGR-Human M99K

<400> SEQUENCE: 39

Met His His His His His His His Gly Gly Gly Gly Gly Ile Glu
1               5                   10                  15

Gly Arg Gly Pro Val Pro Thr Pro Pro Asp Asn Ile Gln Val Gln Glu
                20                  25                  30

Asn Phe Asn Ile Ser Arg Ile Tyr Gly Lys Trp Tyr Asn Leu Ala Ile
                35                  40                  45

Gly Ser Thr Cys Pro Trp Leu Lys Lys Ile Met Asp Arg Met Thr Val
50                  55                  60

Ser Thr Leu Val Leu Gly Glu Gly Ala Thr Glu Ala Glu Ile Ser Met
65                  70                  75                  80

Thr Ser Thr Arg Trp Arg Lys Gly Val Cys Glu Glu Thr Ser Gly Ala
                85                  90                  95

Tyr Glu Lys Thr Asp Thr Asp Gly Lys Phe Leu Tyr His Lys Ser Lys
                100                 105                 110

Trp Asn Ile Thr Lys Glu Ser Tyr Val Val His Thr Asn Tyr Asp Glu
                115                 120                 125

Tyr Ala Ile Phe Leu Thr Lys Lys Phe Ser Arg His His Gly Pro Thr
```

```
              130                 135                 140
Ile Thr Ala Lys Leu Tyr Gly Arg Ala Pro Gln Leu Arg Glu Thr Leu
145                 150                 155                 160

Leu Gln Asp Phe Arg Val Val Ala Gln Gly Val Gly Ile Pro Glu Asp
                165                 170                 175

Ser Ile Phe Thr Met Ala Asp Arg Gly Glu Cys Val Pro Gly Glu Gln
                180                 185                 190

Glu Pro Glu Pro Ile Leu Ile Pro Arg
                195                 200

<210> SEQ ID NO 40
<211> LENGTH: 201
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 17. M8H5GIEGR-Human S101Y

<400> SEQUENCE: 40

Met His His His His His His His Gly Gly Gly Gly Gly Ile Glu
1               5                   10                  15

Gly Arg Gly Pro Val Pro Thr Pro Pro Asp Asn Ile Gln Val Gln Glu
                20                  25                  30

Asn Phe Asn Ile Ser Arg Ile Tyr Gly Lys Trp Tyr Asn Leu Ala Ile
                35                  40                  45

Gly Ser Thr Cys Pro Trp Leu Lys Lys Ile Met Asp Arg Met Thr Val
50                  55                  60

Ser Thr Leu Val Leu Gly Glu Gly Ala Thr Glu Ala Glu Ile Ser Met
65                  70                  75                  80

Thr Ser Thr Arg Trp Arg Lys Gly Val Cys Glu Glu Thr Ser Gly Ala
                85                  90                  95

Tyr Glu Lys Thr Asp Thr Asp Gly Lys Phe Leu Tyr His Lys Ser Lys
                100                 105                 110

Trp Asn Ile Thr Met Glu Tyr Tyr Val Val His Thr Asn Tyr Asp Glu
                115                 120                 125

Tyr Ala Ile Phe Leu Thr Lys Lys Phe Ser Arg His His Gly Pro Thr
130                 135                 140

Ile Thr Ala Lys Leu Tyr Gly Arg Ala Pro Gln Leu Arg Glu Thr Leu
145                 150                 155                 160

Leu Gln Asp Phe Arg Val Val Ala Gln Gly Val Gly Ile Pro Glu Asp
                165                 170                 175

Ser Ile Phe Thr Met Ala Asp Arg Gly Glu Cys Val Pro Gly Glu Gln
                180                 185                 190

Glu Pro Glu Pro Ile Leu Ile Pro Arg
                195                 200

<210> SEQ ID NO 41
<211> LENGTH: 201
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 18. M8H5GIEGR-Human K69.92.118.130R

<400> SEQUENCE: 41
```

```
Met His His His His His His His Gly Gly Gly Gly Ile Glu
1               5                   10                  15

Gly Arg Gly Pro Val Pro Thr Pro Pro Asp Asn Ile Gln Val Gln Glu
            20                  25                  30

Asn Phe Asn Ile Ser Arg Ile Tyr Gly Lys Trp Tyr Asn Leu Ala Ile
        35                  40                  45

Gly Ser Thr Cys Pro Trp Leu Lys Lys Ile Met Asp Arg Met Thr Val
    50                  55                  60

Ser Thr Leu Val Leu Gly Glu Gly Ala Thr Glu Ala Glu Ile Ser Met
65              70                  75                  80

Thr Ser Thr Arg Trp Arg Arg Gly Val Cys Glu Glu Thr Ser Gly Ala
                85                  90                  95

Tyr Glu Lys Thr Asp Thr Asp Gly Lys Phe Leu Tyr His Arg Ser Lys
            100                 105                 110

Trp Asn Ile Thr Met Glu Ser Tyr Val Val His Thr Asn Tyr Asp Glu
        115                 120                 125

Tyr Ala Ile Phe Leu Thr Lys Arg Phe Ser Arg His His Gly Pro Thr
    130                 135                 140

Ile Thr Ala Arg Leu Tyr Gly Arg Ala Pro Gln Leu Arg Glu Thr Leu
145                 150                 155                 160

Leu Gln Asp Phe Arg Val Val Ala Gln Gly Val Gly Ile Pro Glu Asp
                165                 170                 175

Ser Ile Phe Thr Met Ala Asp Arg Gly Glu Cys Val Pro Gly Glu Gln
        180                 185                 190

Glu Pro Glu Pro Ile Leu Ile Pro Arg
        195                 200
```

<210> SEQ ID NO 42
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 19. M8H5GIEGR-Coelacanth

<400> SEQUENCE: 42

```
Met His His His His His His His Gly Gly Gly Gly Ile Glu
1               5                   10                  15

Gly Arg Gly Ser Pro Leu Arg Asp Glu Asp Ile Gln Val Gln Glu Asn
            20                  25                  30

Phe Asp Leu Pro Arg Ile Tyr Gly Lys Trp Tyr Glu Ile Ala Ile Ala
        35                  40                  45

Ser Thr Cys Pro Trp Val Lys Asn His Lys Asp Lys Met Phe Met Gly
    50                  55                  60

Thr Met Val Leu Gln Glu Gly Glu Gln Ser Asp Arg Ile Ser Thr Thr
65              70                  75                  80

Ser Thr Arg Ile Arg Asp Gly Thr Cys Ser Gln Ile Thr Gly Tyr Tyr
                85                  90                  95

Thr Leu Thr Thr Thr Pro Gly Lys Phe Ala Tyr His Asn Ser Lys Trp
            100                 105                 110

Asn Leu Asp Val Asn Ser Tyr Val Val His Thr Asn Tyr Asp Glu Tyr
        115                 120                 125

Ser Ile Val Met Met Gln Lys Tyr Lys Ser Ser Asn Thr Thr Thr
    130                 135                 140
```

-continued

```
Val Arg Leu Tyr Gly Arg Thr Gln Glu Leu Arg Asp Ser Leu His Ala
145                 150                 155                 160

Glu Phe Lys Lys Phe Ala Leu Asp Gln Gly Ile Asp Glu Asp Ser Ile
                165                 170                 175

Tyr Ile Leu Pro Lys Arg Asp Glu Cys Val Pro Gly Glu Pro Lys Ala
            180                 185                 190

Glu Ser Leu Met Ala Arg
            195
```

<210> SEQ ID NO 43
<211> LENGTH: 201
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: 21. M8H5GIEGR-Human L89T

<400> SEQUENCE: 43

```
Met His His His His His His His Gly Gly Gly Gly Gly Ile Glu
1               5                   10                  15

Gly Arg Gly Pro Val Pro Thr Pro Pro Asp Asn Ile Gln Val Gln Glu
            20                  25                  30

Asn Phe Asn Ile Ser Arg Ile Tyr Gly Lys Trp Tyr Asn Leu Ala Ile
        35                  40                  45

Gly Ser Thr Cys Pro Trp Leu Lys Lys Ile Met Asp Arg Met Thr Val
    50                  55                  60

Ser Thr Leu Val Leu Gly Glu Gly Ala Thr Glu Ala Glu Ile Ser Met
65                  70                  75                  80

Thr Ser Thr Arg Trp Arg Lys Gly Val Cys Glu Glu Thr Ser Gly Ala
                85                  90                  95

Tyr Glu Lys Thr Asp Thr Asp Gly Lys Phe Thr Tyr His Lys Ser Lys
            100                 105                 110

Trp Asn Ile Thr Met Glu Ser Tyr Val Val His Thr Asn Tyr Asp Glu
        115                 120                 125

Tyr Ala Ile Phe Leu Thr Lys Lys Phe Ser Arg His His Gly Pro Thr
    130                 135                 140

Ile Thr Ala Lys Leu Tyr Gly Arg Ala Pro Gln Leu Arg Glu Thr Leu
145                 150                 155                 160

Leu Gln Asp Phe Arg Val Val Ala Gln Gly Val Gly Ile Pro Glu Asp
                165                 170                 175

Ser Ile Phe Thr Met Ala Asp Arg Gly Glu Cys Val Pro Gly Glu Gln
            180                 185                 190

Glu Pro Glu Pro Ile Leu Ile Pro Arg
        195                 200
```

<210> SEQ ID NO 44
<211> LENGTH: 201
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: 22. M8H5GIEGR-Human N1796D

<400> SEQUENCE: 44

```
Met His His His His His His His Gly Gly Gly Gly Gly Ile Glu
1               5                   10                  15
```

Gly Arg Gly Pro Val Pro Thr Pro Pro Asp Asn Ile Gln Val Gln Glu
            20                  25                  30

Asn Phe Asp Ile Ser Arg Ile Tyr Gly Lys Trp Tyr Asn Leu Ala Ile
            35                  40                  45

Gly Ser Thr Cys Pro Trp Leu Lys Lys Ile Met Asp Arg Met Thr Val
 50                  55                  60

Ser Thr Leu Val Leu Gly Glu Gly Ala Thr Glu Ala Glu Ile Ser Met
65                  70                  75                  80

Thr Ser Thr Arg Trp Arg Lys Gly Val Cys Glu Glu Thr Ser Gly Ala
                85                  90                  95

Tyr Glu Lys Thr Asp Thr Asp Gly Lys Phe Leu Tyr His Lys Ser Lys
            100                 105                 110

Trp Asp Ile Thr Met Glu Ser Tyr Val Val His Thr Asn Tyr Asp Glu
            115                 120                 125

Tyr Ala Ile Phe Leu Thr Lys Lys Phe Ser Arg His His Gly Pro Thr
130                 135                 140

Ile Thr Ala Lys Leu Tyr Gly Arg Ala Pro Gln Leu Arg Glu Thr Leu
145                 150                 155                 160

Leu Gln Asp Phe Arg Val Val Ala Gln Gly Val Gly Ile Pro Glu Asp
                165                 170                 175

Ser Ile Phe Thr Met Ala Asp Arg Gly Glu Cys Val Pro Gly Glu Gln
            180                 185                 190

Glu Pro Glu Pro Ile Leu Ile Pro Arg
            195                 200

<210> SEQ ID NO 45
<211> LENGTH: 201
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 23. M8H5GIEGR-Human T45K

<400> SEQUENCE: 45

Met His His His His His His Gly Gly Gly Gly Ile Glu
1               5                   10                  15

Gly Arg Gly Pro Val Pro Thr Pro Pro Asp Asn Ile Gln Val Gln Glu
            20                  25                  30

Asn Phe Asn Ile Ser Arg Ile Tyr Gly Lys Trp Tyr Asn Leu Ala Ile
            35                  40                  45

Gly Ser Thr Cys Pro Trp Leu Lys Lys Ile Met Asp Arg Met Lys Val
 50                  55                  60

Ser Thr Leu Val Leu Gly Glu Gly Ala Thr Glu Ala Glu Ile Ser Met
65                  70                  75                  80

Thr Ser Thr Arg Trp Arg Lys Gly Val Cys Glu Glu Thr Ser Gly Ala
                85                  90                  95

Tyr Glu Lys Thr Asp Thr Asp Gly Lys Phe Leu Tyr His Lys Ser Lys
            100                 105                 110

Trp Asn Ile Thr Met Glu Ser Tyr Val Val His Thr Asn Tyr Asp Glu
            115                 120                 125

Tyr Ala Ile Phe Leu Thr Lys Lys Phe Ser Arg His His Gly Pro Thr
130                 135                 140

Ile Thr Ala Lys Leu Tyr Gly Arg Ala Pro Gln Leu Arg Glu Thr Leu
145                 150                 155                 160

-continued

Leu Gln Asp Phe Arg Val Val Ala Gln Gly Val Gly Ile Pro Glu Asp
                165                 170                 175

Ser Ile Phe Thr Met Ala Asp Arg Gly Glu Cys Val Pro Gly Glu Gln
            180                 185                 190

Glu Pro Glu Pro Ile Leu Ile Pro Arg
        195                 200

<210> SEQ ID NO 46
<211> LENGTH: 201
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 24. M8H5GIEGR-Human A135E

<400> SEQUENCE: 46

Met His His His His His His His Gly Gly Gly Gly Ile Glu
1               5                   10                  15

Gly Arg Gly Pro Val Pro Thr Pro Pro Asp Asn Ile Gln Val Gln Glu
            20                  25                  30

Asn Phe Asn Ile Ser Arg Ile Tyr Gly Lys Trp Tyr Asn Leu Ala Ile
        35                  40                  45

Gly Ser Thr Cys Pro Trp Leu Lys Lys Ile Met Asp Arg Met Thr Val
    50                  55                  60
Ser Thr Leu Val Leu Gly Glu Gly Ala Thr Glu Ala Glu Ile Ser Met
65                  70                  75                  80

Thr Ser Thr Arg Trp Arg Lys Gly Val Cys Glu Glu Thr Ser Gly Ala
                85                  90                  95

Tyr Glu Lys Thr Asp Thr Asp Gly Lys Phe Leu Tyr His Lys Ser Lys
            100                 105                 110

Trp Asn Ile Thr Met Glu Ser Tyr Val Val His Thr Asn Tyr Asp Glu
        115                 120                 125

Tyr Ala Ile Phe Leu Thr Lys Lys Phe Ser Arg His His Gly Pro Thr
    130                 135                 140

Ile Thr Ala Lys Leu Tyr Gly Arg Glu Pro Gln Leu Arg Glu Thr Leu
145                 150                 155                 160

Leu Gln Asp Phe Arg Val Val Ala Gln Gly Val Gly Ile Pro Glu Asp
                165                 170                 175

Ser Ile Phe Thr Met Ala Asp Arg Gly Glu Cys Val Pro Gly Glu Gln
            180                 185                 190

Glu Pro Glu Pro Ile Leu Ile Pro Arg
        195                 200

<210> SEQ ID NO 47
<211> LENGTH: 201
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 25. M8H5GIEGR-Human V170S

<400> SEQUENCE: 47

Met His His His His His His His Gly Gly Gly Gly Ile Glu
1               5                   10                  15

Gly Arg Gly Pro Val Pro Thr Pro Pro Asp Asn Ile Gln Val Gln Glu

-continued

```
                20                  25                  30
Asn Phe Asn Ile Ser Arg Ile Tyr Gly Lys Trp Tyr Asn Leu Ala Ile
             35                  40                  45
Gly Ser Thr Cys Pro Trp Leu Lys Lys Ile Met Asp Arg Met Thr Val
 50                  55                  60
Ser Thr Leu Val Leu Gly Glu Gly Ala Thr Glu Ala Glu Ile Ser Met
 65                  70                  75                  80
Thr Ser Thr Arg Trp Arg Lys Gly Val Cys Glu Glu Thr Ser Gly Ala
                 85                  90                  95
Tyr Glu Lys Thr Asp Thr Asp Gly Lys Phe Leu Tyr His Lys Ser Lys
                100                 105                 110
Trp Asn Ile Thr Met Glu Ser Tyr Val Val His Thr Asn Tyr Asp Glu
            115                 120                 125
Tyr Ala Ile Phe Leu Thr Lys Lys Phe Ser Arg His His Gly Pro Thr
        130                 135                 140
Ile Thr Ala Lys Leu Tyr Gly Arg Ala Pro Gln Leu Arg Glu Thr Leu
145                 150                 155                 160
Leu Gln Asp Phe Arg Val Val Ala Gln Gly Val Gly Ile Pro Glu Asp
                165                 170                 175
Ser Ile Phe Thr Met Ala Asp Arg Gly Glu Cys Ser Pro Gly Glu Gln
            180                 185                 190
Glu Pro Glu Pro Ile Leu Ile Pro Arg
        195                 200
```

<210> SEQ ID NO 48
<211> LENGTH: 201
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 26. M8H5GIEGR-Human

<400> SEQUENCE: 48

```
Met His His His His His His His Gly Gly Gly Gly Ile Glu
 1               5                  10                  15
Gly Arg Gly Pro Val Pro Thr Pro Pro Asp Asn Ile Gln Val Gln Glu
                 20                  25                  30
Asn Phe Asn Ile Ser Arg Ile Tyr Gly Lys Trp Tyr Asn Leu Ala Ile
             35                  40                  45
Gly Ser Thr Cys Pro Trp Leu Lys Lys Ile Met Asp Arg Met Thr Val
 50                  55                  60
Ser Thr Leu Val Leu Gly Glu Gly Ala Thr Glu Ala Glu Ile Ser Met
 65                  70                  75                  80
Thr Ser Thr Arg Trp Arg Lys Gly Val Cys Glu Glu Thr Ser Gly Ala
                 85                  90                  95
Tyr Glu Lys Thr Asp Thr Asp Gly Lys Phe Leu Tyr His Lys Ser Lys
                100                 105                 110
Trp Asn Ile Thr Met Glu Ser Tyr Val Val His Thr Asn Tyr Asp Glu
            115                 120                 125
Tyr Ala Ile Phe Leu Thr Lys Lys Phe Ser Arg His His Gly Pro Thr
        130                 135                 140
Ile Thr Ala Lys Leu Tyr Gly Arg Ala Pro Gln Leu Arg Glu Thr Leu
145                 150                 155                 160
Leu Gln Asp Phe Arg Asp Val Ala Gln Gly Val Gly Ile Pro Glu Asp
```

```
                    165                 170                 175

Ser Ile Phe Thr Met Ala Asp Arg Gly Glu Cys Val Pro Gly Glu Gln
                180                 185                 190

Glu Pro Glu Pro Ile Leu Ile Pro Arg
        195                 200

<210> SEQ ID NO 49
<211> LENGTH: 201
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 27. M8H5GIEGR-Human G172Q

<400> SEQUENCE: 49

Met His His His His His His His Gly Gly Gly Gly Ile Glu
1               5                   10                  15

Gly Arg Gly Pro Val Pro Thr Pro Pro Asp Asn Ile Gln Val Gln Glu
            20                  25                  30

Asn Phe Asn Ile Ser Arg Ile Tyr Gly Lys Trp Tyr Asn Leu Ala Ile
        35                  40                  45

Gly Ser Thr Cys Pro Trp Leu Lys Lys Ile Met Asp Arg Met Thr Val
    50                  55                  60

Ser Thr Leu Val Leu Gly Glu Gly Ala Thr Glu Ala Glu Ile Ser Met
65                  70                  75                  80

Thr Ser Thr Arg Trp Arg Lys Gly Val Cys Glu Glu Thr Ser Gly Ala
                85                  90                  95

Tyr Glu Lys Thr Asp Thr Asp Gly Lys Phe Leu Tyr His Lys Ser Lys
            100                 105                 110

Trp Asn Ile Thr Met Glu Ser Tyr Val Val His Thr Asn Tyr Asp Glu
        115                 120                 125

Tyr Ala Ile Phe Leu Thr Lys Lys Phe Ser Arg His His Gly Pro Thr
    130                 135                 140

Ile Thr Ala Lys Leu Tyr Gly Arg Ala Pro Gln Leu Arg Glu Thr Leu
145                 150                 155                 160

Leu Gln Asp Phe Arg Val Val Ala Gln Gly Val Gly Ile Pro Glu Asp
                165                 170                 175

Ser Ile Phe Thr Met Ala Asp Arg Gly Glu Cys Val Pro Gln Glu Gln
            180                 185                 190

Glu Pro Glu Pro Ile Leu Ile Pro Arg
        195                 200

<210> SEQ ID NO 50
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 33. M8H4DK-Human M41K+

<400> SEQUENCE: 50

Met His His His His His His His Asp Asp Asp Asp Lys Gly Pro
1               5                   10                  15

Val Pro Thr Pro Pro Asp Asn Ile Gln Val Gln Glu Asn Phe Asn Ile
            20                  25                  30
```

```
Ser Arg Ile Tyr Gly Lys Trp Tyr Asn Leu Ala Ile Gly Ser Thr Cys
        35                  40                  45

Pro Trp Leu Lys Lys Ile Lys Asp Arg Met Thr Val Ser Thr Leu Val
 50                  55                  60

Leu Gly Glu Gly Ala Thr Glu Ala Glu Ile Ser Met Thr Ser Thr His
 65                  70                  75                  80

Trp Arg Lys Gly Val Cys Glu Glu Thr Ser Gly Ala Tyr Glu Lys Thr
                 85                  90                  95

Asp Thr Asp Gly Lys Phe Leu Tyr His Lys Ser Lys Trp Asn Ile Thr
            100                 105                 110

Met Glu Ser Tyr Val Val His Thr Asn Tyr Asp Glu Tyr Ala Ile Phe
        115                 120                 125

Leu Thr Lys Lys Phe Ser Arg His His Gly Pro Thr Ile Thr Ala Lys
130                 135                 140

Leu Tyr Gly Arg Ala Pro Gln Leu Arg Glu Thr Leu Leu Gln Asp Phe
145                 150                 155                 160

Arg Val Val Ala Gln Gly Val Gly Ile Pro Glu Asp Ser Ile Phe Thr
                165                 170                 175

Met Ala Asp Arg Gly Glu Cys Val Pro Gly Glu Gln Glu Pro Glu Pro
            180                 185                 190

Ile Leu Ile Pro Arg
        195

<210> SEQ ID NO 51
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 34. M8H4DK-Human M41K+N1796D 34

<400> SEQUENCE: 51

Met His His His His His His Asp Asp Asp Asp Lys Gly Pro
 1               5                  10                  15

Val Pro Thr Pro Pro Asp Asn Ile Gln Val Gln Glu Asn Phe Asp Ile
                 20                  25                  30

Ser Arg Ile Tyr Gly Lys Trp Tyr Asn Leu Ala Ile Gly Ser Thr Cys
        35                  40                  45

Pro Trp Leu Lys Lys Ile Lys Asp Arg Met Thr Val Ser Thr Leu Val
 50                  55                  60

Leu Gly Glu Gly Ala Thr Glu Ala Glu Ile Ser Met Thr Ser Thr Arg
 65                  70                  75                  80

Trp Arg Lys Gly Val Cys Glu Glu Thr Ser Gly Ala Tyr Glu Lys Thr
                 85                  90                  95

Asp Thr Asp Gly Lys Phe Leu Tyr His Lys Ser Lys Trp Asp Ile Thr
            100                 105                 110

Met Glu Ser Tyr Val Val His Thr Asn Tyr Asp Glu Tyr Ala Ile Phe
        115                 120                 125

Leu Thr Lys Lys Phe Ser Arg His His Gly Pro Thr Ile Thr Ala Lys
130                 135                 140

Leu Tyr Gly Arg Ala Pro Gln Leu Arg Glu Thr Leu Leu Gln Asp Phe
145                 150                 155                 160

Arg Val Val Ala Gln Gly Val Gly Ile Pro Glu Asp Ser Ile Phe Thr
                165                 170                 175
```

```
Met Ala Asp Arg Gly Glu Cys Val Pro Gly Glu Gln Glu Pro Glu Pro
            180                 185                 190

Ile Leu Ile Pro Arg
        195

<210> SEQ ID NO 52
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 35. M8H4DK-Human R66H+N179SD

<400> SEQUENCE: 52

Met His His His His His His His Asp Asp Asp Asp Lys Gly Pro
1               5                   10                  15

Val Pro Thr Pro Pro Asp Asn Ile Gln Val Gln Glu Asn Phe Asp Ile
            20                  25                  30

Ser Arg Ile Tyr Gly Lys Trp Tyr Asn Leu Ala Ile Gly Ser Thr Cys
        35                  40                  45

Pro Trp Leu Lys Lys Ile Met Asp Arg Met Thr Val Ser Thr Leu Val
    50                  55                  60

Leu Gly Glu Gly Ala Thr Glu Ala Glu Ile Ser Met Thr Ser Thr His
65                  70                  75                  80

Trp Arg Lys Gly Val Cys Glu Glu Thr Ser Gly Ala Tyr Glu Lys Thr
                85                  90                  95

Asp Thr Asp Gly Lys Phe Leu Tyr His Lys Ser Lys Trp Asp Ile Thr
            100                 105                 110

Met Glu Ser Tyr Val Val His Thr Asn Tyr Asp Glu Tyr Ala Ile Phe
        115                 120                 125

Leu Thr Lys Lys Phe Ser Arg His His Gly Pro Thr Ile Thr Ala Lys
    130                 135                 140

Leu Tyr Gly Arg Ala Pro Gln Leu Arg Glu Thr Leu Leu Gln Asp Phe
145                 150                 155                 160

Arg Val Val Ala Gln Gly Val Gly Ile Pro Glu Asp Ser Ile Phe Thr
                165                 170                 175

Met Ala Asp Arg Gly Glu Cys Val Pro Gly Glu Gln Glu Pro Glu Pro
            180                 185                 190

Ile Leu Ile Pro Arg
        195

<210> SEQ ID NO 53
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 36. M8H4DK-Human M41K+R66H+N179SD

<400> SEQUENCE: 53

Met His His His His His His His Asp Asp Asp Asp Lys Gly Pro
1               5                   10                  15

Val Pro Thr Pro Pro Asp Asn Ile Gln Val Gln Glu Asn Phe Asp Ile
            20                  25                  30

Ser Arg Ile Tyr Gly Lys Trp Tyr Asn Leu Ala Ile Gly Ser Thr Cys
        35                  40                  45
```

```
Pro Trp Leu Lys Lys Ile Lys Asp Arg Met Thr Val Ser Thr Leu Val
    50                  55                  60

Leu Gly Glu Gly Ala Thr Glu Ala Glu Ile Ser Met Thr Ser Thr His
65                  70                  75                  80

Trp Arg Lys Gly Val Cys Glu Glu Thr Ser Gly Ala Tyr Glu Lys Thr
                85                  90                  95

Asp Thr Asp Gly Lys Phe Leu Tyr His Lys Ser Lys Trp Asp Ile Thr
            100                 105                 110

Met Glu Ser Tyr Val Val His Thr Asn Tyr Asp Glu Tyr Ala Ile Phe
        115                 120                 125

Leu Thr Lys Lys Phe Ser Arg His His Gly Pro Thr Ile Thr Ala Lys
    130                 135                 140

Leu Tyr Gly Arg Ala Pro Gln Leu Arg Glu Thr Leu Leu Gln Asp Phe
145                 150                 155                 160

Arg Val Val Ala Gln Gly Val Gly Ile Pro Glu Asp Ser Ile Phe Thr
                165                 170                 175

Met Ala Asp Arg Gly Glu Cys Val Pro Gly Glu Gln Glu Pro Glu Pro
            180                 185                 190

Ile Leu Ile Pro Arg
        195

<210> SEQ ID NO 54
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 38. M8H4DK-Human R66H

<400> SEQUENCE: 54

Met His His His His His His His Asp Asp Asp Asp Lys Gly Pro
1               5                   10                  15

Val Pro Thr Pro Pro Asp Asn Ile Gln Val Gln Glu Asn Phe Asn Ile
                20                  25                  30

Ser Arg Ile Tyr Gly Lys Trp Tyr Asn Leu Ala Ile Gly Ser Thr Cys
            35                  40                  45

Pro Trp Leu Lys Lys Ile Met Asp Arg Met Thr Val Ser Thr Leu Val
    50                  55                  60

Leu Gly Glu Gly Ala Thr Glu Ala Glu Ile Ser Met Thr Ser Thr His
65                  70                  75                  80

Trp Arg Lys Gly Val Cys Glu Glu Thr Ser Gly Ala Tyr Glu Lys Thr
                85                  90                  95

Asp Thr Asp Gly Lys Phe Leu Tyr His Lys Ser Lys Trp Asn Ile Thr
            100                 105                 110

Met Glu Ser Tyr Val Val His Thr Asn Tyr Asp Glu Tyr Ala Ile Phe
        115                 120                 125

Leu Thr Lys Lys Phe Ser Arg His His Gly Pro Thr Ile Thr Ala Lys
    130                 135                 140

Leu Tyr Gly Arg Ala Pro Gln Leu Arg Glu Thr Leu Leu Gln Asp Phe
145                 150                 155                 160

Arg Val Val Ala Gln Gly Val Gly Ile Pro Glu Asp Ser Ile Phe Thr
                165                 170                 175

Met Ala Asp Arg Gly Glu Cys Val Pro Gly Glu Gln Glu Pro Glu Pro
            180                 185                 190
```

Ile Leu Ile Pro Arg
        195

<210> SEQ ID NO 55
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 39.M8H4DK-Human

<400> SEQUENCE: 55

Met His His His His His His His Asp Asp Asp Lys Gly Pro
1               5                   10                  15

Val Pro Thr Pro Pro Asp Asn Ile Gln Val Gln Glu Asn Phe Asp Ile
            20                  25                  30

Ser Arg Ile Tyr Gly Lys Trp Tyr Asn Leu Ala Ile Gly Ser Thr Cys
        35                  40                  45

Pro Trp Leu Lys Lys Ile Met Asp Arg Met Thr Val Ser Thr Leu Val
    50                  55                  60

Leu Gly Glu Gly Ala Thr Glu Ala Glu Ile Ser Met Thr Ser Thr Arg
65                  70                  75                  80

Trp Arg Lys Gly Val Cys Glu Glu Thr Ser Gly Ala Tyr Glu Lys Thr
                85                  90                  95

Asp Thr Asp Gly Lys Phe Leu Tyr His Lys Ser Lys Trp Asp Ile Thr
            100                 105                 110

Met Glu Ser Tyr Val Val His Thr Asn Tyr Asp Glu Tyr Ala Ile Phe
        115                 120                 125

Leu Thr Lys Lys Phe Ser Arg His His Gly Pro Thr Ile Thr Ala Lys
    130                 135                 140

Leu Tyr Gly Arg Ala Pro Gln Leu Arg Glu Thr Leu Leu Gln Asp Phe
145                 150                 155                 160

Arg Val Val Ala Gln Gly Val Gly Ile Pro Glu Asp Ser Ile Phe Thr
                165                 170                 175

Met Ala Asp Arg Gly Glu Cys Val Pro Gly Glu Gln Glu Pro Glu Pro
            180                 185                 190

Ile Leu Ile Pro Arg
        195

<210> SEQ ID NO 56
<211> LENGTH: 192
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 40. M8H-Human wt

<400> SEQUENCE: 56

Met His His His His His His His Gly Pro Val Pro Thr Pro Pro
1               5                   10                  15

Asp Asn Ile Gln Val Gln Glu Asn Phe Asn Ile Ser Arg Ile Tyr Gly
            20                  25                  30

Lys Trp Tyr Asn Leu Ala Ile Gly Ser Thr Cys Pro Trp Leu Lys Lys
        35                  40                  45

Ile Met Asp Arg Met Thr Val Ser Thr Leu Val Leu Gly Glu Gly Ala

```
                    50                  55                  60
Thr Glu Ala Glu Ile Ser Met Thr Ser Thr Arg Trp Arg Lys Gly Val
 65                  70                  75                  80

Cys Glu Glu Thr Ser Gly Ala Tyr Glu Lys Thr Asp Thr Asp Gly Lys
                     85                  90                  95

Phe Leu Tyr His Lys Ser Lys Trp Asn Ile Thr Met Glu Ser Tyr Val
                100                 105                 110

Val His Thr Asn Tyr Asp Glu Tyr Ala Ile Phe Leu Thr Lys Lys Phe
            115                 120                 125

Ser Arg His His Gly Pro Thr Ile Thr Ala Lys Leu Tyr Gly Arg Ala
        130                 135                 140

Pro Gln Leu Arg Glu Thr Leu Leu Gln Asp Phe Arg Val Val Ala Gln
145                 150                 155                 160

Gly Val Gly Ile Pro Glu Asp Ser Ile Phe Thr Met Ala Asp Arg Gly
                165                 170                 175

Glu Cys Val Pro Gly Glu Gln Glu Pro Glu Pro Ile Leu Ile Pro Arg
                180                 185                 190
```

<210> SEQ ID NO 57
<211> LENGTH: 192
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 41. M8H-Human R66H+N1796D

<400> SEQUENCE: 57

```
Met His His His His His His His Gly Pro Val Pro Thr Pro Pro
 1               5                  10                  15

Asp Asn Ile Gln Val Gln Glu Asn Phe Asp Ile Ser Arg Ile Tyr Gly
                 20                  25                  30

Lys Trp Tyr Asn Leu Ala Ile Gly Ser Thr Cys Pro Trp Leu Lys Lys
             35                  40                  45

Ile Met Asp Arg Met Thr Val Ser Thr Leu Val Leu Gly Glu Gly Ala
 50                  55                  60

Thr Glu Ala Glu Ile Ser Met Thr Ser Thr His Trp Arg Lys Gly Val
 65                  70                  75                  80

Cys Glu Glu Thr Ser Gly Ala Tyr Glu Lys Thr Asp Thr Asp Gly Lys
                     85                  90                  95

Phe Leu Tyr His Lys Ser Lys Trp Asp Ile Thr Met Glu Ser Tyr Val
                100                 105                 110

Val His Thr Asn Tyr Asp Glu Tyr Ala Ile Phe Leu Thr Lys Lys Phe
            115                 120                 125

Ser Arg His His Gly Pro Thr Ile Thr Ala Lys Leu Tyr Gly Arg Ala
        130                 135                 140

Pro Gln Leu Arg Glu Thr Leu Leu Gln Asp Phe Arg Val Val Ala Gln
145                 150                 155                 160

Gly Val Gly Ile Pro Glu Asp Ser Ile Phe Thr Met Ala Asp Arg Gly
                165                 170                 175

Glu Cys Val Pro Gly Glu Gln Glu Pro Glu Pro Ile Leu Ile Pro Arg
                180                 185                 190
```

<210> SEQ ID NO 58
<211> LENGTH: 594
<212> TYPE: DNA

<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: 60. M8H4DK-Human wt

<400> SEQUENCE: 58

```
atgcatcacc atcaccatca ccatcacgat gacgatgaca agggccctgt gccaacgccg      60
cccgacaaca tccaagtgca ggaaaacttc aatatctctc ggatctatgg gaagtggtac     120
aacctggcca tcggttccac ctgccctgg ctgaagaaga tcatggacag gatgacagtg      180
agcacgctgg tgctgggaga gggcgctaca gaggcggaga tcagcatgac cagcactcgt     240
tggcggaaag gtgtctgtga ggagacgtct ggagcttatg agaaaacaga tactgatggg    300
aagtttctct atcacaaatc caaatggaac ataaccatgg agtccatgt ggtccacacc     360
aactatgatg agtatgccat tttcctgacc aagaaattca gccgccatca tggacccacc    420
attactgcca agctctacgg gcgggcgccg cagctgaggg aaactctcct gcaggacttc    480
agagtggttg cccagggtgt gggcatccct gaggactcca tcttcaccat ggctgaccga    540
ggtgaatgtg tccctgggga gcaggaacca gagcccatct taatcccgag atga          594
```

<210> SEQ ID NO 59
<211> LENGTH: 603
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: 1.M8H5GIEGR-Mouse

<400> SEQUENCE: 59

```
atgcatcacc atcaccatca ccatcacggt ggaggagggg gtatcgaggg ccgcgaccct      60
gcgtcaacac tgccagatat ccaggttcag gagaacttca gtgagtcccg gatctatgga    120
aaatggtaca acctggcggt gggatccacc tgcccgtggc tgagccgcat taaggacaag    180
atgagcgtga gcacgctggt gctgcaggag ggggcgacag aaacagagat cagcatgacc    240
agtactcgat ggcggagagg tgtctgtgag gagatcactg gggcgtacca gaagacggac    300
atcgatggaa agttcctcta ccacaaatcc aaatggaaca taaccttgga atccatgtg    360
gtccacacca actatgacga atatgccatt tccttacca agaagtccag ccaccaccac    420
gggctcacca tcactgccaa gctctatggt cgggagccac agctgaggga cagccttctg    480
caggagttca aggatgtggc cctgaatgtg ggcatctctg agaactccat cattttttatg   540
cctgacagag gggaatgtgt ccctgggat cgggaggtgg agcccacatc aattgccaga    600
tga                                                                  603
```

<210> SEQ ID NO 60
<211> LENGTH: 606
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: 2. M8H5GIEGR-Naked Mole

<400> SEQUENCE: 60

```
atgcatcacc atcaccatca ccatcacggt ggaggagggg gtatcgaggg ccgcaatcct      60
```

```
gtgccgatgc cgccagacaa catccaagtg caggagaact ttgatgaatc ccggatctat      120
gggaaatggt tcaacctggc tacgggctcc acgtgcccgt ggctgaagag gatcaaagac      180
aggctgagtg tgagcacaat ggtgctgggc aaggggacca cggagacaca gatcagcaca      240
acccacaccc actggcggca aggggtgtgc caggagacct caggggttta caagaaaaca      300
gacacggctg gaagttcct ctaccacaag tccaaatgga atgtaaccat ggagtcctat       360
gtggtccaca ccaactatga tgagtatgcc atcattctaa ctaagaagtt cagccaccac      420
catggaccga ccattactgc caagctctat gggagagagc cgcggctgag agacagcctc      480
ctgcaggaat tcagggagat ggccctgggc gtaggcatcc ccgaggattc catcttcaca      540
atggccaaca gagggaatg tgtccctggt gaccaggcac cagagtccac cccagccccg      600
aggtga                                                                606
```

<210> SEQ ID NO 61
<211> LENGTH: 594
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 3. M8H5GIEGR-Frog

<400> SEQUENCE: 61

```
atgcatcacc atcaccatca ccatcacggt ggaggagggg gtatcgaggg ccgctgcagc      60
ccaatccagc cagaggacaa tatccagatc caggagaact ttgatctcca gaggatttat      120
ggcaaatggt acgacattgc catcggctcc acctgcaaat ggctgaagca ccacaaggaa      180
aagttcaaca tggggacact ggagcttagc gatggggaga ccgacgggga ggtgcggatt      240
gtgaacacaa ggatgaggca cggaacctgc tctcagattg ttgggtccta tcagaagaca      300
gagaccccag ggaagttcga ctatttcaac gcacggtggg gaaccacgat ccaaaactac      360
attgtcttca ctaactacaa tgagtatgtc atcatgcaga tgaggaagaa gaagggatcg      420
gagaccacca cgaccgtcaa gctgtatggg cggagcccag acttgcgtcc gaccctcgtt      480
gatgaattca ggcagtttgc cttggctcag ggcattcctg aagactccat cgtgatgcta      540
cctaacaatg gtgagtgctc tccaggggaa atagaagtga gaccacggag atga           594
```

<210> SEQ ID NO 62
<211> LENGTH: 594
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 4. M8H5GIEGR-Chicken

<400> SEQUENCE: 62

```
atgcatcacc atcaccatca ccatcacggt ggaggagggg gtatcgaggg ccgcacgcct      60
gttggggacc aggatgagga cattcaagtg caagagaatt ttgagcctga gcggatgtat      120
gggaaatggt atgacgtagc tgttggcacc acctgcaagt ggatgaagaa ctacaaggag      180
aagttcagca tgggcacact ggtgctgggc cccggcccca gcgctgacca gatcagtacc      240
atcagcacca ggctgcggca aggtgactgc aaacgtgtct caggagagta ccagaaaact      300 gacaccctg gcaaatacac ctactataac cccaagtggg atgtgtctat caagtcctac      360
gtgcttcgca ccaactatga agaatacgca gtcattctga tgaagaagac aagtaatttt      420
```
ggcccaacca ccacactgaa gctgtatggg agaagcccag agctgcggga agagctcacc    480
gaggctttcc agcagctggc tctggagatg ggcatccctg cagattccgt cttcatcctg    540
gccaacaaag gtgaatgtgt cccacaggag actgccactg cccctgagag gtga          594

<210> SEQ ID NO 63
<211> LENGTH: 606
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 5. M8H5GIEGR-Rabbit

<400> SEQUENCE: 63
atgcatcacc atcaccatca ccatcacggt ggaggagggg gtatcgaggg ccgcgacccc    60
gtgcccaccc tgccggacga catccaagtg caggagaact tcgagctctc tcggatctac    120
gggaaatggt acaacctggc tgtggggtcc acctgcccgt ggctgaagag gatcaaggac    180
aggatggccg tgagcacgct ggtgctggga gggggacga gcgagacgga gatcagcatg    240
accagcacgc actggcggag gggcgtctgt gaggagatct ccggggccta tgagaaaacg    300
gacactgacg ggaagttcct gtaccacaaa gccaatgga acttaaccat ggagtcctac    360
gtggtgcaca ccaactacga tgagtatgcc attttttctca ccaagaaatt cagccgccgc    420
cacggcccca ccatcaccgc caagctctat gggcgggagc cgcagctgag ggagagcctc    480
ctgcaggagt tcagggaggt ggctctcggg gtggggatcc ccgagaactc catcttcacc    540
atgatcgaca gaggggaatg tgtgcccggg cagcaggaac caaagcctgc ccccgtgttg    600
agatga                                                                606

<210> SEQ ID NO 64
<211> LENGTH: 606
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 6. M8H5GIEGR-SQ Monkey

<400> SEQUENCE: 64
atgcatcacc atcaccatca ccatcacggt ggaggagggg gtatcgaggg ccgcagccca    60
gtgccgacgc cgcccgaagg cattcaagtg caggaaaact tcaatctctc tcggatctac    120
ggcaagtggt acaacctggc catcggttcc acctgcccct ggctaaagaa gatcatggac    180
aggttgaaag tgagcacgct ggtgctggaa gagggcgcca cggaggcgga gatcagcatg    240
accagcactc gctggcggaa aggtttctgt gagcagacct cttgggctta tgagaaaaca    300
gatactgatg ggaagtttct ctatcacgaa cccaatgga acgtaaccat ggagtcctat    360
gtggcccaca ccaactatga ggagtatgcc attttcctga ccaagaaatt cagccgccat    420
catggaccca ccattactgc caagctctat gggcgggagc cacagctgag ggaaagcctc    480
ctgcaggact tcagagtggt tgcccagggt gtgggcatcc ctgaggattc catcttcacc    540
atggctaacc gaggtgaatg cgtccctggg gagcaggaac acagcccat cctacaccgg    600 agatga                                                                606

<210> SEQ ID NO 65

```
<211> LENGTH: 606
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 7. M8H5GIEGR-Walrus

<400> SEQUENCE: 65
atgcatcacc atcaccatca ccatcacggt ggaggagggg gtatcgaggg ccgcagtccc      60
gtgctgacgc cgcctgacgc catccaagtg caagagaact tcgacatctc tcggatctac     120
gggaagtggt tcatgtggc catgggctcc acctgcccgt ggctgaagaa gttcatggac      180
aggatgtcca tgagcacgct ggtgctgggc gaggggcga cggatgggga gatcagcatg      240
accagcacac gttggcggag aggcacctgt gaggagatct ctggggctta tgagaaaacc     300
agcactaacg gaaagttcct ctatcataat cccaaatgga acatcaccat ggagtcctat     360
gtggtccaca ccgactatga tgagtacgcc atctttctga ccaagaaatt cagccgccac     420
catgggccca ccattactgc caagctctat gggcgacagc cgcagcttcg agaaagcctg     480
ctggaggagt tcagggagct tgccttgggt gtgggcatcc ccgaggactc catcttcacc     540
atggccaaca aggtgagtg tgtccctggg gagcaggaac cagagccctc tccacacatg     600
aggtga                                                               606

<210> SEQ ID NO 66
<211> LENGTH: 603
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 8. M8H5GIEGR-Manatee

<400> SEQUENCE: 66
atgcatcacc atcaccatca ccatcacggt ggaggagggg gtatcgaggg ccgcagccca      60
gtgaaaacac cactcaacga catccaagtg caggagaact ttgacctccc tcggatctac     120
gggaaatggt tcaacatagc cattggctcc acctgccaat ggctgaagag gttgaaggcc     180
gggccgacca tgagcaccct ggtcctggga gaggagcta cagacacaga gatcagcaca      240
accagcactc gttggcggaa aggcttctgt gaggagatct ctggggcata tgagaaaaca     300
gacacagctg ggaagttcct ttatcacgga tccaaatgga atgtaacctt ggagtcctat     360
gtggtccaca ccaactatga tgagtacgcc atttttctga ccaagaaatt cagccgctat     420
ggactcacca ttactgctaa gctctatggg cggcagcctc aggtgaggga gagcctcctg     480
gaggagttca gggaatttgc cctgggtgtg gcatccctg aggattccat cttccacacg      540
gccgacaaag gtgagtgtgt ccctggagag caggagccag aacccaccgc agccctgaga     600
tga                                                                  603

<210> SEQ ID NO 67
<211> LENGTH: 609
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 9. M8H5GIEGR-Plaice
```

-continued

<400> SEQUENCE: 67

| atgcatcacc atcaccatca ccatcacggt ggaggagggg gtatcgaggg ccgcctccct | 60 |
| gtgctccctg aacctctta cccgacacag gagaactttg atctgacccg gtttgtgggg | 120 |
| acatggcacg atgttgcctt gacgagcagc tgcccccata tgcagcgtaa cagggcggat | 180 |
| gcagccattg gtaaactggt tctggagaaa gacactggaa acaaactcaa ggtgacacga | 240 |
| actagactca gacatggaac atgtgtggag atgtctggag aatatgagtt aaccagcaca | 300 |
| ccaggacgaa tcttctacca tattgacagg tgggatgcag acgtggacgc ctacgtggtt | 360 |
| cacaccaact acgacgagta cgcaattata ataatgagca acagaaaac atcgggggag | 420 |
| aacagcacct cactcaagct gtacagtcgg acgatgtctg tgagagacac tgtgctggat | 480 |
| gacttcaaaa ctctggtcag acatcaggga atgagtgacg acaccattat catcaagcag | 540 |
| aacaaaggtg actgtattcc tggagagcag gtggaagaag caccatctca gccagagccc | 600 |
| aagcggtga | 609 |

<210> SEQ ID NO 68
<211> LENGTH: 606
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 10. M8H5GIEGR-Orangutan

<400> SEQUENCE: 68

| atgcatcacc atcaccatca ccatcacggt ggaggagggg gtatcgaggg ccgcggccct | 60 |
| gtgccgacgc cgcccgacaa catccaagtg caggaaaact tcaatatctc tcggatctat | 120 |
| gggaagtggt acaacctggc catcggttcc acctgcccct ggctgaagaa gatcatggac | 180 |
| aggatgacag tgagcaccct ggtgctggga gagggcgcta cagaggcgga gatcagcatg | 240 |
| accagcactc gttggcggaa aggtgtctgt gaggagacat ctggagctta tgagaaaaca | 300 |
| gatactgatg gaagtttct ctatcacaaa tccaaatgga acataaccat ggagtcctat | 360 |
| gtggtccaca ccaactatga tgagtatgcc attttcctga ccaagaaatt cagccgccgt | 420 |
| catggaccca ccattactgc caagctctac gggcgggcgc cgcagctgag ggaaaccctc | 480 |
| ctgcaggact tcagagtggt tgcccagggt gtgggcatcc tgaggactc catcttcacc | 540 |
| atggctgacc gaggtgaatg tgtccctggg gaacaggaac cagagcccat cttaatcccg | 600 |
| agatga | 606 |

<210> SEQ ID NO 69
<211> LENGTH: 606
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 11. M8H5GIEGR-Human P35K

<400> SEQUENCE: 69

| atgcatcacc atcaccatca ccatcacggt ggaggagggg gtatcgaggg ccgcggccct | 60 |
| gtgccaacgc cgcccgacaa catccaagtg caggaaaact tcaatatctc tcggatctat | 120 |
| gggaagtggt acaacctggc catcggttcc acctgcaaat ggctgaagaa gatcatggac | 180 |
| aggatgacag tgagcacgct ggtgctggga gagggcgcta cagaggcgga gatcagcatg | 240 |

```
accagcactc gttggcggaa aggtgtctgt gaggagacgt ctggagctta tgagaaaaca    300
gatactgatg ggaagtttct ctatcacaaa tccaaatgga acataaccat ggagtcctat    360
gtggtccaca ccaactatga tgagtatgcc attttcctga ccaagaaatt cagccgccat    420
catggaccca ccattactgc caagctctac gggcgggcgc cgcagctgag ggaaactctc    480
ctgcaggact tcagagtggt tgcccagggt gtgggcatcc ctgaggactc catcttcacc    540
atggctgacc gaggtgaatg tgtccctggg gagcaggaac cagagcccat cttaatcccg    600
agatga                                                              606

<210> SEQ ID NO 70
<211> LENGTH: 606
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 12. M8H5GIEGR-Human M41K

<400> SEQUENCE: 70
atgcatcacc atcaccatca ccatcacggt ggaggagggg gtatcgaggg ccgcggccct     60
gtgccaacgc cgcccgacaa catccaagtg caggaaaact tcaatatctc tcggatctat    120
gggaagtggt acaacctggc catcggttcc acctgcccct ggctgaagaa gatcaaagac    180
aggatgacag tgagcacgct ggtgctggga gagggcgcta cagaggcgga gatcagcatg    240
accagcactc gttggcggaa aggtgtctgt gaggagacgt ctggagctta tgagaaaaca    300
gatactgatg ggaagtttct ctatcacaaa tccaaatgga acataaccat ggagtcctat    360
gtggtccaca ccaactatga tgagtatgcc attttcctga ccaagaaatt cagccgccat    420
catggaccca ccattactgc caagctctac gggcgggcgc cgcagctgag ggaaactctc    480
ctgcaggact tcagagtggt tgcccagggt gtgggcatcc ctgaggactc catcttcacc    540
atggctgacc gaggtgaatg tgtccctggg gagcaggaac cagagcccat cttaatcccg    600
agatga                                                              606

<210> SEQ ID NO 71
<211> LENGTH: 606
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 13. M8H5GIEGR-Human R66H

<400> SEQUENCE: 71
atgcatcacc atcaccatca ccatcacggt ggaggagggg gtatcgaggg ccgcggccct     60
gtgccaacgc cgcccgacaa catccaagtg caggaaaact tcaatatctc tcggatctat    120
gggaagtggt acaacctggc catcggttcc acctgcccct ggctgaagaa gatcatggac    180
aggatgacag tgagcacgct ggtgctggga gagggcgcta cagaggcgga gatcagcatg    240
accagcactc attggcggaa aggtgtctgt gaggagacgt ctggagctta tgagaaaaca    300
gatactgatg ggaagtttct ctatcacaaa tccaaatgga acataaccat ggagtcctat    360
gtggtccaca ccaactatga tgagtatgcc attttcctga ccaagaaatt cagccgccat    420
catggaccca ccattactgc caagctctac gggcgggcgc cgcagctgag ggaaactctc    480
```

```
ctgcaggact tcagagtggt tgcccagggt gtgggcatcc ctgaggactc catcttcacc    540
atggctgacc gaggtgaatg tgtccctggg gagcaggaac cagagcccat cttaatcccg    600
agatga                                                               606
```

<210> SEQ ID NO 72
<211> LENGTH: 606
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 14. M8H5GIEGR-Human T75K

<400> SEQUENCE: 72

```
atgcatcacc atcaccatca ccatcacggt ggaggagggg gtatcgaggg ccgcggccct    60
gtgccaacgc cgcccgacaa catccaagtg caggaaaact tcaatatctc tcggatctat   120
gggaagtggt acaacctggc catcggttcc acctgcccct ggctgaagaa gatcatggac   180
aggatgacag tgagcacgct ggtgctggga gagggcgcta cagaggcgga gatcagcatg   240
accagcactc gttggcggaa aggtgtctgt gaggagaaat ctggagctta tgagaaaaca   300
gatactgatg gaagtttcct ctatcacaaa tccaaatgga acataaccat ggagtcctat   360
gtggtccaca ccaactatga tgagtatgcc attttcctga ccaagaaatt cagccgccat   420
catggaccca ccattactgc caagctctac gggcgggcgc cgcagctgag ggaaactctc   480
ctgcaggact tcagagtggt tgcccagggt gtgggcatcc ctgaggactc catcttcacc   540
atggctgacc gaggtgaatg tgtccctggg gagcaggaac cagagcccat cttaatcccg   600
agatga                                                               606
```

<210> SEQ ID NO 73
<211> LENGTH: 606
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 15. M8H5GIEGR-Human T75Y

<400> SEQUENCE: 73

```
atgcatcacc atcaccatca ccatcacggt ggaggagggg gtatcgaggg ccgcggccct    60
gtgccaacgc cgcccgacaa catccaagtg caggaaaact tcaatatctc tcggatctat   120
gggaagtggt acaacctggc catcggttcc acctgcccct ggctgaagaa gatcatggac   180
aggatgacag tgagcacgct ggtgctggga gagggcgcta cagaggcgga gatcagcatg   240
accagcactc gttggcggaa aggtgtctgt gaggagtatt ctggagctta tgagaaaaca   300
gatactgatg gaagtttcct ctatcacaaa tccaaatgga acataaccat ggagtcctat   360
gtggtccaca ccaactatga tgagtatgcc attttcctga ccaagaaatt cagccgccat   420
catggaccca ccattactgc caagctctac gggcgggcgc cgcagctgag ggaaactctc   480
ctgcaggact tcagagtggt tgcccagggt gtgggcatcc ctgaggactc catcttcacc   540
atggctgacc gaggtgaatg tgtccctggg gagcaggaac cagagcccat cttaatcccg   600
agatga                                                               606
```

<210> SEQ ID NO 74
<211> LENGTH: 606

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 16. M8H5GIEGR-Human M99K

<400> SEQUENCE: 74
atgcatcacc atcaccatca ccatcacggt ggaggagggg gtatcgaggg ccgcggccct    60
gtgccaacgc cgcccgacaa catccaagtg caggaaaact tcaatatctc tcggatctat   120
gggaagtggt acaacctggc catcggttcc acctgcccct ggctgaagaa gatcatggac   180
aggatgacag tgagcacgct ggtgctggga gagggcgcta cagaggcgga gatcagcatg   240
accagcactc gttggcggaa aggtgtctgt gaggagacgt ctggagctta tgagaaaaca   300
gatactgatg ggaagtttct ctatcacaaa tccaaatgga acataaccaa agagtcctat   360
gtggtccaca ccaactatga tgagtatgcc attttcctga ccaagaaatt cagccgccat   420
catggaccca ccattactgc caagctctac gggcgggcgc cgcagctgag ggaaactctc   480
ctgcaggact tcagagtggt tgcccagggt gtgggcatcc ctgaggactc catcttcacc   540
atggctgacc gaggtgaatg tgtccctggg gagcaggaac cagagcccat cttaatcccg   600
agatga                                                              606

<210> SEQ ID NO 75
<211> LENGTH: 606
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 17. M8H5GIEGR-Human S101Y

<400> SEQUENCE: 75
atgcatcacc atcaccatca ccatcacggt ggaggagggg gtatcgaggg ccgcggccct    60
gtgccaacgc cgcccgacaa catccaagtg caggaaaact tcaatatctc tcggatctat   120
gggaagtggt acaacctggc catcggttcc acctgcccct ggctgaagaa gatcatggac   180
aggatgacag tgagcacgct ggtgctggga gagggcgcta cagaggcgga gatcagcatg   240
accagcactc gttggcggaa aggtgtctgt gaggagacgt ctggagctta tgagaaaaca   300
gatactgatg ggaagtttct ctatcacaaa tccaaatgga acataaccat ggagtattat   360
gtggtccaca ccaactatga tgagtatgcc attttcctga ccaagaaatt cagccgccat   420
catggaccca ccattactgc caagctctac gggcgggcgc cgcagctgag ggaaactctc   480
ctgcaggact tcagagtggt tgcccagggt gtgggcatcc ctgaggactc catcttcacc   540
atggctgacc gaggtgaatg tgtccctggg gagcaggaac cagagcccat cttaatcccg   600
agatga                                                              606

<210> SEQ ID NO 76
<211> LENGTH: 606
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 18. M8H5GIEGR-Human K69.92.118.

<400> SEQUENCE: 76
```

| | |
|---|---|
| atgcatcacc atcaccatca ccatcacggt ggaggagggg gtatcgaggg ccgcggccct | 60 |
| gtgccaacgc cgcccgacaa catccaagtg caggaaaact tcaatatctc tcggatctat | 120 |
| gggaagtggt acaacctggc catcggttcc acctgcccct ggctgaagaa gatcatggac | 180 |
| aggatgacag tgagcacgct ggtgctggga gagggcgcta cagaggcgga gatcagcatg | 240 |
| accagcactc gttggcggcg tggtgtctgt gaggagacgt ctggagctta tgagaaaaca | 300 |
| gatactgatg ggaagtttct ctatcaccgt tccaaatgga acataaccat ggagtcctat | 360 |
| gtggtccaca ccaactatga tgagtatgcc attttcctga ccaagcgttt cagccgccat | 420 |
| catggaccca ccattactgc ccgtctctac gggcgggcgc cgcagctgag ggaaactctc | 480 |
| ctgcaggact tcagagtggt tgcccagggt gtgggcatcc ctgaggactc catcttcacc | 540 |
| atggctgacc gaggtgaatg tgtccctggg gagcaggaac cagagcccat cttaatcccg | 600 |
| agatga | 606 |

<210> SEQ ID NO 77
<211> LENGTH: 597
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 19. M8H5GIEGR-Coelacanth

<400> SEQUENCE: 77

| | |
|---|---|
| atgcatcacc atcaccatca ccatcacggt ggaggagggg gtatcgaggg ccgcggaagt | 60 |
| ccccttcgag atgaagacat ccaagtgcag gagaactttg accttcccag gatttatgga | 120 |
| aaatggtacg aaattgcaat cgcttcgacc tgtccctggg tgaagaatca aaggataag | 180 |
| atgttcatgg aactatggt gctacaagag ggagagcaga gtgaccggat cagtaccacc | 240 |
| tccacccgaa tcagggatgg aacctgctca cagatcactg gatattacac gttaaccaca | 300 |
| acacctggga agttcgctta tcacaattct aaatggaact tggatgtcaa cagttatgtt | 360 |
| gttcacacta actatgacga atactcgatt gtgatgatgc agaaatacaa aagctctaac | 420 |
| tctaccacta cagtccgact ctatggaaga actcaagagc tacgagacag cttgcatgcc | 480 |
| gagttcaaaa agtttgctct ggatcaggga atagatgagg actccattta cattctgcca | 540 |
| aaaagagatg aatgtgtacc tggtgaacct aaagcagaat ctctcatggc acgttga | 597 |

<210> SEQ ID NO 78
<211> LENGTH: 606
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 21. M8H5GIEGR-Human L89T

<400> SEQUENCE: 78

| | |
|---|---|
| atgcatcacc atcaccatca ccatcacggt ggaggagggg gtatcgaggg ccgcggccct | 60 |
| gtgccaacgc cgcccgacaa catccaagtg caggaaaact tcaatatctc tcggatctat | 120 |
| gggaagtggt acaacctggc catcggttcc acctgcccct ggctgaagaa gatcatggac | 180 |
| aggatgacag tgagcacgct ggtgctggga gagggcgcta cagaggcgga gatcagcatg | 240 |
| accagcactc gttggcggaa aggtgtctgt gaggagacgt ctggagctta tgagaaaaca | 300 |

```
gatactgatg ggaagtttac ctatcacaaa tccaaatgga acataaccat ggagtcctat        360
gtggtccaca ccaactatga tgagtatgcc attttcctga ccaagaaatt cagccgccat        420
catggaccca ccattactgc caagctctac gggcgggcgc cgcagctgag ggaaactctc        480
ctgcaggact tcagagtggt tgcccagggt gtgggcatcc ctgaggactc catcttcacc        540
atggctgacc gaggtgaatg tgtccctggg gagcaggaac cagagcccat cttaatcccg        600
agatga                                                                   606
```

<210> SEQ ID NO 79
<211> LENGTH: 606
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 22. M8H5GIEGR-Human N1796D

<400> SEQUENCE: 79

```
atgcatcacc atcaccatca ccatcacggt ggaggagggg gtatcgaggg ccgcggccct         60
gtgccaacgc cgcccgacaa catccaagtg caggaaaact tcgatatctc tcggatctat        120
gggaagtggt acaacctggc catcggttcc acctgccccct ggctgaagaa gatcatggac       180
aggatgacag tgagcacgct ggtgctggga gagggcgcta cagaggcgga gatcagcatg        240
accagcactc gttggcggaa aggtgtctgt gaggagacgt ctggagctta tgagaaaaca        300
gatactgatg ggaagtttct ctatcacaaa tccaaatggg atataaccat ggagtcctat        360
gtggtccaca ccaactatga tgagtatgcc attttcctga ccaagaaatt cagccgccat        420
catggaccca ccattactgc caagctctac gggcgggcgc cgcagctgag ggaaactctc        480
ctgcaggact tcagagtggt tgcccagggt gtgggcatcc ctgaggactc catcttcacc        540
atggctgacc gaggtgaatg tgtccctggg gagcaggaac cagagcccat cttaatcccg        600
agatga                                                                   606
```

<210> SEQ ID NO 80
<211> LENGTH: 606
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 23. M8H5GIEGR-Human T45K

<400> SEQUENCE: 80

```
atgcatcacc atcaccatca ccatcacggt ggaggagggg gtatcgaggg ccgcggccct         60
gtgccaacgc cgcccgacaa catccaagtg caggaaaact tcaatatctc tcggatctat        120
gggaagtggt acaacctggc catcggttcc acctgccccct ggctgaagaa gatcatggac       180
aggatgaaag tgagcacgct ggtgctggga gagggcgcta cagaggcgga gatcagcatg        240
accagcactc gttggcggaa aggtgtctgt gaggagacgt ctggagctta tgagaaaaca        300
gatactgatg ggaagtttct ctatcacaaa tccaaatgga acataaccat ggagtcctat        360
gtggtccaca ccaactatga tgagtatgcc attttcctga ccaagaaatt cagccgccat        420
catggaccca ccattactgc caagctctac gggcgggcgc cgcagctgag ggaaactctc        480
ctgcaggact tcagagtggt tgcccagggt gtgggcatcc ctgaggactc catcttcacc        540
atggctgacc gaggtgaatg tgtccctggg gagcaggaac cagagcccat cttaatcccg        600
```

<210> SEQ ID NO 81
<211> LENGTH: 606
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 24. M8H5GIEGR-Human A135E

<400> SEQUENCE: 81

```
atgcatcacc atcaccatca ccatcacggt ggaggagggg gtatcgaggg ccgcggccct      60
gtgccaacgc cgcccgacaa catccaagtg caggaaaact tcaatatctc tcggatctat     120
gggaagtggt acaacctggc catcggttcc acctgcccct ggctgaagaa gatcatggac     180
aggatgacag tgagcacgct ggtgctggga gagggcgcta cagaggcgga gatcagcatg     240
accagcactc gttggcggaa aggtgtctgt gaggagacgt ctggagctta tgagaaaaca     300
gatactgatg ggaagtttct ctatcacaaa tccaaatgga acataaccat ggagtcctat     360
gtggtccaca ccaactatga tgagtatgcc attttcctga ccaagaaatt cagccgccat     420
catggaccca ccattactgc caagctctac gggcgggaac cgcagctgag ggaaactctc     480
ctgcaggact tcagagtggt tgcccagggt gtgggcatcc tgaggactc catcttcacc      540
atggctgacc gaggtgaatg tgtccctggg gagcaggaac cagagcccat cttaatcccg     600
agatga                                                               606
```

<210> SEQ ID NO 82
<211> LENGTH: 606
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 25. M8H5GIEGR-Human V170S

<400> SEQUENCE: 82

```
atgcatcacc atcaccatca ccatcacggt ggaggagggg gtatcgaggg ccgcggccct      60
gtgccaacgc cgcccgacaa catccaagtg caggaaaact tcaatatctc tcggatctat     120
gggaagtggt acaacctggc catcggttcc acctgcccct ggctgaagaa gatcatggac     180
aggatgacag tgagcacgct ggtgctggga gagggcgcta cagaggcgga gatcagcatg     240
accagcactc gttggcggaa aggtgtctgt gaggagacgt ctggagctta tgagaaaaca     300
gatactgatg ggaagtttct ctatcacaaa tccaaatgga acataaccat ggagtcctat     360
gtggtccaca ccaactatga tgagtatgcc attttcctga ccaagaaatt cagccgccat     420
catggaccca ccattactgc caagctctac gggcgggcgc cgcagctgag ggaaactctc     480
ctgcaggact tcagagtggt tgcccagggt gtgggcatcc tgaggactc catcttcacc      540
atggctgacc gaggtgaatg ttctcctggg gagcaggaac cagagcccat cttaatcccg     600
agatga                                                               606
```

<210> SEQ ID NO 83
<211> LENGTH: 606
<212> TYPE: DNA
<213> ORGANISM: Artificial Sequence
<220> FEATURE:

<223> OTHER INFORMATION: Description of Artificial Sequence: Synthetic
polynucleotide
<220> FEATURE:
<223> OTHER INFORMATION: 26. M8H5GIEGR-Human V148D

<400> SEQUENCE: 83

```
atgcatcacc atcaccatca ccatcacggt ggaggagggg gtatcgaggg ccgcggccct     60
gtgccaacgc cgcccgacaa catccaagtg caggaaaact tcaatatctc tcggatctat    120
gggaagtggt acaacctggc catcggttcc acctgcccct ggctgaagaa gatcatggac    180
aggatgacag tgagcacgct ggtgctggga gagggcgcta cagaggcgga gatcagcatg    240
accagcactc gttggcggaa aggtgtctgt gaggagacgt ctggagctta tgagaaaaca    300
gatactgatg ggaagtttct ctatcacaaa tccaaatgga acataaccat ggagtcctat    360
gtggtccaca ccaactatga tgagtatgcc attttcctga ccaagaaatt cagccgccat    420
catggaccca ccattactgc caagctctac gggcgggcgc cgcagctgag ggaaactctc    480
ctgcaggact tcagagatgt tgcccagggt gtgggcatcc ctgaggactc catcttcacc    540
atggctgacc gaggtgaatg tgtccctggg gagcaggaac cagagcccat cttaatcccg    600
agatga                                                               606
```

<210> SEQ ID NO 84
<211> LENGTH: 606
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: 27. M8H5GIEGR-Human G172Q

<400> SEQUENCE: 84

```
atgcatcacc atcaccatca ccatcacggt ggaggagggg gtatcgaggg ccgcggccct     60
gtgccaacgc cgcccgacaa catccaagtg caggaaaact tcaatatctc tcggatctat    120
gggaagtggt acaacctggc catcggttcc acctgcccct ggctgaagaa gatcatggac    180
aggatgacag tgagcacgct ggtgctggga gagggcgcta cagaggcgga gatcagcatg    240
accagcactc gttggcggaa aggtgtctgt gaggagacgt ctggagctta tgagaaaaca    300
gatactgatg ggaagtttct ctatcacaaa tccaaatgga acataaccat ggagtcctat    360
gtggtccaca ccaactatga tgagtatgcc attttcctga ccaagaaatt cagccgccat    420
catggaccca ccattactgc caagctctac gggcgggcgc cgcagctgag ggaaactctc    480
ctgcaggact tcagagtggt tgcccagggt gtgggcatcc ctgaggactc catcttcacc    540
atggctgacc gaggtgaatg tgtccctcag gagcaggaac cagagcccat cttaatcccg    600
agatga                                                               606
```

<210> SEQ ID NO 85
<211> LENGTH: 594
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: 33. M8H4DK-Human M41K+R66H

<400> SEQUENCE: 85

```
atgcatcacc atcaccatca ccatcacgat gacgatgaca agggccctgt gccaacgccg     60
```

```
cccgacaaca tccaagtgca ggaaaacttc aatatctctc ggatctatgg gaagtggtac    120
aacctggcca tcggttccac ctgcccctgg ctgaagaaga tcaaagacag gatgacagtg    180
agcacgctgg tgctgggaga gggcgctaca gaggcggaga tcagcatgac cagcactcat    240
tggcggaaag gtgtctgtga ggagacgtct ggagcttatg agaaaacaga tactgatggg    300
aagtttctct atcacaaatc caaatggaac ataaccatgg agtcctatgt ggtccacacc    360
aactatgatg agtatgccat tttcctgacc aagaaattca gccgccatca tggacccacc    420
attactgcca agctctacgg gcgggcgccg cagctgaggg aaactctcct gcaggacttc    480
agagtggttg cccagggtgt gggcatccct gaggactcca tcttcaccat ggctgaccga    540
ggtgaatgtg tccctgggga gcaggaacca gagcccatct taatcccgag atga          594
```

<210> SEQ ID NO 86
<211> LENGTH: 594
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 34. M8H4DK-Human M41K+N1796D

<400> SEQUENCE: 86

```
atgcatcacc atcaccatca ccatcacgat gacgatgaca agggccctgt gccaacgccg     60
cccgacaaca tccaagtgca ggaaaacttc gatatctctc ggatctatgg gaagtggtac    120
aacctggcca tcggttccac ctgcccctgg ctgaagaaga tcaaagacag gatgacagtg    180
agcacgctgg tgctgggaga gggcgctaca gaggcggaga tcagcatgac cagcactcgt    240
tggcggaaag gtgtctgtga ggagacgtct ggagcttatg agaaaacaga tactgatggg    300
aagtttctct atcacaaatc caaatgggat ataaccatgg agtcctatgt ggtccacacc    360
aactatgatg agtatgccat tttcctgacc aagaaattca gccgccatca tggacccacc    420
attactgcca agctctacgg gcgggcgccg cagctgaggg aaactctcct gcaggacttc    480
agagtggttg cccagggtgt gggcatccct gaggactcca tcttcaccat ggctgaccga    540
ggtgaatgtg tccctgggga gcaggaacca gagcccatct taatcccgag atga          594
```

<210> SEQ ID NO 87
<211> LENGTH: 594
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 35. M8H4DK-Human R66H+N1796D

<400> SEQUENCE: 87

```
atgcatcacc atcaccatca ccatcacgat gacgatgaca agggccctgt gccaacgccg     60
cccgacaaca tccaagtgca ggaaaacttc gatatctctc ggatctatgg gaagtggtac    120
aacctggcca tcggttccac ctgcccctgg ctgaagaaga tcatggacag gatgacagtg    180
agcacgctgg tgctgggaga gggcgctaca gaggcggaga tcagcatgac cagcactcat    240
tggcggaaag gtgtctgtga ggagacgtct ggagcttatg agaaaacaga tactgatggg    300
aagtttctct atcacaaatc caaatgggat ataaccatgg agtcctatgt ggtccacacc    360
aactatgatg agtatgccat tttcctgacc aagaaattca gccgccatca tggacccacc    420
attactgcca agctctacgg gcgggcgccg cagctgaggg aaactctcct gcaggacttc    480
```

```
agagtggttg cccagggtgt gggcatccct gaggactcca tcttcaccat ggctgaccga    540
ggtgaatgtg tccctgggga gcaggaacca gagcccatct taatcccgag atga         594

<210> SEQ ID NO 88
<211> LENGTH: 594
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 36. M8H4DK-Human M41K+R66H+N1796D

<400> SEQUENCE: 88
atgcatcacc atcaccatca ccatcacgat gacgatgaca agggccctgt gccaacgccg    60
cccgacaaca tccaagtgca ggaaaacttc gatatctctc ggatctatgg gaagtggtac   120
aacctggcca tcggttccac ctgcccctgg ctgaagaaga tcaaagacag gatgacagtg   180
agcacgctgg tgctgggaga gggcgctaca gaggcggaga tcagcatgac cagcactcat   240
tggcggaaag gtgtctgtga ggagacgtct ggagcttatg agaaaacaga tactgatggg   300
aagtttctct atcacaaatc caaatgggat ataaccatgg agtcctatgt ggtccacacc   360
aactatgatg agtatgccat tttcctgacc aagaaattca gccgccatca tggacccacc   420
attactgcca agctctacgg gcgggcgccg cagctgaggg aaactctcct gcaggacttc   480
agagtggttg cccagggtgt gggcatccct gaggactcca tcttcaccat ggctgaccga   540
ggtgaatgtg tccctgggga gcaggaacca gagcccatct taatcccgag atga         594

<210> SEQ ID NO 89
<211> LENGTH: 594
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 37. M8H4DK-Human M41K

<400> SEQUENCE: 89
atgcatcacc atcaccatca ccatcacgat gacgatgaca agggccctgt gccaacgccg    60
cccgacaaca tccaagtgca ggaaaacttc aatatctctc ggatctatgg gaagtggtac   120
aacctggcca tcggttccac ctgcccctgg ctgaagaaga tcaaagacag gatgacagtg   180
agcacgctgg tgctgggaga gggcgctaca gaggcggaga tcagcatgac cagcactcgt   240
tggcggaaag gtgtctgtga ggagacgtct ggagcttatg agaaaacaga tactgatggg   300
aagtttctct atcacaaatc caaatggaac ataaccatgg agtcctatgt ggtccacacc   360
aactatgatg agtatgccat tttcctgacc aagaaattca gccgccatca tggacccacc   420
attactgcca agctctacgg gcgggcgccg cagctgaggg aaactctcct gcaggacttc   480
agagtggttg cccagggtgt gggcatccct gaggactcca tcttcaccat ggctgaccga   540
ggtgaatgtg tccctgggga gcaggaacca gagcccatct taatcccgag atga         594

<210> SEQ ID NO 90
<211> LENGTH: 594
<212> TYPE: DNA
<213> ORGANISM: Artificial Sequence
<220> FEATURE:
<223> OTHER INFORMATION: Description of Artificial Sequence: Synthetic
      polynucleotide
```

<220> FEATURE:
<223> OTHER INFORMATION: 38. M8H4DK-Human R66H

<400> SEQUENCE: 90

```
atgcatcacc atcaccatca ccatcacgat gacgatgaca agggccctgt gccaacgccg    60
cccgacaaca tccaagtgca ggaaaacttc aatatctctc ggatctatgg gaagtggtac   120
aacctggcca tcggttccac ctgcccctgg ctgaagaaga tcatggacag gatgacagtg   180
agcacgctgg tgctgggaga gggcgctaca gaggcggaga tcagcatgac cagcactcat   240
tggcggaaag gtgtctgtga ggagacgtct ggagcttatg agaaaacaga tactgatggg   300
aagtttctct atcacaaatc caatggaac ataaccatgg agtccatgt ggtccacacc    360
aactatgatg agtatgccat tttcctgacc aagaaattca gccgccatca tggacccacc   420
attactgcca agctctacgg gcgggcgccg cagctgaggg aaactctcct gcaggacttc   480
agagtggttg cccagggtgt gggcatccct gaggactcca tcttcaccat ggctgaccga   540
ggtgaatgtg tccctgggga gcaggaacca gagcccatct taatcccgag atga          594
```

<210> SEQ ID NO 91
<211> LENGTH: 594
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 39. M8H4DK-Human N179GD

<400> SEQUENCE: 91

```
atgcatcacc atcaccatca ccatcacgat gacgatgaca agggccctgt gccaacgccg    60
cccgacaaca tccaagtgca ggaaaacttc gatatctctc ggatctatgg gaagtggtac   120
aacctggcca tcggttccac ctgcccctgg ctgaagaaga tcatggacag gatgacagtg   180
agcacgctgg tgctgggaga gggcgctaca gaggcggaga tcagcatgac cagcactcgt   240
tggcggaaag gtgtctgtga ggagacgtct ggagcttatg agaaaacaga tactgatggg   300
aagtttctct atcacaaatc caatggat ataaccatgg agtccatgt ggtccacacc     360
aactatgatg agtatgccat tttcctgacc aagaaattca gccgccatca tggacccacc   420
attactgcca agctctacgg gcgggcgccg cagctgaggg aaactctcct gcaggacttc   480
agagtggttg cccagggtgt gggcatccct gaggactcca tcttcaccat ggctgaccga   540
ggtgaatgtg tccctgggga gcaggaacca gagcccatct taatcccgag atga          594
```

<210> SEQ ID NO 92
<211> LENGTH: 579
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 40. M8H-Human wt

<400> SEQUENCE: 92

```
atgcatcacc atcaccatca ccatcacggc cctgtgccaa cgccgcccga acatccaa      60
gtgcaggaaa acttcaatat ctctcggatc tatgggaagt ggtacaacct ggccatcggt   120
tccacctgcc cctggctgaa gaagatcatg gacaggatga cagtgagcac gctggtgctg   180
ggagagggcg ctacagaggc ggagatcagc atgaccagca ctcgttggcg gaaaggtgtc   240
```

```
tgtgaggaga cgtctggagc ttatgagaaa acagatactg atgggaagtt tctctatcac    300
aaatccaaat ggaacataac catggagtcc tatgtggtcc acaccaacta tgatgagtat    360
gccattttcc tgaccaagaa attcagccgc catcatggac ccaccattac tgccaagctc    420
tacgggcggg cgccgcagct gagggaaact ctcctgcagg acttcagagt ggttgcccag    480
ggtgtgggca tccctgagga ctccatcttc accatggctg accgaggtga atgtgtccct    540
ggggagcagg aaccagagcc catcttaatc ccgagatga                          579
```

<210> SEQ ID NO 93
<211> LENGTH: 579
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 41. M8H-Human R66H+N1796D

<400> SEQUENCE: 93

```
atgcatcacc atcaccatca ccatcacggc cctgtgccaa cgccgcccga caacatccaa    60
gtgcaggaaa acttcgatat ctctcggatc tatgggaagt ggtacaacct ggccatcggt    120
tccacctgcc cctggctgaa gaagatcatg gacaggatga cagtgagcac gctggtgctg    180
ggagagggcg ctacagaggc ggagatcagc atgaccagca ctcattggcg aaaggtgtc     240 tgtgaggaga cgtctggagc ttatgagaaa acagatactg atgggaagtt tctctatcac    300
aaatccaaat gggatataac catggagtcc tatgtggtcc acaccaacta tgatgagtat    360
gccattttcc tgaccaagaa attcagccgc catcatggac ccaccattac tgccaagctc    420
tacgggcggg cgccgcagct gagggaaact ctcctgcagg acttcagagt ggttgcccag    480
ggtgtgggca tccctgagga ctccatcttc accatggctg accgaggtga atgtgtccct    540
ggggagcagg aaccagagcc catcttaatc ccgagatga                          579
```

<210> SEQ ID NO 94
<211> LENGTH: 555
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 42. untagged-Human R66H+N1796D

<400> SEQUENCE: 94

```
atgggccctg tgccaacgcc gcccgacaac atccaagtgc aggaaaactt cgatatctct    60
cggatctatg ggaagtggta caacctggcc atcggttcca cctgcccctg gctgaagaag    120
atcatggaca ggatgacagt gagcacgctg gtgctggag agggcgctac agaggcggag     180
atcagcatga ccagcactca ttggcggaaa ggtgtctgtg aggagacgtc tggagcttat    240
gagaaaacag atactgatgg gaagtttctc tatcacaaat ccaaatggga tataaccatg    300
gagtcctatg tggtccacac caactatgat gagtatgcca ttttcctgac caagaaattc    360
agccgccatc atggacccac cattactgcc aagctctacg ggcgggcgcc gcagctgagg    420
gaaactctcc tgcaggactt cagagtggtt gcccagggtg tgggcatccc tgaggactcc    480
atcttcacca tggctgaccg aggtgaatgt gtccctgggg agcaggaacc agagcccatc    540
ttaatcccga gatga                                                    555
```

-continued

```
<210> SEQ ID NO 95
<211> LENGTH: 555
<212> TYPE: DNA
<213> ORGANISM: Homo sapiens
<220> FEATURE:
<223> OTHER INFORMATION: 61. untagged-Human wt

<400> SEQUENCE: 95
atgggccctg tgccaacgcc gcccgacaac atccaagtgc aggaaaactt caatatctct      60
cggatctatg ggaagtggta caacctggcc atcggttcca cctgcccctg gctgaagaag     120
atcatggaca ggatgacagt gagcacgctg gtgctggagg agggcgctac agaggcggag     180
atcagcatga ccagcactcg ttggcggaaa ggtgtctgtg aggagacgtc tggagcttat     240
gagaaaacag atactgatgg gaagtttctc tatcacaaat ccaaatggaa cataaccatg     300
gagtcctatg tggtccacac caactatgat gagtatgcca ttttcctgac caagaaattc     360
agccgccatc atggacccac cattactgcc aagctctacg ggcgggcgcc gcagctgagg     420
gaaactctcc tgcaggactt cagagtggtt gcccagggtg tgggcatccc tgaggactcc     480
atcttcacca tggctgaccg aggtgaatgt gtccctgggg agcaggaacc agagcccatc     540
ttaatcccga gatga                                                      555

<210> SEQ ID NO 96
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Met His His His His His His His His Gly Gly Gly Gly Gly Ile Glu
1               5                   10                  15

Gly Arg

<210> SEQ ID NO 97
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Met His His His His His His His His Asp Asp Asp Asp Lys
1               5                   10

<210> SEQ ID NO 98
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Met His His His His His His Asp Asp Asp Asp Lys
1               5                   10

<210> SEQ ID NO 99
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 99

Met His His His His His His His
1               5

<210> SEQ ID NO 100
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Asp Asp Asp Lys Ala
1               5

<210> SEQ ID NO 101
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Leu Ile Pro Arg
1

<210> SEQ ID NO 102
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 102

His His His His His His
1               5

<210> SEQ ID NO 103
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 103

His His His His His His His His
1               5

<210> SEQ ID NO 104
<211> LENGTH: 183
<212> TYPE: PRT
<213> ORGANISM: Pongo abelii

<400> SEQUENCE: 104

Gly Pro Val Pro Thr Pro Pro Asp Asn Ile Gln Val Gln Glu Asn Phe
1               5                   10                  15

Asn Ile Ser Arg Ile Tyr Gly Lys Trp Tyr Asn Leu Ala Ile Gly Ser
            20                  25                  30

Thr Cys Pro Trp Leu Lys Lys Ile Met Asp Arg Met Thr Val Ser Thr
```

```
            35                  40                  45
Leu Val Leu Gly Glu Gly Ala Thr Glu Ala Glu Ile Ser Met Thr Ser
 50                  55                  60

Thr Arg Trp Arg Lys Gly Val Cys Glu Glu Thr Ser Gly Ala Tyr Glu
 65                  70                  75                  80

Lys Thr Asp Thr Asp Gly Lys Phe Leu Tyr His Lys Ser Lys Trp Asn
                     85                  90                  95

Ile Thr Met Glu Ser Tyr Val Val His Thr Asn Tyr Asp Glu Tyr Ala
                100                 105                 110

Ile Phe Leu Thr Lys Lys Phe Ser Arg Arg His Gly Pro Thr Ile Thr
                115                 120                 125

Ala Lys Leu Tyr Gly Arg Ala Pro Gln Leu Arg Glu Thr Leu Leu Gln
130                 135                 140

Asp Phe Arg Val Val Ala Gln Gly Val Gly Ile Pro Glu Asp Ser Ile
145                 150                 155                 160

Phe Thr Met Ala Asp Arg Gly Glu Cys Val Pro Gly Glu Gln Glu Pro
                165                 170                 175

Glu Pro Ile Leu Ile Pro Arg
                180

<210> SEQ ID NO 105
<211> LENGTH: 183
<212> TYPE: PRT
<213> ORGANISM: Saimiri boliviensis

<400> SEQUENCE: 105

Ser Pro Val Pro Thr Pro Glu Gly Ile Gln Val Gln Glu Asn Phe
 1               5                  10                  15

Asn Leu Ser Arg Ile Tyr Gly Lys Trp Tyr Asn Leu Ala Ile Gly Ser
                 20                  25                  30

Thr Cys Pro Trp Leu Lys Lys Ile Met Asp Arg Leu Lys Val Ser Thr
             35                  40                  45

Leu Val Leu Glu Glu Gly Ala Thr Glu Ala Glu Ile Ser Met Thr Ser
 50                  55                  60

Thr Arg Trp Arg Lys Gly Phe Cys Glu Gln Thr Ser Trp Ala Tyr Glu
 65                  70                  75                  80

Lys Thr Asp Thr Asp Gly Lys Phe Leu Tyr His Glu Pro Lys Trp Asn
                     85                  90                  95

Val Thr Met Glu Ser Tyr Val Ala His Thr Asn Tyr Glu Glu Tyr Ala
                100                 105                 110

Ile Phe Leu Thr Lys Lys Phe Ser Arg His His Gly Pro Thr Ile Thr
                115                 120                 125

Ala Lys Leu Tyr Gly Arg Glu Pro Gln Leu Arg Glu Ser Leu Leu Gln
130                 135                 140

Asp Phe Arg Val Val Ala Gln Gly Val Gly Ile Pro Glu Asp Ser Ile
145                 150                 155                 160

Phe Thr Met Ala Asn Arg Gly Glu Cys Val Pro Gly Glu Gln Glu Pro
                165                 170                 175

Gln Pro Ile Leu His Arg Arg
                180

<210> SEQ ID NO 106
<211> LENGTH: 182
<212> TYPE: PRT
<213> ORGANISM: Mus musculus
```

```
<400> SEQUENCE: 106

Asp Pro Ala Ser Thr Leu Pro Asp Ile Gln Val Gln Glu Asn Phe Ser
1               5                   10                  15

Glu Ser Arg Ile Tyr Gly Lys Trp Tyr Asn Leu Ala Val Gly Ser Thr
            20                  25                  30

Cys Pro Trp Leu Ser Arg Ile Lys Asp Lys Met Ser Val Gln Thr Leu
        35                  40                  45

Val Leu Gln Glu Gly Ala Thr Glu Thr Glu Ile Ser Met Thr Ser Thr
    50                  55                  60

Arg Trp Arg Arg Gly Val Cys Glu Glu Ile Thr Gly Ala Tyr Gln Lys
65                  70                  75                  80

Thr Asp Ile Asp Gly Lys Phe Leu Tyr His Lys Ser Lys Trp Asn Ile
                85                  90                  95

Thr Leu Glu Ser Tyr Val Val His Thr Asn Tyr Asp Glu Tyr Ala Ile
            100                 105                 110

Phe Leu Thr Lys Lys Ser Ser His His His Gly Leu Thr Ile Thr Ala
        115                 120                 125

Lys Leu Tyr Gly Arg Glu Pro Gln Leu Arg Asp Ser Leu Leu Gln Glu
    130                 135                 140

Phe Lys Asp Val Ala Leu Asn Val Gly Ile Ser Glu Asn Ser Ile Ile
145                 150                 155                 160

Phe Met Pro Asp Arg Gly Glu Cys Val Pro Gly Asp Arg Glu Val Glu
                165                 170                 175

Pro Thr Ser Ile Ala Arg
            180

<210> SEQ ID NO 107
<211> LENGTH: 183
<212> TYPE: PRT
<213> ORGANISM: Oryctolagus cuniculus

<400> SEQUENCE: 107

Asp Pro Val Pro Thr Leu Pro Asp Ile Gln Val Gln Glu Asn Phe
1               5                   10                  15

Glu Leu Ser Arg Ile Tyr Gly Lys Trp Tyr Asn Leu Ala Val Gly Ser
            20                  25                  30

Thr Cys Pro Trp Leu Lys Arg Ile Lys Asp Arg Met Ala Val Ser Thr
        35                  40                  45

Leu Val Leu Gly Glu Gly Thr Ser Glu Thr Glu Ile Ser Met Thr Ser
    50                  55                  60

Thr His Trp Arg Arg Gly Val Cys Glu Glu Ile Ser Gly Ala Tyr Glu
65                  70                  75                  80

Lys Thr Asp Thr Asp Gly Lys Phe Leu Tyr His Lys Ala Lys Trp Asn
                85                  90                  95

Leu Thr Met Glu Ser Tyr Val Val His Thr Asn Tyr Asp Glu Tyr Ala
            100                 105                 110

Ile Phe Leu Thr Lys Lys Phe Ser Arg Arg His Gly Pro Thr Ile Thr
        115                 120                 125

Ala Lys Leu Tyr Gly Arg Glu Pro Gln Leu Arg Glu Ser Leu Leu Gln
    130                 135                 140

Glu Phe Arg Glu Val Ala Leu Gly Val Gly Ile Pro Glu Asn Ser Ile
145                 150                 155                 160

Phe Thr Met Ile Asp Arg Gly Glu Cys Val Pro Gly Gln Gln Glu Pro
                165                 170                 175
```

```
Lys Pro Ala Pro Val Leu Arg
            180

<210> SEQ ID NO 108
<211> LENGTH: 183
<212> TYPE: PRT
<213> ORGANISM: Heterocephalus glaber

<400> SEQUENCE: 108

Asn Pro Val Pro Met Pro Pro Asp Asn Ile Gln Val Gln Glu Asn Phe
1               5                   10                  15

Asp Glu Ser Arg Ile Tyr Gly Lys Trp Phe Asn Leu Ala Thr Gly Ser
            20                  25                  30

Thr Cys Pro Trp Leu Lys Arg Ile Lys Asp Arg Leu Ser Val Ser Thr
        35                  40                  45

Met Val Leu Gly Lys Gly Thr Thr Glu Thr Gln Ile Ser Thr Thr His
    50                  55                  60

Thr His Trp Arg Gln Gly Val Cys Gln Glu Thr Ser Gly Val Tyr Lys
65                  70                  75                  80

Lys Thr Asp Thr Ala Gly Lys Phe Leu Tyr His Lys Ser Lys Trp Asn
                85                  90                  95

Val Thr Met Glu Ser Tyr Val Val His Thr Asn Tyr Asp Glu Tyr Ala
            100                 105                 110

Ile Ile Leu Thr Lys Lys Phe Ser His His Gly Pro Thr Ile Thr
        115                 120                 125

Ala Lys Leu Tyr Gly Arg Glu Pro Arg Leu Arg Asp Ser Leu Leu Gln
    130                 135                 140

Glu Phe Arg Glu Met Ala Leu Gly Val Gly Ile Pro Glu Asp Ser Ile
145                 150                 155                 160

Phe Thr Met Ala Asn Arg Gly Glu Cys Val Pro Gly Asp Gln Ala Pro
                165                 170                 175

Glu Ser Thr Pro Ala Pro Arg
            180

<210> SEQ ID NO 109
<211> LENGTH: 183
<212> TYPE: PRT
<213> ORGANISM: Odobenus rosmarus

<400> SEQUENCE: 109

Ser Pro Val Leu Thr Pro Pro Asp Ala Ile Gln Val Gln Glu Asn Phe
1               5                   10                  15

Asp Ile Ser Arg Ile Tyr Gly Lys Trp Phe His Val Ala Met Gly Ser
            20                  25                  30

Thr Cys Pro Trp Leu Lys Lys Phe Met Asp Arg Met Ser Met Ser Thr
        35                  40                  45

Leu Val Leu Gly Glu Gly Ala Thr Asp Gly Glu Ile Ser Met Thr Ser
    50                  55                  60

Thr Arg Trp Arg Arg Gly Thr Cys Glu Glu Ile Ser Gly Ala Tyr Glu
65                  70                  75                  80

Lys Thr Ser Thr Asn Gly Lys Phe Leu Tyr His Asn Pro Lys Trp Asn
                85                  90                  95

Ile Thr Met Glu Ser Tyr Val Val His Thr Asp Tyr Asp Glu Tyr Ala
            100                 105                 110

Ile Phe Leu Thr Lys Lys Phe Ser Arg His His Gly Pro Thr Ile Thr
        115                 120                 125
```

Ala Lys Leu Tyr Gly Arg Gln Pro Gln Leu Arg Glu Ser Leu Leu Glu
    130                 135                 140

Glu Phe Arg Glu Leu Ala Leu Gly Val Gly Ile Pro Glu Asp Ser Ile
145                 150                 155                 160

Phe Thr Met Ala Asn Lys Gly Glu Cys Val Pro Gly Glu Gln Glu Pro
                165                 170                 175

Glu Pro Ser Pro His Met Arg
            180

<210> SEQ ID NO 110
<211> LENGTH: 182
<212> TYPE: PRT
<213> ORGANISM: Trichechus manatus

<400> SEQUENCE: 110

Ser Pro Val Lys Thr Pro Leu Asn Asp Ile Gln Val Gln Glu Asn Phe
1               5                   10                  15

Asp Leu Pro Arg Ile Tyr Gly Lys Trp Phe Asn Ile Ala Ile Gly Ser
            20                  25                  30

Thr Cys Gln Trp Leu Lys Arg Leu Lys Ala Gly Pro Thr Met Ser Thr
        35                  40                  45

Leu Val Leu Gly Glu Gly Ala Thr Asp Thr Glu Ile Ser Thr Thr Ser
    50                  55                  60

Thr Arg Trp Arg Lys Gly Phe Cys Glu Glu Ile Ser Gly Ala Tyr Glu
65                  70                  75                  80

Lys Thr Asp Thr Ala Gly Lys Phe Leu Tyr His Gly Ser Lys Trp Asn
                85                  90                  95

Val Thr Leu Glu Ser Tyr Val Val His Thr Asn Tyr Asp Glu Tyr Ala
            100                 105                 110

Ile Phe Leu Thr Lys Lys Phe Ser Arg Tyr Gly Leu Thr Ile Thr Ala
        115                 120                 125

Lys Leu Tyr Gly Arg Gln Pro Gln Val Arg Glu Ser Leu Leu Glu Glu
    130                 135                 140

Phe Arg Glu Phe Ala Leu Gly Val Gly Ile Pro Glu Asp Ser Ile Phe
145                 150                 155                 160

Thr Thr Ala Asp Lys Gly Glu Cys Val Pro Gly Glu Gln Glu Pro Glu
                165                 170                 175

Pro Thr Ala Ala Leu Arg
            180

<210> SEQ ID NO 111
<211> LENGTH: 179
<212> TYPE: PRT
<213> ORGANISM: Gallus gallus

<400> SEQUENCE: 111

Thr Pro Val Gly Asp Gln Asp Glu Asp Ile Gln Val Gln Glu Asn Phe
1               5                   10                  15

Glu Pro Glu Arg Met Tyr Gly Lys Trp Tyr Asp Val Ala Val Gly Thr
            20                  25                  30

Thr Cys Lys Trp Met Lys Asn Tyr Lys Glu Lys Phe Ser Met Gly Thr
        35                  40                  45

Leu Val Leu Gly Pro Gly Pro Ser Ala Asp Gln Ile Ser Thr Ile Ser
    50                  55                  60

Thr Arg Leu Arg Gln Gly Asp Cys Lys Arg Val Ser Gly Glu Tyr Gln
65                  70                  75                  80

```
Lys Thr Asp Thr Pro Gly Lys Tyr Thr Tyr Tyr Asn Pro Lys Trp Asp
                85                  90                  95

Val Ser Ile Lys Ser Tyr Val Leu Arg Thr Asn Tyr Glu Glu Tyr Ala
            100                 105                 110

Val Ile Leu Met Lys Lys Thr Ser Asn Phe Gly Pro Thr Thr Thr Leu
            115                 120                 125

Lys Leu Tyr Gly Arg Ser Pro Glu Leu Arg Glu Leu Thr Glu Ala
        130                 135                 140

Phe Gln Gln Leu Ala Leu Glu Met Gly Ile Pro Ala Asp Ser Val Phe
145                 150                 155                 160

Ile Leu Ala Asn Lys Gly Glu Cys Val Pro Gln Glu Thr Ala Thr Ala
                165                 170                 175

Pro Glu Arg
```

```
<210> SEQ ID NO 112
<211> LENGTH: 180
<212> TYPE: PRT
<213> ORGANISM: Latimeria chalumnae

<400> SEQUENCE: 112

Gly Ser Pro Leu Arg Asp Glu Asp Ile Gln Val Gln Glu Asn Phe Asp
1               5                   10                  15

Leu Pro Arg Ile Tyr Gly Lys Trp Tyr Glu Ile Ala Ile Ala Ser Thr
            20                  25                  30

Cys Pro Trp Val Lys Asn His Lys Asp Lys Met Phe Met Gly Thr Met
        35                  40                  45

Val Leu Gln Glu Gly Glu Gln Ser Asp Arg Ile Ser Thr Thr Ser Thr
    50                  55                  60

Arg Ile Arg Asp Gly Thr Cys Ser Gln Ile Thr Gly Tyr Tyr Thr Leu
65                  70                  75                  80

Thr Thr Thr Pro Gly Lys Phe Ala Tyr His Asn Ser Lys Trp Asn Leu
                85                  90                  95

Asp Val Asn Ser Tyr Val Val His Thr Asn Tyr Asp Glu Tyr Ser Ile
            100                 105                 110

Val Met Met Gln Lys Tyr Lys Ser Ser Asn Ser Thr Thr Thr Val Arg
            115                 120                 125

Leu Tyr Gly Arg Thr Gln Glu Leu Arg Asp Ser Leu His Ala Glu Phe
        130                 135                 140

Lys Lys Phe Ala Leu Asp Gln Gly Ile Asp Glu Asp Ser Ile Tyr Ile
145                 150                 155                 160

Leu Pro Lys Arg Asp Glu Cys Val Pro Gly Glu Pro Lys Ala Glu Ser
                165                 170                 175

Leu Met Ala Arg
            180
```

```
<210> SEQ ID NO 113
<211> LENGTH: 179
<212> TYPE: PRT
<213> ORGANISM: Xenopus laevis

<400> SEQUENCE: 113

Cys Ser Pro Ile Gln Pro Glu Asp Asn Ile Gln Ile Gln Glu Asn Phe
1               5                   10                  15

Asp Leu Gln Arg Ile Tyr Gly Lys Trp Tyr Asp Ile Ala Ile Gly Ser
            20                  25                  30

Thr Cys Lys Trp Leu Lys His His Lys Glu Lys Phe Asn Met Gly Thr
```

```
            35                  40                  45
Leu Glu Leu Ser Asp Gly Glu Thr Asp Gly Glu Val Arg Ile Val Asn
 50                  55                  60

Thr Arg Met Arg His Gly Thr Cys Ser Gln Ile Val Gly Ser Tyr Gln
 65                  70                  75                  80

Lys Thr Glu Thr Pro Gly Lys Phe Asp Tyr Phe Asn Ala Arg Trp Gly
                 85                  90                  95

Thr Thr Ile Gln Asn Tyr Ile Val Phe Thr Asn Tyr Asn Glu Tyr Val
                100                 105                 110

Ile Met Gln Met Arg Lys Lys Lys Gly Ser Glu Thr Thr Thr Thr Val
                115                 120                 125

Lys Leu Tyr Gly Arg Ser Pro Asp Leu Arg Pro Thr Leu Val Asp Glu
130                 135                 140

Phe Arg Gln Phe Ala Leu Ala Gln Gly Ile Pro Glu Asp Ser Ile Val
145                 150                 155                 160

Met Leu Pro Asn Asn Gly Glu Cys Ser Pro Gly Glu Ile Glu Val Arg
                165                 170                 175

Pro Arg Arg

<210> SEQ ID NO 114
<211> LENGTH: 184
<212> TYPE: PRT
<213> ORGANISM: Pleuronectes platessa

<400> SEQUENCE: 114

Leu Pro Val Leu Pro Glu Pro Leu Tyr Pro Thr Gln Glu Asn Phe Asp
 1                5                  10                  15

Leu Thr Arg Phe Val Gly Thr Trp His Asp Val Ala Leu Thr Ser Ser
                 20                  25                  30

Cys Pro His Met Gln Arg Asn Arg Ala Asp Ala Ala Ile Gly Lys Leu
                 35                  40                  45

Val Leu Glu Lys Asp Thr Gly Asn Lys Leu Lys Val Thr Arg Thr Arg
 50                  55                  60

Leu Arg His Gly Thr Cys Val Glu Met Ser Gly Glu Tyr Glu Leu Thr
 65                  70                  75                  80

Ser Thr Pro Gly Arg Ile Phe Tyr His Ile Asp Arg Trp Asp Ala Asp
                 85                  90                  95

Val Asp Ala Tyr Val Val His Thr Asn Tyr Asp Glu Tyr Ala Ile Ile
                100                 105                 110

Ile Met Ser Lys Gln Lys Thr Ser Gly Glu Asn Ser Thr Ser Leu Lys
                115                 120                 125

Leu Tyr Ser Arg Thr Met Ser Val Arg Asp Thr Val Leu Asp Asp Phe
130                 135                 140

Lys Thr Leu Val Arg His Gln Gly Met Ser Asp Asp Thr Ile Ile Ile
145                 150                 155                 160

Lys Gln Asn Lys Gly Asp Cys Ile Pro Gly Glu Gln Val Glu Glu Ala
                165                 170                 175

Pro Ser Gln Pro Glu Pro Lys Arg
                180
```